(12) United States Patent
Li et al.

(10) Patent No.: US 8,097,253 B2
(45) Date of Patent: Jan. 17, 2012

(54) METHODS FOR INHIBITING ANGIOGENESIS

(75) Inventors: Dean Y. Li, Salt Lake City, UT (US); Kyle Won Park, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 12/271,825

(22) Filed: Nov. 14, 2008

(65) Prior Publication Data

US 2010/0040622 A1    Feb. 18, 2010

Related U.S. Application Data

(63) Continuation of application No. 11/183,136, filed on Jul. 14, 2005, now Pat. No. 7,456,151.

(60) Provisional application No. 60/587,796, filed on Jul. 14, 2004.

(51) Int. Cl.
*A61K 39/00* (2006.01)
*C07K 16/00* (2006.01)
*C07K 16/18* (2006.01)

(52) U.S. Cl. ............... 424/139.1; 424/130.1; 530/387.1; 530/387.9

(58) Field of Classification Search .................. None
See application file for complete search history.

(56) References Cited

U.S. PATENT DOCUMENTS

| | | | |
|---|---|---|---|
| 5,747,262 | A | 5/1998 | Hinck et al. |
| 5,824,775 | A | 10/1998 | Swimmer et al. |
| 5,939,271 | A | 8/1999 | Tessier-Lavigne et al. |
| 6,017,714 | A | 1/2000 | Tessier-Lavigne et al. |
| 6,028,173 | A | 2/2000 | Landes et al. |
| 6,030,806 | A | 2/2000 | Landes et al. |
| 6,087,326 | A | 7/2000 | Hinck et al. |
| 6,096,866 | A | 8/2000 | Tessier-Lavigne et al. |
| 6,218,526 | B1 | 4/2001 | Swimmer et al. |
| 6,277,585 | B1 | 8/2001 | Tessier-Lavigne et al. |
| 6,309,638 | B1 | 10/2001 | Tessier-Lavigne et al. |
| 6,428,965 | B1 | 8/2002 | Ginty et al. |
| 6,448,054 | B1 | 9/2002 | Poznansky et al. |
| 6,495,674 | B1 | 12/2002 | Lamke et al. |
| 6,566,094 | B1 | 5/2003 | Kimura et al. |
| 7,456,151 | B2 | 11/2008 | Li et al. |
| 2003/0003163 | A1 | 1/2003 | Hodosh |
| 2003/0040046 | A1 | 2/2003 | Tessier-Lavigne et al. |
| 2003/0049248 | A1 | 3/2003 | Tessier-Lavigne et al. |
| 2003/0207347 | A1 | 11/2003 | Olson et al. |

FOREIGN PATENT DOCUMENTS

| | | |
|---|---|---|
| FR | 2814077 | 3/2002 |
| WO | WO 95/13367 | 5/1995 |
| WO | WO 97/14424 | 4/1997 |
| WO | WO 97/40064 | 10/1997 |
| WO | WO 98/37085 | 8/1998 |
| WO | WO 00/32746 | 6/2000 |
| WO | WO 00/053735 | 9/2000 |
| WO | WO 01/64837 | 9/2001 |
| WO | WO 02/33080 | 4/2002 |

OTHER PUBLICATIONS

First Preliminary Amendment filed Jan. 24, 2006 in co-pending U.S. Appl. No. 11/183,136.
Restriction Requirement issued Dec. 21, 2006 in co-pending U.S. Appl. No. 11/183,136.
Reply to Restriction Requirement filed Jan. 22, 2007 in co-pending U.S. Appl. No. 11/183,136.
Restriction Requirement issued Apr. 18, 2007 in co-pending U.S. Appl. No. 11/183,136.
Reply to Restriction Requirement filed May 11, 2007 in co-pending U.S. Appl. No. 11/183,136.
Office Action issued Aug. 7, 2007 in co-pending U.S. Appl. No. 11/183,136.
Amendment and Response filed Feb. 7, 2008 in co-pending U.S. Appl. No. 11/183,136.
Notice of Non-Compliant Amendment issued Feb. 19, 2008 in co-pending U.S. Appl. No. 11/183,136.
Response to Notice of Non-Compliant Amendment filed Mar. 19, 2008 in co-pending U.S. Appl. No. 11/183,136.
Notice of Allowance issued Jul. 23, 2008 in co-pending U.S. Appl. No. 11/183,136.
Notification of Transmittal of the International Search Report and the Written Opinion of the International Searching Authority issued Oct. 24, 2005 in International Application No. PCT/US2005/024980.
Borisy et al. (2003). Systematic discovery of multicomponent therapeutics. Proc. Natl. Acad. Sci. USA. 100(13):7977-7982.
Nico et al. (2001). Vascular stem cells and angiogenesis. Journal of Hematotherapy & Stem Cell Research. 10:905-912.
Park et al. (2005). Identification of new netrin family members in zebrafish: developmental expression of netrin2 and netrin4. Developmental Dynamics. 234:726-731.
Puschel, A.W. (1999). Divergent properties of mouse netrins. Mechanisms of Development. 83:65-75.
Park et al. (2004). The axonal attractant netrin-1 is an angiogenic factor. Proc. Natl. Acad. Sci. USA. 101(46):16210-16215.
Wells, J.A. (1990). Additivity of mutational effects in proteins. Biochemistry. 29(37):8509-8517.
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.
Skolnick et al. (2000). From genes to protein structure and function: novel applications of computational approaches in the genomic era. Trends in Biotech. 18(1):34-39.
Corset, V., et al., "Netrin-1-mediated axon outgrowth and cAMP production requires interaction with adenosine A2b receptor," Nature, 407:747-750 (2000).

(Continued)

*Primary Examiner* — Christine J Saoud
*Assistant Examiner* — Jon M Lockard
(74) *Attorney, Agent, or Firm* — Samuel E. Webb; Yury M. Colton; Stoel Rives LLP

(57) ABSTRACT

The present invention provides methods and compositions for modulating proliferation, differentiation, migration, and adhesion of cardiovascular cell types.

1 Claim, 11 Drawing Sheets

OTHER PUBLICATIONS

Culotti, J.G., and Merz, D.C., "DCC and netrins," Curr Opin Cell Biol, 10:609-613 (1996).

Dickson, Barry J., "Molecular Mechanisims of Axon Guidance", Science, 298(5600), pp. 1959-1964 (2002) Abstract.

Dubey, R.K., et al., "A.sub.2B Adenosine Receptors Stimulate Growth of Porcine and Rat Arterial Endothelial Cells," Hypertension, 39:530-535 (2002).

Folkman, J., and D'Amore, P.A., "Blood Vessel Formation: What Is Its Molecular Basis?" Cell, 87:1153-1155 (1996).

Huber, A.B., et al., "Signaling at the Growth Cone: Ligand-Receptor Complexes and the Control of Axon Growth and Guidance," Annu. Rev. Neurosci., 26:509-563 (2003).

Keleman, K., and Dickson, B.J., "Short- and Long-Range Repulsion by the *Drosophila* Unc5 Netrin Receptor," Neuron, 32:605-617 (2001).

Kusano, K.F., et al., "Sonic Hedgehog Induces Arteriogenesis in Diabetic Vasa Nervorum and Restores Function in Diabetic Neuropathy," Arterioscler Thromb Vasc Biol, 24:2102-2107 (2004).

Lu, X., et al., "The netrin receptor UNC5B mediates guidance events controlling morphogenesis of the vascular system", Nature, 432 (7014), pp. 179-186 (2004).

Nakashiba, T., et al., "Complementary expression and neurite outgrowth activity of netrin-G subfamily members," Mechanisms of Development, 111:47-60 (2002).

Nakashiba, T., et al., "Netrin-G1: a Novel Glycosyl Phosphatidylinositol-Linked Mammalian Netrin That Is Functionally Divergent from Classical Netrins," Journal of Neuroscience, 20(17):6540-6550 (2000).

Tessier-Lavigne, M. and Goodman, C. S., "The Molecular Biology of Axon Guidance", Science, 274:1123-1133 (1996) Abstract.

Thiebault, K. et al., "The netrin-1 receptors UNC5H are putative tumor suppressors controlling cell death commitment", Proceedings of the National Academy of Sciences of USA, National Academy of Science, 100(7), pp. 4173-4178 (2003).

Weinstein, B.M., "Vessels and Nerves: Marching to the Same Tune," Cell, 120:299-302 (2005).

Yin, Y., et al., "Identification and expression of mouse netrin-4," Mechanisms of Development, 96:115-119 (2000).

Schematic Depicting Domain Structure of a Netrin Polypeptide

Fig 6
a RT-PCR
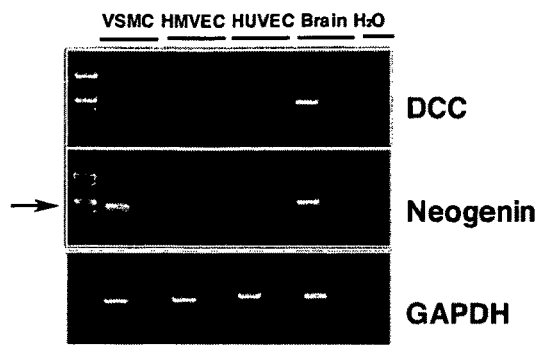
b Western Blot
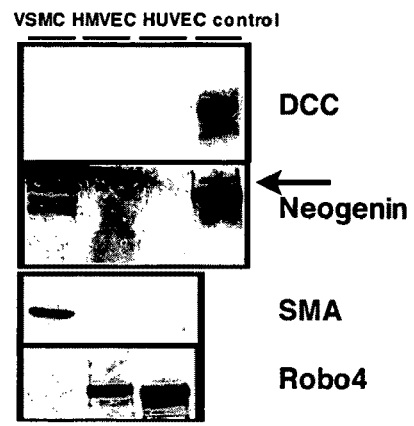
c Migration
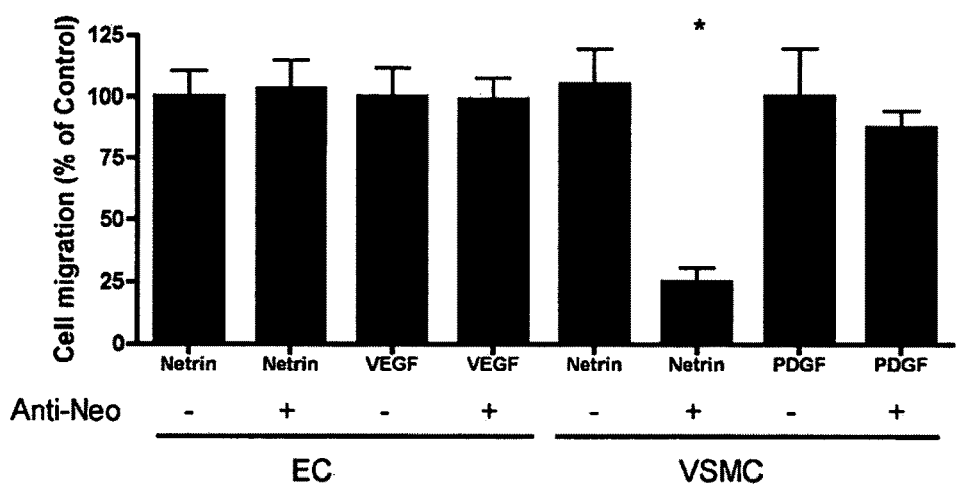
d Adhesion
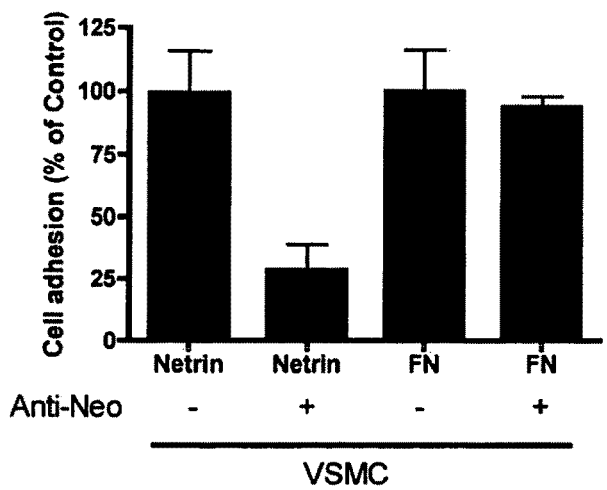

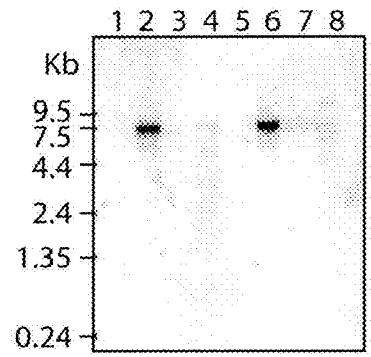

1. Promyelocytic Leukemia HL-60
2. Hela 53
3. Chronic Myelogenous Leukemia K-562
4. Lymphoblast Leukemia MOLT-4
5. Burkett's Lymphoma Raji
6. Colorectal Adenocarcinoma S-W480
7. Lung Carcinoma A549
8. Melanoma G-361

Fig. 8A

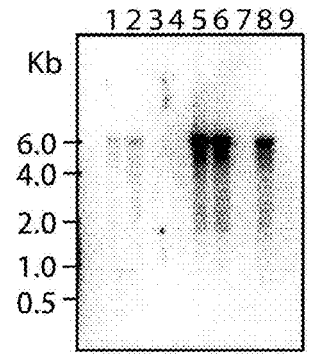

1. Acute T-Cell Leukemia (Jurkat)
2. Burkett's Lymphoma (CA46)
3. Breast Carcinoma (MDA-MB-453)
4. Burkett's Lymphoma (Namalwa)
5. Epidermal Carcinoma (A-431)
6. Uterine Carcinoma (UES-SA)
7. Burkett's Lymphoma (Ray)
8. Osteocarcinoma (WG-03)
9. Histocytic Lymphoma (U-937)

Fig. 8B

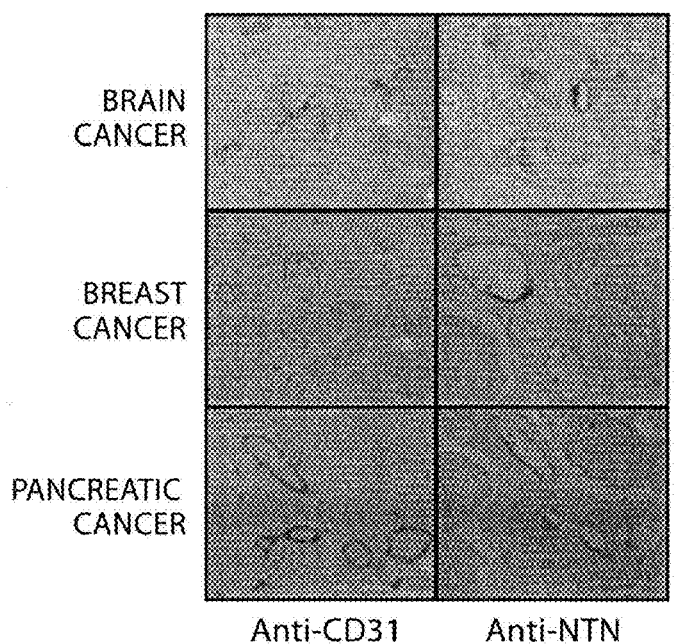

METHODS FOR INHIBITING ANGIOGENESIS

RELATED APPLICATIONS

This application is a continuation of U.S. patent application Ser. No. 11/183,136, filed Jul. 14, 2005, issued as U.S. Pat. No. 7,456,151, which claims the benefit of U.S. Provisional Application No. 60/587,796, filed Jul. 14, 2004, incorporated herein by reference.

BACKGROUND OF THE INVENTION

The cardiovascular system is the first organ system to develop and function during embryogenesis. As its name implies, the cardiovascular system involves a network of complex vasculature, vascular cells (e.g., endothelial cells and vascular smooth muscle cells), blood cells, immune cells, as well as the multiple cell types (e.g., myocardial, endocardial, pericardial) required to form a functioning heart.

Given the important role of the heart and vasculature, not only in maintaining the very life of an organism but also in delivering oxygen and nutrients throughout a body, tremendous resources have focused on identifying factors that promote or otherwise modulate vascular growth and migration. These factors include members of the fibroblast growth factor (FGF) family, the platlet-derived growth factor (PDGF) family, the vascular endothelial growth factor (VEGF) family, and the angiopoietins.

Despite the tremendous advances in cardiovascular research, there remains a substantial need in the art to improve our understanding of the cardiovascular and vascular systems throughout embryonic and adult development. Through an increased understanding of cardiovascular and vascular development and the identification of the molecular signals involved in regulating one or more of the proliferation, differentiation, migration, survival, and adhesion of cells of these systems, methods and compositions useful in modulating cells of the cardiovascular system can be developed for in vitro and in vivo purposes. The present invention provides such methods and compositions.

Furthermore, there exists a need in the art to improve our understanding of the mechanisms by which normal cardiovascular growth and behavior goes awry in numerous conditions and disease states. Through an increased understanding of the molecular mechanisms underlying normal and pathological development of the heart and vasculature, methods and compositions useful in modulating one or more of the proliferation, differentiation, migration, survival, and adhesion of cells of the cardiovascular system can be developed. The present invention provides such methods and compositions.

BRIEF SUMMARY OF THE INVENTION

The present invention provides methods and compositions using netrin, netrin-related compositions, and agents that inhibit the expression and/or activity of netrin or of netrin signaling. The present invention is based on the discovery that netrin polypeptides and netrin signaling, known for its role in axon guidance, also function to modulate the proliferation and migration of vascular cells and endothelial cells. Based on this discovery, the present invention provides novel methods and compositions for using netrin and netrin-related compositions to influence the proliferation, migration, and adhesion of various vascular and endothelial cell types, as well as methods for treating diseases and conditions of the vascular system.

In a first aspect, the invention provides a method for promoting angiogenesis. The method comprises administering an amount of a netrin polypeptide effective to promote angiogenesis. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 39, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 39, 40, 42, 44, or a bioactive fragment thereof. In still another embodiment, the netrin polypeptide comprises an amino acid sequence identical to SEQ ID NO: 2, 4, 6, 8, 10, 12, 39, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In any of the foregoing embodiments, the invention contemplates further administering one or more angiogenic factors. In one embodiment, the angiogenic factors are selected from a vascular endothelial growth factor (VEGF), a fibroblast growth factor (FGF), a platlet-derived growth factor (PDGF), or an angiopoietin polypeptide. The combination of a netrin polypeptide and one or more angiogenic factors may act additively or synergistically, and may be administered consecutively or concomitantly.

In a second aspect, the present invention provides a method for inhibiting angiogenesis. The method comprises administering an amount of an agent effective to inhibit angiogenesis, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In a third aspect, the present invention provides the use of a netrin polypeptide in the manufacture of a medicament for promoting angiogenesis.

In a fourth aspect, the present invention provides the use of an agent that inhibits the expression and/or activity of a netrin polypeptide in the manufacture of a medicament for inhibiting angiogenesis.

In a fifth aspect, the present invention provides a method for promoting proliferation of smooth muscle cells. The method comprises contacting smooth muscle cells with an amount of a netrin polypeptide effective to promote proliferation of said smooth muscle cells. In one embodiment, the netrin polypeptide is a human netrin-1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 39, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 39, 40, 42, 44, or a bioactive fragment thereof. In still another embodiment, the netrin polypeptide comprises an amino acid sequence identical to SEQ ID NO: 2, 4, 6, 8, 10, 12, 39, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In one embodiment, the smooth muscle cells are vascular smooth muscle cells.

In a sixth aspect, the invention provides a method for inhibiting the proliferation of smooth muscle cells. The method comprises contacting cells with an amount of an agent effective to inhibit proliferation of smooth muscle cells, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In one embodiment, the smooth muscle cells are vascular smooth muscle cells.

In a seventh aspect, the invention provides the use of a netrin polypeptide in the manufacture of a medicament for promoting the proliferation of smooth muscle cells. In one embodiment, the smooth muscle cells are vascular smooth muscle cells.

In an eighth aspect, the invention provides the use of an agent that inhibits the expression and/or activity of a netrin polypeptide in the manufacture of a medicament for inhibiting the proliferation of smooth muscle cells. In one embodiment, the smooth muscle cells are vascular smooth muscle cells.

In a ninth aspect, the invention provides a method for promoting proliferation of endothelial cells. The method comprises contacting endothelial cells with an amount of a netrin polypeptide effective to promote proliferation of said endothelial cells. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 39, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 39, 40, 42, 44, or a bioactive fragment thereof. In still another embodiment, the netrin polypeptide comprises an amino acid sequence identical to SEQ ID NO: 2, 4, 6, 8, 10, 12, 39, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In a tenth aspect, the present invention provides a method for inhibit the proliferation of endothelial cells. The method comprises contacting endothelial cells with an amount of an agent effective to inhibit proliferation of said endothelial cells, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In an eleventh aspect, the invention provides the use of a netrin polypeptide in the manufacture of a medicament for promoting proliferation of endothelial cells.

In a twelfth aspect, the invention provides the use of an agent that inhibits the expression and/or activity of a netrin polypeptide in the manufacture of a medicament for inhibiting the proliferation of endothelial cells.

In a thirteenth aspect, the invention provides a method for promoting migration of endothelial cells. The method comprises contacting endothelial cells with an amount of a netrin polypeptide effective to promote migration of said endothelial cells. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In a fourteenth aspect, the present invention provides a method for inhibiting the migration of endothelial cells. The method comprises contacting said cells with am amount of an agent effective to inhibit the migration of endothelial cells, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In a fifteenth aspect, the present invention provides the use of a netrin polypeptide in the manufacture of a medicament for promoting migration of endothelial cells.

In a sixteenth aspect, the present invention provides the use of an agent that inhibits the expression and/or activity of a netrin polypeptide in the manufacture of a medicament for promoting migration of endothelial cells.

In a seventeenth aspect, the present invention provides a method of promoting migration of an endothelial tube. The method comprises administering an amount of a netrin polypeptide effective to promote the migration of the endothelial tube, wherein said netrin polypeptide is an attractive signal thereby promoting migration of the endothelial tube to the netrin polypeptide. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In an eighteenth aspect, the present invention provides a method of inhibiting migration of an endothelial tube. The method comprises administering an amount of an agent effective to inhibit migration of an endothelial tube, wherein the agent inhibits the expression and/or activity of a netrin polypeptide, and wherein said agent is a repulsive signal thereby inhibiting migration of said endothelial tube to said agent. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In a nineteenth aspect, the present invention provides the use of a netrin polypeptide in the manufacture of a medicament for promoting migration of an endothelial tube.

In a twentieth aspect, the present invention provides the use of an agent that inhibits the expression and/or activity of a netrin polypeptide in the manufacture of a medicament for inhibiting the migration of an endothelial tube.

In a twenty-first aspect, the present invention provides a method for promoting proliferation of stem cells. The method comprises administering an amount of a netrin polypeptide effective to promote proliferation of said stem cells. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In any of the foregoing, the invention contemplates that the stem cells can be embryonic, fetal, or adult stem cells. The stem cells can be cultured and maintained in vitro, in which case the netrin polypeptide is administered to the cells in vitro. The stem cells can be endogenous stem cells in the body of an animal, in which case the netrin polypeptide is administered to the animal to promote the proliferation of stem cells in vivo.

In one embodiment, the stem cells are hematopoietic stem cells or endothelial stem cells.

In a twenty-second aspect, the invention provides a method for promoting migration of stem cells. The method comprises administering an amount of a netrin polypeptide effective to promote migration of the stem cells. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In any of the foregoing, the invention contemplates that the stem cells can be embryonic, fetal, or adult stem cells. The stem cells can be cultured and maintained in vitro, in which case the netrin polypeptide is administered to the cells in vitro. The stem cells can be endogenous stem cells in the body of an animal, in which case the netrin polypeptide is administered to the animal to promote the migration of stem cells in vivo.

In one embodiment, the stem cells are hematopoietic stem cells or endothelial stem cells.

In a twenty-third aspect, the present invention provides the use of a netrin polypeptide in the manufacture of a medicament for promoting proliferation of stem cells.

In a twenty-fourth aspect, the present invention provides the use of a netrin polypeptide in the manufacture of a medicament for promoting migration of stem cells.

In a twenty-fifth aspect, the present invention provides a method of promoting adhesion of smooth muscle cells. The method comprises contacting smooth muscle cells with an amount of a netrin polypeptide effective to promote adhesion of said smooth muscle cells. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In one embodiment, the smooth muscle cells are vascular smooth muscle cells.

In a twenty-sixth aspect, the present invention provides the use of a netrin polypeptide in the manufacture of a medicament to promote adhesion of smooth muscle cells.

In a twenty-seventh aspect, the present invention provides a pharmaceutical composition comprising a modified netrin polypeptide, or bioactive fragment thereof. The modified netrin polypeptide can be modified on one or more of an N-terminal, C-terminal, or internal amino acid residue with one or more moiety. Each moiety can be independently selected from exemplary hydrophobic or hydrophilic moieties. Particularly preferred modified netrin polypeptides for use in the methods of the present invention retain one or more of the biological activities of the un-modifed netrin polypeptide. Furthermore, particularly preferred modified netrin polypeptides possess one or more advantageous physio-chemical properties in comparison to the un-modified polypeptide.

Modified polypeptides can be modified one, two, three, four, five, or more than five times. Furthermore, modified polypeptides can be modified on the N-terminal amino acid residue, the C-terminal amino acid residue, and/or on an internal amino acid residue. In one embodiment, the modified amino acid reside is a cysteine. In another embodiment, the modified amino acid residue is not a cysteine.

In one embodiment of any of the foregoing, the modified compositions comprise a polypeptide appended with one or more hydrophobic moieties. Exemplary hydrophobic moieties include, but are not limited to, sterols, fatty acids, hydrophobic amino acid residues, and hydrophobic peptides. When a polypeptide is appended with more than one hydrophobic moiety, each hydrophobic moiety is independently selected. The independently selected moieties can be the same or different. Furthermore, when a polypeptide is appended with more than one moiety, the moieties may include hydrophobic moieties and non-hydrophobic moieties.

In another embodiment of any of the foregoing, the modified compositions comprise a polypeptide appended with one or more hydrophilic moieties. Exemplary hydrophilic moieties include, but are not limited to, PEG containing moieties, cyclodextran, or albumin. When a polypeptide is appended with more than one hydrophilic moiety, each hydrophilic moiety is independently selected. The independently selected moieties can be the same or different. Furthermore, when a polypeptide is appended with more than one moiety, the moieties may include hydrophilic moieties and non-hydrophilic moieties.

In a twenty-eighth aspect, the invention provides pharmaceutical compositions comprising a netrin polypeptide, a modified netrin polypeptide, or an agent that inhibits the expression and/or activity or a netrin polypeptide. Such pharmaceutical compositions may optionally be attached to a biocompatible support or dissolved in a biocompatible matrix. Preferred pharmaceutical compositions for use in the methods of the present invention retain one or more of the biological activities of the native composition (e.g., native netrin, etc).

In one embodiment, the biocompatible support is an intraluminal device. In another embodiment, the intraluminal device is a stent, catheter, or wire.

In a twenty-ninth aspect, the invention provides a method for the prophylaxis or treatment of vascular stenosis.

In a thirtieth aspect, the invention provides a method for the treatment of obstructive vascular disease. In one embodiment, the obstructive vascular disease is atherosclerosis, restenosis, vascular bypass graft stenosis, transplant arteriopathy, aneurysm, or dissection.

In a thirty-first aspect, the invention provides a method for the prophylaxis or treatment of stenosis. In one embodiment, the site of stenosis is selected from any of the common bile duct, the pancreatic duct, the esophagus, the urethra, the bladder, the uterus, or the ovarian duct.

In a thirty-second aspect, the invention provides a method for decreasing restenosis following angioplasty, bypass grafting, or cardiac catheterization.

In a thirty-third aspect, the invention provides a method for treating an ischemic condition in an animal. The method comprises administering to a patient in need thereof an amount of a netrin polypeptide effective to decrease ischemia. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In any of the foregoing embodiments, the invention contemplates further administering one or more angiogenic factors. In one embodiment, the angiogenic factors are selected from a vascular endothelial growth factor (VEGF), a fibroblast growth factor (FGF), a platlet-derived growth factor (PDGF), or an angiopoietin polypeptide. The combination of a netrin polypeptide and one or more angiogenic factors may act additively or synergistically, and may be administered consecutively or concomitantly.

In a thirty-fourth aspect, the present invention provides a method for decreasing inflammation. The method comprises administering an amount of an agent effective to inhibit the proliferation and/or migration of one or more inflammatory cell type, wherein said agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In one embodiment, the one or more inflammatory cell types is selected from any of macrophages, lymphocytes, mast cells, platlets, or eosinophils.

In a thirty-fifth aspect, the present invention provides a method for inhibiting the growth or survival of a tumor. The method comprises administering an amount of an agent sufficient to inhibit angiogenesis and thereby inhibiting the growth or survival of a tumor, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In a thirty-sixth aspect, the present invention provides a method for promoting wound healing. The method comprises administering to an animal an amount of a netrin polypeptide effective to promote angiogenesis and thereby promote wound healing. In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide.

In still another embodiment, the netrin polypeptide comprises an amino acid sequence at least 80% identical to any of SEQ ID NO: 2, 4, 6, 8, 10, 12, 38, 40, 42, 44, or a bioactive fragment thereof. In another embodiment, the netrin polypeptide comprises an amino acid sequence at least 85%, 90%, 95%, 97%, 98%, 99%, or greater than 99% identical to any of SEQ ID NO: 2, 4, 6, 8, 10, 12, 38, 40, 42, 44, or a bioactive fragment thereof. In still another embodiment, the netrin polypeptide comprises an amino acid sequence identical to SEQ ID NO: 2, 4, 6, 8, 10, 12, 38, 40, 42, 44, or a bioactive fragment thereof. In yet another embodiment, the netrin polypeptide is encoded by a nucleic acid sequence that hybridizes under stringent conditions, including a wash step of 0.2×SSC at 65° C. to a nucleic acid sequence represent in any of SEQ ID NO: 1, 3, 5, 7, 9, 11, 37, 39, 41, or 43.

In any of the foregoing embodiments, the invention contemplates further administering one or more angiogenic factors. In one embodiment, the angiogenic factors are selected from a vascular endothelial growth factor (VEGF), a fibroblast growth factor (FGF), a platlet-derived growth factor (PDGF), or an angiopoietin polypeptide. The combination of a netrin polypeptide and one or more angiogenic factors may act additively or synergistically, and may be administered consecutively or concomitantly.

In a thirty-seventh aspect, the present invention provides a method for treating or preventing adhesions following surgery or medical wounding. The method comprises administering an amount of an agent effective to inhibit angiogenesis and thereby inhibiting scar formation and adhesions following surgery or medical wounding, wherein the agent inhibits the expression and/or activity of a netrin polypeptide. In one embodiment, the agent that inhibits the expression and/or activity of a netrin polypeptide is selected from an anti-netrin antibody, an Unc5h receptor, an Unc5h receptor ectodomain, or an anti-neogenin antibody. In another embodiment, the agent that inhibits the expression and/or activity of a netrin polypeptide is selected from an antisense oligonucleotide that binds to and inhibits the expression and/or activity of netrin, an RNAi construct that binds to and inhibits the expression and/or activity of netrin, a ribozyme that inhibits the expression and/or activity of netrin, a small molecule that binds to and inhibits the expression and/or activity of netrin, or a small molecule that inhibits the expression and/or activity of netrin by interfering with the binding of netrin to a netrin receptor.

In a thirty-eighth aspect, the present invention provides the use of a netrin polypeptide in the manufacture of a medicament for treating ischemia.

In a thirty-ninth aspect, the present invention provides the use of an agent that inhibits the expression and/or activity of a netrin polypeptide in the manufacture of a medicament for decreasing inflammation.

In a fortieth aspect, the invention provides the use of an agent that inhibits the expression and/or activity of a netrin polypeptide in the manufacture of a medicament for inhibiting the growth or survival of a tumor.

In a forty-first aspect, the invention provides the use of a netrin polypeptide in the manufacture of a medicament for promoting wound healing.

In a forty-second aspect, the invention provides the use of an agent that inhibits the expression and/or activity of a netrin polypeptide in the manufacture of a medicament for preventing or decreasing adhesions following surgery or medical wounding.

In a forty-third aspect, the invention provides methods for screening to identify, characterize, or optimize variants, modified polypeptides, or bioactive fragments of any of the polypeptides of the present invention. In one embodiment, the method comprises screening to identify, characterize, or optimize modified polypeptides that retain one or more of the biological activities of the native or un-modified polypeptide. Preferable variants possess one or more advantageous physiochemical properties in comparison to the native or un-modified polypeptide.

In a further aspect, the present invention provides a method of treating a neuropathy in an animal. The method comprises administering to the animal an amount of a netrin polypeptide effective to treat the neuropathy in the animal (e.g., a human). In one embodiment, the netrin polypeptide is a human netrin1, netrin2, netrin4, netrin G1, or netrin G2 polypeptide. In another embodiment, the netrin polypeptide is a rodent (e.g., mouse or rat) netrin1, netrin3, netrin4, netrin G1, or netrin G2 polypeptide. In yet another embodiment, the netrin polypeptide is a human or rodent netrin1 polypeptide. To illustrate, the neuropathy is peripheral neuropathy or diabetic neuropathy.

In one embodiment, the method comprises screening to identify, characterize, or optimize variants, modified polypeptides, or bioactive fragments of netrin.

For any of the foregoing aspects, the invention contemplates administering a composition comprising polypeptides, as well as compositions comprising nucleic acids. By way of example, in methods calling for administration of a netrin polypeptide, the invention additionally contemplates administration of a nucleic acid sequence encoding a netrin polypeptide. In one embodiment, the nucleic acid sequence encodes a human netrin polypeptide selected from netrin1, netrin2, netrin4, netrin G1, or netrin G2. In another embodiment, the nucleic acid sequence encodes a mouse netrin polypeptide selected from netrin1, netrin3, netrin4, netrin G1, or netrin G2. In another embodiment, the nucleic acid sequence encodes a polypeptide at least 80%, 85%, 90%, 95%, 96%, 97%, 98%, 99%, or 100% identical to SEQ ID NO: 2, 4, 6, 8, 10, 12, 38, 40, 42, 44, or to a bioactive fragment thereof. In another embodiment, the nucleic acid sequence hybridizes under stringent conditions, including a wash step of 0.2×SSC at 65° C., to a sequence represented in SEQ ID NO: 1, 3, 5, 7, 9, 11, 37, 39, 41, or 43. In still another embodiment, the composition comprises a nucleic acid sequence at least 80%, 85%, 90%, 95%, 96%, 97%, 98%, 99%, or 100% identical to SEQ ID NO: 1, 3, 5, 7, 9, 11, 37, 39, 41, or 43, or a bioactive fragment thereof.

In any of the foregoing methods directed to administration of compositions comprising nucleic acids, the compositions can be formulated and administered using appropriate methodologies outlined for administration of polypeptides.

For each of the above aspects of this invention, it is contemplated that any one of the embodiments may be combined with any other embodiments wherever applicable.

The methods and compositions described herein will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

DETAILED DESCRIPTION OF THE DRAWINGS

FIG. 1 shows a schematic representation of the domain structure of a full-length netrin polypeptide. This domain structure is conserved across netrin polypeptides isolated from a range of organisms including humans and rodents. Briefly, a full-length polypeptide is approximately 600 amino acid residues in length. The polypeptide is often glycosylated, and has a molecular weight of approximately 70-80 kDa. The N-terminal two-thirds of the polypeptide (domains VI and v1, v2, and v3) are homologous to the N-termini of polypeptide chains A, B1, and B2 of laminin. Additionally, domains v1, v2, and v3 mediate binding between netrin and the receptors DCC and neogenin. The carboxy terminal third of he protein is highly basic and may mediate interaction between netrin and integrins.

FIG. 2 shows the expression of netrin1 in mouse embryonic and adult tissues. Panels (a-f) show netrin1 expression in mouse E9-E10 tissues by in situ hybridization using an antisense netrin1 probe. Panels (a-c) show expression of netrin1 in whole mount and panels (d-f) show expression of netrin1 in cross-section. Note the strong expression of netrin1 in the floorplate (indicated with a black arrowhead) and in the somites (indicated with a red arrowhead). Panels (g-j) show the expression of Netrin1 protein in 8 micron sections of adult human breast and brain tissue. Sections were stained with an antibody immunoreactive with netrin1 protein (panels g and i) or with an antibody immunoreactive with the endothelial marker CD31 (panels h and j). Note the netrin expression surrounding blood vessels in both the brain and the breast, as well as expression throughout ductal tissue of the breast.

FIG. 6 shows that the receptor neogenin mediated netrin signaling in vascular smooth muscle cells.

FIG. 8 shows the expression of netrin in a variety of tumors and tumor cell lines.

Figure 9:
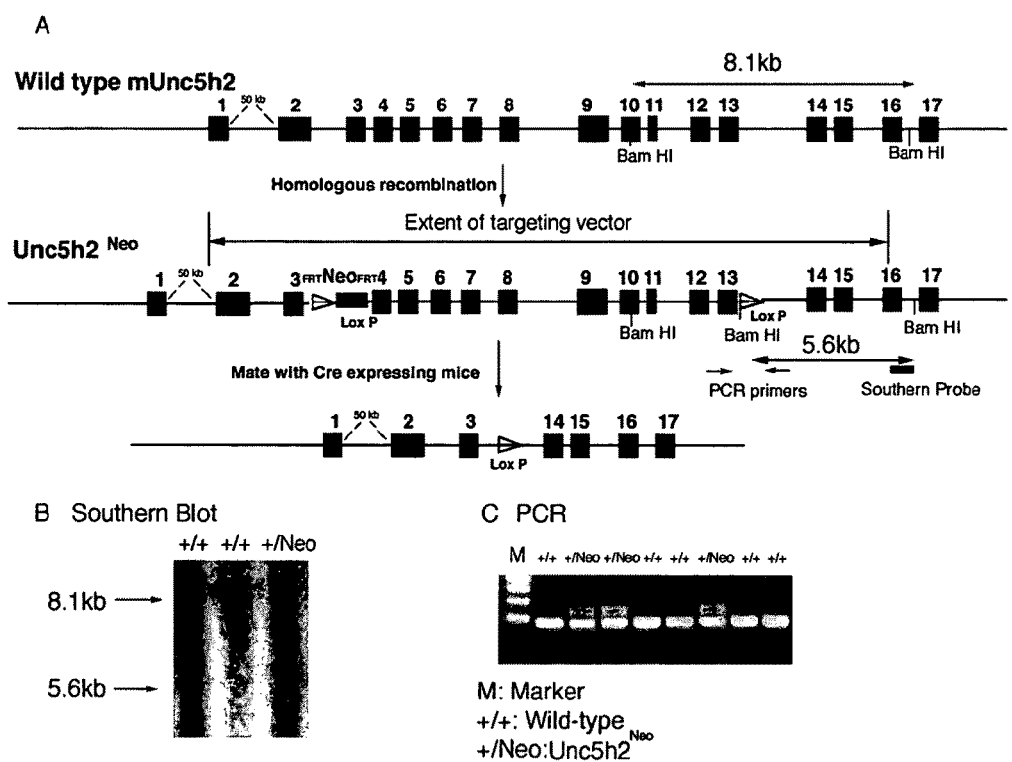

FIG. 9 shows generation of mice with a conditional allele for Unc5h2. Panel A shows targeting strategy with PCR primers and southern probe used for genotyping. Homologous recombination results in the Unc5h2Neo allele. Neomycin cassette is flanked by Frt sites and is removed by Flp recombinase resulting in Unc5h2C allele. Cells that have the Unc5h2C allele and Cre recombinase delete exons 4-14, the region between lox P sites have an Unc5h2-allele. The transmembrane domain encoded in exon 9 is marked by black bar. Panels B and C show Southern blot and PCR analysis of offspring from two independent founder chimeras confirm germline transmission.

Figure 10:
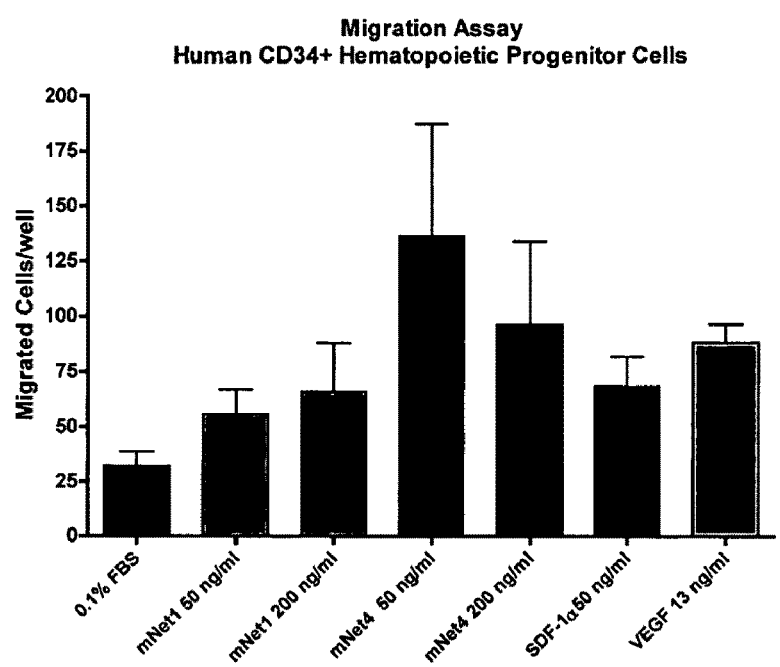

FIG. 10 shows that netrins are chemoattractants for human hematopoietic stem cells (HSC). HSCs were enriched for CD34 expression using magnetic beads. Netrin-1 and Netrin-4 were as chemotactic as serum derived factor-1a and VEGF.

Figure 11:
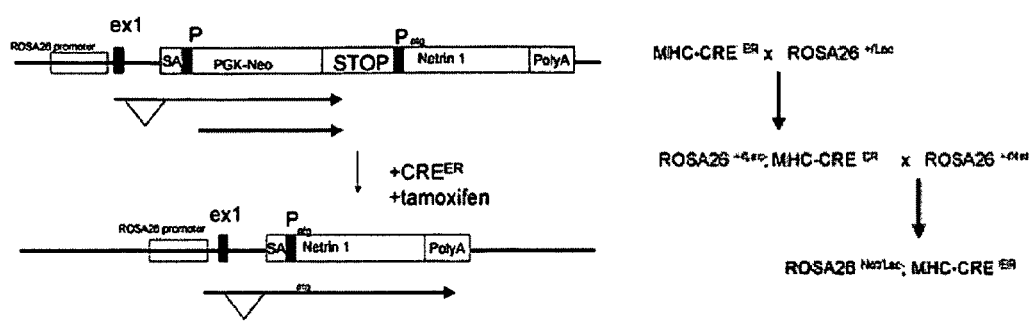

FIG. 11 shows constructs and matings that generate mice overexpressing Netrin-1 in the heart upon induction with tamoxifen. The left panel shows that only in presence of Cre recombinase, PGK-Neo cassette and Stop signal can be removed by recombination, and the ROSA26 promoter drive Netrin-1 expression. The right panel shows that by appropriate matings between ROSA26+/lac and MHC-CREER, a mouse expressing Netrin-1 in the heart is generated when treated with tamoxifen. The vectors described above enable insertion of any cDNA of choice in a single cloning step.

DETAILED DESCRIPTION OF THE INVENTION (i) Overview

The present invention provides methods and compositions for modulating the proliferation, differentiation, adhesion, and migration of cells of the cardiovascular and vascular system. Specifically, the present invention provides methods and compositions that modulate the behavior of primary vascular cells including endothelial cells, vascular smooth muscle cells, and cells derived from the same lineages such as primary blood and immune cells. Methods and compositions useful for modulating (promoting or inhibiting) the proliferation, differentiation, migration, and adhesion of these cell types have a range of in vitro and in vivo uses including, but not limited to, uses in a therapeutic context to treat or prevent a variety of diseases or conditions.

The present invention is based on the discovery that certain ligands and receptors involved in axon guidance in the nervous system also function to modulate cell behavior of primary vascular cells. Previous studies had shown that certain proteins that provide repulsive cues to axons also provide repulsive cues to some vascular cell types. However, to our knowledge, this is the first report that a role for attractive cues is conserved between the nervous system and the vasculature.

Based on the discovery that netrin polypeptides and netrin signaling can promote angiogenesis, as well as proliferation, migration, and adhesion of smooth muscle and endothelial cells, the present invention provides methods and compositions for modulating the proliferation, differentiation, migration, and adhesion of primary vascular cells including smooth muscle cells and endothelial cells. Methods and compositions of the present invention include methods of promoting proliferation, migration, or adhesion of smooth muscle cells or endothelial cells using an agent that promotes expression or activity of netrin or of netrin signaling. Exemplary agents include netrin polypeptides, modified netrin polypeptides, and bioactive fragments thereof. Further, exemplary agents are described herein.

Methods and compositions of the present invention also include methods of inhibiting angiogenesis, as well as methods of inhibiting proliferation, migration, and adhesion of smooth muscle and endothelial cells. Exemplary agents include all or a portion of an Unc5h receptor, neogenin blocking antibodies, neogenin antisense oligonucleotides, neogenin RNAi constructs, neogenin ribozymes, and various small molecules agents.

Before outlining the methods and compositions of the present invention in further detail, we provide a brief overview of netrin and various netrin receptors. Much of the knowledge of netrin comes from studies in the nervous system where netrin plays an important role as an attractive cue for axons. Netrin polypeptides were originally purified from chick due to their ability to promote axon outgrowth. Multiple orthologs have been isolated in numerous species. The human orthologs include netrin1, netrin2, netrin4, netrin G1, and netrin G2. The mouse orthologs include netrin1, netrin3, netrin4, netrin G1, and netrin G2, although the polypeptide referred to as mouse netrin3 is the mouse family member of human netrin2.

Figure 1:
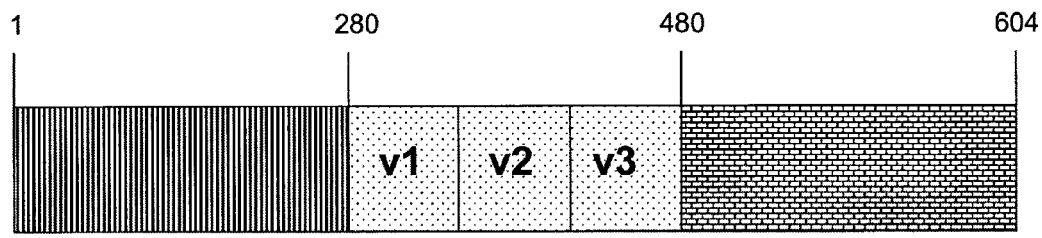

A schematic diagram of a netrin polypeptide is provided in FIG. 1. Full-length netrin polypeptides are approximately 600 amino acid residues in length and have an approximate molecular weight of 70-80 kDa. The protein is often found in a glycosylated form. The N-terminal two-thirds of the protein (domain VI and domain v1, v2, and v3) are homologous to the N-termini of the polypeptide chains (A, B1, and B2) of laminin. Domains v1, v2, and v3 encompass EGF-like repeats and mediate the binding of netrins to the netrin receptors DCC and neogenin. The C-terminal third of netrin is highly basic, and may mediate interactions between netrins and integrins, at least in certain cell types.

Netrins can interact with several different receptors. In the nervous system, the attractant activity of netrins is mediated by neogenin and DCC (deleted in colorectal cancer). Both DCC and neogenin encode transmembrane receptors with an ectodomain comprising four immunoglobulin domains and six fibronectin repeats. Although the cytoplasmic domains of DCC and neogenin have no obvious catalytic domains, multiple pathways including small GTPases, MAP kinase, phopholipase C, and PI-3 kinase have been implicated in netrin signaling.

Additionally, at least two families of receptors mediate a repulsive activity of netrin polypeptides. In the nervous system, repulsive activity of netrins is mediated by members of the Robo and Unc5h families of receptors.

In light of the discoveries described in the present application and in light of the known mediators of netrin's activity in the nervous system, the present invention contemplates a variety of methods based on compositions that promote netrin activity or netrin signaling or based on compositions that inhibit netrin activity or netrin signaling (e.g., inhibit the attractant activity of netrin).

In addition to in vitro and in vivo methods for modulating the behavior of cardiovascular cell types, the methods and compositions of the present invention are useful in a range of assays for identifying and characterizing (i) netrin receptors that mediate netrin's activity on a particular cell type or under a particular set of cellular or environmental circumstances, (ii) components of the netrin signaling pathway, or (iii) agents that mimic or antagonize a biological activity of netrin.

(ii) Definitions

Unless defined otherwise, all technical and scientific terms have the same meaning as is commonly understood by one of skill in the art to which this invention belongs.

The articles "a" and "an" are used herein to refer to one or to more than one (i.e., to at least one) of the grammatical object of the article. By way of example, "an element" means one element or more than one element.

A "marker" is used to determine the state of a cell. Markers are characteristics, whether morphological or biochemical (enzymatic), particular to a cell type, or molecules expressed by the cell type. A marker may be a protein marker, such as a protein marker possessing an epitope for antibodies or other binding molecules available in the art. A marker may also consist of any molecule found in a cell, including, but not limited to, proteins (peptides and polypeptides), lipids, polysaccharides, nucleic acids and steroids. Additionally, a marker may comprise a morphological or functional characteristic of a cell. Examples of morphological traits include, but are not limited to, shape, size, and nuclear to cytoplasmic ratio. Examples of functional traits include, but are not limited to, the ability to adhere to particular substrates, ability to incorporate or exclude particular dyes, ability to migrate under particular conditions, and the ability to differentiate along particular lineages.

Markers may be detected by any method available to one of skill in the art. In addition to antibodies (and all antibody derivatives) that recognize and bind at least one epitope on a marker molecule, markers may be detected using analytical techniques, such as by protein dot blots, sodium dodecyl sulfate polyacrylamide gel electrophoresis (SDS-PAGE), or any other gel system that separates proteins, with subsequent visualization of the marker (such as Western blots), gel filtration, affinity column purification; morphologically, such as fluorescent-activated cell sorting (FACS), staining with dyes that have a specific reaction with a marker molecule (such as ruthenium red and extracellular matrix molecules), specific morphological characteristics (such as the presence of microvilli in epithelia, or the pseudopodia/filopodia in migrating cells, such as fibroblasts and mesenchyme); and biochemically, such as assaying for an enzymatic product or intermediate, or the overall composition of a cell, such as the ratio of protein to lipid, or lipid to sugar, or even the ratio of two specific lipids to each other, or polysaccharides. In the case of nucleic acid markers, any known method may be used. If such a marker is a nucleic acid, PCR, RT-PCR, in situ hybridization, dot blot hybridization, Northern blots, Southern blots and the like may be used, coupled with suitable detection methods. If such a marker is a morphological and/or functional trait, suitable methods include visual inspection using, for example, the unaided eye, a stereomicroscope, a dissecting microscope, a confocal microscope, or an electron microscope.

"Differentiation" describes the acquisition or possession of one or more characteristics or functions different from that of the original cell type. A differentiated cell is one that has a different character or function from the surrounding structures or from the precursor of that cell (even the same cell). The process of differentiation gives rise from a limited set of cells (for example, in vertebrates, the three germ layers of the embryo: ectoderm, mesoderm and endoderm) to cellular diversity, creating all of the many specialized cell types that comprise an individual.

Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway. In many, but not all tissues, the process of differentiation is coupled with exit from the cell cycle. In these cases, the cells typically lose or greatly restrict their capacity to proliferate and such cells are commonly referred to as being "terminally differentiated. However, we note that the term "differentiation" or "differentiated" refers to cells that are more specialized in their fate or function than at a previous point in their development, and includes both cells that are terminally differentiated and cells that, although not terminally differentiated, are more specialized than at a previous point in their development.

"Proliferation" refers to an increase in the number of cells in a population by means of cell division. Cell proliferation results from the coordinated activation of multiple signal transduction pathways, often in response to growth factors and other mitogens. Cell proliferation may also be promoted when cells are released from the actions of intra- or extracellular signals and mechanisms that block or down-regulate cell proliferation. An increase in cell proliferation can be assessed by an increase in DNA synthesis.

The term "netrin-related composition" refers to a composition comprising a netrin polypeptide, a modified netrin polypeptide, or a variant or bioactive fragment thereof. The term is used interchangeably with netrin composition throughout the application. A "netrin-related polypeptide" refers to a polypeptide comprising a netrin amino acid sequence, a variant netrin amino acid sequence, or a bioactive fragment thereof. Such polypeptides may be modified or un-modified. Particularly preferred netrin-related polypeptides of the invention are human and mouse netrin-related polypeptides (e.g., mouse netrin1, human netrin1, human netrin2, mouse netrin2, human netrin4, mouse netrin4, mouse netrin G1 and G2, human netrin G1 and G2, as well as variants, bioactive fragments, and modified polypeptides thereof). In certain embodiment, the netrin-related polypeptides of the invention comprise an amino acid sequence at least 70%, 75%, 80%, 85%, 90%, 95%, 96%, 97%, 98%, 99%, or 100% identical to any of SEQ ID NO: 2, 4, 6, 8, 10, 12, 38, 40, 42, 44, or a bioactive fragment thereof. In any of the foregoing, a netrin-related polypeptide or a netrin-related composition of the invention retains one or more of the biological activities of the corresponding netrin polypeptide. Exemplary biological activities of netrin include the following: (i) binds a netrin receptor; (ii) promotes attraction of axons; (iii) promotes angiogenesis; (iv) promotes cell migration; (v) promotes cell adhesion; and (vi) promotes cell proliferation.

In certain embodiments, netrin-related compositions refer to netrin-related nucleic acid compositions. Such compositions comprise nucleic acid sequences encoding a netrin-related polypeptide. The netrin-related nucleic acid composition can be delivered, and the delivered netrin-related nucleic acid composition encodes a netrin-related polypeptide that retains one or more of the biological activities of netrin. Exemplary netrin-related nucleic acid compositions comprise a nucleic acid sequence at least 70%, 75%, 80%, 85%, 90%, 95%, 96%, 97%, 98%, 99%, or 100% identical to any of SEQ ID 1, 3, 5, 7, 9, 11, 37, 39, 41, 43, or a bioactive fragment thereof. Further exemplary nucleic acid compositions comprise a nucleic acid sequence the encodes a polypeptide at least 70%, 75%, 80%, 85%, 90%, 95%, 96%, 97%, 98%, 99%, or 100% identical to any of SEQ ID NO: 2, 4, 6, 8, 10, 12, 38, 40, 42, 44, or a bioactive fragment thereof. Still further exemplary nucleic acid compositions comprise a nucleic acid sequence that hybridizes under stringent conditions, including a wash step of 0.2×SSC at 65 C, to a nucleic acid sequence represented in any of SEQ ID 1, 3, 5, 7, 9, 11, 37, 39, 41, or 43.

In addition to full-length netrin-related polypeptides, the invention contemplates the use of bioactive fragments of netrin-related polypeptides that retain one or more of the biological activities of a full-length netrin-related polypeptide. Exemplary bioactive fragment are bioactive fragments of SEQ ID NO: 2, 4, 6, 8, 10, 12, 38, 40, 42, or 44. Further exemplary bioactive fragments are fragments of a polypeptide at least 80% identical to SEQ ID NO: 2, 4, 6, 8, 10, 12, 38, 40, 42, or 44.

Table 1 below provides exemplary sequences referred to in the specification. GenBank Accession numbers are provided for the nucleic acid and amino acid sequences referenced in the application.

TABLE 1

A list of sequences disclosed in the application.

| | |
|---|---|
| SEQ ID NO: 1 | Netrin-1 nucleic acid sequence - mouse (NM_008744) |
| SEQ ID NO: 2 | Netrin-1 amino acid sequence - mouse (NM_008744 and NP_032770) |
| SEQ ID NO: 3 | Netrin-1 nucleic acid sequence - human (NM_004822) |
| SEQ ID NO: 4 | Netrin-1 amino acid sequence - human (NM_004822 and NP_004813) |
| SEQ ID NO: 5 | Netrin-2 nucleic acid sequence - human (NM_006181) |
| SEQ ID NO: 6 | Netrin-2 amino acid sequence - human (NM_006181 and NP_006172) |
| SEQ ID NO: 7 | Netrin-3 nucleic acid sequence - mouse (NM_010947) |
| SEQ ID NO: 8 | Netrin-3 amino acid sequence - mouse (NM_010947 and NP_035077) |
| SEQ ID NO: 9 | Netrin-4 nucleic acid sequence - mouse (NM_021320) |
| SEQ ID NO: 10 | Netrin-4 amino acid sequence - mouse (NM_021320 and NP_067295) |
| SEQ ID NO: 11 | Netrin-4 nucleic acid sequence - human (NM_021229) |
| SEQ ID NO: 12 | Netrin-4 amino acid sequence - human (NM_021229 and NP_067052) |
| SEQ ID NO: 13 | UNC5H1 nucleic acid sequence - mouse (NM_153131) |
| SEQ ID NO: 14 | UNC5H1 amino acid sequence - mouse (NM_153131 and NP_694771) |
| SEQ ID NO: 15 | UNC5H1 nucleic acid sequence - human (XM_030300) |
| SEQ ID NO: 16 | UNC5H1 amino acid sequence - human (XM_030300 and XP_030300) |
| SEQ ID NO: 17 | UNC5H2 nucleic acid sequence - mouse (NM_029770) |
| SEQ ID NO: 18 | UNC5H2 amino acid sequence - mouse (NM_029770 and NP_084046) |
| SEQ ID NO: 19 | UNC5H2 nucleic acid sequence - human (NM_170744) |
| SEQ ID NO: 20 | UNC5H2 amino acid sequence - human (NM_170744 and NP_734465) |
| SEQ ID NO: 21 | UNC5H3 nucleic acid sequence - mouse (NM_009472) |
| SEQ ID NO: 22 | UNC5H3 amino acid sequence - mouse (NM_009472 and NP_033498) |
| SEQ ID NO: 23 | UNC5H3 nucleic acid sequence - human (NM_003728) |
| SEQ ID NO: 24 | UNC5H3 amino acid sequence - human (NM_003728 and NP_003719) |
| SEQ ID NO: 25 | Neogenin nucleic acid sequence - mouse (NM_008684) |
| SEQ ID NO: 26 | Neogenin amino acid sequence - mouse (NM_008684 and NP_032710) |
| SEQ ID NO: 27 | Neogenin nucleic acid sequence - human (NM_02499) |
| SEQ ID NO: 28 | Neogenin amino acid sequence - human (NM_002499 and NP_002490) |
| SEQ ID NO: 29 | human DCC forward primer |
| SEQ ID NO: 30 | human DCC reverse primer |
| SEQ ID NO: 31 | human neogenin forward primer |
| SEQ ID NO: 32 | human neogenin reverse primer |
| SEQ ID NO: 33 | human Unc5h2 forward primer |
| SEQ ID NO: 34 | human Unc5h2 reverse primer |
| SEQ ID NO: 35 | GAPDH forward primer |
| SEQ ID NO: 36 | GAPDH reverse primer |
| SEQ ID NO: 37 | Netrin G1 nucleic acid sequence- mouse (NM_030699) |
| SEQ ID NO: 38 | Netrin G1 amino acid sequence - mouse (NM_030699 and NP_109624) |
| SEQ ID NO: 39 | Netrin G1 nucleic acid sequence - human (NM_014917) |
| SEQ ID NO: 40 | Netrin G1 amino acid sequence - human (NM_014917 and NP_55732) |
| SEQ ID NO: 41 | Netrin G2 nucleic acid sequence - mouse (NM_133501) |

TABLE 1-continued

A list of sequences disclosed in the application.

| | |
|---|---|
| SEQ ID NO: 42 | Netrin G2 amino acid sequence - mouse (NM_133501 and NP_598008) |
| SEQ ID NO: 43 | Netrin G2 nucleic acid sequence - human (NM_032536) |
| SEQ ID NO: 44 | Netrin G2 amino acid sequence - human (NM_032536 and NP_115925) |

By bioactive fragment is meant that a given portion of the protein maintains one or more of the functional attributes of the full length protein. In the context of the present invention, a bioactive fragment retains one or more of the biological functions of full length netrin including, but not limited to, any of the following: retains the ability to promote netrin signaling. Additional biological activities include, but are not limited to, (i) binds a netrin receptor; (ii) promotes attraction of axons; (iii) promotes angiogenesis; (iv) promotes cell migration; (v) promotes cell adhesion; and (vi) promotes cell proliferation. The invention contemplates the use not only of bioactive fragments of netrin, but also peptidomimetics (modified fragments). Furthermore, as outlined below, the invention contemplates modified netrin-related polypeptides, and modified bioactive fragments thereof. Exemplary modified netrin-related polypeptides and modified bioactive fragments thereof retain one or more of the biological activities of the corresponding native and/or un-modified netrin.

Variants may be full length or other than full length. Variants of the nucleic acids or proteins of the invention include, but are not limited to, molecules comprising regions that are substantially identical to the nucleic acids or proteins of the invention. In various embodiments, the variants are at least about 70%, 75%, 80%, 85%, 90%, 95%, 96%, 97%, 98%, 99%, or greater than 99% identical to a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions (Ausubel et al., 1987). Variants for use in the methods and compositions of the present invention retain one or more of the biological activities of native and/or of un-modified netrin.

Although many of the definitions outlined above regarding exemplary variants and fragments for use in the methods of the present invention are described in terms of netrin polypeptides, the present invention includes compositions and uses for others agents. Such agents modulate the expression and/or activity of netrin and of netrin signaling, but such agents are not a netrin polypeptide itself. The invention contemplates that when other non-netrin polypeptide or nucleic acid agents are used, variants, bioactive fragment, and modified forms of that polypeptide or nucleic acid are within the scope of the present invention.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)", "protein(s)" and "polypeptide(s)" are used interchangeably herein.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wildtype polynucleotide sequence or any change in a wildtype protein sequence. The term "variant" is used interchangeably with "mutant". Although it is often assumed that a change in the genetic material results in a change of the function of the protein, the terms "mutant" and "variant" refer to a change in the sequence of a wildtype protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause expression in other tissues as well.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

In general, a "growth factor" is a substance that promotes cell growth and development by directing cell maturation and differentiation. Growth factors also mediate tissue maintenance and repair. Growth factors affect cell behavior by binding to specific receptors on the surface of cells. The binding of ligand to a growth factor receptor activates a signal transduction pathway that influences, for example, cell behavior. Growth factors typically exert an affect on cells at very low concentrations. A number of growth factors are specifically recognized as having particular potency in vascular cells. These growth factors include members of the fibroblast growth factor (FGF) family, members of the platlet derived growth factor (PDGF) family, members of the vascular endothelial growth factor (VEGF) family, and angiopoietins. Such growth factors will similarly be referred to interchangeably herein as "angiogenic factors," "angiogenic growth factors," and "vascular growth factors."

"Fibroblast growth factors" (Fgfs) belong to a class of growth factors consisting of a large family of short polypeptides that are released extracellularly and bind with heparin to dimerize and activate specific receptor tyrosine kinases (Fgfrs). Fgf signaling is involved in mammalian wound healing and tumor angiogenesis (Ortega et al., 1998; Zetter, 1998) and has numerous roles in embryonic development, including induction and/or patterning during organogenesis of the limb, tooth, brain, and heart (Crossley et al., 1996; Martin, 1998; Ohuchi et al., 1997; Peters and Balling, 1999; Reifers et al., 1998; Vogel et al., 1996; Zhu et al., 1996). Fgfs can easily be detected using either functional assays (Baird and Klagsbrun, 1991; Moody, 1993) or antibodies (Research Diagnostics; Flanders, N.J. or Promega, Wis.).

The term "preventing" is art-recognized, and when used in relation to a condition, such as a local recurrence (e.g., pain), a disease such as cancer, a syndrome complex such as heart failure or any other medical condition, is well understood in the art, and includes administering, prior to onset of the condition, a composition that reduces the frequency of, reduces the severity of, or delays the onset of symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, reducing the severity of, or alternatively delaying, pain sensations experienced by subjects in a treated population versus an untreated control population.

The term "agent" refers to compounds of the invention including nucleic acids, peptides, polypeptides, and small organic molecules. The invention contemplates agents that inhibit the expression or activity of netrin or netrin signaling (e.g., agents that inhibit the pro-angiogenesis, attractant activity of netrin). The invention further contemplates agents that promote the expression or activity of netrin or netrin signaling (e.g., agents that promote the pro-angiogenesis, attractant activity of netrin).

The term "modified" refers to the derivatization of a polypeptide with one or more moieties by appending (e.g., attaching via covalent or non-covalent interactions) one or more moieties to one or more amino acid residues of that polypeptide. Exemplary modifications include hydrophobic moieties such as lipophilic moieties and fatty acid moieties, glycosylation, phosphorylation. Further exemplary modifications include hydrophilic modifications. Polypeptides for use in the methods of the present invention, including netrin polypeptides, can be modified. Modified polypeptides for use in the methods of the present invention retain one or more of the biological activities of the native polypeptide, and preferably additional possess one or more advantageous physiochemical properties in comparison to the corresponding native and/or un-modified polypeptide. In certain embodiment, the invention provides modified netrin-related polypeptides. We note that native netrin polypeptides are often glycosylated. However, the invention contemplates the use of a range of modified and unmodified polypeptides. By way of example, the invention contemplates the following: (i) the use of netrin polypeptides that are not glycosylated or otherwise modified, (ii) the use of netrin polypeptides that are glycosylated but that are not otherwise modified, (iii) the use of netrin polypeptides that are not glycosylated but that are modified with one or more moieties on either the same or different residues as are typically glycosylated, and (iv) the use of netrin polypeptides that are glycosylated and are additionally modified with one or more moieties on the same or different residues as are typically glycosylated. For any of the above examples of modified or unmodified netrin polypeptides, bioactive fragments thereof, or other polypeptides for use in the methods of the present invention, preferred modified polypeptides or fragments retain the biological activity of the native polypeptide and preferably possess one or more advantageous physiochemical activity.

The term "appended" refers to the addition of one or more moieties to an amino acid residue. The term refers, without limitation, to the addition of any moiety to any amino acid residue. The term includes attachment of a moiety via covalent or non-covalent interactions.

The term "N-terminal amino acid residue" refers to the first amino acid residue (amino acid number 1) of a polypeptide or peptide.

The term "C-terminal amino acid residue" refers to the last amino acid residue (amino acid number n, wherein n=the total number of residues in the peptide or polypeptide) of a polypeptide or peptide.

The term "hydrophobic" refers to the tendency of chemical moieties with nonpolar atoms to interact with each other rather than water or other polar atoms. Materials that are "hydrophobic" are, for the most part, insoluble in water. Natural products with hydrophobic properties include lipids, fatty acids, phospholipids, sphingolipids, acylglycerols, waxes, sterols, steroids, terpenes, prostaglandins, thromboxanes, leukotrienes, isoprenoids, retenoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms.

The term "lipophilic group", in the context of being attached to a polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

The phrase "internal amino acid" means any amino acid in a peptide sequence that is neither the N-terminal amino acid nor the C-terminal amino acid.

In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, omithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

A "reversed" or "retro" peptide sequence as disclosed herein refers to that part of an overall sequence of covalently-bonded amino acid residues (or analogs or mimetics thereof)

wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrastemal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

The phrase "effective amount" as used herein means that the amount of one or more agent, material, or composition comprising one or more agents as described herein which is effective for producing some desired effect in a subject.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

(iii) Exemplary Compositions and Methods

Polypeptides and peptide fragments: The present invention provides compositions comprising netrin-related polypeptides, modified netrin-related polypeptides, and bioactive fragments thereof. As outlined in detail herein, exemplary netrin-related polypeptides include netrin1, netrin2/3, netrin4, netrin G1, and netrin G2 related polypeptides, modified netrin related polypeptides, and bioactive fragments thereof. Below we describe various polypeptides for use in the methods and compositions of the present invention. The invention contemplates that any of the polypeptides and polypeptide fragments described in detail below can be appended to produce a modified polypeptide or modified polypeptide fragment.

Additionally, we note that the polypeptides and peptide fragments for use in the methods of the present invention are not limited to netrin polypeptides. The invention additionally contemplates a variety of agents, including polypeptide and peptide agents. These agents are described in detail herein. Nevertheless, we note that although netrin polypeptides are provided as specific examples of the range of modified and variant polypeptides and bioactive fragments thereof, the invention similarly contemplates the methods and compositions comprising other variant and modified forms of polypeptides (e.g., polypeptide agents that inhibit or promote the expression and/or activity of netrin or of netrin signaling).

In certain embodiments, the composition comprises a netrin-related polypeptide, or a bioactive fragment thereof. Such polypeptides or fragments can include either a wildtype peptide sequence or a variant sequence, and variant sequences can be readily constructed and tested to ensure that the variant sequence retains one or more of the biological activities of the native polypeptide. One of skill in the art can readily make variants comprising an amino acid sequence at least 60%, 70%, 75%, 80%, 85%, 90%, 95%, 96%, 97%, 98% or 99% identical to a particular polypeptide, and identify variants that activate netrin signaling and retain one or more of the biological activities of the native polypeptide. To further illustrate, the present invention contemplates netrin-related polypeptides comprising an amino acid sequence at least 60%, 70%, 75%, 80%, 85%, 90%, 95%, 96%, 97%, 98%, 99%, or 100% identical to a netrin polypeptides (SEQ ID NO: 2, 4, 6, 8, 10, 12, 38, 40, 42, or 44). Furthermore, the invention contemplates netrin-related polypeptides that differ from SEQ ID NO: 2, 4, 6, 8, 10, 12, 38, 40, 42, or 44 at from one-ten positions (e.g., one, two, three, four, five, six, seven, eight, nine, or ten positions).

In any of the foregoing, the invention contemplates compositions comprising bioactive fragments of any of the foregoing netrin-related polypeptides or modified netrin-related polypeptides. Exemplary bioactive fragments include fragments of at least 25, 50, 60, 70, 80, 90, 100, 125, 150, 200, 250, 300, 325, 350, 400, 450, 500, 550, 600, or greater than 600 amino acid residues of a netrin polypeptide (e.g., of SEQ ID NO: 2, 4, 6, 8, 10, 12, 38, 40, 42, or 44) that retain the biological activity of the full-length netrin polypeptide. Exemplary fragments include, but are not limited to, domains of netrin outlined in detail in FIG. 1. Such domains include the N-terminal most VI domain; v1, v2, v3 (wherein v1, v2, and v3 can be provided alone or in combination); and the C-terminal most basic domain. Exemplary biological activities of netrin include the following: (i) binds a netrin receptor; (ii) promotes attraction of axons; (iii) promotes angiogenesis, (iv) promotes cell migration; (v) promotes cell adhesion; and (vi) promotes cell proliferation.

The present invention contemplates a wide range of compositions and pharmaceutical compositions comprising netrin-related polypeptides, modified netrin-related polypeptides, and bioactive fragments thereof. Furthermore, the present invention contemplates a wide range of compositions and pharmaceutical compositions comprising agents (including polypeptide and peptide agents) that promote or inhibit the expression or activity of netrin or of netrin signaling (e.g., promotes or inhibits the pro-angiogenic, attractant activity of netrin).

In certain embodiments, where the present invention provides agents (e.g., polypeptide, peptide agents, or nucleic acids) that promote the expression or activity of netrin or of netrin signaling, such agents are referred to herein as netrin agonists. To illustrate, netrin agonists include, but are not limited to, a netrin polypeptide, a modified netrin polypeptide, a mimic or variant of a netrin polypeptide, and an agent that enhances interaction between a netrin and a netrin receptor.

In other embodiments, where the present invention provides agents (e.g., polypeptide, peptide agents, or nucleic acids) that inhibit the expression or activity of netrin or of netrin signaling, such agents are referred to herein as netrin antagonists. To illustrate, netrin antagonists include, but are not limited to, an Unc5h receptor, a soluble netrin receptor that binds to netrin but cannot mediate netrin signaling (e.g., a netrin receptor ectodomain), an antibody against a netrin polypeptide, an antibody against a netrin receptor, a mutant or variant of a netrin polypeptide that binds to a netrin receptor but cannot activate the netrin signaling, a nucleic acid that inhibits expression of a netrin (e.g., an antisense nucleic acid or an siRNA), an agent that inhibits or disrupts interaction between a netrin polypeptide and a netrin receptor.

The subject polypeptides, modified polypeptides, bioactive fragments, compositions, and pharmaceutical compositions have a variety of uses which will be outlined in greater detail herein. Generally, however, the invention contemplates pharmaceutical compositions comprising one netrin-related polypeptide (e.g., one netrin-related polypeptide, one modified netrin-related polypeptide, or one bioactive fragment), as well as pharmaceutical compositions comprising more than one netrin-related polypeptide (e.g., two, three, four, five, or more than five netrin-related polypeptides).

Similarly, the invention contemplates pharmaceutical compositions comprising one agent that promotes or inhibits the expression or activity of netrin or of netrin signaling, as well as pharmaceutical compositions comprising more than one agent (e.g., two, three, four, five, or more than five agents) that promotes or inhibits the expression or activity of netrin or of netrin signaling. For example, the invention provides a netrin related composition which comprises at least two netrin related polypeptides of different types, such as two or more polypeptides selected from human netrin1, human netrin3, human netrin4, human netrin G1, and human netrin G2. Similarly, two or more different polypeptides can be selected from mouse netrin1, mouse netrin2, mouse netrin4, mouse netrin G1, and mouse netrin G2. In the cases of netrin antagonists, the invention provides a netrin related composition which comprises two or more netrin antagonists for inhibiting two or more different netrin family members. Optionally, such composition may comprise two or more soluble netrin receptors of different types. To illustrate, two or more netrin antagonists are selected from a soluble DCC receptor, a soluble neogenin receptor, a soluble Robo receptor, and a soluble Unc5h2 receptor. Similarly, two or more netrin antagonists can be selected from an antibody against DCC receptor, an antibody against neogenin receptor, an antibody against Robo receptor, and an antibody against Unc5h2 receptor. To further illustrate, two or more netrin antagonists can be selected from an antibody against human netrin1, an antibody against human netrin3, an antibody against human netrin4, an antibody against human netrin G1, and an antibody against human netrin G 2.

The invention contemplates the use of compositions and pharmaceutical compositions administered alone, or in combination with one or more additional agents. Such additional agents include (i) growth factors and (ii) angiogenic factors. Additionally, the invention contemplates administering polypeptides according to the present invention together with other compounds or therapies appropriate in light of the particular disease or condition being treated. Similarly, in methods of screening to identify or characterize additional modified netrin-related polypeptides, the invention contemplates that putative modified polypeptides may be screened singly or in combination.

In addition to the polypeptides and fragments described in detail above, the present invention also pertains to isolated nucleic acids comprising nucleotide sequences that encode said polypeptides and fragments. The term nucleic acid as used herein is intended to include fragments as equivalents, wherein such fragments have substantially the same function as the full length nucleic acid sequence from which it is derived. Equivalent nucleotide sequences will include sequences that differ by one or more nucleotide substitutions, additions or deletions, such as allelic variants; and will, therefore, include sequences that differ from the nucleotide sequence of, for example, a wildtype netrin (SEQ ID NO: 1, 3, 5, 7, 9, 11, 37, 39, 41, or 43). Equivalent sequences include those that vary from a known wildtype or variant sequence due to the degeneracy of the genetic code. Equivalent sequences may also include nucleotide sequences that hybridize under stringent conditions (i.e., equivalent to about 20-27° C. below the melting temperature ($T_m$) of the DNA duplex formed in about 1M salt) to the nucleotide sequence of netrin-related polypeptide. Further examples of stringent hybridization conditions include a wash step of 0.2×SSC at 65° C. For the foregoing examples of equivalents to the netrin-related polypeptides of the present invention, one of skill in the art will recognize that an equivalent sequence encodes a polypeptide that retains one or more of the biological activities of a native and/or un-modified netrin. Specifically, the polypeptide retains one or more of the following biological activities: Exemplary biological activities of netrin include the following: (i) binds a netrin receptor; (ii) promotes attraction of axons; (iii) promote angiogenesis, (iv) promotes cell migration, (v) promotes cell adhesion, and (vi) promotes cell proliferation.

In one example, the invention contemplates a netrin-related polypeptide, modified netrin-related polypeptide, or bioactive fragment thereof encoded or encodable by a nucleic acid sequence which hybridizes under stringent conditions, including a wash step of 0.2×SSC at 65° C., to a nucleic acid sequence of SEQ ID NO: 1, 3, 5, 7, 9, 11, 37, 39, 41, or 43.

Equivalent nucleotide sequences for use in the methods described herein also include sequences which are at least 60% identical to a give nucleotide sequence. In another embodiment, the nucleotide sequence is at least 70%, 75%, 80%, 85%, 90%, 95%, 96%, 97%, 98%, 99%, or 100% identical to the nucleotide sequence of a native sequence that encodes a netrin-related polypeptide and retains one or more of the biological activities of a native netrin-related polypeptide.

Nucleic acids having a sequence that differs from nucleotide sequences which encode a particular netrin-related polypeptide due to degeneracy in the genetic code are also within the scope of the invention. Such nucleic acids encode functionally equivalent peptides but differ in sequence from wildtype sequences known in the art due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist. One skilled in the art will appreciate that these variations in one or more nucleotides (up to about 3-5% of the nucleotides) of the nucleic acids encoding polypeptides having one or more of the biological activities of a native netrin-related polypeptide may exist among individuals of a given species due to natural allelic variation.

In the context of the present invention, compositions comprising netrin-related polypeptides can be administered as recombinant polypeptides or compositions comprising recombinant polypeptides. Furthermore, compositions of the invention comprising netrin-related polypeptides can be administered as conditioned medium prepared from cells expressing and secreting a netrin-related polypeptide.

Peptidomimetics: In other embodiments, the invention contemplates that the netrin-related polypeptide, modified netrin-related polypeptide, or bioactive fragment thereof is a peptidomimetic (herein referred to interchangeably as a mimetic or a peptide mimetic). Preferable peptidomimetics retain one or more of the biological activities of native a netrin-related polypeptide. Peptidomimetics are compounds based on, or derived from, peptides and proteins. The peptidomimetics of the present invention can be obtained by structural modification of the amino acid sequence of a known netrin-related polypeptide using unnatural amino acids, conformational restraints, isosteric replacement, and the like. The subject peptidomimetics constitute the continuum of structural space between peptides and non-peptide synthetic structures. As used herein, the term peptide mimetic will apply to any netrin-related polypeptide containing a structural modification at one or more positions. For example, a full-length netrin-related polypeptide modified at one, two, three, four, or more than four positions is a peptide mimetic. Similarly, a netrin-related polypeptide modified at every position is a peptide mimetic. Furthermore, a bioactive fragment of a netrin-related polypeptide modified at one or more positions, or at every position, is a netrin-related polypeptide.

Exemplary peptidomimetics can have such attributes as being non-hydrolyzable (e.g., increased stability against proteases or other physiological conditions which degrade the corresponding peptide), having increased specificity and/or potency, and having increased cell permeability for intracellular localization. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988, p 123), C-7 mimics (Huffman et al. in *Peptides: Chemistry and Biologyy*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modified (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988)

In addition to a variety of sidechain replacements which can be carried out to generate the subject peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Additionally, peptidomimietics based on more substantial modifications of the backbone of a peptide can be used. Peptidomimetics which fall in this category include (i) retro-inverso analogs, and (ii) N-alkyl glycine analogs (so-called peptoids).

Furthermore, the methods of combinatorial chemistry are being brought to bear, e.g., PCT publication WO 99/48897, on the development of new peptidomimetics. For example, one embodiment of a so-called "peptide morphing" strategy focuses on the random generation of a library of peptide analogs that comprise a wide range of peptide bond substitutes.

In an exemplary embodiment, the peptidomimetic can be derived as a retro-inverso analog of the peptide. Retro-inverso analogs can be made according to the methods known in the art, such as that described by the Sisto et al. U.S. Pat. No. 4,522,752. As a general guide, sites which are most susceptible to proteolysis are typically altered, with less susceptible amide linkages being optional for mimetic switching. The final product, or intermediates thereof, can be purified by HPLC.

In another illustrative embodiment, the peptidomimetic can be derived as a retro-enatio analog of the peptide. Retro-enantio analogs such as this can be synthesized using commercially available D-amino acids (or analogs thereof) and standard solid- or solution-phase peptide-synthesis techniques. For example, in a preferred solid-phase synthesis method, a suitably amino-protected (t-butyloxycarbonyl, Boc) residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid is introduced by coupling with diisopropylcarbodiimide. The resin is again washed, and the cycle repeated for each of the remaining amino acids in turn. When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for any of the subject polypeptides. A trans olefin analog can be synthesized according to the method of Y. K. Shue et al. (1987) *Tetrahedron Letters* 28:3225 and also according to other methods known in the art. It will be appreciated that variations in the cited procedure, or other procedures available, may be necessary according to the nature of the reagent used.

It is further possible to couple the pseudodipeptides synthesized by the above method to other pseudodipeptides, to make peptide analogs with several olefinic functionalities in place of amide functionalities.

Still other classes of peptidomimetic derivatives include phosphonate derivatives. The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in designing peptidomimetics. To illustrate, the peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic, heteroaromatic, or biheteroaromatic nucleus.

The subject peptidomimetics can be optimized by, e.g., combinatorial synthesis techniques combined with high throughput screening techniques, and furthermore can be tested to ensure that the peptidomimetic retains one or more of the biological activities of a native netrin-related polypeptide. Any of the foregoing peptidomimetics can be modified with one or more hydrophobic and/or hydrophilic moieties, as described herein for other netrin-related polypeptides. Exemplary modified netrin-related polypeptide peptidomimetics retain one or more of the biological activities of a native netrin-related polypeptide and additionally possess one or more advantageous physiochemical properties.

Hydrophobically Modified Polypeptides

In addition to providing netrin-related compositions comprising polypeptides and bioactive fragments thereof, as described herein, the present invention recognizes that certain compositions comprising modified netrin-related polypeptides and bioactive fragments thereof will have certain other advantages in comparison to their native and/or un-modified counter-parts. Such modified netrin-related polypeptides (including full-length polypeptides and bioactive fragments) not only retain one or more of the biological activities of the corresponding native or un-modified polypeptide, but may also possess one or more additional, advantageous physiochemical properties in comparison to a native and/or un-modified netrin. Exemplary physiochemical properties include, but are not limited to, increased in vitro half-life, increased in vivo half-life, decreased immunogenicity, increased solubility, increased potency, increased bioavailability, and increased biodistribution. The present invention contemplates compositions comprising modified netrin-related polypeptide. For example, the present invention contemplates modified netrin-related polypeptides. Compositions comprising modified netrin-related polypeptides area also referred to herein as modified netrin-related compositions. Exemplary modified netrin-related compositions for use in the methods of the present invention include modified human netrin1, modified human netrin2, modified human netrin4, modified human netrin G1, modified human netrin G2, modified mouse netrin1, modified mouse netrin3, modified mouse netrin4, modified mouse netrin G1, and modified mouse netrin G2. Further exemplary modified netrin-related compositions comprise and amino acid sequence at least 70%, 75%, 80%, 85%, 90%, 95%, 97%, 98%, 99%, or 100% identical to an amino acid sequence represented in SEQ ID NO: 2, 4, 6, 8, 10, 12, 38, 40, 42, 44, or a bioactive fragment thereof.

The present invention recognizes that native netrin polypeptides are often glycosylated. Accordingly, the present invention contemplates a range of modified and un-modified netrin polypeptides that retain a biological activity of a native or un-modified netrin polypeptide. Exemplary netrin-related polypeptides include the following: (i) netrin polypeptides that possess a native glycosylation, but are not otherwise modified; (ii) netrin polypeptides that possess no modifications, (iii) netrin polypeptides that possess a native glycosylation, and also possess one or more additional modifications, (iv) netrin polypeptide that do not possess a native glycosylation, but are otherwise modified.

Modified netrin polypeptides are one illustrative embodiment of the range of modified polypeptides for use in the methods of the present invention. The application contemplates that any polypeptide or peptide for use in the methods of the present invention can be modified to impart one or more advantageous physiochemical properties.

By way of further example, where the present invention provides netrin agonists or antagonists, netrin agonists or antagonists include modified polypeptides, or modified bioactive fragments thereof. Optionally, modified polypeptides or modified bioactive fragments retain one or more of the biological activities of the native polypeptide, and preferably possess one or more advantageous physiochemical activity in comparison to the native polypeptide.

In one embodiment, the modified netrin-related polypeptide is a hydrophobically modified netrin-related polypeptide.

The invention contemplates that a netrin-related polypeptide may be appended with one or more moieties to produce a modified netrin-related polypeptide. For example, a modified netrin-related polypeptide may be appended with two, three, four, five, or more than five moieties. The moieties may be the same or may be different. When said one or more moieties are hydrophobic moieties, the modified netrin-related polypeptide is also known as a hydrophobically modified netrin-related polypeptide.

Furthermore, the invention contemplates that the one or more moieties (e.g., one or more independently selected hydrophobic moieties) may be appended to the N-terminal amino acid residue, the C-terminal amino acid residue, and/or one or more internal amino acid residues. When a modified netrin-related polypeptide is appended with two or more moieties, the moieties may be appended to the same amino acid residue and/or to different amino acid residues. Additionally, as detailed above, the moieties may be the same or different.

The present invention provides modified netrin-related polypeptides, and methods of using these modified netrin-related polypeptides in vitro and in vivo. The modified netrin-related polypeptides of the present invention should retain one or more of the biological activities of the corresponding native and/or un-modified netrin. Additionally, preferable modified netrin-related polypeptides possess one or more advantageous physiochemical characteristics in comparison to the corresponding native and/or un-modified netrin.

Accordingly, modified netrin-related polypeptides not only provide additional possible compositions for manipulating netrin signaling in vitro or in vivo, such modified netrin-related polypeptides may also provide netrin-related polypeptides with improved properties in comparison to the prior art. Exemplary modified netrin-related polypeptides include hydrophobically modified netrin-related polypeptides.

Modifying a polypeptide or peptide (i.e, adding or appending one or more hydrophobic moieties to an existing amino acid residue or substituting one or more hydrophobic moieties for an amino acid) can alter the physiochemical properties of the polypeptide in useful way. For example, such hydrophobically modified netrin-related polypeptides may have increased biological activity, increased stability, increased in vivo or in vitro half-life, or decreased immunogenicity in comparison to a native and/or un-modified netrin-related polypeptide.

The overall hydrophobic character of a polypeptide can be increased in any of a number of ways. Regardless of how the polypeptide is modified in order to increase its hydrophobicity, one of skill in the art will recognize that preferable modified netrin-related polypeptides retain one or more of the biological activities of the corresponding native and/or un-modified netrin. Additionally, particularly preferred modified polypeptides possess one or more advantageous physiochemical properties.

Briefly, the hydrophobicity of a polypeptide can be increased by (a) chemically modifying an amino acid residue or (b) replacing an amino acid residue with one or more hydrophobic amino acid residues. By way of further example, a polypeptide can be chemically modified in any of a number of ways. A chemical moiety can be directly appended via a reactive amino acid residue (e.g., via reaction with a sulfhydryl and/or an alpha-amine of a cysteine residue or via reaction with another reactive amino acid residue). Such a reactive amino acid residue may exist in the native polypeptide sequence or such a reactive amino acid residue may be added to the native sequence to provide a site for addition of a hydrophobic moiety. Similarly, when the hydrophobicity of a polypeptide is increased by addition of hydrophobic amino acid residues, such additional hydrophobic amino acid residues may either replace amino acid residue of the native polypeptide, or such amino acid residue may be appended to the native amino acid residues.

Exemplary hydrophobic moieties may be appended to the N-terminal, C-terminal, and/or one or more internal amino acid residues. One class of hydrophobic moieties that may be appended to a netrin-related polypeptide includes lipids such as fatty acid moieties and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: CH3(CH2)nCOOH. Table 2 below lists examples of some fatty acids that can be conveniently appended to a netrin-related polypeptide using conventional chemical methods.

TABLE 2

Exemplary Saturated and Unsaturated Fatty Acids.

| Value of n | Common Name |
|---|---|
| Saturated Acids: CH3 (CH2)n COOH | |
| 2 | butyric acid |
| 4 | caproic acid |
| 6 | caprylic acid |
| 8 | capric acid |
| 10 | lauric acid |
| 12 | myristic acid |
| 14 | palmitic acid |
| 16 | stearic acid |
| 18 | arachidic acid |
| 20 | behenic acid |
| 22 | lignoceric acid |
| Unsaturated Acids | |
| CH3CH=CHCOOH | crotonic acid |
| CH3(CH2)3CH=CH(CH2)7COOH | myristoleic acid |
| CH3(CH2)5CH=CH (CH2)7COOH | palmitoleic acid |
| CH3(CH2)7CH=CH(CH2)7COOH | oleic acid |
| CH3(CH2)3(CH2CH=CH)2(CH2)7COOH | linoleic acid |
| CH3(CH2CH=CH)3(CH2)7COOH | linolenic acid |
| CH3(CH2)3(CH2CH=CH)4(CH2)3COOH | arachidonic acid |

Other lipids that can be attached to a netrin-related polypeptide include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups.

There are a wide range of hydrophobic moieties with which a netrin-related polypeptide can be derivatized. A hydrophobic group can be, for example, a relatively long chain alkyl or cycloalkyl (preferably n-alkyl) group having approximately 7 to 30 carbons. The alkyl group may terminate with a hydroxy or primary amine "tail". To further illustrate, such molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as hydrophobic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2-CH(OH)—O—(C12-C18)-alkyl, and in particular conjugates with pyrene derivatives. The hydrophobic moiety can be a lipophilic dye suitable for use in the invention including, but not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B, and the BODIPY dyes available from Molecular Probes Inc.

Other exemplary lipophilic moieties include aliphatic carbonyl radical groups including 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(−)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

As outlined in detail above, the invention contemplates modified netrin-related polypeptides containing one or more hydrophobic moieties, and further contemplates that said one or more moieties can be appended to the N-terminal amino acid residue, the C-terminal amino acid residue, and/or an internal amino acid residue. When the modified netrin-related polypeptide is appended with two or more moieties, these moieties may be the same or may be different. Furthermore, such moieties may be appended to the same amino acid residue and/or to different amino acid residues.

The invention further contemplates that the hydrophobicity of a netrin-related polypeptide may be increased by appending one or more hydrophobic amino acid residues to the polypeptide or by replacing one or more amino acid residue with one or more hydrophobic amino acid residues. For example, phenylalanine, isoleucine, and methionine are hydrophobic amino acid residues. Accordingly, appending one or more of these residues to a netrin-related polypeptide would increase the hydrophobicity of the netrin-related polypeptide. Similarly, replacing one or more of the amino acid residues of the native polypeptide with one or more of these amino acid residues would increase the hydrophobicity of the netrin-related polypeptide. In one example, the substitution of a hydrophobic amino acid residue for a native residue may be a conservative substitution, and thus one of skill in the art would not expect the substitution to alter the function of the netrin-related polypeptide. Further exemplary hydrophobic amino acid residues include tryptophan, leucine, valine, alanine, proline, and tyrosine.

The foregoing examples illustrate the varieties of modified netrin-related polypeptide contemplated by the present invention. Any of these modified netrin-related polypeptide can be synthesized using techniques well known in the art, and these modified netrin-related polypeptide can be tested using in vitro and in vivo assays to identify modified compositions that (i) retain one or more of the biological activities of the corresponding native and/or un-modified netrin polypeptide and, preferably (ii) possess one or more advantageous physiochemical characteristics in comparison to the native and/or un-modified netrin polypeptide.

The present invention recognizes that certain native forms (e.g., major form or a minor form) of netrin-related polypeptides may be glycosylated. The present invention contemplates hydrophobically or otherwise modifying polypeptides that either possess or do not possess a native glycosylation pattern. Furthermore, the present invention contemplates modifying polypeptides at either the same or at different residues as are typically glycosylated.

As outlined briefly above, any of a number of methods well known in the art can be used to modify a netrin-related polypeptide (e.g., to append one or more moiety, such as a hydrophobic moiety, to one or more amino acid residue). Exemplary methods include, but are not limited to, the following: (i) derivatization of an amino acid residue; (ii) derivatization of a reactive amino acid residue; (iii) addition of a reactive amino acid residue to the native sequence, and derivatization of the added amino acid residue; (iv) replacement of an amino acid residue in the native sequence with a reactive amino acid residue, and derivatization of the reactive amino acid residue; (v) addition of a hydrophobic amino acid residue or hydrophobic peptide; and (vi) replacement of an amino acid residue in the native sequence with one or more hydrophobic amino acids or peptides.

If an appropriate amino acid is not available at a specific position, site-directed mutagenesis can be used to place a reactive amino acid at that site. Similarly, when synthesizing a netrin-related polypeptide, an appropriate reactive amino acid can be added to the polypeptide (e.g., added to the N-terminus or C-terminus, or internally). Of course, any such variant sequences must be assessed to confirm that the variant retains one or more of the biological activities of the corresponding native and/or un-modified polypeptide. Reactive amino acids include cysteine, lysine, histidine, aspartic acid, glutamic acid, serine, threonine, tyrosine, arginine, methionine, and tryptophan, and numerous methods are well known in the art for appending moieties to any of these reactive amino acids. Furthermore, methodologies exist for appending various moieties to other amino acids, and one of skill in the art can readily select the appropriate techniques for appending a moiety to an amino acid residue.

There are specific chemical methods for the modification of many amino acids, including reactive amino acids. Therefore, a route for synthesizing a modified netrin-related polypeptide would be to chemically attach a hydrophobic moiety to an amino acid in a netrin-related polypeptide. Such amino acid may be a reactive amino acid. Such amino acid may exist in the native sequence or may be added to the native sequence prior to modification. If an appropriate amino acid is not available at the desired position, site-directed mutagenesis at a particular site can be used. Reactive amino acids would include cysteine, lysine, histidine, aspartic acid, glutamic acid, serine, threonine, tyrosine, arginine, methionine, and tryptophan. Thus the goal of creating a modified netrin-related polypeptide could be attained by many chemical means and we do not wish to be restricted by a particular chemistry or site of modification. One of skill in the art can readily make a wide range of modified netrin-related polypeptides using well-known techniques in chemistry, and one of skill in the art can readily test the modified netrin-related polypeptides in any of a number of in vitro or in vivo assays to identify the modified netrin-related polypeptides which retain one or more of the biological activities of the corresponding native and/or un-modified netrin polypeptide. Furthermore, one of skill in the art can readily evaluate which modified netrin-related polypeptides which retain one or more of the biological activities of the corresponding native and/or un-modified netrin polypeptide also possess advantageous physiochemical properties.

The polypeptide can be linked to the hydrophobic moiety in a number of ways including by chemical coupling means, or by genetic engineering. To illustrate, there are a large number of chemical cross-linking agents that are known to those skilled in the art. One class of cross-linking agents are heterobifunctional cross-linkers, which can be used to link the polypeptides and hydrophobic moieties in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl)cyclohexane-1-carboxylate (SMCC), m-Maleimidobenzoyl-N-hydroxysuccinimide ester (MBS); N-succinimidyl(4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-tolune (SMPT), N-succinimidyl 3-(2-pyridyldithio)propionate (SPDP), succinimidyl 6-[3-(2-pyridyldithio)propionate]hexanoate (LC-SPDP).

Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate.2 HCl (DMP) are examples of useful homobifunctional cross-linking agents, and bis-[.beta.-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) Bioconjugate Chemistry 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75).

The reaction buffer should be free of extraneous amines and sulfhydryls. The pH of the reaction buffer should be 7.0-7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the lipophilic group chosen for reaction with maleimides, activated halogens, or pyridyl disulfides must contain a free sulfhydryl. Alternatively, a primary amine may be modified with to add a sulfhydryl.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5-7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing lipophilic group under the appropriate buffer conditions. The conjugates can be isolated from the reaction mixture by methods such as gel filtration or by dialysis.

Exemplary activated lipophilic moieties for conjugation include: N-(1-pyrene)maleimide; 2,5-dimethoxystilbene-4'-maleimide, eosin-5-maleimide; fluorescein-5-maleimide; N-(4-(6-dimethylamino-2-benzofuranyl)phenyl)maleimide; benzophenone-4-maleimide; 4-dimethylaminophenylazophenyl-4'-maleimide (DABMI), tetramethylrhodamine-5-maleimide, tetramethylrhodamine-6-maleimide, RHODAMINE RED™ C2 maleimide, N-(5-aminopentyl) maleimide, trifluoroacetic acid salt, N-(2-aminoethyl)maleimide, trifluoroacetic acid salt, OREGON GREEN™ 488 maleimide, N-(2-((2-(((4-azido-2,3,5,6-tetrafluoro)benzoyl) amino)ethyl) dithio)ethyl)maleimide (TFPAM-SS1), 2-(1-(3-dimethylaminopropyl)-indol-3-yl)-3-(indol-3-yl) maleimide (bisindolylmaleimide; GF 109203x), BODIPY™. FL N-(2-aminoethyl)maleimide, N-(7-dimethylamino-4-methylcoumarin-3-yl)maleimide (DACM), ALEXA™ 488 C5 maleimide, ALEXA™ 594 C5 maleimide, sodium saltN-(1-pyrene)maleimide, 2,5-dimethoxystilbene-4'-maleimide, eosin-5-maleimide, fluorescein-5-maleimide, N-(4-(6-dimethylamino-2-benzofuranyl)phenyl)maleimide, benzophenone-4-maleimide, 4-dimethylaminophenylazophenyl-4'-maleimide, 1-(2-maleimidylethyl)-4-(5-(4-methoxyphenyl)oxazol-2-yl)pyridinium methanesulfonate, tetramethylrhodamine-5-maleimide, tetramethylrhodamine-6-maleimide, RHODAMINE RED™ C2 maleimide, N-(5-aminopentyl)maleimide, N-(2-aminoethyl)maleimide, N-(2-((2-(((4-azido-2,3,5,6-tetrafluoro)benzoyl)amino)ethyl)dithio)ethyl)maleimide, 2-(1-(3-dimethylaminopropyl)-indol-3-yl)-3-(indol-3-yl)maleimide, N-(7-dimethylamino-4-methylcoumarin-3-yl)maleimide (DACM), 11H-Benzo[a]fluorene, Benzo[a]pyrene.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

The foregoing methods are merely provided to illustrate the techniques that one of skill in the art can readily employ in making a wide range of modified netrin-related polypeptides. Further methods are described in U.S. Pat. No. 6,444,793, which is hereby incorporated by reference in its entirety.

Hydrophilically Modified Polypeptides

In addition to providing netrin-related compositions comprising polypeptides and bioactive fragments thereof, as described herein, the present invention recognizes that certain compositions comprising modified netrin-related polypeptides and bioactive fragments thereof will have certain other advantages in comparison to their native and/or un-modified counter-parts. Such modified netrin-related polypeptides (including full-length polypeptides and bioactive fragments) not only retain one or more of the biological activities of native or un-modified netrin, but also possess one or more additional, advantageous physiochemical properties in comparison to a native and/or un-modified netrin. Exemplary physiochemical properties include, but are not limited to, increased in vitro half-life, increased in vivo half-life, decreased immunogenicity, increased solubility, increased potency, increased bioavailability, and increased biodistribution. One class of preferred modified polypeptides include hydrophilically modified polypeptides such as polypeptides appended with one or more cyclodextran moieties, polypeptides appended with one or more PEG moieties, polypeptides appended with one or more laminin moieties, and polypeptides appended with one or more antibody moieties. One preferred class of modified polypeptides and compositions according to the present invention are pegylated polypeptides and compositions. A pegylated netrin-related polypeptides is appended with a PEG containing moiety comprising one or more PEG [(poly(ethylene)glycol or (poly(ethylene)glycol derivative] moieties.

The invention provides compositions comprising modified netrin-related polypeptides and methods for using these modified netrin-related polypeptides. In one embodiment, the modified netrin-related polypeptide is a pegylated netrin polypeptide (e.g., the netrin-related polypeptide is appended with one or more PEG containing moieties). Appending PEG containing moieties to polypeptides may be used to obtain modified compositions that retain one or more of the biological properties of the native or un-modified polypeptide, and further possess one or more advantageous physiochemical properties The term "PEG containing moiety" and "PEG containing moiety comprising one or more PEG moiety" are used throughout this application to refer to the modified netrin-related polypeptides of the invention. A PEG containing moiety may comprise one or more PEG moieties. PEG moieties may exist as a polymer of virtually any size, and the invention contemplates that PEG containing moieties comprising 1, 2, 3, 4, 5, 6, 8, 10, 20, 40, 50, 100, or greater than 100 PEG moieties can be appended to a netrin-related polypeptide. Furthermore, the invention contemplates modification with PEG-containing which further contain reactive groups for appending to a netrin-related polypeptide.

The polymer backbone is a water soluble, substantially non-immunogenic polymer, and is preferably poly(ethylene) glycol. However, as used throughout the specification, the term "PEG", "PEG moiety", and "PEG containing moiety" refer to poly(ethylene glycol) containing moieties, as well as other related polymers. Suitable polymer backbones include, but are not limited to, linear and branched poly(ethylene glycol), linear and branched poly(alkylene oxide), linear and branched poly(vinyl pyrrolidone), linear and branched poly (vinyl alcohol), linear and branched polyoxazoline, linear and branched poly(acryloylmorpholine), and derivatives thereof. Additionally, when the PEG containing moiety comprises more than one PEG moiety, the invention contemplates that the PEG moieties may be the same (e.g., each PEG moiety is polyethylene glycol) or that the PEG moieties may be different (e.g., one or more polyethylene glycol moiety and one or more polyvinyl alcohol moiety).

PEG moieties are useful in biological applications because they have properties that are highly desirable and are generally approved for biological applications in vivo and in vitro. PEG typically is clear, colorless, odorless, soluble in water, stable to heat, inert to many chemical agents, does not hydrolyze or deteriorate, and is generally nontoxic. Poly(ethylene) glycol and other PEG related polymers are considered to be biocompatible, which is to say that PEG is capable of coexistence with living tissues or organisms without causing harm. More specifically, PEG is non-immunogenic, which is to say that PEG does not tend to produce an immune response in the body. When attached to a molecule having some desirable function in the body, such as a biologically active agent, to form a conjugate, the PEG tends to mask the agent and can reduce or eliminate any immune response so that an organism can tolerate the presence of the agent. Accordingly, the conjugate is substantially non-toxic. PEG conjugates tend not to produce a substantial immune response or cause clotting or other undesirable effects.

PEG having the formula —$CH_2CH_2$—$(CH_2CH_2O)_n$—$CH_2CH_2$—, where n is from about 8 to about 4000, is one useful polymer in the practice of the invention. Preferably PEG having a molecular weight of from about 200 to about 100,000 Da is used as polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol.

Many other water soluble substantially non-immunogenic polymers than PEG are also suitable for the present invention. These other polymers can be either in linear form or branched form, and include, but are not limited to, other poly(alkylene oxides) such as poly(propylene glycol) ("PPG"), copolymers of ethylene glycol and propylene glycol and the like; poly (vinyl alcohol) ("PVA") and the like. The polymers can be homopolymers or random or block copolymers and terpolymers based on the monomers of the above polymers, straight chain or branched.

Specific examples of suitable additional polymers include, but are not limited to, difunctional poly(acryloylmorpholine) ("PAcM"), and poly(vinylpyrrolidone) ("PVP"). PVP and poly(oxazoline) are well known polymers in the art and their preparation should be readily apparent to the skilled artisan. PAcM and its synthesis and use are described in U.S. Pat. Nos. 5,629,384 and 5,631,322. Although the molecular weight of each chain of the polymer backbone can vary, it is typically in the range of from about 100 to about 100,000, preferably from about 6,000 to about 80,000.

Those of ordinary skill in the art will recognize that the foregoing list for substantially water soluble non-immunogenic polymer backbone is by no means exhaustive and is merely illustrative, and that all polymeric materials having the qualities described above are contemplated.

In addition to PEG moieties, preferred PEG containing moieties of the invention also contain a reactive group to facilitate attachment of the PEG containing moiety to the netrin-related polypeptide. The reactive group allows the PEG containing moiety to be readily appended to a free amine of an amino acid residue. For example, via the reactive group, a PEG containing moiety can be appended to the primary amine of the N-terminal amino acid residue of a netrin-related polypeptide. Via the reactive group, a PEG containing moiety can be appended to an amine containing amino acid residue including an internal amino acid residue or a C-terminal amino acid residue. An amine containing amino acid residue may be naturally present in a particular polypeptide. However, if an amine containing amino acid residue is not present, an amine containing amino acid residue can be added to a polypeptide at either the N-terminus, C-terminus, or internally, and this added amine containing amino acid residue can supply a site for appending a PEG containing moiety. Following addition of an amine containing amino acid residue, the polypeptide should retain the function of the native polypeptide. Furthermore, if an amine containing amino acid residue is not present, an amine containing amino acid residue can be substituted for a residue already present in the polypeptide. Following substitution of an amine containing amino acid residue for an amino acid residue that does not contain a free amine, the polypeptide should retain the activity of the native polypeptide.

The reactive group (also referred to herein as the reactive moiety) is a moiety capable of reacting with a moiety in another molecule, e.g., a biologically active agent such as proteins, peptides, etc. Examples of suitable reactive moieties include, but are not limited to, active esters, active carbonates, aldehydes, isocyanates, isothiocyanates, epoxides, alcohols, maleimides, vinylsulfones, hydrazides, dithiopyridines, N-succinimidyl, and iodoacetamides. The selection of a free reactive moiety is determined by the moiety in another molecule to which the free reactive moiety is to react. For example, when the moiety in another molecule is a thiol moiety, then a vinyl sulfone moiety is preferred for the free reactive moiety of the activated polymer. On the other hand, an N-succinimidyl moiety is preferred to react to an amino moiety in a biologically active agent.

The invention contemplates any of a number of modified netrin-related polypeptides. The modified netrin-related polypeptides will vary with respect to the number and/or identity of the PEG moieties comprising the PEG containing moiety, and with respect to the reactive group through which the PEG containing moiety is appended to the netrin-related polypeptide. Nevertheless, the present invention contemplates that any such pegylated netrin-related polypeptide can be readily constructed and tested to identify modified netrin-related polypeptides that retain one or more of the biological activities of native or un-modified netrin and which possess one or more advantageous physiochemical property in comparison to native or un-modified netrin. Particularly advantageous PEG containing moieties and methods for appending said PEG containing moieties to a netrin-related polypeptide are further summarized in, for example, the following issued patents and publications. The disclosures of each of the following references are hereby incorporated by reference in their entirety: U.S. Pat. No. 6,664,331, U.S. Pat. No. 6,624,246, U.S. Pat. No. 6,610,281, WO03/070805, U.S. Pat. No. 6,602,952, U.S. Pat. No. 6,602,498, U.S. Pat. No. 6,541,543, U.S. Pat. No. 6,541,015, U.S. Pat. No. 6,515,100, U.S. Pat. No. 6,514,496, U.S. Pat. No. 6,514,491, U.S. Pat. No. 6,495,659, U.S. Pat. No. 6,461,603, U.S. Pat. No. 6,461,602, U.S. Pat. No. 6,436,386, U.S. Pat. No. 5,900,461, WO03/040211, WO03/000777, U.S. Pat. No. 6,448,369, U.S. Pat. No. 6,437,025, and Roberts et al. (2002) *Advanced Drug Delivery Reviews* 54: 459-476.

In addition, pegylated netrin-related polypeptides according to the present invention may have any of the following properties. In certain embodiments, a pegylated netrin-related polypeptide is modified with a moiety comprising one or more PEG (or PEG-related) moieties. Such one or more PEG moieties can be arranged linearly with respect to the netrin-related polypeptide or can be arranged in a branched configuration. The PEG containing moiety may be covalently appended to the primary amine of the N-terminal amino acid residue of the netrin-related polypeptide although the invention contemplates other well known methods for appending PEG moieties to polypeptides. Other preferred embodiments include appending one or more PEG containing moieties to an internal amino acid residue containing a free amine, appending one or more PEG containing moieties to a C-terminal amino acid residue containing a free amine, or appending one or more PEG containing moieties to a reactive lysine or cysteine residue (e.g., an N-terminal, internal, or C-terminal reactive lysine or cysteine residue). We note that certain polypeptides may not contain a convenient free amine for appending one or more PEG moieties. Accordingly, the invention further contemplates the addition or substitution of a free amine containing amino acid residue to a polypeptide to serve as a site of attachment for one or more PEG containing moiety. Following addition or substitution of an amino acid residue to the N-terminus, C-terminus, or internally, the variant polypeptide should retain one or more of the biological activities of the native polypeptide (e.g., addition or substitution of the free amine containing amino acid residue should not disrupt the activity of the polypeptide). For any of the foregoing, the invention contemplates that one or more PEG containing moieties can be appended to the same or to different amino acid residues.

The pegylated netrin-related polypeptides according to the present invention can additionally be described in a number of ways. For example, the invention contemplates appending netrin-related polypeptides with PEG containing moieties totaling approximately 5 kDa, 10 kDa, 20 kDa, 30 kDa, 40 kDa, 60 kDa, 80 kDa, or greater than 80 kDa (e.g., the PEG containing moiety increases the molecular weight of the netrin-related polypeptide by approximately 5, 10, 20, 30, 40, 60, 80, or greater than 80 kDa).

Furthermore, the pegylated netrin-related polypeptides of the invention can be described in terms of the polydispersity of the PEG containing moiety. In one embodiment, the polydispersity is approximately 1.01-1.02 MW/MN (molecular weight/molecular number). In another embodiment, the polydispersity is less than 1.05 MW/MN. In yet another embodiment, the polydispersity is greater than 1.05 MW/MN.

The present invention contemplates the attachment of PEG containing moieties (e.g., moieties comprising one or more PEG or PEG-related moieties) to netrin-related polypeptides. For example, the present invention contemplates the attachment of PEG containing moieties to the primary amine of the N-terminal amino acid residue of a netrin-related polypeptide. The present invention further contemplates the attachment of PEG containing moieties to any amine containing amino acid residue of a netrin-related polypeptide (e.g., an N-terminal, C-terminal, or internal amine containing amino acid residue). Such attachment may be a covalant attachment, and such covalent attachment may occur via an active group of the PEG containing moiety. For example, attachment may occur via an active ester, an active aldehyde, or an active carbonate. Further examples of reactive groups used to covalently append a PEG containing moiety include but are not limited to, isocyanates, isothiocyanates, epoxides, alcohols, maleimides, vinylsulfones, hydrazides, dithiopyridines, and iodoacetamides.

In addition to the foregoing pegylated netrin-related polypeptides, the invention contemplates netrin-related polypeptides modified with other moieties that increase the hydrophilicity of the modified netrin-related polypeptides. Such hydrophilic netrin-related polypeptides retain one or more of the biological activities of un-modified or native netrin, and preferably have one or more advantageous physiochemical properties in comparison to un-modified and/or native netrin-related polypeptide. Exemplary physiochemical properties include, but are not limited to, increased in vitro half-life, increased in vivo half-life, decreased immunogenicity, increased solubility, increased potency, increased solubility, increased bioavailability, and increased biodistribution. Exemplary hydrophilic netrin-related polypeptides include netrin-related polypeptides appended with one or more cyclodextran moieties, or netrin-related polypeptides that are otherwise appended with one or more glycosyl moieties. Other particularly preferred moieties with which a netrin-related polypeptide can be appended include one or more albumin moieties or one or more antibody moieties.

In any of the foregoing, the invention contemplates modified netrin-related polypeptides or bioactive fragments thereof, as well as mimetics of full-length netrin or mimetics of a bioactive fragment of netrin.

As outlined in detail above, the present invention contemplates a variety of modified netrin-related polypeptides, wherein the modified netrin-related polypeptide retains one or mote of the biological activities of native or un-modified netrin polypeptide and further possesses one or more advantageous physiochemical properties. By way of another example of modified netrin-related polypeptides, and methods for using such polypeptides, the present invention contemplates modified netrin-related polypeptides appended with one or more albumin moieties. As outlined in detail for pegylated netrin-related polypeptides, albumin modified netrin-related polypeptides can be modified with one or more albumin moieties and such albumin moieties can be appended to an N-terminal, C-terminal, and/or an internal amino acid residue. Detailed descriptions of albumin and exemplary methods that can be used to append albumin moieties to a netrin-related polypeptide can be found in US application 2004/0010134, the disclosure of which is hereby incorporated by reference in its entirety.

Additional modified netrin-related polypeptides are also contemplated by the present invention and include netrin-related polypeptides modified with one or more albumin moiety, netrin-related polypeptides modified with one or more antibody moiety (e.g., IgG moiety, IgM moiety, IgE moiety, etc), and netrin-related polypeptides otherwise modified so as to increase their hydrophilicity. A variety of methods can be used to append one or more moieties to a netrin-related polypeptide, and exemplary methods are found in the following references which are hereby incorporated by reference in their entirety: US application no. 2004/0010134, U.S. Pat. No. 6,664,331, U.S. Pat. No. 6,624,246, U.S. Pat. No. 6,610,281, WO03/070805, U.S. Pat. No. 6,602,952, U.S. Pat. No. 6,602,498, U.S. Pat. No. 6,541,543, U.S. Pat. No. 6,541,015, U.S. Pat. No. 6,515,100, U.S. Pat. No. 6,514,496, U.S. Pat. No. 6,514,491, U.S. Pat. No. 6,495,659, U.S. Pat. No. 6,461,603, U.S. Pat. No. 6,461,602, U.S. Pat. No. 6,436,386, U.S. Pat. No. 5,900,461, WO03/040211, WO03/000777, U.S. Pat. No. 6,448,369, U.S. Pat. No. 6,437,025, and Roberts et al. (2002) *Advanced Drug Delivery Reviews* 54: 459-476.

For any of the foregoing, we note that modified netrin polypeptides are just one illustrative embodiment of the range of modified polypeptides for use in the methods of the present invention. The application contemplates that any polypeptide or peptide for use in the methods of the present invention can be modified to impart one or more advantageous physiochemical properties. By way of further example, where the present invention provides agents (e.g., polypeptide or peptide agents) that inhibit the expression or activity of netrin or of netrin signaling, such agents include modified polypeptides, or modified bioactive fragments thereof. Modified polypeptides or modified bioactive fragments retain one or more of the biological activities of the native polypeptide, and preferably possess one or more advantageous physiochemical activity in comparison to the native polypeptide. For example, when an agent that inhibits the expression or activity of netrin or of netrin signaling is an Unc5h receptor or an Unc5h receptor ectodomain, the invention contemplates modified Unc5h receptors or modified Unc5h receptor ectodomains.

Classes of Modifications

The present invention contemplates compositions comprising modified polypeptides. In one embodiment, the modified polypeptide is a hydrophilically modified polypeptide. In another embodiment, the modified polypeptide is a pegylated polypeptide. The invention contemplates that a modified polypeptide may be appended with one or more moieties (or with a moiety containing one or more PEG moieties). The moieties may be the same or may be different, and the moieties may be arranged linearly or in a branched configuration. In one embodiment, the modified polypeptide is a modified netrin-related polypeptide.

In embodiments comprising a modified netrin-related polypeptide, the invention contemplates modified polypeptides that also retain a native glycosylation pattern, as well as modified polypeptides that do not possess a native glycosylation pattern.

The invention contemplates that the polypeptides (e.g., netrin polypeptides, Unc polypeptides, etc) can be modified by appending a moiety to the N-terminal amino acid residue (e.g., by appending a PEG containing moiety to the primary amine of the N-terminal amino acid residue). Furthermore, the invention contemplates that the polypeptides can be modified by appending a moiety to an internal amino acid residue or to the C-terminal amino acid residue (e.g., by appending a PEG containing moiety to an amine containing amino acid residue). Additionally, the invention contemplates addition or substitution of a free amine containing amino acid residue to a polypeptide to provide a site for attachment of one or more PEG containing moiety.

The present invention provides modified polypeptides, and methods of using these modified polypeptides in vitro and in vivo. The modified polypeptides of the present invention should retain one or more of the biological activities of un-modified and/or native polypeptide. Additionally, preferable modified polypeptides possess one or more advantageous physiochemical characteristics in comparison to native and/or un-modified polypeptide. Accordingly, modified polypeptides not only provide additional possible compositions for manipulating signaling in vitro or in vivo, such modified polypeptides may also provide polypeptides with improved properties in comparison to the prior art. Exemplary modified polypeptides include pegylated polypeptides.

The present invention contemplates appending polypeptides with any of a number of PEG containing moieties, as well as any of a number of methods for appending such PEG containing moieties to the primary amine of the N-terminal amino acid residue, an amine of an amine containing internal amino acid residues, and/or an amine of an amine containing C-terminal amino acid residue. Furthermore, the invention contemplates appending PEG containing moieties via reactive amino acid residues including cysteine residues.

Various PEG containing moieties are well known in the art. For example, several companies manufacture and market a variety of PEG containing reagents for use in pegylating peptides. In the earlier days of pegylation technology, pegylation occurred via reactive amino acid residues such as cysteines. Although powerful, such methodologies required either that the peptide of interest contain a cysteine residue, or required mutating or appending a cysteine residue to the peptide of interest. Such methodologies are extremely useful, and are well-known in the art. Given that polypeptides, for example netrin polypeptides, contain a number of cysteine residues, methods of appending moieties via a cysteine residue offer a potentially powerful approach for appending moieties to polypeptides.

Additionally, the present invention describes pegylated polypeptides, wherein the PEG containing moiety is attached via a free amine (e.g., the primary amine of the N-terminal amino acid residue, a free amine of an internal amino acid reside, a free amine of a C-terminal amino acid residue, etc.).

Activated PEG containing moieties readily allow the conjugation of PEG containing moieties to primary amine of peptides. Thus, the methods and compositions of the present invention specifically contemplate PEG containing moieties comprising a reactive group (e.g., reactive PEG containing moieties), the invention further contemplates that attachment of the PEG containing moiety to the polypeptides occurs via the reactive group.

Preferable reactive PEG containing moieties readily react with polypeptides at physiological pH (e.g., 7.0, 7.5, 8.0, 8.5, 9.0, and 9.5) and at room temperature. In certain embodiment, the PEG containing moiety is capped with a methoxy PEG. Accordingly, the invention contemplates PEG containing moieties which may include methoxy PEG.

In one aspect, the PEG containing moiety is a lysine-active PEG (also referred to as an active ester containing PEG moiety). Such lysine active PEG containing moieties are particularly useful for either appending a PEG containing moiety to the primary amine of the N-terminal amino acid residue, as well as for appending a PEG containing moiety to an amino acid residue containing an imidazole group or a hydroxyl group (e.g., histidine, tyrosine). Exemplary active esters include, but are not limited to, N-hydroxylsuccinimide (NHS) active esters, succinimidyl propionate (SPA) active esters and, succinimidyl butanate (SBA) active esters. Examples of lysine active PEG containing moieties include, but are not limited to, PEG-N-hydroxylsuccinimide (PEG-NHS), succinimidyl ester of PEG propionic acid (PEG-SPA), and succinimidyl ester of PEG butanoic acid (PEG-SBA).

In another aspect, the PEG containing moiety is a PEG aldehyde (also referred to as a PEG thioester). PEG-thioester containing moieties are specifically designed for conjugation to the N-terminus, and preferable are designed for appending to a cysteine or a histidine.

In another aspect, the PEG containing moiety is a PEG double ester.

In another aspect, the PEG containing moiety is a PEG benzotriazole carbonate (PEG-BTC). Such PEG containing moieties are especially useful for producing modified proteins under mild conditions, and results in the attachment of PEG-BTC to the polypeptide via a stable urethane (carbamate) linkage.

In another aspect, the PEG containing moiety is an amine selective reagent such as PEG-ButyrALD. Such selective reagents allow for more stable modified compositions than previously attainable. However, the invention contemplates the use of other PEG containing moieties bearing aldehyde groups. One specifically contemplated class of aldehyde bearing moieties reacts with primary amines in the presence of sodium cyanoborohydride and includes PEG aldehydes, PEG acetaldehydes, and PEG propionaldehydes.

In another aspect, the PEG containing moiety is a PEG acetaldehyde diethyl acetal (PEG-ACET). Such PEG containing moieties are particularly stable against aldol condensation.

In another aspect, the PEG containing moiety is a sulfhydryl-selective PEG. Exemplary sulfhydryl-selective PEGs include PEG-maleimide (PEG-MAL) and PEG-vinylsulfone (PEG-VS). Such PEG containing moieties are especially useful for reaction with thiol groups.

The foregoing examples illustrate the varieties of modified polypeptides contemplated by the present invention. Any of these modified polypeptides can be synthesized using techniques well known in the art, and these modified polypeptides can be tested using in vitro and in vivo assays to identify modified polypeptides that (i) retain one or more of the biological activities of the corresponding native and/or un-modified polypeptide and, preferably (ii) possess one or more advantageous physiochemical characteristics in comparison to the corresponding native and/or un-modified polypeptide.

In addition, one of skill in the art can readily select from amongst a great many additional PEG containing moieties and select appropriate PEG chemistries to append a PEG containing moiety to one or more of an N-terminal amino acid residue, an internal amino acid residue, or a C-terminal amino acid residue of a polypeptide. Examples of additional PEG containing moieties and PEG chemistries are described, for example, in Roberts et al. (2002) Advanced Drug Delivery Reviews 54: 459-476, U.S. Pat. No. 6,664,331, U.S. Pat. No. 6,624,246, U.S. Pat. No. 6,610,281, WO03/070805, U.S. Pat. No. 6,602,952, U.S. Pat. No. 6,602,498, U.S. Pat. No. 6,541,543, U.S. Pat. No. 6,541,015, U.S. Pat. No. 6,515,100, U.S. Pat. No. 6,514,496, U.S. Pat. No. 6,514,491, U.S. Pat. No. 6,495,659, U.S. Pat. No. 6,461,603, U.S. Pat. No. 6,461,602, U.S. Pat. No. 6,436,386, U.S. Pat. No. 5,900,461, WO03/040211, WO03/000777, U.S. Pat. No. 6,448,369, U.S. Pat. No. 6,437,025, the disclosures of which are hereby incorporated by reference in their entirety.

Additional Modified Polypeptides

The foregoing examples of hydrophobically and hydrophilically modified polypeptides were meant to illustrate the modified polypeptides contemplated by the present invention. As should be clear from the examples provided herein, modified polypeptides of the invention can be appended with 1 or more, 2 or more, 3 or more, 4 or more, 5 or more, or more than 5 moieties. When a polypeptide is appended with more than one moiety, the moieties can be appended to the same amino acid residues or to different amino acid residues. When a polypeptide is appended with more than one moiety, the moieties are independently selected. The independent selection of moieties may include not only various hydrophobic moieties together to produce a hydrophobically modified polypeptide, or various hydrophilic moieties together to produce a hydrophilically modified polypeptide. The invention also contemplates appending a polypeptide with both hydrophobic and hydrophilic moieties to produce a mixed-modified polypeptide. Such a modified polypeptide can be readily evaluated to confirm that it retains one or more biological activities of the corresponding native and/or un-modified polypeptide, and further evaluated to assess whether the modified polypeptide possess one or more advantageous physiochemical properties in comparison to the corresponding native and/or un-modified polypeptide.

Agents

In addition to the nucleic acid and polypeptide compositions of the present invention outlined is detail above, the present invention also contemplates additional agents that can be used in the methods of the present invention. In one embodiment, the agent inhibits the expression or activity of a netrin or of netrin signaling. In another embodiment, such an agent that inhibits the expression or activity of a netrin or of netrin signaling (e.g., inhibit the pro-angiogenic, pro-attractant activity of netrin) is selected from any of the following: (i) an Unc5h polypeptide; (ii) an Unc5h nucleic acid; (iii) a modified or bioactive fragment of Unc5h; (iv) an Unc5h ectodomain; (v) an anti-neogenin antibody (e.g., a blocking antibody); (vi) a neogenin antisense oligonucleotide; (vii) a neogenin RNAi construct; (viii) a neogenin ribozyme; (ix) a small molecule that inhibits the activity or expression of netrin or of netrin signaling; (x) a small molecule that binds to neogenin to inhibit the activity of netrin or of netrin signaling; (xi) a small molecule that binds to netrin to inhibit the activity of netrin or of netrin signaling.

In another embodiment, the agent promotes the expression or activity of a netrin or of netrin signaling (e.g., promotes the pro-angiogenic, pro-attractant activity of netrin). In another embodiment, such an agent that promotes the expression or activity of a netrin or of netrin signaling is selected from any of the following: (i) an anti-Unc5h antibody (a blocking antibody); (ii) an Unc5h antisense oligonucleotide; (iii) a Unc5h RNAi construct; (iv) a Unc5h ribozyme; (v) a small molecule that promotes the activity or expression of netrin or of netrin signaling; (vi) a small molecule that binds to netrin to promote the activity of netrin or of netrin signaling; (vii) a small molecule that binds to neogenin to promote the activity of netrin or of netrin signaling; (viii) a small molecule that binds to and inhibits Unc5h, thereby promoting netrin activity.

The present invention contemplates compositions and pharmaceutical compositions comprising one or more agents of the present invention. The present invention contemplates that numerous agents can be used. The agents of the present invention act to either promote netrin activity or signaling or to inhibit netrin activity or signaling by modulating netrin activity at the level of (i) the ligand netrin, itself; (ii) the receptor neogenin; (iii) the negative regulator Unc5h. Agents that promote or inhibit netrin signaling can then be used in vitro or in vivo, including as a therapeutic agent, as described herein.

A. Classes of Agents

Numerous mechanisms exist to inhibit the expression and/or activity of a particular mRNA or protein. Without being bound by theory, the present invention contemplates any of a number of methods for inhibiting the expression and/or activity of a particular mRNA. Furthermore, the invention contemplates any of a number of methods for inhibiting the expression and/or activity of a particular protein. Still furthermore, the invention contemplates combinatorial methods comprising either (i) the use of two or more inhibitors that decrease the expression and/or activity of a particular mRNA or protein, or (ii) the use of one or more inhibitors that decrease the expression and/or activity of a particular mRNA or protein plus the use of one or more inhibitors that decrease the expression and/or activity of a second mRNA or protein.

The following are illustrative examples of methods for inhibiting the expression and/or activity of an mRNA or protein. These examples are in no way meant to be limiting, and one of skill in the art can readily select from among known methods of inhibiting expression and/or activity. One of skill in the art will readily recognize that inhibitory agents can be used to inhibit the activity of a given protein, and thereby inhibit signaling. Furthermore, inhibitory agents can be used to inhibit the activity of a given protein that endogenously functions to inhibit signaling via a particular protein. In such scenarios, antagonism of the inhibitory protein has a net positive effect, thereby promoting signaling via a particular protein.

Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089/10134, published Apr. 25, 1988), hybridization-triggered cleavage agents (See, e.g., Krol et al., 1988, BioTechniques 6:958-976) or intercalating agents.

(See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier et al., 1987, Nucl. Acids Res. 15:6625-6641). The oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

In another example, it may be desirable to design an antisense oligonucleotide that binds to and mediates the degradation of more than one message. In one example, the messages may encode related protein such as isoforms or functionally redundant protein. In such a case, one of skill in the art can align the nucleic acid sequences that encode these related proteins, and design an oligonucleotide that recognizes both messages.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc Natl Acad Sci USA*, 98:9742-9747; Elbashir, et al. (2001) *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; McManus et al., *RNA,* 2002, 8:842-50; Yu et al., *Proc Natl Acad Sci USA,* 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

Ribozymes molecules designed to catalytically cleave an mRNA transcripts can also be used to prevent translation of mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

Antibodies can be used as inhibitors of the activity of a particular protein (e.g., blocking antibodies). Antibodies can have extraordinary affinity and specificity for particular epitopes. Antibodies that bind to a particular protein in such a way that the binding of the antibody to the epitope on the protein can interfere with the function of that protein. For example, an antibody may inhibit the function of the protein by sterically hindering the proper protein-protein interactions or occupying active sites. Alternatively the binding of the antibody to an epitope on the particular protein may alter the conformation of that protein such that it is no longer able to properly function. In the context of the present application, a preferred antibody may bind to and inhibit the function of a receptor required for netrin signaling in a cell. Alternatively, the antibody may bind to a different site on the enzyme to sterically hinder the protein-protein interactions required for function. In still another example, the antibody may bind to a different site on the protein and alter the conformation of the protein such that the protein is no longer able to function. Exemplary antibodies include anti-neogenin antibodies (e.g., antibodies immunoreactive with all or a portion of a neogenin polypeptide).

Monoclonal or polyclonal antibodies can be made using standard protocols (See, for example, Antibodies: A Laboratory Manual ed. by Harlow and Lane (Cold Spring Harbor Press: 1988)). A mammal, such as a mouse, a hamster, a rat, a goat, or a rabbit can be immunized with an immunogenic form of the peptide. Techniques for conferring immunogenicity on a protein or peptide include conjugation to carriers or other techniques well known in the art.

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a particular polypeptide and monoclonal antibodies isolated from a culture comprising such hybridoma cells.

In the context of the present invention, antibodies can be screened and tested to identify those antibodies that can inhibit the function of a particular protein. One of skill in the art will recognize that not every antibody that is specifically immunoreactive with a particular protein will interfere with the function of that protein. However, one of skill in the art can readily test antibodies to identify those that are capable of blocking the function of a particular protein.

The term antibody as used herein is intended to include fragments thereof which are also specifically reactive with a particular polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a particular protein conferred by at least one CDR region of the antibody.

Both monoclonal and polyclonal antibodies (Ab) directed against a particular polypeptides, and antibody fragments such as Fab, F(ab)$_2$, Fv and scFv can be used to block the action of a particular protein. Such antibodies can be used either in an experimental context to further understand the role of a particular protein in a biological process, or in a therapeutic context.

For any of the foregoing examples of antibodies, the invention contemplates antibodies capable of blocking the function of a given protein in multiple species, as well as species specific antibodies. Furthermore the invention contemplates that some antibodies will cross-reactive with multiple family members related to a given protein (e.g., immunoreactive with netrin1, netrin2, netrin4, netrin G1, or netrin G2), while other antibodies specifically react with one a single family member.

Small organic molecules can agonize or antagonize the function of a particular protein. By small organic molecule is meant a carbon contain molecule having a molecular weight less than 2500 amu, more preferably less than 1500 amu, and even more preferably less than 750 amu.

Small organic molecules can be readily identified by screening libraries of organic molecules and/or chemical compounds to identify those compounds that have a desired function. Without being bound by theory, small organic molecules may exert their function in any of a number of ways.

In addition to screening readily available libraries to identify small organic molecules with a particular function (e.g., promote or inhibit netrin signaling), the present invention contemplates the rational design and testing of small organic molecules. For example, based on molecular modeling of the binding site of a particular enzyme, one of skill in the art can design small molecules that can occupy that binding pocket. Such small organic molecules would be candidate inhibitors of the function of the particular enzyme.

The present invention contemplates a large number of agents that function as inhibitors including nucleic acid, peptide, polypeptide, small organic molecule, antisense oligonucleotide, RNAi construct, antibody, and ribozyme based agents that function as inhibitors. Depending on their particular target, such agents may either promote expression or activity of netrin or of netrin signaling or such agents my inhibit expression or activity of netrin or of netrin signaling.

Agents that function as inhibitors and either promote or inhibit netrin can be used in any of the methods in vitro or in vivo methods of the present invention. Without being bound by theory, an inhibitor for use in the methods of the present invention may function in any of a number of ways. Exemplary agents that inhibit the expression or activity of a netrin or of netrin signaling (e.g., inhibit the pro-angiogenic, pro-attractant activity of netrin) may include the following: (i) an Unc5h polypeptide; (ii) an Unc5h nucleic acid; (iii) a modified or bioactive fragment of Unc5h; (iv) an Unc5h ectodomain; (v) an anti-neogenin antibody (e.g., a blocking antibody) that binds to and inhibits the activity of neogenin;

(vi) a neogenin antisense oligonucleotide binds to and inhibits the activity of neogenin; (vii) a neogenin RNAi construct binds to and inhibits the activity of neogenin; (viii) a neogenin ribozyme binds to and inhibits the activity of neogenin; (ix) a small molecule that inhibits the activity or expression of netrin or of netrin signaling; (x) a small molecule that binds to neogenin to inhibit the activity of netrin or of netrin signaling; (xi) a small molecule that binds to netrin to inhibit the activity of netrin or of netrin signaling. Exemplary agents that promote the expression or activity of a netrin or of netrin signaling (e.g., promote the pro-angiogenic, pro-attractant activity of netrin) by antagonizing the function of an inhibitor of netrin signaling, may include the following: (i) an anti-Unc5h antibody (e.g., a blocking antibody) that binds to and inhibits the activity of Unc5h; (ii) an Unc5h antisense oligonucleotide that binds to and inhibits the activity of Unc5h; (iii) a Unc5h RNAi construct that binds to and inhibits the activity of Unc5h; (iv) a Unc5h ribozyme that binds to and inhibits the activity of Unc5h; (v) a small molecule that promotes the activity or expression of netrin or of netrin signaling; (vi) a small molecule that binds to netrin to promote the activity of netrin or of netrin signaling; (vii) a small molecule that binds to neogenin to promote the activity of netrin or of netrin signaling; (viii) a small molecule that binds to and inhibits Unc5h, thereby promoting netrin activity.

To provide further illustrative examples of agents for use in the subject methods, the invention contemplates the following. Exemplary agents that inhibit the expression or activity of a netrin or of netrin signaling may include: (i) an Unc5h polypeptide comprising an amino acid sequence at least 80%, 85%, 90%, 95%, 97%, 98%, 99%, or 100% identical to all or a portion of an amino acid sequence represented in SEQ ID NO: 14, SEQ ID NO: 16, SEQ ID NO: 18, SEQ ID NO: 20, SEQ ID NO: 22, SEQ ID NO: 24, or a bioactive fragment thereof; (ii) an Unc5h nucleic acid comprising an nucleic acid sequence that can hybridize under stringent conditions to any of SEQ ID NO: 13, SEQ ID NO: 15, SEQ ID NO: 17, SEQ ID NO: 19, SEQ ID NO: 21, or SEQ ID NO: 23; (iii) a modified or bioactive fragment of Unc5h; (iv) an Unc5h ectodomain; (v) an anti-neogenin antibody (e.g., a blocking antibody) that binds to and inhibits the activity of neogenin (e.g., an antibody immunoreactive with all or a portion of any of SEQ ID NO: 26 or SEQ ID NO: 28); (vi) a neogenin antisense oligonucleotide that binds to and inhibits the activity of neogenin (e.g., that hybridizes under strigent conditions to a portion of a neogenin nucleic acid sequence represented in SEQ ID NO: 25 or SEQ ID NO: 27); (vii) a neogenin RNAi construct that binds to and inhibits the activity of neogenin (e.g., that hybridizes under strigent conditions to a portion of a neogenin nucleic acid sequence represented in SEQ ID NO: 25 or SEQ ID NO: 27); (viii) a neogenin ribozyme that binds to and inhibits the activity of neogenin (e.g., that hybridizes under strigent conditions to a portion of a neogenin nucleic acid sequence represented in SEQ ID NO: 25 or SEQ ID NO: 27); (ix) a small molecule that inhibits the activity or expression of netrin or of netrin signaling; (x) a small molecule that binds to neogenin to inhibit the activity of netrin or of netrin signaling; (xi) a small molecule that binds to netrin to inhibit the activity of netrin or of netrin signaling. Exemplary agents that promote the expression or activity of a netrin or of netrin signaling by antagonizing the function of an inhibitor of netrin signaling, may include the following: (i) an anti-Unc5h antibody (e.g., a blocking antibody) that binds to and inhibits the activity of Unc5h (e.g., an antibody immunoreactive with all or a portion of any of SEQ ID NO: 14, SEQ ID NO: 16, SEQ ID NO: 18, SEQ ID NO: 20, SEQ ID NO: 22, SEQ ID NO: 24); (ii) an Unc5h antisense oligonucleotide that binds to and inhibits the activity of Unc5h (e.g., that hybridizes under strigent conditions to a portion of a Unc5h nucleic acid sequence represented in SEQ ID NO: 13, SEQ ID NO: 15, SEQ ID NO: 17, SEQ ID NO: 19, SEQ ID NO: 21, SEQ ID NO: 23); (iii) a Unc5h RNAi construct that binds to and inhibits the activity of Unc5h (e.g., that hybridizes under strigent conditions to a portion of a Unc5h nucleic acid sequence represented in SEQ ID NO: 13, SEQ ID NO: 15, SEQ ID NO: 17, SEQ ID NO: 19, SEQ ID NO: 21, SEQ ID NO: 23); (iv) a Unc5h ribozyme that binds to and inhibits the activity of Unc5h (e.g., that hybridizes under strigent conditions to a portion of a Unc5h nucleic acid sequence represented in SEQ ID NO: 13, SEQ ID NO: 15, SEQ ID NO: 17, SEQ ID NO: 19, SEQ ID NO: 21, SEQ ID NO: 23); (v) a small molecule that promotes the activity or expression of netrin or of netrin signaling; (vi) a small molecule that binds to netrin to promote the activity of netrin or of netrin signaling; (vii) a small molecule that binds to neogenin to promote the activity of netrin or of netrin signaling; (viii) a small molecule that binds to and inhibits Unc5h, thereby promoting netrin activity.

(iv) Exemplary Expression Methods

The systems and methods described herein also provide expression vectors containing a nucleic acid encoding a polypeptide operably linked to at least one transcriptional regulatory sequence. Exemplary nucleic acids encoding a polypeptide for use in the methods of the present invention include, but are not limited to, a nucleic acid encoding a netrin-related polypeptide, a nucleic acid encoding a bioactive fragment of a netrin-related polypeptide, a nucleic acid encoding an Unc5h receptor, and a nucleic acid encoding an Unc5h receptor ectodomain. Accordingly, the invention contemplates delivery of a polypeptide, modified polypeptide, or bioactive fragment thereof, as well as delivery of a nucleic acid sequence encoding a polypeptide, or bioactive fragment thereof. The invention contemplates that delivery of either a composition comprising a nucleic acid sequence or delivery of a composition comprising a polypeptide can be used to influence the proliferation, migration, adhesion, or differentiation of a cardiovascular cell type in vivo or in vitro. Furthermore, the invention contemplates that delivery of either a composition comprising a nucleic acid sequence or delivery of a composition comprising a polypeptide can be used to influence (e.g., promote or inhibit) angiogenesis, stem cell proliferation and/or migration, etc. In short, the methods and treatment methods described in the present application include delivery of polypeptide compositions and pharmaceutical compositions, as well as the delivery of nucleic acid compositions.

Regulatory sequences are art-recognized and are selected to direct expression of the subject proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences may be used in these vectors to express nucleic acid sequences encoding the agents of this invention. Such useful expression control sequences, include, for example, a viral LTR, such as the LTR of the Moloney murine leukemia virus, the LTR of the Herpes Simplex virus-1, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Moreover, the gene constructs can be used to deliver nucleic acids encoding the subject polypeptides. Thus, another aspect of the invention features expression vectors for in vivo or in vitro transfection, viral infection and expression of a subject polypeptide in particular cell types. In one embodiment, such recombinantly produced polypeptides can be modified using standard techniques described herein, as well as other methodologies well known to one of skill in the art.

Expression constructs of the subject agents may be administered in biologically effective carriers, e.g. any formulation or composition capable of effectively delivering the recombinant gene to cells in vivo or in vitro. Approaches include insertion of the subject gene in viral vectors including recombinant retroviruses, adenovirus, adeno-associated virus, herpes simplex virus-1, lentivirus, mammalian baculovirus or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct, electroporation or $CaPO_4$ precipitation. One of skill in the art can readily select from available vectors and methods of delivery in order to optimize expression in a particular cell type or under particular conditions.

Retrovirus vectors and adeno-associated virus vectors have been frequently used for the transfer of exogenous genes. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes. Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions through the use of a helper virus by standard techniques which can be used to infect a target cell. Protocols for producing recombinant retroviruses and for infecting cells in vitro or in vivo with such viruses can be found in *Current Protocols in Molecular Biology*, Ausubel, F. M. et al. (eds.) Greene Publishing Associates, (2000), and other standard laboratory manuals. Examples of suitable retroviruses include pBPSTR1, pLJ, pZIP, pWE and pEM which are known to those skilled in the art. Examples of suitable packaging virus lines for preparing both ecotropic and amphotropic retroviral systems include ψCrip, ψCre, ψ2, ψAm, and PA317.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein; or coupling cell surface receptor ligands to the viral env proteins. Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Moreover, use of retroviral gene delivery can be further enhanced by the use of tissue- or cell-specific transcriptional regulatory sequences which control expression of the gene of the retroviral vector such as tetracycline repression or activation.

Another viral gene delivery system which has been employed utilizes adenovirus-derived vectors. The genome of an adenovirus can be manipulated so that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they can be used to infect a wide variety of cell types, including airway epithelium, endothelial cells, hepatocytes, and muscle cells. Furthermore, the virus particle is relatively stable and amenable to purification and concentration, and as above, can be modified so as to affect the spectrum of infectivity.

Yet another viral vector system is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158: 97-129). It is also one of the few viruses that may integrate its DNA into non-dividing cells, and exhibits a high frequency of stable integration.

Another viral delivery system is based on herpes simplex-1 (HSV-1). HSV-1 based vectors have been shown to infect a variety of cells including post mitotic cells such as neuronal cells (Agudo et al. (2002) *Human Gene Therapy* 13: 665-674; Latchman (2001) *Neuroscientist* 7: 528-537; Goss et al. (2002) *Diabetes* 51: 2227-2232; Glorioso (2002) *Current Opin Drug Discov Devel* 5: 289-295; Evans (2002) *Clin Infect Dis* 35: 597-605; Whitley (2002) *Journal of Clinical Invest* 110: 145-151; Lilley (2001) *Curr Gene Ther* 1: 339-359).

The above cited examples of viral vectors are by no means exhaustive. However, they are provided to indicate that one of skill in the art may select from well known viral vectors, and select a suitable vector for expressing a particular protein in a particular cell type.

In addition to viral transfer methods, such as those illustrated above, non-viral methods can be used to express a subject polypeptide. Many nonviral methods of gene transfer rely on normal mechanisms used by cells for the uptake and intracellular transport of macromolecules. Exemplary gene delivery systems of this type include liposomal derived systems, poly-lysine conjugates, and artificial viral envelopes.

It may sometimes be desirable to introduce a nucleic acid directly to a cell, for example a cell in culture or a cell in an animal. Such administration can be done by injection of the nucleic acid (e.g., DNA, RNA) directly at the desired site. Such methods are commonly used in the vaccine field, specifically for administration of "DNA vaccines", and include condensed DNA (U.S. Pat. No. 6,281,005).

In addition to administration of nucleic acids, the systems and methods described herein contemplate that polypeptides may be administered directly. Some proteins, for example factors that act extracellularly by contacting a cell surface receptor, such as growth factors, may be administered by simply contacting cells with said protein. For example, cells are typically cultured in media which is supplemented by a number of proteins such as FGF, TGFβ, insulin, etc. These proteins influence cells by simply contacting the cells.

In another embodiment, a polypeptide is directly introduced into a cell. Methods of directly introducing a polypeptide into a cell include, but are not limited to, protein transduction and protein therapy. For example, a protein transduction domain (PTD) can be fused to a nucleic acid encoding a particular agent, and the fusion protein is expressed and purified. Fusion proteins containing the PTD are permeable to the cell membrane, and thus cells can be directly contacted with a fusion protein (Derossi et al. (1994) *Journal of Biological Chemistry* 269: 10444-10450; Han et al. (2000) *Molecules and Cells* 6: 728-732; Hall et al. (1996) *Current Biology* 6: 580-587; Theodore et al. (1995) *Journal of Neuroscience* 15: 7158-7167).

Although some protein transduction based methods rely on fusion of a polypeptide of interest to a sequence which mediates introduction of the protein into a cell, other protein transduction methods do not require covalent linkage of a protein of interest to a transduction domain. At least two commercially available reagents exist that mediate protein transduction without covalent modification of the protein (CHARIOT™, produced by Active Motif, and BIOPORTER® Protein Delivery Reagent, produced by Gene Therapy Systems).

Briefly, these protein transduction reagents can be used to deliver proteins, peptides and antibodies directly to cells including mammalian cells. Delivery of proteins directly to cells has a number of advantages. Firstly, many current techniques of gene delivery are based on delivery of a nucleic acid sequence which must be transcribed and/or translated by a cell before expression of the protein is achieved. This results in a time lag between delivery of the nucleic acid and expression of the protein. Direct delivery of a protein decreases this delay. Secondly, delivery of a protein often results in transient expression of the protein in a cell.

As outlined herein, protein transduction mediated by covalent attachment of a PTD to a protein can be used to deliver a protein to a cell. These methods require that individual proteins be covalently appended with PTD moieties. In contrast, methods such as CHARIOT™ and BIOPORTER® facilitate transduction by forming a noncovalent interaction between the reagent and the protein. Without being bound by theory, these reagents are thought to facilitate transit of the cell membrane, and following internalization into a cell the reagent and protein complex disassociates so that the protein is free to function in the cell.

In another aspect, this application includes compositions which are polypeptides, modified polypeptides, or bioactive fragments. Recombinant polypeptides of the present invention include, but are not limited to, netrin polypeptide (SEQ ID NO: 2, 4, 6, 8, 10, 12, 38, 40, 42, or 44), and bioactive fragments thereof that retain one or more of the biological activities of a netrin polypeptide. Further recombinant polypeptides of the present invention include, but are not limited to, Unc5h polypeptides and ectodomains (SEQ ID NO: 14, SEQ ID NO: 16, SEQ ID NO: 18, SEQ ID NO: 20, SEQ ID NO: 22, SEQ ID NO: 24), or bioactive fragments thereof. The invention further contemplates the use of variants of such proteins that retain the biological function of the native protein. Exemplary variants are at least 60% identical, more preferably 70% identical and most preferably 80% identical with any of the aforementioned sequences, or a bioactive fragment thereof. Additional preferred embodiments include recombinant polypeptides comprising an amino acid sequence at least 80%, 85%, 90%, 95%, 96%, 97%, 98%, or 99% identical to an amino acid sequence of any of the aforementioned sequences, or a bioactive fragment thereof.

This application also describes methods for producing the subject polypeptides. For example, a host cell transfected with a nucleic acid vector directing expression of a nucleotide sequence encoding the subject polypeptides can be cultured under appropriate conditions to allow expression of the peptide to occur. The polypeptide may be secreted and isolated from a mixture of cells and medium containing the recombinant polypeptide. Alternatively, the peptide may be expressed cytoplasmically and the cells harvested, lysed and the protein isolated. A cell culture includes host cells, media and other by-products. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In one example, the recombinant polypeptide is a fusion protein containing a domain which facilitates its purification, such as a GST fusion protein. In another example, the subject recombinant polypeptide may include one or more additional domains which facilitate immunodetection, purification, and the like. Exemplary domains include HA, FLAG, GST, His, and the like. Further exemplary domains include a protein transduction domain (PTD) which facilitates the uptake of proteins by cells. Recombinantly expressed proteins can be modified using methods disclosed herein, as well as those well known to one of skill in the art.

This application also describes a host cell which expresses a recombinant form of the subject polypeptides. The host cell may be a prokaryotic or eukaryotic cell. Thus, a nucleotide sequence derived from the cloning of a protein encoding all or a selected portion (either an antagonistic portion or a bioactive fragment) of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant polypeptides by microbial means or tissue-culture technology in accord with the subject invention. Such methods are used to produce experimentally useful proteins that include all or a portion of the subject nucleic acids. For example, such methods are used to produce fusion proteins including domains which facilitate purification or immunodetection, and to produce recombinant mutant forms of a protein).

The recombinant genes can be produced by ligating a nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pGEX-derived plasmids, pTrc-His-derived plasmids, pBTac-derived plasmids and pUC-derived plasmids for expression in prokaryotic cells, such as *E. coli.*

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae.*

Many mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo, pBacMam-2, and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. For other suitable expression systems for both prokaryotic and eukaryotic cells, as well as general recombinant procedures, see *Molecular Cloning A Laboratory Manual,* 3rd Ed., ed. by Sambrook and Russell (Cold Spring Harbor Laboratory Press: 2001).

In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The present invention also makes available isolated polypeptides which are isolated from, or otherwise substantially free of other cellular and extracellular proteins. The term "substantially free of other cellular or extracellular proteins" (also referred to herein as "contaminating proteins") or "substantially pure or purified preparations" are defined as encompassing preparations having less than 20% (by dry weight) contaminating protein, and preferably having less than 5% contaminating protein. Functional forms of the subject proteins can be prepared as purified preparations by using a cloned gene as described herein. By "purified", it is meant, when referring to peptide or nucleic acid sequences, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water and buffers can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. Chemically synthesized proteins can be modified using methods described herein, as well as methods well known in the art.

The recombinant polypeptides of the present invention also include versions of those proteins that are resistant to proteolytic cleavage. Variants of the present invention also include proteins which have been post-translationally modified in a manner different than the authentic protein. Modification of the structure of the subject polypeptides can be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the polypeptides described in more detail herein. Such modified peptides can be produced, for instance, by amino acid substitution, deletion, or addition.

For example, it is reasonable to expect that, in some instances, an isolated replacement of a leucine with an isoleucine or valine, an aspartate with a glutamate, a threonine with a serine, or a similar replacement of an amino acid with a structurally related amino acid (e.g., isosteric and/or isoelectric mutations) may not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry,* 5th ed. by Berg, Tymoczko and Stryer, W H Freeman and Co.: 2002). Whether a change in the amino acid sequence of a peptide results in a functional variant (e.g. functional in the sense that it acts to mimic or antagonize the wild-type form) can be determined by assessing the ability of the variant peptide to produce a response in cells in a fashion similar to the wild-type protein, or competitively inhibit such a response. Polypeptides in which more than one replacement has taken place can readily be tested in the same manner.

Advances in the fields of combinatorial chemistry and combinatorial mutagenesis have facilitated the making of polypeptide variants (Wissmanm et al. (1991) *Genetics* 128: 225-232; Graham et al. (1993) *Biochemistry* 32: 6250-6258; York et al. (1991) *Journal of Biological Chemistry* 266: 8495-8500; Reidhaar-Olson et al. (1988) *Science* 241: 53-57). Given one or more assays for testing polypeptide variants, one can assess whether a given variant retains one or more of the biological activities of the corresponding native polypeptide.

To further illustrate, the invention contemplates a method for generating sets of combinatorial mutants, as well as truncation mutants, and is especially useful for identifying potential variant sequences that retain one or more of the biological activities of a native polypeptide. In one embodiment, the native polypeptide is a netrin polypeptide. The purpose of screening such combinatorial libraries is to generate, for example, novel variants.

In one aspect of this method, the amino acid sequences for a population of polypeptides (e.g., netrin polypeptides) are aligned, preferably to promote the highest homology possible. Amino acids which appear at each position of the aligned sequences are selected to create a degenerate set of combinatorial sequences. In one example, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

The library of potential variants can be generated from a degenerate oligonucleotide sequence using a variety of methods. Chemical synthesis of a degenerate gene sequence can be carried out in an automatic DNA synthesizer, and the synthetic genes then ligated into an appropriate expression vector. One purpose of a degenerate set of genes is to provide, in one mixture, all the sequences encoding the desired set of potential variant sequences. The synthesis of degenerate oligonucleotides is known in the art.

A range of techniques are known for screening gene products of combinatorial libraries made by point mutations, and for screening cDNA libraries for gene products having a certain property. Such techniques will be generally adaptable for rapid screening of the gene libraries generated by the combinatorial mutagenesis of related polypeptides. These techniques are also applicable for rapid screening of other gene libraries. One example of the techniques used for screening large gene libraries includes cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

(v) Methods of Screening

The present application describes methods and compositions for promoting angiogenesis; for promoting proliferation, migration, and/or adhesion of smooth muscle cells and endothelial cells, and for treating a variety of conditions. Furthermore, the present invention provides methods for inhibiting angiogenesis; for inhibiting proliferation, migration, and/or adhesion of smooth muscle cells and endothelial cells, and for treating a variety of conditions. One aspect of the present invention relates to compositions comprising netrin-related polypeptides or agents that promote the expression or activity of netrin or of netrin signaling. Another aspect of the present invention relates to compositions comprising agents that inhibit the expression or activity of netrin or of netrin signaling.

Such polypeptides and agents included modified polypeptides and agents. Modified polypeptides and agents for use in the present invention retain one or more of the biological activities of the native polypeptide or agents, and may also possess one or more advantageous physiochemical activities in comparison to native and/or un-modified polypeptide or agent. Exemplary biological activities of a netrin polypeptide or of an agent that promotes the expression or activity of a netrin polypeptide or of netrin signaling include: (i) binds a netrin receptor; (ii) promotes attraction of axons; (iii) promote angiogenesis, (iv) promotes cell migration, (v) promotes cell adhesion, and (vi) promotes cell proliferation. Exemplary biological activities of an agent that inhibits the expression or activity of netrin or of netrin signaling include: (i) inhibits attraction of axons; (ii) inhibits angiogenesis, (iii) inhibits cell migration, (iv) inhibits cell adhesion, (v) inhibits cell proliferation, (vi) promotes repulsion of axons, and (vii) promotes repulsion of migrating cells.

In light of the importance of providing improved methods and compositions for treating the wide range of conditions of the cardiovascular system, as well as the range of other conditions that can be treated by modulating angiogenesis, and in light of the finding that certain modified polypeptides retain the functional activity of native or un-modified polypeptides but possess one or more advantageous physiochemical properties, the present invention further provides screening methods to identify, characterize, and/or optimize modified polypeptides for use in the methods of the present invention. Exemplary modified polypeptides identified, characterized, and/or optimized by the methods of the present invention retain one or more of the following biological activities of the corresponding native polypeptide.

For example, when the polypeptide is a netrin polypeptide or an agent that promotes the expression or activity of a netrin polypeptide or of netrin signaling, exemplary biological activities retained by a modified polypeptide for use in the methods of the present invention include one or more of the following: (i) binds a netrin receptor; (ii) promotes attraction of axons; (iii) promote angiogenesis, (iv) promotes cell migration, (v) promotes cell adhesion, and (vi) promotes cell proliferation. When the polypeptide is an agent that inhibits the expression or activity of netrin or of netrin signaling, exemplary biological activities retained by a modified polypeptide for use in the methods of the present invention include one or more of the following: (i) inhibits attraction of axons; (ii) inhibits angiogenesis, (iii) inhibits cell migration, (iv) inhibits cell adhesion, (v) inhibits cell proliferation, (vi) promotes repulsion of axons, and (vii) promotes repulsion of migrating cells. Additionally, modified polypeptides that retain one or more of the biological activities of the corresponding native and/or un-modified polypeptide can be further screened to identify modified polypeptides that possess one or more advantageous physiochemical activities in comparison to the corresponding native and/or un-modified polypeptide.

The screening methods described herein can be used to identify polypeptides comprising one or more modifications appended to a native or variant amino acid sequence. The invention contemplates any of a number of modified polypeptides, wherein the modification increases the hydrophilicity of the polypeptide. Exemplary modifications include PEG containing moieties. Further exemplary modifications include albumin moieties, cyclodextran moieties, antibody moieties, or combinations thereof. In any of the foregoing, preferable modified polypeptides identified, characterized, and/or optimized by the methods of the invention retain one or more of the biological activities of the corresponding native and/or un-modified polypeptide. Additionally, modified polypeptides so identified can be further examined to determine if the modified polypeptide possesses one or more advantageous, physiochemical property in comparison to the corresponding native and/or un-modified polypeptide.

The invention further contemplates any of a number of modified polypeptides, wherein the modification increases the hydrophobicity of the polypeptide. Exemplary modifications include sterols, fatty acids, hydrophobic amino acid residues, and hydrophobic peptides. In any of the foregoing, preferable modified polypeptides identified, characterized, and/or optimized by the methods of the invention retain one or more of the biological activities of the corresponding native and/or un-modified polypeptide. Additionally, modified polypeptides so identified can be further examined to determine if the modified polypeptide possesses one or more advantageous, physiochemical property in comparison to the corresponding native and/or un-modified polypeptide.

Furthermore, the invention contemplates any of a number of modified polypeptides containing a combination of hydrophilic and hydrophobic moieties. The screening methods of the invention are not biased based on modifications likely to retain biological activity or moieties likely to impart advantageous physiochemical properties. Accordingly, the screening methods of the invention provide the opportunity to identify, characterize, and/or optimize virtually any possible modification.

The screening methods contemplated include screening single candidate modified polypeptides, multiple modified polypeptides, and libraries of modified polypeptides. In many screening programs that test libraries of nucleic acids, polypeptides, chemical compounds and natural extracts, high throughput assays are desirable to increase the number of agents surveyed in a given period of time. Assays that are performed in cell-free systems, such as may be derived with purified or semi-purified proteins, are often preferred as "primary" screens in that they can be generated to permit rapid development and relatively easy detection of an alteration in a molecular target which is mediated by a test agent. Cell free systems include in vitro systems (preparations of proteins and agents combined in a test tube, Petri dish, etc.), as well as cell free systems such as those prepared from egg extracts or reticulocyte lysates. Moreover, the effects of cellular toxicity and/or bioavailability of the test agents can be generally ignored in such a system, the assay instead being focused primarily on the effect of the agent. Thus, in the context of the present invention, large numbers of candidate, modified polypeptides can be tested in a cell free assay to rapidly assess whether the modified polypeptide retains a biological activity of the corresponding native polypeptide. By way of specific example, modified polypeptides, for example netrin polypeptides, can be tested in a cell free assay to measure binding to their receptor or ligand.

The efficacy of the agent can be assessed by generating dose response curves from data obtained using various concentrations of the test agent. Moreover, a control assay can also be performed to provide a baseline for comparison. Such candidates can be further tested for efficacy in promoting or inhibiting a particular response in cells in culture. The examples provided below provide a number of cell-based assays using endothelial cells, smooth muscle cells, cancer cell lines, and primary cancer tissue sample, and any such cell-based system provides an exemplary system in which to evaluate whether a modified polypeptide retains one or more biological activity of the native polypeptide.

The foregoing cell free and cell-based assays provide examples of the methods that can be used to rapidly screen modified polypeptides to identify, characterize, and/or optimize modified polypeptides that retain one or more of the biological activities of the corresponding native and/or un-modified polypeptide. Additionally, the modified polypeptides that retain one or more of the biological activities of the corresponding native and/or un-modified polypeptide can be further tested to determine whether it possesses one or more advantageous physiochemical property in comparison to the corresponding native and/or un-modified polypeptide.

Additionally, we note that methods of screening can be conducted in vivo in either wildtype or mutant animals. Exemplary mutant animals include animal models of particular cancers (e.g., cancers that expression netrin), animal models of cardiac disease, animal models of ischemia, animal models of stroke, animal models of immunodeficiencies, animal models of inflammation, animal models of anemia, etc. Such animals may be homozygous or hemizygous for a particular mutation. Exemplary wildtype animals include, but are not limited to, any non-human animal such as mice, rats, rabbits, cats, dogs, sheep, pigs, goats, cows, and non-human primates.

Regardless of the methodology used to identify, characterize, and/or optimize a modified polypeptide, such modified polypeptide will have a range of in vitro and in vivo applications. For example, modified polypeptides that retain the biological activity of the native polypeptide provide additional reagents for use in vitro and in vivo. Furthermore, certain modified polypeptides that retain the biological activity of the native and/or un-modified polypeptide also possess one or more advantageous physiochemical property in comparison to the native and/or un-modified polypeptide. These modified polypeptides represent a novel class of polypeptides that may be particularly well suited for particular therapeutic or laboratory use. Accordingly, the invention further contemplates the use of a modified polypeptides identified by the screening methods of the invention. Identified polypeptides may be used alone or in combination with other agents, or may be formulated in a pharmaceutically acceptable carrier. In one embodiment of any of the foregoing, the modified polypeptides are modified netrin polypeptides, or bioactive fragments thereof, for use in promoting one or more of the biological activities of a native netrin polypeptide. In another embodiment, the modified polypeptides are modified Unc5h polypeptides for use in inhibiting one or more of the biological activities of a native netrin polypeptide or of netrin signaling. In yet another embodiment, the modified polypeptides are modified Unc5h ectodomains for use in inhibiting one or more of the biological activities of a native netrin polypeptide or of netrin signaling.

(vi) Exemplary Injuries and Conditions

The methods and compositions of the present invention provide a treatment for any of a wide range of injuries and diseases that can be treated in whole or in part by modulating the proliferation, differentiation, adhesion, or migration of endothelial cells or smooth muscle cells. Accordingly, the present invention has broad applicability to a wide range of conditions, including use in the treatment of ischemia, myocardial infarction, stroke, obstructive vascular disease (e.g., restenosis following angioplasty), cancer, wound healing, inflammation, neuropathies, anemia, and surgical adhesions. Furthermore, the present invention has broad applicability in modulating the behavior of stem cells, particularly stem cells that generate primary blood cells and cells of the endothelial lineage. Exemplary stem cells include hematopoietic stem cells (HSCs).

As outlined in detail throughout the application, the invention contemplates administration of any of the compositions of the invention alone, in combination with other compositions of the invention, or in combination with any of a number of other factors or therapies appropriate for the particular condition being treated. Multiple compositions can be administered consecutively or concurrently.

Unless otherwise defined in conjunction with specific diseases or disorders, the term "treating" or "treatment" refers to: (i) preventing a disease, disorder or condition from occurring in an animal that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

By way of non-limiting example, we provide a brief description of exemplary conditions that can be treated using the methods and compositions of the present invention.
Conditions that Can be Treated by Increasing the Expression or Activity of Netrin or of Netrin Signaling.

The compositions of the present invention (e.g., netrin-related compositions) can be used to promote the activity of netrin or of netrin signaling. Such compositions can be used to promote the proliferation, migration, and adhesion of smooth muscle cells and endothelial cells. Such compositions can also be used to promote angiogenesis. Compositions with one or more of these activities can be useful in the prevention and/or treatment of a number of conditions. Exemplary conditions are described below.

Ischemia: Ischmia results from a period of restricted blood and/or oxygen flow to tissues. In a relatively brief period of time, this restriction of blood and oxygen results in cell and tissue damages or death. Such cell damage or death can lead to reduction in function of the particular effected organ or organ system.

In one aspect, the present invention provides methods and compositions to promote angiogenesis. Such compositions can be used to reduce the blood and oxygen deprivation caused by any of a number of ischemic conditions. Accordingly, methods and compositions that promote angiogenesis can be used in the treatment of ischemia or of an ischemic condition. Exemplary ischemic conditions are described below.

Myocardial infarction: Myocardial infarction is defined as myocardial cell death due to prolonged ischemia. Cell death is categorized pathologically as either coagulation or contraction band necrosis, or both, which usually evolves through necrosis, but can result to a lesser degree from apoptosis.

After the onset of myocardial ischemia, cell death is not immediate but takes a finite period to develop (as little as 15 minutes in some animal models, but even this may be an overestimate). It takes 6 hours before myocardial necrosis can be identified by standard macroscopic or microscopic post-mortem examination. Complete necrosis of all myocardial cells at risk requires at least 4-6 hours or longer, depending on the presence of collateral blood flow into the ischemic zone, persistent or intermittent coronary artery occlusion and the sensitivity of the myocytes.

Infarcts are usually classified by size—microscopic (focal necrosis), small (<10% of the left ventricle), medium (10% to 30% of the left ventricle) or large (>30% of the left ventricle)—as well as by location (anterior, lateral, inferior, posterior or septal or a combination of locations). The pathologic identification of myocardial necrosis is made without reference to morphologic changes in the epicardial coronary artery tree or to the clinical history.

The term MI in a pathologic context may be preceded by the words "acute, healing or healed." An acute or evolving infarction is characterized by the presence of polymorpho-nuclear leukocytes. If the interval between the onset of infarction and death is brief (e.g., 6 hours), minimal or no polymorphonuclear leukocytes may be seen. The presence of mononuclear cells and fibroblasts and the absence of polymorphonuclear leukocytes characterize a healing infarction. A healed infarction is manifested as scar tissue without cellular infiltration. The entire process leading to a healed infarction usually requires five to six weeks or more. Furthermore, reperfusion alters the gross and microscopic appearance of the necrotic zone by producing myocytes with contraction bands and large quantities of extravasated erythrocytes.

Infarcts are classified temporally according to the pathologic appearance as follows: acute (6 hours to 7 days); healing (7 to 28 days), healed (29 days or more). It should be emphasized that the clinical and ECG timing of an acute ischemic event may not be the same as the pathologic timing of an acute infarction. For example, the ECG may still demonstrate evolving ST-T segment changes, and cardiac troponin may still be elevated (implying a recent infarct) at a time when, pathologically, the infarct is in the healing phase.

Myocardial necrosis results in and can be recognized by the appearance in the blood of different proteins released into the circulation due to the damaged myocytes: myoglobin, cardiac troponins T and I, creatine kinase, lactate dehydrogenase, as well as many others. Myocardial infarction is diagnosed when blood levels of sensitive and specific biomarkers, such as cardiac troponin and the MB fraction of creatine kinase (CK-MB), are increased in the clinical setting of acute ischemia. These biomarkers reflect myocardial damage but do not indicate its mechanism. Thus, an elevated value in the absence of clinical evidence of ischemia should prompt a search for other causes of cardiac damage, such as myocarditis.

The presence, absence, and amount of myocardial damage resulting from prolonged ischemia can be assessed by a number of different means, including pathologic examination, measurement of myocardial proteins in the blood, ECG recordings (ST-T segment wave changes, Q waves), imaging modalities such as myocardial perfusion imaging, echocardiography and contrast ventriculography. For each of these techniques, a gradient can be distinguished from minimal to small to large amounts of myocardial necrosis. Some clinicians classify myocardial necrosis as microscopic, small, moderate and large on the basis of the peak level of a particular biomarker. The sensitivity and specificity of each of these techniques used to detect myocardial cell loss, quantitate this loss and recognize the sequence of events over time, differ markedly. We note that the term myocardial necrosis refers to any myocardial cell death regardless of its cause. Although myocardial infarction is one cause of myocardial necrosis, many other conditions result in necrosis. The methods and compositions of the invention can be used to promote angiogenesis, and thus reduce the blood and oxygen deprivation caused by ischemia. Such methods are useful in reducing myocardial damage following myocardial infarction.

Stroke: Every 45 seconds, someone in America has a stroke. Approximately, 700,000 Americans will suffer a stroke this year, and stroke is a leading cause of death and severe, long-term disability both in this country and around the world.

Stroke is a type of cardiovascular disease. It affects the arteries leading to and within the brain. A stroke occurs when a blood vessel that carries oxygen and nutrients to the brain is either blocked by a clot or bursts. When that occurs, regions of the brain are deprived of blood and oxygen, and those regions begin to die. Given the generally low rate of neuronal regeneration, damaged or dead neuronal tissue results in a loss of cognitive, motor, or other neurological skills. One method of reducing the damage caused by a stroke or coronary event is to restore blood and oxygen flow to the effected area. The methods and compositions of the present invention accomplish this goal and offer an effective treatment for stroke.

There are two basic types of strokes. Ischemic strokes are caused by clots that block an artery. This is the most common type of stroke, accounting for approximately 88 percent of all strokes. Hemorrhagic strokes or bleeding strokes are caused by ruptured blood vessels. Although the two types of strokes arise via differing mechanisms, each can result in deprivation of blood and oxygen to all or a portion of the brain. Accordingly, the methods and compositions of the present invention offer an effective treatment for either ischemic or hemorrhagic strokes, as well as for strokes of unknown or unidentified cause.

Extensive clinical and statistical studies have identified several factors that increase the risk of stroke. Some of these risk factors can be modified to reduce the risk of stroke. Accordingly, the methods of the present invention contemplate combinatorial treatment regimens which also address one or more of the risk factors of stroke. We note that many of these risk factors also increase one's risk of other coronary and cardiovascular conditions, and thus methods of decreasing any of these factors may be used as part of a method of the present invention.

The following factors increase one's risk of stroke:

a. High blood pressure (140/90 mm Hg or higher) is the most important risk factor for stroke. High blood pressure often has no specific symptoms, and often goes undiagnosed until the occurrence of a serious cardiovascular or coronary incident.

b. Cigarette smoking and other tobacco use is a major, preventable risk factor for stroke. The nicotine and carbon monoxide in tobacco smoke reduce the amount of oxygen in the blood. Furthermore, these agents damage the walls of blood vessels, making clots more likely to form.

c. Diabetes is defined as a fasting plasma glucose (blood sugar) of 126 mg/dL or more measured on two occasions. While diabetes is treatable, it still increases a person's risk of stroke. Many people with diabetes also have high blood pressure, high blood cholesterol, and are overweight. Each of these factors further increases the risk of stroke.

d. The carotid arteries in the neck supply blood to your brain. A carotid artery narrowed by fatty deposits from atherosclerosis (plaque buildups in artery walls) may become blocked by a blood clot. Carotid artery disease is also called carotid artery stenosis.

e. Peripheral artery disease increases the risk of carotid artery disease, which raises the risk of stroke. Peripheral artery disease is the narrowing of blood vessels carrying blood to leg and arm muscles. It is caused by fatty buildups of plaque in artery walls.

f. Atrial fibrillation is a heart rhythm disorder that raises the risk for stroke. The heart's upper chambers quiver instead of beating effectively, which can let the blood pool and clot. If a clot breaks off, enters the bloodstream, and lodges in an artery leading to the brain, a stroke results.

g. Other heart diseases increase the risk of stroke. For example, individuals with coronary heart disease or heart failure have a higher risk of stroke than those with hearts that work normally. Dilated cardiomyopathy (an enlarged heart), heart valve disease and some types of congenital heart defects also raise the risk of stroke.

h. Transient ischemic attacks (TIAS) are "warning strokes" that produce stroke-like symptoms without lasting damage. Recognizing and treating TIAs can reduce the risk of a major stroke.

i. Certain blood disorders, particularly disorders that cause a high red blood cell count, can increase the risk of stroke. A high red blood cell count thickens the blood and increases clots, thus increasing the risk of stroke.

j. Sickle cell disease, also known as sickle cell anemia, is a genetic disorder that mainly affects African Americans. "Sickled" red blood cells are less able to carry oxygen to the body's tissues and organs. Such red blood cells also tend to stick to blood vessel walls, which can block arteries to the brain and cause a stroke.

k. A high level of total cholesterol in the blood (240 mg/dL or higher) is a major risk factor for heart disease and stroke. Recent studies show that high levels of LDL ("bad") cholesterol (greater than 100 mg/dL) and triglycerides (blood fats, 150 mg/dL or higher) increase the risk of stroke in people with previous coronary heart disease, ischemic stroke or transient ischemic attack (TIA). Low levels (less than 40 mg/dL) of HDL ("good") cholesterol also may raise stroke risk.

l. Physical inactivity, obesity, or both can increase the risk of high blood pressure, high blood cholesterol, diabetes, heart disease and stroke.

m. Excessive alcohol consumption may increase the risk of stroke. Furthermore, certain illegal drugs may increase the risk of stroke. Such drugs include cocaine, as well as intravenous drugs like heroine.

The above risk factors for stroke and heart disease can be addressed with a variety of medications, life-style modifications, and non-medical therapies. Additionally, however, many of the risk factors for stroke and cardiovascular disease cannot be managed. These include increasing age, gender, and hereditary factors.

Wound healing: The methods and compostions of the present invention can be used to promote would healing. Without being bound by theory, a significant portion of the wound healing process involves proliferation and revascularization of the wounded area. The methods and compositions of the present invention promote angiogenesis and furthermore promote proliferation of smooth muscle and endothelial cell types. The promotion of angiogenesis can be used to promote and augment proliferation and revascularization of the wound area. Thus, the methods and compostions of the present invention can be used to promote wound healing.

Wounding can occur following virtually any injury including, but not limited to, burns, cuts, punctures, abrasions, blunt trauma, and the like. Furthermore, wounding may occur anytime tissue is broken, burned, poisoned, cut, or torn, for example by a surgical procedure, radiological treatment, chemotherapeutic treatment, implantation of a device, and the like. Exemplary devices include, but are not limited to, dental implants, stents, catheters, wires, protheses, and the like. The methods and compositions of the present invention can be used to promote the healing of any wound regardless of the location of the wound or the mechanism by which it was caused.

In addition to wounds caused by particular traumas, chronic wounds are a significant problem associated with many conditions and disease states. For example, chronic wounds (e.g., bedsores) are a frequently encountered problem in elderly and bedridden patients and are produced by trauma or pathologic insult. Characteristics of chronic wounds include a loss of skin or underlying tissue which does not heal with conventional types of treatment. Additional examples of chronic wounds are those associated with a particular chronic medical condition such as diabetic ulcers; or catheter site infection and scarring in colonoscopy patients, patients receiving dialysis, patients receiving long-term intravenous therapy, or patients receiving long-term chemotherapy.

The methods and compositions of the present invention promote wound healing. These methods and compositions are useful regardless of whether the wound is a chronic wound resulting from a particular condition (e.g., diabetes or periodontal disease) or an acute wound caused by a particular traumatic injury or isolated treatment. By way of further brief description, we provide a summary of the current understanding of the wound healing process. This summary is provided merely to illustrate the extensive knowledge in the art regarding wound healing. Nevertheless, the utility of the methods and composition of the present invention in promoting wound healing is not limited by any particular theory, as described herein.

The healing response is initiated at the moment of injury, and the first several days following injury are often characterized by an inflammatory response to the injury. Surgical or traumatic wounds disrupt the tissue architecture and cause haemorrhage. Initially, blood fills the wound defect and exposure of this blood to collagen in the wound leads to platelet degranulation and activation of Hageman factor. This in turn sets into motion a number of biological amplification systems including the complement kinin and clotting cascades and plasmin generation. These serve to amplify the original injury signal and lead not only to clot formation, which unites the wound edges, but also to the accumulation of a number of mitogens and chemoattractants at the site of wounding.

Production of both kinins and prostaglandins leads to vasodilatation and increased small vessel permeability in the region of the wound. This results in edema in the area of the injury and is responsible for the pain and swelling which occurs early after injury. Within 6 hours, circulating immune cells start to appear in the wound. Polymorphonuclear leucocytes (PMN) are the first blood leucocytes to enter the wound site. They initially appear in the wound shortly after injury and subsequently their numbers increase steadily, peaking at 24-48 hours. Their main function appears to be phagocytosis of the bacteria which have been introduced into the wound during injury. The presence of PMN in the wound following injury does not appear to be essential in order for normal wound healing to take place, with healing proceeding normally in their absence provided that bacterial contamination has not occurred. In the absence of infection, PMN have a relatively short life span in the wound and their numbers decrease rapidly after the third day.

The next cellular, immune elements to enter the wound are macrophages. These cells are derived from circulating monocytes by a combination of migration and chemotaxis. They first appear within 48-96 hours post-injury and reach a peak around the third day post-injury. These macrophages have a much longer life span than the PMN and persist in the wound until healing is complete. Their appearance is followed somewhat later by T lymphocytes, which appear in significant numbers around the fifth day post-injury, with peak numbers occurring about the seventh day after injury. In contrast to PMN, the presence and activation of both macrophages and lymphocytes in the wound is critical to the progress of the normal healing process. Macrophages phagocytose and digest pathological organisms and tissue debris. In addition, macrophages release many biologically active substances that facilitate the recruitment of additional inflammatory cells and aid the macrophage in tissue decontamination and debridement.

In the absence of significant infection or contamination, the inflammatory phase is short, and after the wound has been successfully cleared of devitalized and unwanted material it gives way to the proliferative phase of healing. The proliferative phase is characterized by the formation of granulation tissue in the wound. Granulation tissue consists of a combination of cellular elements, including fibroblasts and inflammatory cells, along with new capillaries embedded in a loose extra cellular matrix of collagen, fibronectin and hyaluronic acid.

Fibroblasts first appear in significant numbers in the wound on the third day post-injury and achieve peak numbers around the seventh day. This rapid expansion in the fibroblast population at the wound site occurs via a combination of proliferation and migration. Fibroblasts are derived from local mesenchymal cells, particularly those associated with blood vessel adventitia, which are induced to proliferate and attracted into the wound by a combination of cytokines produced initially by platelets and subsequently by macrophages and lymphocytes. Fibroblasts are the primary synthetic element in the repair process and are responsible for production of the majority of structural proteins used during tissue reconstruction. In particular, fibroblasts produce large quantities of collagen, a family of triple-chain glycoproteins, which form the main constituent of the extracellular wound matrix and which are ultimately responsible for imparting tensile strength to the scar.

Collagen is first detected in the wound around the third day post-injury, and thereafter the levels increase rapidly for approximately 3 weeks. It then continues to accumulate at a more gradual pace for up to 3 months post wounding. The collagen is initially deposited in a seemingly haphazard fashion and these individual collagen fibrils are subsequently reorganized, by cross-linking, into regularly aligned bundles oriented along the lines of stress in the healing wound. Fibroblasts are also responsible for the production of other matrix constituents including fibronectin, hyaluronic acid and the glycosaminoglycans. The process of fibroblast proliferation and synthetic activity is known as fibroplasia.

Revascularization of the wound proceeds in parallel with fibroplasia. Capillary buds sprout from blood vessels adjacent to the wound and extend into the wound space. On the second day post-injury, endothelial cells from the side of the venule closest to the wound begin to migrate in response to angiogenic stimuli. These capillary sprouts eventually branch at their tips and join to form capillary loops, through which blood begins to flow. New sprouts then extend from these loops to form a capillary plexus. The soluble factors responsible for angiogenesis remain incompletely defined. It appears that angiogenesis occurs by a combination of proliferation and migration. Putative mediators for endothelial cell growth and chemotaxis include cytokines produced by platelets, macrophages and lymphocytes in the wound, low oxygen tension, lactic acid, and biogenic amines. Of the potential cytokine mediators of neovascularization, basic fibroblast growth factor (bFGF), acidic FGF (aFGF), transforming growth factors-$\alpha$ and $\beta$ (TGF-$\alpha$ and -$\beta$) and epidermal growth factor (EGF) have all been shown to be potent stimuli for new vessel formation. FGF, in particular, has been shown to be a potent inducer of in vivo neovascularization.

While these events are proceeding deep in the wound, restoration of epithelial integrity is taking place at the wound surface. Re-epithelialization of the wound begins within a couple of hours of the injury. Epithelial cells, arising from either the wound margins or residual dermal epithelial appendages within the wound bed, begin to migrate under the scab and over the underlying viable connective tissue. The epidermis immediately adjacent to the wound edge begins thickening within 24 hours after injury. Marginal basal cells at the edge of the wound loose their firm attachment to the underlying dermis, enlarge and begin to migrate across the surface of the provisional matrix filling the wound. Fixed basal cells in a zone near the cut edge undergo a series of rapid mitotic divisions, and these cells appear to migrate by moving over one another in a leapfrog fashion until the defect is covered. Once the defect is bridged, the migrating epithelial cells loose their flattened appearance, become more columnar in shape and increase in mitotic activity. Layering of the epithelium is re-established and the surface layer eventually keratinized. Reepithelialization is complete in less than 48 hours in the case of approximated incised wounds, but may take substantially longer in the case of larger wounds where there is a significant tissue defect. If only the epithelium is damaged, such as occurs in split thickness skin graft donor sites, then repair consists primarily of re-epithelization with minimal or absent fibroplasia and granulation tissue formation. The stimuli for re-epithelization remain incompletely determined, but it appears that the process is mediated by a combination of loss of contact inhibition, exposure of constituents of the extracellular matrix, particularly fibronectin, and by cytokines produced by immune mononuclear cells. EGF, TGF-β, bFGF, platelet-derived growth factor (PDGF) and insulinlike growth factor-λ (IGF-λ) in particular, have been shown to promote epithelialization.

Stem Cell Mobilization: The methods and compositions of the present invention can be used to promote priloferation and mobilization of stem cells, particularly stem cells that give rise to primary vascular cell types including primary blood cells, smooth muscle cells and endothelial cells. Exemplary stem cells include hematopoietic stem cells, mesenchymal stem cells, and endothelial stem cells.

In recent years, there have been significant advances in the stem cell field. At this point, it is widely believed that resident stem cells exist within the body. Such stem cells may be mobilized in response to injury or disease, and given the proper instruction, may prove useful in the treatment of such injury or disease. Given that the compositions of the present invention promote the proliferation and mobility of primary vascular cells, the invention contemplates their use in stimulating the proliferation and mobilization of their precursor cells (e.g., the stem and progenitor cells that give rise to primary vascular cells including blood cells, smooth muscle cells, and endothelial cells).

The methods and compositions of the present invention can be used to stimulate stem cells in vitro or in vivo. Furthermore, the methods and compositions of the present invention can be used to stimulate embryonic, fetal, or adult stem cells derived from any mammalian organism.

Stimulation of stem cell proliferation and/or migration may be useful in any of a number of applications. By way of non-limiting example, promotion of stem cell proliferation in vitro may be useful for developing improved laboratory techniques for maintaining stem cells in culture. By way of further non-limiting example, promotion of stem cell proliferation, for example, hematopoietic stem cell proliferation or mesenchymal stem cell proliferation, may be useful in the treatment of anemia; to improve or augment recovery and engraftment following a stem cell or bone marrow transplant; and in the treatment of immunodeficiencies, lymphomas, or leukemias.

Neuropathies: The methods and compostions of the present invention can be used to treat neuropathies. "Neuropathy" refers to any disease or malfunction of the nerves. Neuropathy includes, without limitation, peripheral neuropathy, diabetic neuropathy, autonomic neuropathy and mononeuropathy. As used herein, "peripheral neuropathy" refers to a disorder affecting a segment of the peripheral nervous system. For instance, the methods and compostions of the present invention can be used as part of a treatment program in the management of neuropathies associated with systemic disease, e.g., viral infections, diabetes, inflamation; as well as genetically acquired (hereditary) neuropathies, e.g., Charcot-Marie-Tooth disease; and neuropathies caused by a toxic agent, e.g., a chemotherapeutic agent such as vincristine; and neuropathies caused by trauma, such as crushed nerves.

To further illustrate, the subject methods and compostions can be used in the treatment of such acquired neuropathies as diabetic neuropathies; immune-mediated neuropathies such as Guillain-Barre syndrome (GBS) and variants, chronic inflammatory demyelinating polyneuropathy (CIDP), chronic polyneuropathies with antibodies to peripheral nerves, neuropathies associated with vasculitis or inflammation of the blood vessels in peripheral nerve, brachial or lumbosacral plexitis, and neuropathies associated with monoclonal gammopathies; neuropathies associated with tumors or neoplasms such as sensory neuropathy associated with lung cancer, neuropathy associated with multiple myeloma, neuropathy associated with waldenstrom's macroglobulemia, chronic lymphocytic leukemia, or B-cell lymphoma; neuropathy associated with amyloidosis; neuropathies caused by infections; neuropathies caused by nutritional imbalance; neuropathy in kidney disease; hypothyroid neuropathy; neuropathy caused by alcohol and toxins; neuropathies caused by drugs; neuropathy resulting from local irradiation; neuropathies caused by trauma or compression; idiopathic neuropathies.

Likewise, the subject method can be used in the treatment of such hereditary neuropathies as Charcot-Marie Tooth Disease (CMT); Familial Amyloidotic Neuropathy and other Hereditary Neuropathies; and Hereditary Porphyria.

In another embodiment, the subject methods and compositions can be used to inhibit or otherwise slow neurodegenerative events associated with age-related neuropathology.

In a specific embodiment, the subject methods and compostions can be used to treat diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

Conditions that Can be Treated by Inhibiting the Expression or Activity of Netrin or of Netrin Signaling.

The present invention also provides methods and compositions comprising agents that inhibit the activity of netrin or that inhibit netrin signaling. Such compositions can be used to inhibit the proliferation, migration, and adhesion of smooth muscle cells and endothelial cells. Such compositions can also be used to inhibit angiogenesis. Compositions with one or more of these activities can be useful in the prevention and/or treatment of a number of conditions. Exemplary conditions are described below.

Cancer: Cancer is a catch-all phrase that refers to any of a number of hyper-proliferation conditions affecting nearly every tissue. For example, cancers of the breast, colon, prostate, ovary, testicles, cervix, esophagus, pancreas, bone, lung, brain, skin, liver, stomach, and tongue are well known. Further well known examples of cancers include cancers of the blood such as leukemias and lymphomas.

The dangers posed by cancers are two-fold. First, cancer in a particular tissue may grow, thereby inhibiting the normal function of a particular organ or tissue. Second, cancer may metastasize to other parts of the body, thereby inhibiting the normal function of multiple organs and tissues.

One currently recognized method for treating or otherwise inhibiting the progression of cancer is based on the concept of anti-angiogenesis. Without being bound by theory, the inhibition of angiogenesis prevents tumor growth and survival by depriving those cells of the blood, oxygen, and nutrients necessary to maintain cell growth and survival. In the presence of anti-angiogenic compounds, tumor growth and metastasis is inhibited. Such anti-angiogenesis therapy can be used alone, or in combination with out cancer therapies to treat and/or otherwise prevent the progression of cancer.

The invention provides methods and compositions for inhibiting angiogenesis. In light of the well-recognized role for anti-angiogenics in the treatment of many types of cancer, the present invention provides methods and compositions for the treatment of cancer. For example, the present invention provides methods and compositions to inhibit the growth, survival, or metastasis of a tumor or of tumor cells.

Inflammation: The methods and compositions of the present invention can similarly be used to decrease inflammation. Inflammation is a defensive reaction caused by tissue damage, injury, or infection and is characterized by redness, heat, swelling, and pain. The primary objective of inflammation is to localize and eradicate the irritant and repair the surrounding tissue. For the survival of the host, inflammation is a necessary and beneficial process. However, sometimes the inflammatory response is hyperactivated and actually results in further tissue damage. For example, hyper-immune responses are seen in certain allergic responses. Further hyper-immune responses include autoimmune responses. Accordingly, while recognizing the beneficial aspect of inflammation, the invention contemplates methods and compositions to prevent excessive inflammation, as for example, during a hyper-immune response.

The goal of developing improved methods and compositions for decreasing inflammation is by no means a new one. Aspirin, Tylenol, and Advil are amongst the readily available and time honored treatment for everyday inflammatory responses including sprained ligaments, arthritis, and the like. The present invention provides novel methods and compositions for the treatment of inflammation, and contemplates administration of the compositions of the invention alone or in combination with other anti-inflammatory agents known in the art and appropriate for the particular indication.

Retinopathy: Based in part on a combination of their anti-angiogenic and anti-inflammatory properties, the methods and compositions of the present invention can be used in the treatment of retinopathies. Briefly, we outline below two subclasses of retinopathy: diabetic retinopathy and retinopathy of prematurity (ROP).

Among the more than 10 million people in the United States who have or will develop diabetes, over half will ultimately have some degree of visual loss. Such visual loss is caused in large part by retinopathy.

A cascade of subtle changes that occur in the blood vessel walls, the blood itself, and the very special structures in the retina lead to swelling of the central retinal tissue (macular edema) that blurs the vision of millions of diabetics. More severe prolonged abnormalities will lead to development of abnormal weak blood vessels that can rupture or be the scaffold for scar tissue. Dense blood clots in the central cavity (vitreous gel) of the eye or retinal detachment from traction of scar tissue can lead to profound visual loss or total blindness. Significant retinal changes can occur before any visual changes are noted by the patient, so an annual ophthalmic eye exam has been recommended by the Federal Center for Disease Control (CDC) in Atlanta. Blurring of vision, increased trouble with glare and an onset of "floaters" may be evidence of beginning visual problems.

Examination for retinopathy includes basic tests of visual acuity, eye pressure (to rule out glaucoma), and an exam through a dilated pupil to see both panoramic and high magnification views of the retina. In addition to the commonly performed fluorescein angiography test that identifies both early and late blood vessel changes by their special forms of excessive leakage, macular tissue damage can be measured by a special electroretinogram (ERG) (principle similar to the electrocardiogram), small central blind spot changes by the scanning laser ophthalmoscope (SL0), hidden changes in a blood filled eye by a sonar-like ultra-sound echo system, and subtle circulatory changes in the retinal blood vessels with the Laser Doppler Flow meter (LDF).

The methods and compositions of the present invention can be used in the treatment of retinopathy, for example in the treatment of diabetic retinopathy. Such methods and compositions can be used alone or in combination with other recognized therapies for retinopathy. Such therapies include laser photocoagulation and closed vitrectomy. Such therapies also include management of diabetes, for example, methods of stabilizing one's blood glucose and thereby avoiding frequent hyper- and hypo-glycemic states.

Laser treatment is more common than vitrectomy. It is done in an office, with the patient sitting in front of a laser machine. The eye is numbed by anesthesia drops to allow a special contact lens to be placed on the eye to deliver the laser beam. The beam can be changed to minimize discomfort while delivering sufficient energy to create the desired retinal reaction. The laser treatment is performed either to decrease the macular swelling or to reduce the risk of bleeding from abnormal, weak blood vessels.

Vitrectomy is Necessary if Extensive Blood has Remained in the Eye without Spontaneous Clearing or if Scar Tissue is Destroying Vision.

Retinopathy of Prematurity (ROP) is a disease of the retina, the light sensitive membrane covering the inside of the eye. It affects small, prematurely born babies. It consists of abnormal retinal vessels that grow mostly in an area where normal vessels have not yet grown in the retina. ROP is divided into stages 1 to 5. Stages 1 and 2 do not usually require treatment. Some babies who have developed stage 3 ROP require treatment usually involving laser or cryotherapy.

Peripheral retinal treatment can reduce, but not eliminate, the chance of the ROP progressing to the potentially blinding stages 4 and 5. When stage 4 or 5 ROP is reached, the retina is detached and other therapies can be performed. One such therapy is scleral buckling, which involves encircling the eyeball with a silicone band to try and reduce the pulling on the retina. Other therapies include vitrectomy (removal of the gel-like substance called the vitreous that fills the back of the eye). Sometimes the removal of the lens as well is required during vitrectomy to try and eliminate as much pulling as possible from the retinal surface. Removal of the lens is performed if the retina is touching the back surface of the lens.

Surgical adhesions: Adhesions occur when tissues, which are normally free, scar together, sometimes as a result of surgery. Abnormal connections between tissues can cause a variety of problems, such as infertility or bowel obstruction. Adhesions typically occur 40 to 90 percent of the time after surgery, typically at the site where the surgery occurred.

Adhesions often occur when tissues heal following suturing, incision, infection, foreign bodies, and trauma (tissue damage) that are caused by virtually any kind of surgery. When the tissue heals, it may scar. The preferred outcome after surgery is to have tissues heal without sticking (adhering) together. Although scarring typically accompanies the healing of wounded tissues, the preferred surgical outcome is for any scarring to occur absent adhesions.

Adhesions can be life threatening and can make surgical re-entry hazardous, impeding orientation and visibility. Dissecting adhesions may cause injury to surrounding organs or blood vessels, increasing blood loss and prolong operating time. Adhesions often cause severe pain, discomfort, limited range of motion and organ dysfunction. In order to relieve pain or free an obstruction caused by adhesions, additional surgery may be required to dissect the adhesions. Adhesions can occur in virtually any tissue. However, the following are illustrative examples of adhesions and the resulting consequences of adhesions in several tissue types.

Adhesions are commonly associated with pelvic pain. In fact, as high as 38 percent of women who suffer from pelvic pain have adhesions. Because normally separate organs are bound together by scar, the stretching and pulling of this tissue from everyday body movements can cause pain. Adhesions are also a leading cause of female infertility. Certain gynecological surgeries can lead to the formation of adhesions between the ovaries and the fallopian tubes. Such scarring can interfere with the transportation of the egg and sperm, making it difficult to conceive.

Bowel obstruction is caused by adhesions involving the intestines, and can occur shortly after surgery or even years later. Such obstruction can lead to nausea, vomiting, debilitating pain, and even death. If left untreated, the bowel may eventually rupture.

Adhesions are caused, in part, by hyper-proliferative wound healing activity following surgery or other injury. The methods of the present invention can be used to limit the rate or extent of hyper-proliferation following surgery, thereby decreasing the incidence or severity of adhesions.

Obstructive vascular disease: The term "obstructive vascular disease" refers to a range of conditions characterized by occlusion of a vessel. By way of example, obstructive vascular diseases include atherosclerosis and vascular stenosis. By way of further example, obstructive vascular diseases also include the occlusion of vessels that often occurs following angioplasty or other intraluminal intervention. The methods and compositions of the present invention can be used to treat or prevent obstructive vascular diseases. Such compositions can be delivered alone or in combination, and can be delivered directly to the site of obstruction or systemically.

Without being bound by theory, the methods and compositions of the present invention can be used to decrease proliferation and migration of endothelial cells that occlude vessels. Such vessels include not only blood vessels but other vessels including endothelial tubes. Exemplary endothelial tubes that may become occluded include the nephric duct, the common bile duct, the pancreatic duct, the esophagus, the urethra, the ureter, the bladder, the Fallopian tubes, the ovarian duct, and the bladder.

Weight-Management: Obesity has become a chronic health problem in this country, and around the world. Obesity and other chronic weight problems have a variety of consequences including social and psychological consequences. Additionally, obesity is a major factor that increases one's risk of diseases including, but not limited to, cardiovascular disease, stroke, high cholesterol, diabetes, colon cancer, gout, chronic joint pain, arthritis, and respiratory difficulties.

In an effort to manage the growing problem of obesity, a variety of diet aids, diet regimens, and exercise regimens have been developed to help people manage their weight and avoid obesity. The methods and compositions of the present invention provide another tool that can be used to reduce fat, and thereby decrease weight gain in an individual. By inhibiting angiogenesis, the compositions of the present invention can be used to reduce fat. Such compositions can be used alone, or in combination with other diet and exercise regimens used to help reduce fat in an individual.

In addition to their use as part of a diet regimen to reduce fat in an individual, the anti-angiogenic compositions and methods of the present invention may additionally be used to augment the treatment of a condition that is exacerbated by obesity. Exemplary conditions include, but are not limited to, cardiovascular disease, stroke, high cholesterol, diabetes, colon cancer, gout, chronic joint pain, arthritis, and respiratory difficulties.

The foregoing examples are merely illustrative of the broad range of diseases and injuries of vastly different mechanisms that can be treated using the methods and compositions of the present invention. Generally, the invention contemplates that any condition that can be treated, in whole or in part, by increasing angiogenesis or by promoting proliferation, migration, or adhesion of endothelial cells or of smooth muscle cells may be treated using a composition of the present invention that promotes expression or activity of netrin or of netrin signaling. Similarly, the invention contemplates that any condition that can be treated, in whole or in pary, by decreasing angiogenesis or by inhibiting proliferation, migration, or adhesion of endothelial cells or of smooth muscle cells may be treated using a composition of the present invention that inhibits the expression or activity of netrin or of netrin signaling.

(vii) Pharmaceutical Compositions and Methods of Administration

The invention further contemplates pharmaceutical compositions comprising netrin polypeptides and agents that inhibit the expression or activity of netrin polypeptides. Exemplary pharmaceutical compositions include pharmaceutical compositions comprising (i) a netrin polypeptide, (ii) an active fragment of a netrin polypeptide, (iii) a modified netrin polypeptide, or (iv) a modified active fragment of a netrin polypeptide, (v) an anti-netrin antibody, (vi) an Unc5h receptor or ectodomain, (vii) an anti-neogenin antibody, formulated in a pharmaceutically acceptable carrier or excipient. Further exemplary pharmaceutical compositions include pharmaceutical compositions comprising one or more netrin polypeptides, modified netrin polypeptides, or active fragments thereof. Additional exemplary pharmaceutical compositions include pharmaceutical compositions comprising one or more agents that promote the activity of netrin or of netrin signaling (e.g., promote the pro-angiogenic, pro-attractant activity of netrin). Further exemplary pharmaceutical compositions include pharmaceutical compositions comprising one or more agents that inhibit the activity of netrin or of netrin signaling (e.g., inhibit the pro-angiogenic, pro-attractant activity of netrin). Still further exemplary pharmaceutical compositions include pharmaceutical compositions comprising one or more netrin polypeptides, modified netrin polypeptides, or active fragments thereof, and one or more other agents. Such agents include, but are not limited to, angiogenic factors.

The pharmaceutical compositions of the present invention are formulated according to conventional pharmaceutical compounding techniques. See, for example, Remington's Pharmaceutical Sciences, 18th Ed. (1990, Mack Publishing Co., Easton, Pa.). Pharmaceutical formulations of the invention can contain the active polypeptide and/or agent, or a pharmaceutically acceptable salt thereof. These compositions can include, in addition to an active polypeptide and/or agent, a pharmaceutically acceptable excipient, carrier, buffer, stabilizer or other material well known in the art. Such materials should be non-toxic and should not interfere with the efficacy of the active agent. Preferable pharmaceutical compositions are non-pyrogenic. The carrier may take a wide variety of forms depending on the route of administration, e.g., intravenous, intravascular, oral, intrathecal, epineural or parenteral, transdermal, etc. Furthermore, the carrier may take a wide variety of forms depending on whether the pharmaceutical composition is administered systemically or administered locally, as for example, via a biocompatible device such as a catheter, stent, wire, or other intraluminal device. Additional methods of local administration include local administration that is not via a biocompatible device. Furthermore, local delivery and/or topical delivery may be, for example, via a biocompatible matrix such as a bandage, dressing, suture, or gauze.

Illustrative examples of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

In one embodiment, the pharmaceutical composition is formulated for sustained-release. An exemplary sustained-release composition has a semi permeable matrix of a solid biocompatible polymer to which the composition is attached or in which the composition is encapsulated. Examples of suitable polymers include a polyester, a hydrogel, a polylactide, a copolymer of L-glutamic acid and ethyl-L-glutamase, non-degradable ethylene-vinyl acetate, a degradable lactic acid-glycolic acid copolymer, and poly-D+-hydroxybutyric acid.

Polymer matrices can be produced in any desired form, such as a film, or microcapsules.

Other sustained-release compositions include liposomally entrapped modified compositions. Liposomes suitable for this purpose can be composed of various types of lipids, phospholipids, and/or surfactants. These components are typically arranged in a bilayer formation, similar to the lipid arrangement of biological membranes. Liposomes containing the compositions of the present invention are prepared by known methods (see, for example, Epstein, et al. (1985) PNAS USA 82:3688-92, and Hwang, et al., (1980) PNAS USA, 77:4030).

Pharmaceutical compositions according to the invention include implants, i.e., compositions or device that are delivered directly to a site within the body and are, preferably, maintained at that site to provide localized delivery. The compositions, including the pharmaceutical compositions described in the present application can be administered systemically, or locally. Locally administered compositions can be delivered, for example, to the pericardial sac, to the pericardium, to the endocardium, to the great vessels surrounding the heart (e.g., intravascularly to the heart), via the coronary arteries, or directly to the myocardium. When delivering to the myocardium to promote proliferation and repair damaged myocardium, the invention contemplates delivering directly to the site of damage or delivery to another site at some distance from the site of damage. Exemplary methods of administering compositions systemically or locally will be described in more detail herein.

The compositions, and pharmaceutical compositions thereof, of the invention also include implants comprising a composition attached to a biocompatible support. This combination of a biocompatible support and a composition can be used to deliver the composition in vivo. Preferable biocompatible supports include, without limitation, stents, wires, catheters, and other intraluminal devices. In one embodiment, the biocompatible support can be delivered intravascularly or intravenously.

The support can be made from any biologically compatible material, including gpolymers, such as polytetrafluorethylene (PFTE), polyethylene terphthalate, Dacronftpolypropylene, polyurethane, polydimethyl siloxame, fluorinated ethylene propylene (FEP), polyvinyl alcohol, poly(organo) phosphazene (POP), poly-1-lactic acid (PLLA), polyglycolic/polylactic acid copolymer, methacrylphosphorylcholine and laurylmethacrylate copolymer, phosphorylcholine, polycaprolactone, silicone carbide, cellulose ester, polyacrylic acid, and the like, as well as combinations of these materials. Metals, such as stainless steel, nitinol, titanium, tantalum, and the like, can also be employed as or in the support. Preferably, the support is sufficiently porous to permit diffusion of compositions or products thereof across or out of the support.

Supports can provide pharmaceutical compositions of the invention with desired mechanical properties. Those skilled in the art will recognize that minimum mechanical integrity requirements exist for implants that are to be maintained at a given target site.

Preferred intravascular implants, for example, should resist the hoop stress induced by blood pressure without rupture or aneurysm formation.

The size and shape of the support is dictated by the particular application. If the support is to be maintained at a vascular site, a tubular support is conveniently employed.

"Attachment" of compositions to support is conveniently achieved by adsorption of the compositions on a support surface. However, any form of attachment, e.g., via covalent or non-covalent bonds is contemplated. In one embodiment, the composition is prepared as a solution, preferably containing a carrier, such as bovine serum albumin (BSA). This solution is crosslinked using an agent such as glutaraldehyde, gamma irradiation, or a biocompatible epoxy solution and then applied to the surface of the support by coating or immersion.

Alternatively, compositions can be mechanically entrapped in a microporous support (e.g., PTFE). The composition solution employed for this method need not be crosslinked. After wetting the support (e.g., with 100% ethanol), the solution is forced into the pores of the support using positive or negative pressure. For tubular supports, a syringe containing the solution can be attached to the tube so that the solution is forced into the lumen of the tube and out through the tube wall so as to deposit the composition on internal and external support surfaces.

Compositions can also be dissolved and suspended within a biocompatible polymer matrix, such as those described above, that can then be coated on a support or prosthetic device. Preferably, the polymerized matrix is porous enough to allow cellular interaction with the composition.

Composition matrix/support assemblies intended for intravascular use may have the matrix attached to the outside surface of a tubular support. The matrix could also be attached to the interior of the support, provided the matrix was sufficiently firmly attached to the support. Loose matrix would predispose to intravascular flow disturbances and could result in thrombus formation.

In other embodiments, the composition is delivered via a biocompatible, intraluminal device, however, the composition is not crosslinked or otherwise desolved in the device. For example, the invention contemplates use of a catheter or other device to deliver a bolus of a composition. In such embodiments, the composition may not necessarily be associated with the catheter. The use of a catheter, or other functionally similar intraluminal device, allows localized delivery via the vasculature. For example, an intraluminal device can be used to deliver a bolus of composition directly to the myocardium, endocardium, or pericardium/pericardial space. Alternatively, an intraluminal device can be used to locally deliver a bolus of composition in the vascular adjacent to cardiac tissue.

As outlined above, biocompatible devices for use in the various methods of delivery contemplated herein can be composed of any of a number of materials. The biocompatible devices include wires, stents, catheters, balloon catheters, and other intraluminal devices. Such devices can be of varying sizes and shapes depending on the intended vessel, duration of implantation, particular condition to be treated, and overall health of the patient. A skilled physician or cardiovascular surgeon can readily select from among available devices based on the particular application.

By way of further illustration, exemplary biocompatible, intraluminal devices are currently produced by several companies including Cordis, Boston Scientific, Guidant, and Medtronic.

The invention also provides articles of manufacture including pharmaceutical compositions of the invention and related kits. The invention encompasses any type of article including a pharmaceutical composition of the invention, but the article of manufacture is typically a container, preferably bearing a label identifying the composition contained therein.

The container can be formed from any material that does not react with the contained composition and can have any shape or other feature that facilitates use of the composition for the intended application. A container for a pharmaceutical composition of the invention intended for parental administration generally has a sterile access port, such as, for example, an intravenous solution bag or a vial having a stopper pierceable by a hypodermic injection needle.

Kits of the invention generally include one or more such articles of manufacture and preferably include instructions for use. Preferred kits include one or more devices that facilitate delivery of a pharmaceutical composition of the invention to a target site.

Compositions for use in the methods of the present invention, as well as compositions identified by the subject methods may be conveniently formulated for administration with a biologically acceptable medium, such as water, buffered saline, polyol (for example, glycerol, propylene glycol, liquid polyethylene glycol and the like) or suitable mixtures thereof. Exemplary modified compositions include hydrophobically modified, hydrophilically modified, and mixed-modified compositions. Such modified compositions may be modified with one or more moieties. Such one or more moieties may be appended to the N-terminal amino acid residue, the C-terminal amino acid residue, and/or one or more internal amino acid residue. When a modified composition is modified with more than one moiety, the invention contemplates that the moieties may be the same or different, and may be attached to the same amino acid residue or to different amino acid residues.

Throughout this section of the application, the term agent will be used interchangeably to refer to one or more composition or modified composition for use in the methods of the present invention.

Optimal concentrations of the active ingredient(s) in the chosen medium can be determined empirically, according to procedures well known to medicinal chemists. As used herein, "biologically acceptable medium" includes solvents, dispersion media, and the like which may be appropriate for the desired route of administration of the one or more agents. The use of media for pharmaceutically active substances is known in the art. Except insofar as a conventional media or agent is incompatible with the activity of a particular agent or combination of agents, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations".

Methods of introduction may also be provided by delivery via a biocompatible, device. Biocompatible devices suitable for delivery of the subject agents include intraluminal devices such as stents, wires, catheters, sheaths, and the like. However, administration is not limited to delivery via a biocompatible device. As detailed herein, the present invention contemplates any of number of routes of administration and methods of delivery. Furthermore, when an agent is delivered via a biocompatible device, the invention contemplates that the agent may be crosslinked to or otherwise associated with or dissolved in the device, or may not be so associated.

The agents identified using the methods of the present invention may be given orally, parenterally, or topically. They are of course given by forms suitable for each administration route. For example, they are administered in tablets or capsule form, by injection, inhalation, ointment, controlled release device or patch, or infusion.

The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

The one or more agents can be administered as such or in admixtures with pharmaceutically acceptable and/or sterile carriers and can also be administered in conjunction with other compounds. These additional compounds may be administered sequentially to or simultaneously with the agents for use in the methods of the present invention.

Agents can be administered alone, or can be administered as a pharmaceutical formulation (composition). Said agents may be formulated for administration in any convenient way for use in human or veterinary medicine. In certain embodiments, the agents included in the pharmaceutical preparation may be active themselves, or may be a prodrug, e.g., capable of being converted to an active compound in a physiological setting.

Thus, another aspect of the present invention provides pharmaceutically acceptable compositions comprising an effective amount of one or more agents, formulated together with one or more pharmaceutically acceptable carriers (additives) and/or diluents. As described below, the pharmaceutical compositions of the present invention may be specially formulated for administration in solid or liquid form, including those adapted for the following: (1) delivery via a stent or other biocompatible, intraluminal device; (2) oral administration, for example, drenches (aqueous or non-aqueous solutions or suspensions), tablets, boluses, powders, granules, pastes for application to the tongue; (3) parenteral administration, for example, by subcutaneous, intramuscular or intravenous injection as, for example, a sterile solution or suspension; (4) topical application, for example, as a cream, ointment or spray applied to the skin; or (5) opthalamic administration, for example, for administration following injury or damage to the retina; (6) intramyocardial, intraperi-cardial, or intraendocardial administration; (7) intravascularly, intravenously, or via the coronary artiers. However, in certain embodiments the subject agents may be simply dissolved or suspended in sterile water. In certain embodiments, the pharmaceutical preparation is non-pyrogenic, i.e., does not elevate the body temperature of a patient.

Some examples of the pharmaceutically acceptable carrier materials that may be used include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, one or more agents may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of agent of the present invention. These salts can be prepared in situ during the final isolation and purification of the agents of the invention, or by separately reacting a purified agent of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the agents include the conventional nontoxic salts or quaternary ammonium salts of the agents, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more agents may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of agents of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the agent which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent of the present invention as an active ingredient. An agent of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the agents of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agents, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Transdermal patches have the added advantage of providing controlled delivery of an agent of the present invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the agent in a polymer matrix or gel.

Pharmaceutical compositions of this invention suitable for parenteral administration comprise one or more agents of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an agent, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally administered agent form is accomplished by dissolving or suspending the agent in an oil vehicle.

For any of the foregoing, the invention contemplates administration to neonatal, adolescent, and adult patients, and one of skill in the art can readily adapt the methods of administration and dosage described herein based on the age, health, size, and particular disease status of the patient. Furthermore, the invention contemplates administration in utero to treat conditions in an affected fetus.

EXEMPLIFICATIONS

The invention now being generally described, it will be more readily understood by reference to the following examples, which are included merely for purposes of illustration of certain aspects and embodiments of the present invention, and are not intended to limit the invention.

Example 1

Netrin1 is Expressed in Embryonic and Adult Tissues

To confirm that vascular cell types such as smooth muscle cells and endothelial cells would likely respond to modulation of netrin and netrin signaling, we examined expression of one member of the netrin family during embryonic and adult development. Our results, which are summarized in FIG. 2, confirm that netrin1 is expressed during embryonic and adult development in a pattern consistent with a role in modulating behavior of cell types including cardiovascular cell type. Expression of a netrin family member indicates that such cell types can be modulated by manipulating netrin polypeptides and netrin signaling.

Figure 2:
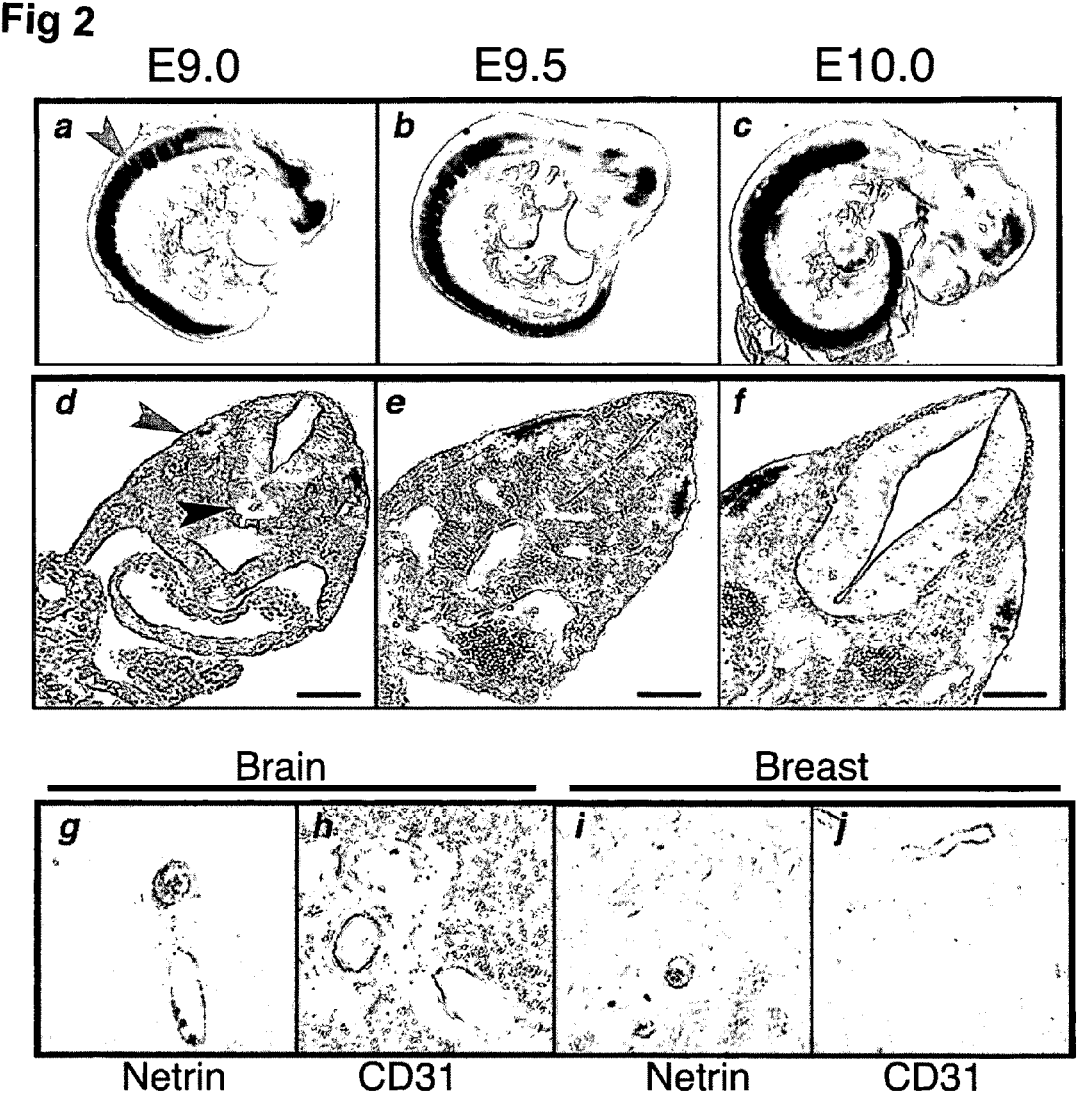

Briefly, FIG. 2 shows the expression of netrin1 in mouse embryonic and adult tissues. Panels (a-f) show netrin1 expression in mouse E9-E10 tissues by in situ hybridization using an antisense netrin1 probe. Panels (a-c) show expression of netrin1 in whole mount and panels (d-f) show expression of netrin1 in cross-section. Note the strong expression of netrin1 in the floorplate (indicated with a black arrowhead) and in the somites (indicated with a red arrowhead).

Panels (g-j) show the expression of netrin1 protein in 8 micron sections of adult human breast and brain tissue. Sections were stained with an antibody immunoreactive with netrin1 protein (panels g and i) or with an antibody immunoreactive with the endothelial marker CD31 (panels h and j). Note the netrin expression surrounding blood vessels in both the brain and the breast, as well as expression throughout ductal tissue of the breast.

Example 2

Netrin Promotes Proliferation of Endothelial Cells and Smooth Muscle Cells

Given the expression of a netrin polypeptide in endothelial and vascular cell types, we examined the mitogenic potential of a netrin polypeptide. Furthermore, we compared the proliferative capacity of a netrin polypeptide to the known vascular growth factor VEGF. The results of several studies are summarized in FIG. 3 which shows that a netrin polypeptide, netrin1, promoted proliferation of both endothelial cells and smooth muscle cells. Furthermore, these results indicated that a netrin polypeptide promoted proliferation with a potency similar to that of the known vascular growth factor, VEGF.

Figure 3:
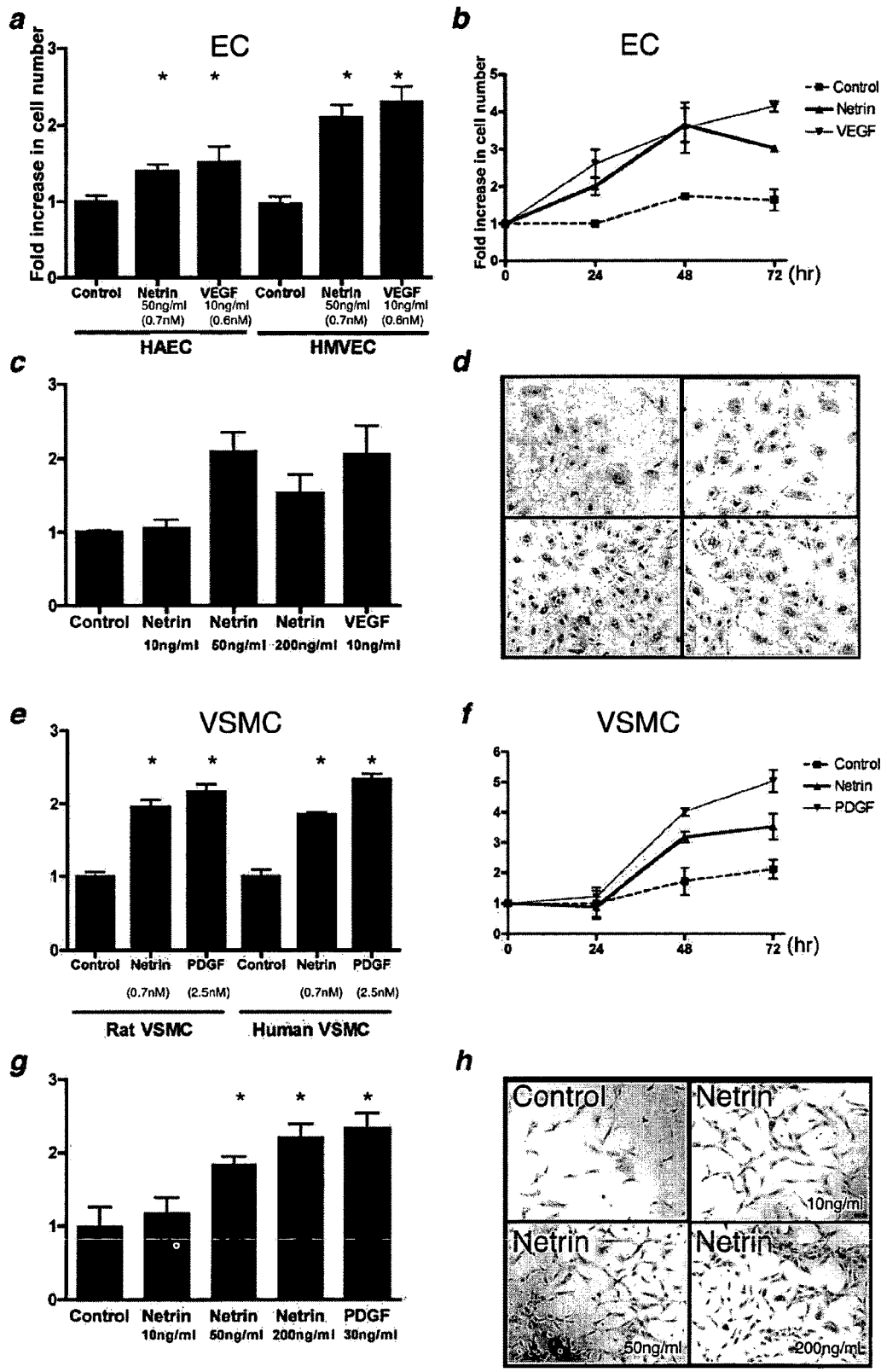
FIG. 3 shows that netrin stimulated proliferation of endothelial and smooth muscle cells, and that the proliferative effect of netrin is comparable to that of VEGF.

Briefly, FIG. 3 summarizes the following experiments. Panels (a-d) summarize experiments that examined the effect of netrin1 or VEGF on endothelial cells (EC). Panels (e-h) summarize experiments that examined the effect of netrin1 or VEGF on vascular smooth muscle cells. All of the experiments provided in FIG. 3 measured the fold increase in cell number (as a measure of the change in cell proliferation) over cells treated with BSA in serum free media. The panels provided in FIG. 3 represent the results of at least three independent experiments each performed in triplicate.

Panels (a-d) show that netrin stimulated proliferation of endothelial cells at levels similar to that of VEGF. Briefly, after 48 hours of treatment, netrin1 (50 ng/ml) or the known endothelial growth factor VEGF (10 ng/ml) each stimulated proliferation of both primary human microvascular endothelial cells (HMVEC) and human aortic endothelial cells (HAEC) (panel a). As summarized in the graph presented in panels (b and c) proliferation of endothelial cells, in this case HMVEC, following treatment with either netrin1 or VEGF was time and dose dependent. In these experiments, the optimal response of endothelial cells to netrin treatment was observed at 48 hours and at a done of 50 ng/ml. Panel (d) provides representative fields of cell culture wells containing HMVECs following 48 hours of treatment with the indicated amounts of netrin1 or BSA.

Panels (e-h) show that netrin stimulated proliferation of smooth muscle cells at levels similar to PDGF. Briefly, after 48 hours of treatment, netrin1 or the known growth factor PDGF stimulated proliferation of human or rat vascular smooth muscle cells (VSMC). Panel (e) shows that following 48 hours of treatment with either Netrin1 (50 ng/ml) or PDGF (30 ng/ml), there was a two fold increase in the number of primary rat and human VSMC when compared to BSA treated (control) cells. Panels (f and g) show that the proliferation of smooth muscle cells, in this case vascular smooth muscle cells, following treatment with either netrin1 or PDGF was time and dose dependent. Panel (h) provides representative fields of cell culture wells containing VSMCs following 48 hours of treatment with the indicated concentrations of netrin1 or BSA.

Example 3

Netrin Promotes Migration of Endothelial Cells and Smooth Muscle Cells

Given the expression of a netrin polypeptide in endothelial and vascular cell types, we examined the chemoattractant activity of a netrin polypeptide using a modified Boyden chamber assay. Furthermore, we compared the chemoattractant activity of a netrin polypeptide to known chemoattractants (VEGF and PDGF). The results of several studies are summarized in FIG. 4 which shows that a netrin polypeptide, netrin1, is chemotactic (a chemoattractant that is directional such that cells respond to a gradient of the factor) for both endothelial cells and smooth muscle cells.

Figure 4:
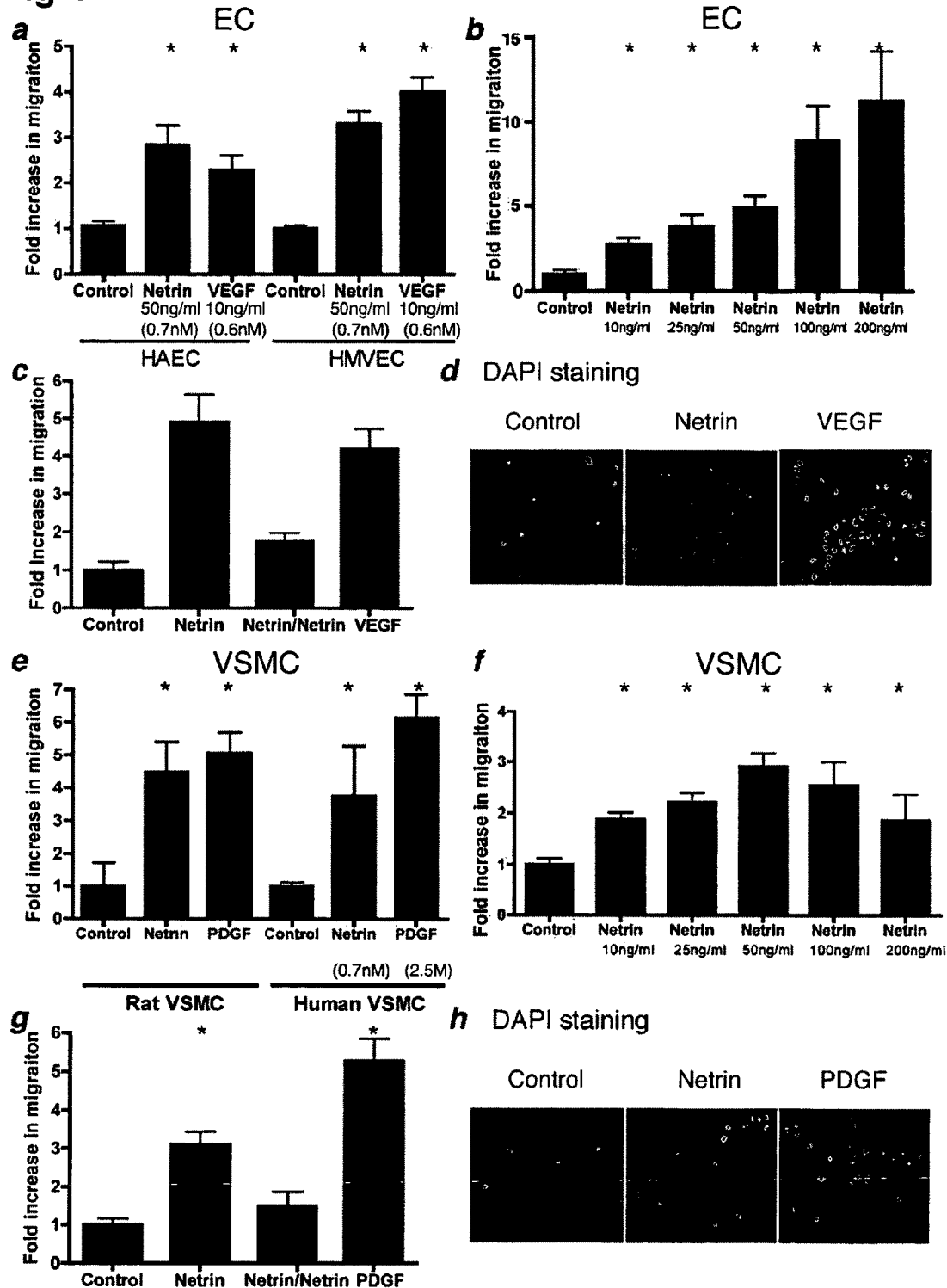
FIG. 4 shows that netrin induced migration of endothelial and smooth muscle cells, and that the chemotactic effect of netrin is comparable to that of VEGF.

In the experiments summarized in FIG. 4, the number of cells that migrated to either netrin1 or to a known chemoattractant were measured. Panels (a-d) summarize experiments performed using endothelial cells (EC) and panels (e-h) summarize experiments performed using smooth muscle cells. The data is presented as the relative increase in migration observed in cells treated with test factor over those treated with BSA. The figures represent the results of at least three independent experiments each performed in triplicate.

Panels (a-d) show that netrin1 is chemotactic for endothelial cells, and that the activity of netrin1 is similar to that of VEGF. Panel (a) shows that netrin1 (50 ng/ml) and VEGF (10 ng/m) each induced migration of both HAEC and HMVEC in the modified Boyden chamber assay. Panel (b) shows that migration of endothelial cells, in this case HMVECs, is directly proportional to the concentration of netrin1. Panel (c) shows that netrin1 induced direction migration (e.g., is chemotactic), as equal molar amounts of netrin1 polypeptide in each chamber (e.g., the elimination of a gradient of netrin) reduced endothelial cell migration. Panel (d) provides representative fields of endothelial cells, in this case HMVECs, migrating in response to netrin1 (50 ng/ml) or VEGF (10 ng/ml). The cells in panel (d) are stained with DAPI to facilitate visualization.

Panels (e-h) show that netrin1 is chemotactic for smooth muscle cells, and that the activity of netrin1 is similar to that of PDGF. Panel (e) shows that netrin1 (50 ng/ml) and PDGF (30 ng/ml) each induced migration of rat and human VSMC. Panel (f) shows that migration to netrin1 is biphasic and peaks at 50 ng/ml. Panel (g) shows that netrin1 induced directional migration (e.g., is chemotactic), as equal molar amounts of netrin1 in each chamber (e.g., the elimination of a gradient of netrin) reduced VSMC migration. Panel (h) provides representative fields of smooth muscle cells, in this case VSMCs, migrating in response to netrin1 (50 ng/ml) or PDGF (30 ng/ml). The cells in panel (d) are stained with DAPI to facilitate visualization.

Example 4

Promotes Adhesion of Smooth Muscle Cells

Netrin promotes adhesion of at least certain cell type. Without being bound by theory, netrin-mediated adhesion may be via an interaction with integrins or other cell-type specific receptors. Accordingly, we examined whether a netrin polypeptide could promote adhesion of one or more cardiovascular cell types. The results of these experiments are summarized in FIG. 5 which shows that the netrin polypeptide netrin1 promoted adhesion of smooth muscle cells, specifically vascular smooth muscle cells, but did not promote adhesion of either HAECs or HMVECs.

Figure 5:
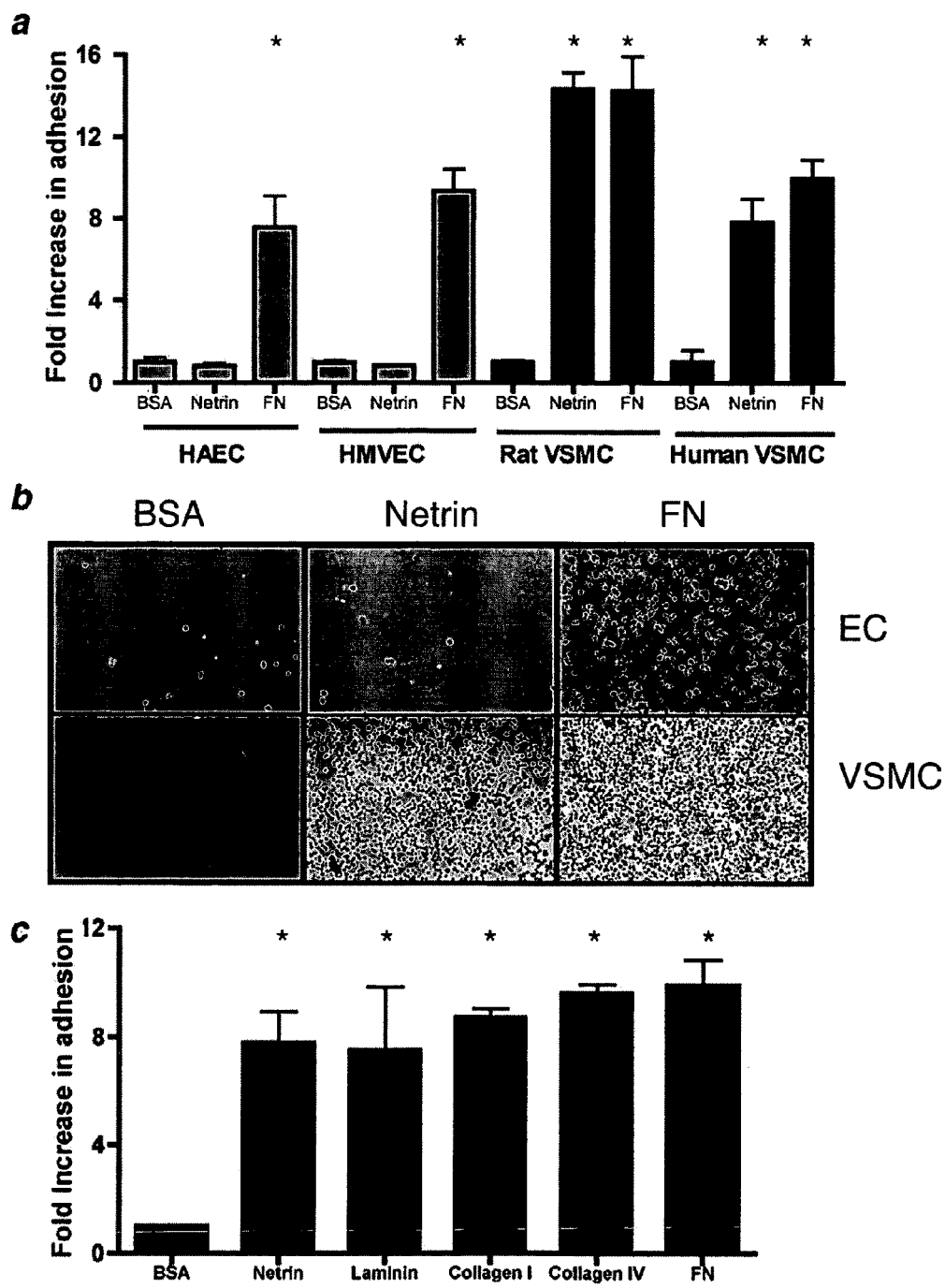
FIG. 5 shows that netrin promoted the adhesion of smooth muscle cells.

Panels (a-c) of FIG. 5 provide a quantitative analysis of adhesion of vascular smooth muscle cells (VSMC) and two endothelial cell types (EC) in response to netrin1, fibronectin (FN), laminin, collagen I, or collagen IV. Briefly, the wells of cell culture dishes were coated with netrin1 or with a test matrix element (e.g., BSA, FN, lamini, collagen I, or collagen IV). Endothelial cells or smooth muscle cells were plated and allowed to adhere to the coated wells for 30 minutes. Following the 30 minute incubation period, the cells were washed off. Adhesion (e.g., the ability of the particular coating to mediate adhesion of the cells) was measured by comparing the number of cells that adhered to a test coating versus a BSA coated well. The figures represent the results of at least three independent experiments each performed in triplicate.

Panel (a) shows that primary rat and human smooth muscle cells, specifically VSMCs, adhered to both netrin1 coated and FN coated dishes. In contrast, two endothelial cell types, HAECs and HMVECs, did not adhere to the netrin1 coated dishes. However, these endothelial cell types did adhere to dishes coated with FN. Panel (b) provides representative fields of H&E stained cells adhering to dishes coated with either BSA, netrin1, or FN.

Given that netrin1 promoted adhesion of vascular smooth muscle cells, we compared netrin-mediated to adhesion mediated by known matrix proteins. Panel (c) shows that adhesion of VSMC to netrin1 is comparable to adhesion mediated by FN, laminin1, collagen I, and collagen IV.

Example 5

The Netrin Receptor Neogenin Mediates Netrin Signaling in Vascular Smooth Muscle Cells We attempted to identify which, if any, of the known netrin receptors mediated netrin signaling in smooth muscle cells and endothelial cells. FIG. 6 summarizes the results of numerous experiments aimed at identifying the netrin receptor in these cells types. These results show that the netrin receptor neogenin mediates netrin signaling in vascular smooth muscle cells. However, neogenin does not appear to mediate netrin signaling in endothelial cells.

Panels (a and b) provide expression analysis of various netrin receptors in vascular smooth muscle cells and endothelial cells. Panel (a) provides the results of RT-PCR analysis, and shows that neogenin mRNA is expressed in vascular smooth muscle cells, and to a lesser extent in endothelial cells. Panel (b) provides Western blot analysis showing that neogenin protein is expressed in vascular smooth muscle cells. Neogenin does not appear to be expressed in endothelial cells. However, it is possible that neogenin expressed in endothelial cells differs in such a way that it is not immunoreactive with the same antibody capable of detecting expression in VSMCs. In the experiments summarized in panels (a and b), no DCC receptor expression was detected in either endothelial cells or VSMCs.

Given the expression of neogenin in VSMCs, we conducted experiments using a neogenin blocking antibody to assess whether neogenin mediated netrin signaling in VSMCs. Panel (c) summarizes the results of migration assays and shows that a neogenin blocking antibody inhibited the netrin1-mediated migration of VSMCs. The neogenin blocking antibody did not, however, inhibit PDGF-mediated migration of VSMCs. Furthermore, the neogenin blocking antibody did not inhibit netrin-mediated or VEGF-mediated migration of endothelial cells.

Additionally, we conducted experiments using a neogenin blocking antibody to assess whether neogenin mediated netrin-mediated adhesion of VSMCs. Panel (d) summarizes the results of adhesion assays and shows that a neogenin blocking antibody inhibited netrin-mediated adhesion in VSMCs. The neogenin blocking antibody did not, however, inhibit adhesion of VSMCs to fibronectin (FN).

Example 6

Netrin Promotes Angiogensis In Vivo

Figure 7:
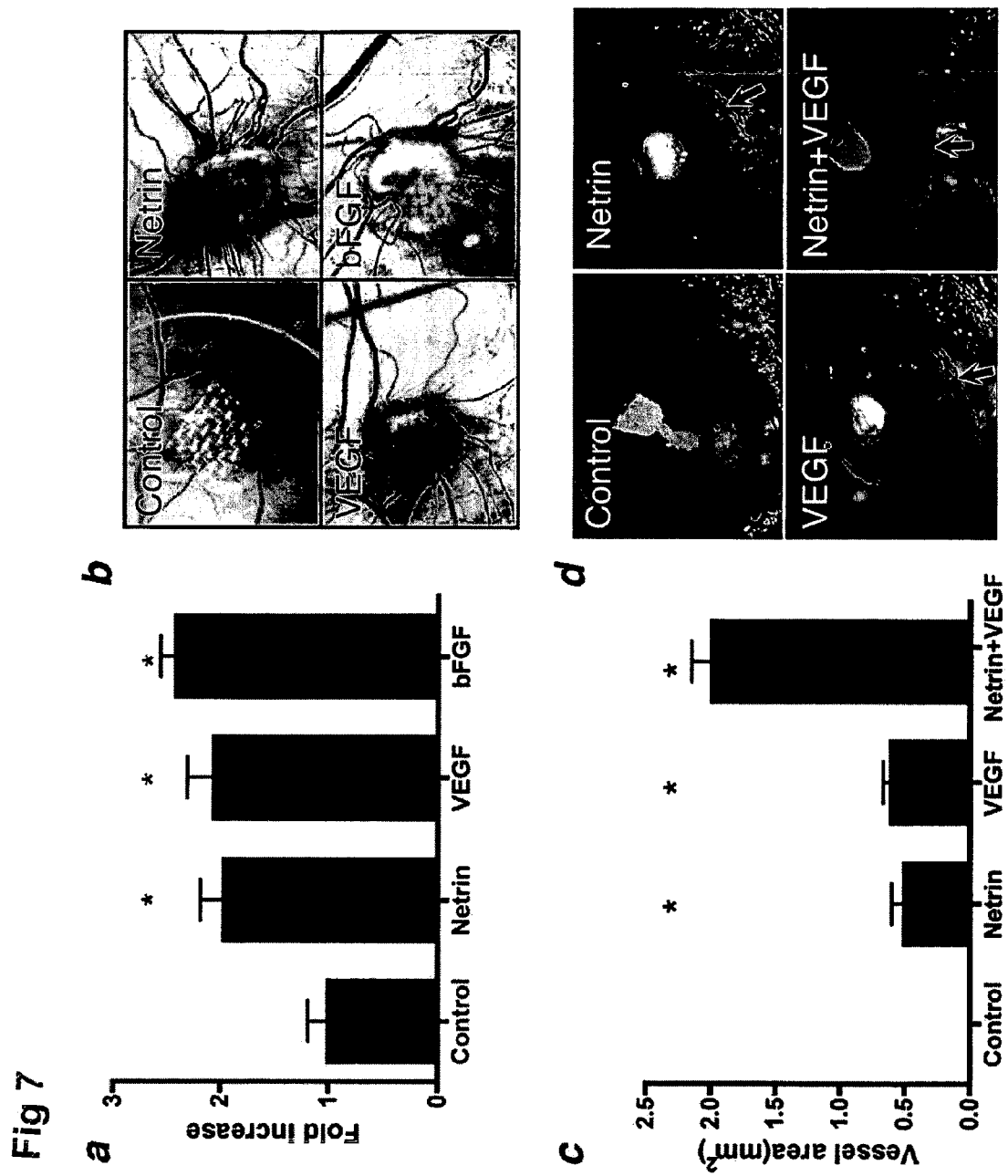
FIG. 7 shows that netrin promoted angiogenesis in vivo.

The above examples demonstrate that netrin polypeptides and netrin signaling can modulate the proliferation, migration, and adhesion of cardiovascular cell types. We further analyzed whether manipulation of netrin and netrin signaling can modulate cellular behavior in vivo using two in vivo angiogenesis assays. The results summarized in FIG. 7 show that netrin polypeptides and the manipulation of netrin signaling promoted angiogenesis in vivo.

Panels (a and b) show the results of experiments performed using a chorioallantoic membrane (CAM) assay. Netrin1 induced angiogenesis and vascular sprouting in the (CAM) assay. Furthermore, netrin1 induced angiogenesis at a level comparable to the known angiogenic factors VEGF and bFGF. Briefly, sponges were soaked with netrin1, VEGF, FGF, or BSA and were placed on chick CAMs. The number of vessels sprouting into the sponges after 72 hours were counted and quantified as the fold increase over BSA treated sponges. For each test factor, a total of 24 CAM assays were performed.

Panels (c and d) show the results of experiments performed using a murine corneal micropocket assay. Netrin1 induced angiogenesis in the murine corneal micropocket assay, and the level of netrin-mediated induction of angiogenesis was comparable to that of VEGF. Additionally, we assessed the angiogenic effect of administering a combination of netrin1 and VEGF and found that the two factors acted synergistically to promote angiogenesis.

Briefly, hydron pellets containing either 3.0 nM of netrin1 or VEGF stimulated comparable levels of blood vessel growth. When netrin1 and VEGF were combined, however, the two factors had a synergistic effect on angiogenesis. In other words, the response caused by the combination of netrin1 and VEGF was greater than the sum of the responses to each factor individually. In a single experiment, each test factor was placed on six corneas. Each experiment has been repeated a minimum of three times.

Materials and Methods

The following methods were used throughout the experiments outlined in the above examples:

Staging of mouse embryos and in situ hybridization were according to standard methods (see, for example, Umess et al., 2000). For in situ hybridization, Digoxygenin (DIG)-labeled cRNA probes were prepared using standard methods.

For isolation of RNA, total RNA was isolated from HUVEC, HMVEC and hAoSMC using TRIZOL (Gibco-BRL). Brain RNA was purchased from BD Biosciences. RNA was reverse-transcribed using the RETROscript kit (Ambion) and used for PCR according to the manufacturer's instructions. The following primer pairs were used:

```
human DCC:
forward
5'-acaggcctcaaaccaaacac-3'     (SEQ ID NO: 29)

reverse
5'-acctccatctccatgacgac-3'     (SEQ ID NO: 30)

human neogenin:
forward
5'-accccagcctgtgattagtg-3'     (SEQ ID NO: 31)

reverse
5'-tgtgatggttcagagcttgc-3'     (SEQ ID NO: 32)

human Unc5h2:
forward
5'-agttgcctctcctcctcctc-3'     (SEQ ID NO: 33)

reverse
5'ctttgccttttgcttttgg-3'       (SEQ ID NO: 34)

GAPDH:
forward
5'-acccagaagactgtggatgg-3'     (SEQ ID NO: 35)

reverse
5'-tgctgtagccaaattcgttg-3'.    (SEQ ID NO: 36)
```

The following conditions were used to amplify DCC, neogenin and Unc5h2: denaturation at 94° C. for 30 seconds, annealing at 58° C. for 30 seconds and extension at 72° C. for 45 seconds, 35 cycles. The conditions used to amplify GAPDH were denaturation at 94° C. for 30 seconds, annealing at 58° C. for 30 seconds and extension at 72° C. for 45 seconds, 30 cycles.

Immunohistochemistry and Western blot analyses were performed as described previously (see, for example, Urness et al., 2000). Primary antibodies that recognize Netrin-1 (Oncogene), DCC (Oncogene), Neogenin (Santa Cruz Biotech), Unc5h2 (gift of Lindsay Hinck, UC Santa Cruz) and CD31 (Dako) were used.

In Vitro Assays

BSA and PDGF-BB were obtained from Sigma. Recombinant human VEGF-165, FGF-2 and Netrin1 were purchased from R&D systems. Fibronectin, laminin-1, collagen I and collagen IV were purchased from BD Biosciences. Human aortic vascular smooth muscle cells (VSMC), human aortic endothelial cells (HAEC) and human microvascular endothelial cells (HMVEC) were cultured according to supplier's instructions (Cambrex). All of the cell biological assays described above were performed by individuals blinded to the specific treatments. Each assay was repeated on at least two independent samples of primary cells, and reproduced three separate times. Furthermore, each condition within an experiment was performed in triplicate.

A. Proliferation: The read-out for mitogenic activity in the in vitro assay was change in cell number. This is the most direct measurement of mitogenic activity. Low passage primary endothelial cells or vascular smooth muscle cells were seeded onto 24 well plates at equal density and serum starved for 16 hours. Following starvation, factors (BSA, PDGF-BB, VEGF-165, netrin1) were added at the indicated concentrations. After 24, 48, and 72 hours of treatment, the number of cells were measured using either a hemocytometer or by counting fixed and stained cells. The fold increase in cell number was calculated in comparison to BSA treated wells at 24 hours. Representative fields of cells were stained with H&E (Sigma) and photographed.

B. Migration: For assays measuring migration, vascular endothelial cells were serum starved overnight and then seeded at a density of 40,000 cells/well onto 5 μm transwell inserts. Test factors were added in serum free media and placed in the lower chamber. After incubation at 37° C. for 3 hours, filters were fixed with Zamboni's fixative and stained with DAPI stain Kit (Fisher). The total number of migrated cells was calculated by counting five random fields at 400× magnification. This number of migrated cells was then expressed as fold increase.

Assays measuring migration of vascular smooth muscle cells were conducted as described above for endothelial cells, with two exceptions. 30 ng/ml PDGF-BB was used as the positive control in experiments using vascular smooth muscle cells, and vascular smooth muscle cells were seeded onto 8 μm transwell inserts—rather than the 5 μm inserts used to assess migration of endothelial cells.

For experiments analyzing the ability of particular netrin receptors to block an effect of netrin, cells were pretreated with 0.1 μg/ml of neogenin or DCC for 30 minutes prior to addition to the upper chamber.

C. Adhesion: For assays measuring adhesion, 96 well plates were coated with BSA, netrin1, fibronectin, laminin-1, collagen I and collagen IV for 16 to 20 hours at 4° C. Prior to the addition of cells, wells were blocked with PBS containing 1% BSA for 1 hour at room temperature. Cells were harvested by trypsinization, neutralized with growth media, washed twice, and then resuspended in serum-free DMEM containing 0.5% BSA. $5 \times 10^4$ cells were added to each well and allowed to attach for 30 min at 37° C. in a $CO_2$ incubator. After washing three times with PBS, cells were fixed, stained with H&E and counted. For blocking experiments, cells were pretreated for 30 min with 10 μg/ml of neogenin antibody.

In Vivo Assays

To assess the ability of netrin related compositions to promote angiogenesis or otherwise modulate vascular cells in vivo, the chorioallantoic membrane (CAM) assay was used. Fertilized Leghorn chicken eggs were incubated under conditions of constant humidity (60%) at 37° C. Eggs were opened into sterile cling wrap hammocks and incubated at 37° C. with 2.0% $CO_2$ and 90% relative humidity until day 6 of incubation. Methylcellulose sponges (Gelfoam, Upjohn, Kalamazoo, Mich.) adsorbed with test factors were placed on the CAM at day 6 of incubation. Sponges containing BSA alone, FGF-2, or VEGF were used as controls. Mesh (Tetko) was placed on top of the sponges to mark their location. The CAM was incubated at 37° C. for a treatment period of 72 hours and fixed in 4% paraformaldehyde/2% glutaraldehyde/PBS.

Following treatment, the average number of microvessels surrounding the implanted mesh was calculated using either Image J software or a blinded reviewer. The change in the number of microvessels, in comparison to the control, was calculated and expressed as a fold increase.

A second in vivo assay referred to as the murine corneal micropocket assay was also used to assess the ability of a netrin composition to modulate vascular cell types. For the murine corneal micropocket assay, hydron (Hydro Med Sciences) pellets containing sucralfate (Sigma) and the indicated growth factors were prepared as previously described. The pellets were implanted, and the degree of vascularizafion induced by the growth factor containing pellets was evaluated.

Briefly, 7-8 week old male C57BL/6 mice were anesthetized with an intraperitoneal injection of avertin (Sigma-Aldrich), and the eyes were topically anesthetized with proparacaine. An incision was made lateral to the pupil with a #10 surgical blade, and a corneal micropocket was dissected from this incision toward the limbus with a von Graefe knife #3. A pellet was implanted in this micropocket and topical erythromycin was applied. Five to six days after implantation of the pellet implantation, neovascularization was quantitated by visualization with a slit lamp microscope. Vascularized area was computed with the following formula: $2\pi/10$*Clock hours*Vessel length (mm), and the degree of vascularization compared to animals implanted with control pellets.

Example 7

Expression of Netrin in Cancer Cell Lines and Human Tumors

The role of angiogenesis in maintaining tumors, and in allowing the growth and metastasis of many types of cancer is well known. In fact, several current cancer therapies are based on inhibiting angiogenesis, thereby preventing the growth and survival of tumors. As outlined in detail in the present application, netrin polypeptides and netrin signaling can promote angiogenesis. Similarly, agents that inhibit the activity or expression of netrin can inhibit angiogenesis. Such agents that inhibit the activity or expression of netrin, thereby inhibiting angiogenesis, can be used in the treatment of many types of cancer.

This aspect of the present invention is further supported by the experiments summarized in FIG. 8. Briefly, FIG. 8 shows that a netrin polypeptide, netrin1, is expressed in several cancer cell lines. Furthermore, netrin1 is expressed in human cancer tissue. The expression of netrin in cancer cell lines and in primary cancer tissue indicates that cancer cells and tumors are likely responsive to modulation of netrin.

Briefly, panels (a) and (b) show Northern blot analysis of netrin1 expression in a variety of cancer cell lines. The following cell lines were examined in panel (A): (1) promyelocytic leukemia HL-60, (2) Hela S3, (3) chronic myelogenous leukemia K-562, (4) lymphoblastic leukemia MOLT-4, (5) Burkitt's lymphoma Raji, (6) colorectal adenocarcinoma SW480, (7) lung carcinoma A549, and (8) melanoma G-361. The following cell lines were examined in panel B: (1) acute T-cell leukemia jurkat, (2) Burkitt's lymphoma CA46, (3) breast carcinoma MDA-MB-453, (4) Burkitt's lymphoma namalwa, (5) epidermal carcinoma A-431, (6) uterine carcinoma MES-SA, (7) Burkitt's lymphoma Raji, (8) osteosarcoma MG-63, and (9) histocytic lymphoma U-937.

By Northern blot analysis, netrin1 was strongly expressed in Hela S3 cells (panel A, lane 2), colorectal adenocarcinoma (SW480, panel A, lane 6), epidermal carcinoma (A-431, panel B, lane 5), uterine carcinoma (MES-SA, panel B, lane 6), and osteosarcoma (MG-63, panel B, lane 8). Netrin1 expression was also detected, although to a lesser extent, in lymphoblastic leukemia (MOLT-4, panel A, lane 4), lung carcinoma (A549, panel A, lane 7), melanoma (G-361, panel A, lane 8), acute T-cell leukemia Ourkat, panel B, lane 1), and Burkitt's lymphoma (CA46, panel B, lane 2).

We note that Northern blot analysis is less sensitive that RT-PCR. Thus, additional cell lines may express one or more netrin polypeptides, and the absence of a strong signal by Northern blot analysis does not necessarily indicate the absence of expression.

Panel C shows that netrin1 protein is expressed in a variety of human primary tumors from multiple cell types. Sections of human tumor tissue (brain cancer, breast cancer, and pancreatic cancer) were analyzed by immunohistochemistry using either an antibody immunoreactive with netrin1 or an antibody immunoreactive for the endothelial marker CD31. Netrin1 was expressed in all three human tumor tissues. Furthermore, colocalization of netrin1 expression and CD31 expression indicated that netrin is expressed in vasculature within these tumors.

Example 8

Identification of an Angiogenic Netrin Receptor

In the previous sections, we showed that Netrin-1 and Netrin-4 induced endothelial proliferation and migration. Our preliminary studies showed that virtually no expression of the known netrin receptors, except for Unc5h2, is observed in endothelial cells. These findings support our hypotheses that the pro-angiogenic effects of Netrin-1 are mediated via an unidentified receptor, and that Unc5h2 blocks or reduces the attractive effects of Netrin-1.

To identify the endothelial receptor responsible for netrin's pro-angiogenic or attractive effects, our initial experiments focused on examining the role of an obvious candidate receptor such as an adenosine receptor. Adenosine is an endogenous nucleoside that has well known roles in controlling vascular tone, cardiac myocyte contractility, modulation of neurotransmission, and cell growth. Four subtypes of adenosine receptor have been cloned and are expressed in endothelial cells: $A_1$, $A_{2A}$, $A_{2B}$, and $A_3$. We hypothesized that adenosine receptors mediate endothelial response to Netrin-1.

First, we reproduced published reports that showed Netrin-1 binds to the $A_{2B}$ receptor. We extended these experiments and found that Netrin-4 did not bind to the $A_{2B}$ receptor. Second, we determined whether adenosine receptors could be important for netrin signaling by using DPSPX, a non-selective adenosine receptor inhibitor. Our initial results indicated that DPSPX inhibited Netrin-1 mediated endothelial migration, and has little effect on VEGF mediated endothelial migration. These preliminary findings are consistent with the possibility that the $A_{2B}$ receptor mediates the pro-angiogenic effects of Netrin-1. Whether any of the candidate $A_{2B}$ receptors is responsible for the mitogenic and chemoattractant properties of netrins on endothelial cells is to be determined.

Further, the pro-angiogenic netrin receptor in endothelial cells can be identified by expression cloning. For this purpose, we have endothelial cDNA expression libraries with an average cDNA length of 2 kb that are ideal for screening. We also labeled Netrin-1 with either biotin or alkaline phosphatase, and showed that these modifications do not affect their functional or binding properties. Labeled Netrin-1 binds to canonical receptors and is active in endothelial migration assays. These reagents and assays allow us to screen endothelial expression libraries.

Example 9

Charaterization of the Role of the "Repulsive" Netrin Receptor Unc5h2

First, we generated in mice two mutant alleles of Unc5h2, a null allele and a conditional null allele (FIG. 9). The salient features for these alleles are: (1) Unc5h2 is inactivated by a deletion that removes a significant portion of the gene, including regions encoding much of the ligand binding domain, the transmembrane domain and over 50% of the cytoplasmic signaling domain reducing the likelihood of partial or dominant-negative activity; this was accomplished by inserting lox P sites in the $3^{rd}$ and $13^{th}$ INTRON of the Unc5h2 genomic sequence; and (2) neither allele contains large tracts of foreign DNA, such as antibiotic resistance genes, eliminating cis-effects known to influence gene expression.

Mice homozygous for the conditional allele or compound heterozygotes containing the conditional and the null allele are fully viable and fertile. Homozygosity for the null allele, however, results in embryonic lethality. Consistent with report of Lu et al, we found vascular defects in Unc5h2−/− embryos to be subtle and only a small percentage of mice developed dysmorphic hearts and pericardial effusion. In contrast to Lu et al, we observed other deficiencies including anemia, cranio-facial abnormalities, hypopigmented optic discs, neural tube dysmorphia, and overall developmental arrest by embryonic day 12.5, which are more severe than any observed vascular defects. To ascertain which of these phenotypes directly resulted from the absence of Unc5h2, we have assembled a number of Cre driver mice that permit temporal and spatial control over the deletion of Unc5h2 in mice containing the conditional allele.

The defects in E12.5 Unc5h2−/− embryos do not exist at E11.5, and cannot be used to distinguish Unc5h2−/− from Unc5h2+/+ embryos in observers blinded to the genotype. At present, the only phenotypic differences that such observers can distinguish Unc5h2−/− from +/+ mice at E11.5 are reduced heart rate and blood flow. Cursory inspection of the cardiac morphology indicates no gross defects in cardiac myocyte number, hypertrophy or turning.

Second, we studied the functional role of netrin receptors in different primary cells isolated from murine embryos (e.g., knockout mice and their wild type siblings). For example, we isolated endothelial cells from wild type embryos, performed immunostains for endothelial markers and showed that the cells migrated to Netrin-1. The functional role of netrin receptors is to be determined.

Example 10

Investigation of the Effect of Netrins on Stem Cells and Cardiac Disorders

To establish the therapeutic potential of netrins, we examined the effect of netrins on each of the cell types (e.g., stem cells and cardiac myocytes) involved in enhancing angiogenesis and improving heart function. First, our published report and preliminary data demonstrated that netrins stimulate endothelial sprouting. Second, we showed that Netrin-1 and Netrin-4 induce migration of human CD34+ hematopoietic stem cells (FIG. 10). Bone marrow derived stem cells reduce myocardial damage following infarction when injected into the heart, and these cells contribute between 10-15% of the endothelial cells in newly formed vessels cells. Third, Netrin-1 or Netrin-4 do not inhibit (nor stimulate) survival or growth of cardiac myocytes in culture. Together, these studies suggest that netrins may have therapeutic benefit by inducing angiogenesis and homing of circulating stem cells to regions of ischemic hearts.

Next, we examine whether overexpression of netrins can enhance angiogenesis and reduce cardiac injury following chronic ligation of coronary arteries 94-96. We have established this assay in an established cardiac infarct model. Our perioperative mortality is 0%, while our 14-day mortality is 10%. Mortality is secondary to ventricular rupture, and occurs between 2-5 days after coronary ligation. The infarct size quantitated by pathology is 40% with a left ventricular ejection fraction of 40% (normal 70%). Thus, we can assay in vivo for the effects of netrins on myocardial infarction.

Next, we generate mice in which the ectopic expression of netrins can be controlled spatially and temporally. The initial focus is on expressing Netrin-1 in adult cardiomyocytes (FIG. 11). First, an artificial exon containing Netrin-1 cDNA is targeted to the first intron of the ROSA 26 locus. This loci has a high recombination frequency making it easy to target, and others have used its promoter to drive expression of paracrine factors 99. Netrin-1 expression is silenced by the presence of a loxP-flanked transcriptional stop signal preceding the Netrin-1 coding sequences. Netrin-1 expression can be induced by removal of this signal following activation of the CRE recombinase. A second allele of ROSA 26 containing a CRE-activatable lacZ gene is available and is used to assess the fidelity of the system. The ROSA loci are notable for the ease of recombination and the robustness of the promoter to drive expression of paracrine factors 99. The embryonic stem cells bearing either Netrin-1 or Netrin-4 targeted to the ROSA 26 loci will be identified by southern blot analysis shortly. Second, genetic crossing allows us to generate mice containing the two ROSA 26 alleles, Netrin-1 (net) and Lac Z (lac), as well as a transgene in which CRE is under: (1) transcriptional control of the MHC promoter, activated in mature cardiomyocytes; and (2) post-translational regulation by virtue of fusion to a tamoxifen-responsive estrogen receptor element. These mice, ROSA26 net/lac; MHC-CREer are thus predicted to express Netrin-1 from the ROSA26 locus only in heart tissue and only after exposure to tamoxifen.

Example 11

Investigation of the Effect of Netrins on Ischemic Neuropathy & Hindlimb

Peripheral vascular disease caused by atherosclerosis and/or diabetes can be modeled in rodents and rabbits by surgical ligation of the femoral artery and removal of a segment of the artery distal to the ligation. It is known that the limb ischemia produced by the ligation also results in limb neuropathy. Ischemic injury of healthy animals and humans activates a number of pathways which subsequently induce the regeneration and recovery of the damaged tissue. For example, VEGF is induced in response to hindlimb ischemia and can accelerate recovery when given pharmacologically following this ischemic insult. We investigate the possibility that netrins modulate limb ischemia in animals and humans, and that netrin related therapeutic agents are beneficial both in the endogenous and pharmacological settings to revascularization and recovery from ischemic neuropathy.

For these purposes, we can carry out studies in animal models, such as Hindlimb Ischemia (HLI) model on FVB mice (nondiabetic) and diabetic mouse model (mutant mice db/db). The animals are treated with netrin, and the effect of netrin on diabetic/ischemic neuropathy and ischemic hindlimb (HLI model) is then evaluated. Alternatively, studies can be carried out in BMT model (Rosa 26 BMT db/db mice). We evaluate bone marrow-derived cell contribution to ischemic site after netrin treatment.

The animal models can be treated (administered) with a gene such as a plasmid DNA encoding a netrin, or a protein such as a recombinant mouse netrin-1 protein.

Evaluations of the animal models can be done include: 1) neurophysiological measurement such as sensory nerve conduction velocity (SNCV), motor nerve conduction velocity (MNCV), and tailflick test; 2) Laser Doppler Imaging (LDI), for example, for ischemic limb (HLI model); 3) histology/fluorescent staining, for example, for nerve & muscle (capillary by FITC-BS1 lectin); and 4) double immunofluorescent staining, such as with eNOS, VEGF and Netrin1 with Isolectin B4/actinin and S100.

In addition, we can carry out in vitro studies, for example, in mouse endothelial cell & Schwann cell treated with Netrin. Effects of netrin can be determined by various assays, including migration assay, proliferation assay, adhesion assay, apoptosis assay, tube formation assay, angiogenesis cDNA gene array, and western blot for VEGF, eNOS and other markers. In particular, we determine whether netrin modulates one of the following signaling pathways: 1) UNC5B receptor (a repulsive netrin receptor in endothelial cells controlling morphogenesis of the vascular system); 2) MAP1B (a neuron-specific microtubule-associated protein implicated in the crosstalk between microtubules and actin filaments); and 3) FAK (focal Ahesion Kinase, implicated in regulating cell adhesion and migration).

INCORPORATION BY REFERENCE

All publications, patents and patent applications are herein incorporated by reference in their entirety to the same extent as if each individual publication, patent or patent application was specifically and individually indicated to be incorporated by reference in its entirety.

EQUIVALENTS

While specific embodiments of the subject invention have been discussed, the above specification is illustrative and not restrictive. Many variations of the invention will become apparent to those skilled in the art upon review of this specification and the claims below. Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting angiogenesis in a subject in need thereof, comprising administering an antibody that binds a netrin1 polypeptide, in an amount effective to inhibit angiogenesis, wherein said netrin1 polypeptide comprises the amino acid sequence SEQ ID NO: 2 or SEQ ID NO: 4, and wherein said antibody inhibits the angiogenic activity of said netrin1 polypeptide.

* * * * *

UNITED STATES PATENT AND TRADEMARK OFFICE
CERTIFICATE OF CORRECTION

| | | Page 1 of 1 |
|---|---|---|
| PATENT NO. | : 8,097,253 B2 | |
| APPLICATION NO. | : 12/271825 | |
| DATED | : January 17, 2012 | |
| INVENTOR(S) | : Dean Y. Li and Kyle Won Park | |

It is certified that error appears in the above-identified patent and that said Letters Patent is hereby corrected as shown below:

In the Specification

Column 1, insert a new paragraph after Line 11, --This invention was made with government support under HL065648 awarded by the National Institutes of Health. The government has certain rights in the invention.--

Signed and Sealed this
Twenty-second Day of December, 2015

Michelle K. Lee
*Director of the United States Patent and Trademark Office*

SEQUENCE LISTING

```
<160> NUMBER OF SEQ ID NOS: 44

<210> SEQ ID NO 1
<211> LENGTH: 1812
<212> TYPE: DNA
<213> ORGANISM: Mouse

<400> SEQUENCE: 1
atgatgcgcg ctgtgtggga ggcgctggcg gcgctggcgg cggtggcgtg cctggtgggc      60
gcggtccgcg ggcccgggct tagcatgttc gccggccagg cggcgcagcc tgatccttgc     120
tcggatgaga atggacaccc gcgccgctgc atcccggact ttgtcaacgc cgccttcggc     180
aaggacgtgc gcgtgtccag cacctgcggc cggcccccgg cgcgctactg cgtggtgagc     240
gagcgtggtg aagagcgcgt gcgctcctgt cacctctgca actcttcgga tcccaagaaa     300
gcgcacccgc ccgccttcct caccgacctc aataacccgc acaacctgac gtgctggcag     360
tccgagaact acctgcagtt cccgcacaac gtgacgctca ctctgtcgct cggcaagaag     420
tttgaggtga cctatgtgag cctgcaattc tgctcgccgc ggccagagtc catggccatc     480
tacaagtcca tggactacgg gcgcacgtgg gtgcccttcc agttctattc cacgcagtgc     540
cgcaaaatgt acaaccggcc gcaccgcgcg cctatcacca aacagaacga gcaggaggcc     600
gtgtgcaccg actcgcacac cgacatgcgc ccgctctctg gcgggctgat cgctttcagc     660
acgctggacg ggcggccctc ggcgcacgac ttcgacaact cgccggtgct gcaggactgg     720
gtcacggcca ccgacatccg cgtggctttc agccgcctga cacgttcgg cgacgagaac     780 gaagacgact cggagctggc gcgcgactcc tattactatg cagtgtctga cctgcaggtt     840
ggcggccgct gcaagtgcaa cggccacgcg gcgcgttgcg tgcgcgaccg agacgacagt     900
ctggtgtgtg actgtaggca caacacggcc ggccctgaat gcgaccgttg caagcccttc     960
cactacgacc ggccctggca gcgcgccacg gcccgcgagg ccaacgagtg cgtggcctgc    1020
aactgcaacc tccatgctcg gcgctgcaga ttcaacatgg agctctataa gctatcaggg    1080
cgcaagagcg ggggagtstg tctcaactgc cgccacaaca ctgcgggccg ccactgccac    1140
tactgcaagg agggcttcta ccgagacatg ggcaagccta tcacccaccg gaaggcttgc    1200
aaagcctgtg attgccaccc agtgggtgct gctggcaaga cctgcaatca aaccactggc    1260
caatgtccct gcaaggacgg cgtgacgggc atcacctgca accgatgtgc caaaggctac    1320
cagcagagcc gttcccccat cgcccttgc atcaagattc ctgtggcgcc gcccaccact    1380
gcagccagca gcgtggagga accggaagac tgtgattcct attgcaaggc ctccaaaggc    1440
aagctgaaga tgaacatgaa gaaatactgc aggaaggact atgctgtcca gatccacatc    1500
ctgaaggccg acaaagcagg ggactggtgg aagttcaccg tgaacatcat ctccgtgtac    1560
aagcagggca caagtcgtat tcgccgtggt gaccagagtt tgtggatccg ctcacgagac    1620
atcgcctgca agtgtcccaa aatcaagccc ctcaagaagt acttgctgtt gggtaatgcc    1680
gaggactcac ctgaccagag tggcatcgtg gcagacaaga gcagcctggt gatccagtgg    1740
cgggacacat gggcacggcg gctgcgcaag ttccagcaac gggagaagaa gggcaagtgc    1800
aagaaggcct ag                                                        1812
```

<210> SEQ ID NO 2
<211> LENGTH: 603
<212> TYPE: PRT
<213> ORGANISM: Mouse

<400> SEQUENCE: 2

```
Met Met Arg Ala Val Trp Glu Ala Leu Ala Leu Ala Ala Val Ala
 1               5                  10                  15

Cys Leu Val Gly Ala Val Arg Gly Pro Gly Leu Ser Met Phe Ala Gly
                20                  25                  30

Gln Ala Ala Gln Pro Asp Pro Cys Ser Asp Glu Asn Gly His Pro Arg
            35                  40                  45

Arg Cys Ile Pro Asp Phe Val Asn Ala Ala Phe Gly Lys Asp Val Arg
        50                  55                  60

Val Ser Ser Thr Cys Gly Arg Pro Pro Ala Arg Tyr Cys Val Val Ser
 65              70                  75                  80

Glu Arg Gly Glu Glu Arg Val Arg Ser Cys His Leu Cys Asn Ser Ser
                85                  90                  95

Asp Pro Lys Lys Ala His Pro Pro Ala Phe Leu Thr Asp Leu Asn Asn
            100                 105                 110

Pro His Asn Leu Thr Cys Trp Gln Ser Glu Asn Tyr Leu Gln Phe Pro
        115                 120                 125

His Asn Val Thr Leu Thr Leu Ser Leu Gly Lys Lys Phe Glu Val Thr
130                 135                 140

Tyr Val Ser Leu Gln Phe Cys Ser Pro Arg Pro Glu Ser Met Ala Ile
145                 150                 155                 160

Tyr Lys Ser Met Asp Tyr Gly Arg Thr Trp Val Pro Phe Gln Phe Tyr
                165                 170                 175

Ser Thr Gln Cys Arg Lys Met Tyr Asn Arg Pro His Arg Ala Pro Ile
            180                 185                 190

Thr Lys Gln Asn Glu Gln Glu Ala Val Cys Thr Asp Ser His Thr Asp
        195                 200                 205

Met Arg Pro Leu Ser Gly Gly Leu Ile Ala Phe Ser Thr Leu Asp Gly
    210                 215                 220

Arg Pro Ser Ala His Asp Phe Asp Asn Ser Pro Val Leu Gln Asp Trp
225                 230                 235                 240

Val Thr Ala Thr Asp Ile Arg Val Ala Phe Ser Arg Leu His Thr Phe
                245                 250                 255

Gly Asp Glu Asn Glu Asp Asp Ser Glu Leu Ala Arg Asp Ser Tyr Tyr
            260                 265                 270

Tyr Ala Val Ser Asp Leu Gln Val Gly Gly Arg Cys Lys Cys Asn Gly
        275                 280                 285

His Ala Ala Arg Cys Val Arg Asp Arg Asp Asp Ser Leu Val Cys Asp
    290                 295                 300

Cys Arg His Asn Thr Ala Gly Pro Glu Cys Asp Arg Cys Lys Pro Phe
305                 310                 315                 320

His Tyr Asp Arg Pro Trp Gln Arg Ala Thr Ala Arg Glu Ala Asn Glu
                325                 330                 335

Cys Val Ala Cys Asn Cys Asn Leu His Ala Arg Arg Cys Arg Phe Asn
            340                 345                 350

Met Glu Leu Tyr Lys Leu Ser Gly Arg Lys Ser Gly Gly Val Cys Leu
        355                 360                 365

Asn Cys Arg His Asn Thr Ala Gly Arg His Cys His Tyr Cys Lys Glu
    370                 375                 380
```

| Gly | Phe | Tyr | Arg | Asp | Met | Gly | Lys | Pro | Ile | Thr | His | Arg | Lys | Ala | Cys |
| 385 | | | | | 390 | | | | | 395 | | | | | 400 |

| Lys | Ala | Cys | Asp | Cys | His | Pro | Val | Gly | Ala | Ala | Gly | Lys | Thr | Cys | Asn |
| | | | 405 | | | | | 410 | | | | | 415 | | |

| Gln | Thr | Thr | Gly | Gln | Cys | Pro | Cys | Lys | Asp | Gly | Val | Thr | Gly | Ile | Thr |
| | | | 420 | | | | | 425 | | | | | 430 | | |

| Cys | Asn | Arg | Cys | Ala | Lys | Gly | Tyr | Gln | Gln | Ser | Arg | Ser | Pro | Ile | Ala |
| | | 435 | | | | | 440 | | | | | 445 | | | |

| Pro | Cys | Ile | Lys | Ile | Pro | Val | Ala | Pro | Pro | Thr | Thr | Ala | Ala | Ser | Ser |
| | 450 | | | | | 455 | | | | | 460 | | | | |

| Val | Glu | Glu | Pro | Glu | Asp | Cys | Asp | Ser | Tyr | Cys | Lys | Ala | Ser | Lys | Gly |
| 465 | | | | | 470 | | | | | 475 | | | | | 480 |

| Lys | Leu | Lys | Met | Asn | Met | Lys | Lys | Tyr | Cys | Arg | Lys | Asp | Tyr | Ala | Val |
| | | | | 485 | | | | | 490 | | | | | 495 | |

| Gln | Ile | His | Ile | Leu | Lys | Ala | Asp | Lys | Ala | Gly | Asp | Trp | Trp | Lys | Phe |
| | | | 500 | | | | | 505 | | | | | 510 | | |

| Thr | Val | Asn | Ile | Ile | Ser | Val | Tyr | Lys | Gln | Gly | Thr | Ser | Arg | Ile | Arg |
| | | 515 | | | | | 520 | | | | | 525 | | | |

| Arg | Gly | Asp | Gln | Ser | Leu | Trp | Ile | Arg | Ser | Arg | Asp | Ile | Ala | Cys | Lys |
| | 530 | | | | | 535 | | | | | 540 | | | | |

| Cys | Pro | Lys | Ile | Lys | Pro | Leu | Lys | Lys | Tyr | Leu | Leu | Gly | Asn | Ala |
| 545 | | | | | 550 | | | | | 555 | | | | | 560 |

| Glu | Asp | Ser | Pro | Asp | Gln | Ser | Gly | Ile | Val | Asp | Lys | Ser | Ser | Leu |
| | | | | 565 | | | | | 570 | | | | | 575 | |

| Val | Ile | Gln | Trp | Arg | Asp | Thr | Trp | Ala | Arg | Arg | Leu | Arg | Lys | Phe | Gln |
| | | | 580 | | | | | 585 | | | | | 590 | | |

| Gln | Arg | Glu | Lys | Lys | Gly | Lys | Cys | Lys | Lys | Ala |
| | | 595 | | | | | 600 | | | |

```
<210> SEQ ID NO 3
<211> LENGTH: 1989
<212> TYPE: DNA
<213> ORGANISM: Homo sapiens

<400> SEQUENCE: 3
agcttcgggg gcgagcgctc gtgtgtgtga gtgcgcgccg ccagcgcgc cttctgcggc      60 aggcggacag atcctcggcg cggcagggcc ggggcaagct ggacgcagca tgatgcgcgc    120
agtgtgggag gcgctggcgg cgctggcggc ggtggcgtgc ctggtgggcg cggtgcgcgg    180
cgggcccggg ctcagcatgt tcgcgggcca ggcggcgcag cccgatccct gctcggacga    240
gaacggccac ccgcgccgct gcatcccgga cttt gtcaat gcggccttcg gcaaggacgt    300
gcgcgtgtcc agcacctgcg gccggccccc ggcgcgctac tgcgtggtga gcgagcgcgg    360
cgaggagcgg ctgcgctcgt gccacctctg caacgcgtcc gaccccaaga aggcgcaccc    420
gcccgccttc ctcaccgacc tcaacaaccc gcacaacctg acgtgctggc agtccgagaa    480
ctacctgcag ttcccgcaca cgtcacgct cacactgtcc ctcggcaaga agttcgaagt    540
gacctacgtg agcctgcagt tctgctcgcc gcggcccgag tccatggcca tctacaagtc    600
catggactac gggcgcacgt gggtgccctt ccagttctac tccacgcagt gccgcaagat    660
gtacaaccgg ccgcaccgcg cgcccatcac caagcagaac gagcaggagg ccgtgtgcac    720
cgactcgcac accgacatgc gcccgctctc gggcggcctc atcgccttca gcacgctgga    780
cgggcggccc tcggcgcacg acttcgacaa ctcgcccgtg ctgcaggact gggtcacggc    840
cacagacatc cgcgtggcct tcagccgcct gcacacgttc ggcgacgaga acgaggacga    900
```

-continued

```
ctcggagctg gcgcgcgact cgtacttcta cgcggtgtcc gacctgcagg tgggcggccg    960
gtgcaagtgc aacggccacg cggcccgctg cgtgcgcgac cgcaccgaca gcctggtgtg   1020
cgactgcagg cacaacacgg ccggcccgga gtgcgaccgc tgcaagccct tccactacga   1080
ccggccctgg cagcgcgcca cagcccgcga agccaacgag tgcgtggcct gtaactgcaa   1140
cctgcatgcc cggcgctgcc gcttcaacat ggagctctac aagctttcgg ggcgcaagag   1200
cggaggtgtc tgcctcaact gtcgccacaa caccgccggc cgccactgcc attactgcaa   1260
ggagggctac taccgcgaca tgggcaagcc catcacccac cggaaggcct gcaaagcctg   1320
tgattgccac cctgtgggtg ctgctggcaa aacctgcaac caaaccaccg ccagtgtcc   1380 ctgcaaggac ggcgtgacgg gtatcacctg caaccgctgc gccaaaggct accagcagag   1440
ccgctctccc atcgccccct gcataaagat ccctgtagcg ccgccgacga ctgcagccag   1500
cagcgtggag gagcctgaag actgcgattc ctactgcaag gcctccaagg ggaagctgaa   1560
gattaacatg aaaaagtact gcaagaagga ctatgccgtc cagatccaca tcctgaaggc   1620
ggacaaggcg ggggactggt ggaagttcac ggtgaacatc atctccgtgt ataagcaggg   1680
cacgagccga atccgccgcg gtgaccgag cctgtggatc cgctcgcggg acatcgcctg   1740
caagtgtccc aaaatcaagc ccctcaagaa gtacctgctg ctgggcaacg cggaggactc   1800
tccggaccag agcggcatcg tggccgataa aagcagcctg gtgatccagt ggcgggacac   1860
gtgggcgcgg cggctgcgca agttccagca gcgtgagaag aagggcaagt gcaagaaggc   1920
ctagcgccga ggcagcgggc gggcgggccg ggcgggcccg agggcggggc gagcgagacg   1980
gcgcttggc                                                           1989
```

<210> SEQ ID NO 4
<211> LENGTH: 604
<212> TYPE: PRT
<213> ORGANISM: Homo sapiens

<400> SEQUENCE: 4

```
Met Met Arg Ala Val Trp Glu Ala Leu Ala Ala Leu Ala Ala Val Ala
 1               5                  10                  15

Cys Leu Val Gly Ala Val Arg Gly Gly Pro Gly Leu Ser Met Phe Ala
                20                  25                  30

Gly Gln Ala Ala Gln Pro Asp Pro Cys Ser Asp Glu Asn Gly His Pro
            35                  40                  45

Arg Arg Cys Ile Pro Asp Phe Val Asn Ala Ala Phe Gly Lys Asp Val
        50                  55                  60

Arg Val Ser Ser Thr Cys Gly Arg Pro Pro Ala Arg Tyr Cys Val Val
 65                  70                  75                  80

Ser Glu Arg Gly Glu Glu Arg Leu Arg Ser Cys His Leu Cys Asn Ala
                85                  90                  95

Ser Asp Pro Lys Lys Ala His Pro Ala Phe Leu Thr Asp Leu Asn Asn
               100                 105                 110

Pro His Asn Leu Thr Cys Trp Gln Ser Glu Asn Tyr Leu Gln Phe Pro
           115                 120                 125

His Asn Val Thr Leu Thr Leu Ser Leu Gly Lys Lys Phe Glu Val Thr
       130                 135                 140

Tyr Val Ser Leu Gln Phe Cys Ser Pro Arg Pro Glu Ser Met Ala Ile
145                 150                 155                 160

Tyr Lys Ser Met Asp Tyr Gly Arg Thr Trp Val Pro Phe Gln Phe
               165                 170                 175
```

-continued

```
Tyr Ser Thr Gln Cys Arg Lys Met Tyr Asn Arg Pro His Arg Ala Pro
                180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Asp Ser Glu Leu Ala Arg Asp Ser Tyr
            260                 265                 270

Phe Tyr Ala Val Ser Asp Leu Gln Val Gly Gly Arg Cys Lys Cys Asn
        275                 280                 285

Gly His Ala Ala Arg Cys Val Arg Asp Arg Thr Asp Ser Leu Val Cys
    290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
            340                 345                 350

Asn Met Glu Leu Tyr Lys Leu Ser Gly Arg Lys Ser Gly Gly Val Cys
        355                 360                 365

Leu Asn Cys Arg His Asn Thr Ala Gly Arg His Cys His Tyr Cys Lys
    370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
            420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
    450                 455                 460

Ser Val Glu Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
                485                 490                 495

Val Gln Ile His Ile Leu Lys Ala Asp Lys Ala Gly Asp Trp Trp Lys
            500                 505                 510

Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
    530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
        595                 600
```

<210> SEQ ID NO 5
<211> LENGTH: 1986
<212> TYPE: DNA
<213> ORGANISM: Homo sapiens

<400> SEQUENCE: 5

| | | | | | |
|---|---|---|---|---|---|
| gaggacgcgc | caacatcccc | gctgctgtgc | tgggcccggg | gcgtgcccgc | cgctgctccc | 60 |
| acctctgggc | cgggctgggg | ccgcccgggg | gccctgttcc | tcggcattgc | gggcctggtg | 120 |
| ggcagaaccg | cggagagggc | ttcttttccc | caagggcagc | gtcttggggc | ccggccactg | 180 |
| gctgacccgc | agcggctccg | gccatgcctg | gctggccctg | ggggctgctg | ctgacggcag | 240 |
| gcacgctctt | cgccgccctg | agtcctgggc | cgcggcgcc | cgccgacccc | tgccacgatg | 300 |
| aggggggtgc | gccccgcggc | tgcgtgccag | gactggtgaa | cgccgccctg | ggccgcgagg | 360 |
| tgctggcttc | cagcacgtgc | gggcggccgg | ccactcgggc | ctgcgacgcc | tccgacccgc | 420 |
| gacgggcaca | ctcccccgcc | ctccttactt | ccccagggg | cacggccagc | cctctgtgct | 480 |
| ggcgctcgga | gtccctgcct | cgggcgcccc | tcaacgtgac | tctcacggtg | ccctgggca | 540 |
| aggcttttga | gctggtcttc | gtgagcctgc | gcttctgctc | agctccccca | gcctccgtgg | 600 |
| ccctgctcaa | gtctcaggac | catggccgca | gctgggcccc | gctgggcttc | ttctcctccc | 660 |
| actgtgacct | ggactatggc | cgtctgcctg | ccctgccaa | tggcccagct | ggcccagggc | 720 |
| ctgaggccct | gtgcttcccc | gcaccctgg | ccagcctga | tggcagcggc | cttctggcct | 780 |
| tcagcatgca | ggacagcagc | ccccaggcc | tggacctgga | cagcagccca | gtgctccaag | 840 |
| actgggtgac | cgccaccgac | gtccgtgtag | tgctcacaag | gcctagcacg | gcaggtgacc | 900 |
| ccagggacat | ggaggccgtc | gtcccttact | cctacgcagc | caccgacctc | caggtgggcg | 960 |
| ggcgctgcaa | gtgcaatgga | catgcctcac | ggtgcctgct | ggacacacag | ggccacctga | 1020 |
| tctgcgactg | tcggcatggc | accgagggcc | ctgactgcgg | ccgctgcaag | cccttctact | 1080 |
| gcgacaggcc | atgcagcgg | gccactgccc | gggaatccca | cgcctgcctc | gcttgctcct | 1140 |
| gcaacggcca | tgcccgccgc | tgccgcttca | acatggagct | gtaccgactg | tccgccgcc | 1200 |
| gcagcggggg | tgtctgtctc | aactgccggc | acaacaccgc | cggccgccac | tgccactact | 1260 |
| gccgggaggc | cttctatcga | gaccctggcc | gtgccctgag | tgaccgtcgg | gcttgcaggg | 1320 |
| cctgcgactg | tcacccggtt | ggtgctgctg | gcaagacctg | caaccagacc | acaggccagt | 1380 |
| gtccctgcaa | ggatggcgtc | actggcctca | cctgcaaccg | ctgcgcgcct | ggcttccagc | 1440 |
| aaagccgctc | cccagtggcg | ccctgtgtta | agaccccctat | ccctggaccc | actgaggaca | 1500 |
| gcagccctgt | gcagcccag | gactgtgact | cgcactgcaa | acctgcccgt | ggcagctacc | 1560 |
| gcatcagcct | aaagaagttc | tgcaagaagg | actatgcggt | gcaggtggcg | gtgggtgcgc | 1620 |
| gcggcgaggc | gcgcgcgcg | tggacacgct | tcccggtggc | ggtgctcgcc | gtgttccgga | 1680 |
| gcggagagga | gcgcgcgcgg | cgcggagta | gcgcgctgtg | ggtgcccgcc | ggggatgcgg | 1740 |
| cctgcggctg | cccgcgcctg | ctccccggcc | gccgctacct | cctgctgggg | ggcgggcctg | 1800 |
| gagccgcggc | tgggggcgcg | ggggccggg | ggcccggct | catcgccgcc | cgcggaagcc | 1860 |
| tcgtgctacc | ctggagggac | gcgtggacgc | ggcgcctgcg | gaggctgcag | cgacgcgaac | 1920 |
| ggcggggcg | ctgcagcgcc | gcctgagccc | ccggctggg | cagggcggcc | gctgctccca | 1980 |
| catcta | | | | | 1986 |

<210> SEQ ID NO 6
<211> LENGTH: 580

<212> TYPE: PRT
<213> ORGANISM: Homo sapiens

<400> SEQUENCE: 6

```
Met Pro Gly Trp Pro Trp Gly Leu Leu Leu Thr Ala Gly Thr Leu Phe
 1               5                  10                  15

Ala Ala Leu Ser Pro Gly Pro Pro Ala Pro Asp Pro Cys His Asp
            20                  25                  30

Glu Gly Gly Ala Pro Arg Gly Cys Val Pro Gly Leu Val Asn Ala Ala
        35                  40                  45

Leu Gly Arg Glu Val Leu Ala Ser Ser Thr Cys Gly Arg Pro Ala Thr
 50                  55                  60

Arg Ala Cys Asp Ala Ser Asp Pro Arg Arg Ala His Ser Pro Ala Leu
 65                  70                  75                  80

Leu Thr Ser Pro Gly Gly Thr Ala Ser Pro Leu Cys Trp Arg Ser Glu
                85                  90                  95

Ser Leu Pro Arg Ala Pro Leu Asn Val Thr Leu Thr Val Pro Leu Gly
                100                 105                 110

Lys Ala Phe Glu Leu Val Phe Val Ser Leu Arg Phe Cys Ser Ala Pro
        115                 120                 125

Pro Ala Ser Val Ala Leu Leu Lys Ser Gln Asp His Gly Arg Ser Trp
 130                 135                 140

Ala Pro Leu Gly Phe Phe Ser Ser His Cys Asp Leu Asp Tyr Gly Arg
145                 150                 155                 160

Leu Pro Ala Pro Ala Asn Gly Pro Ala Gly Pro Gly Pro Glu Ala Leu
                165                 170                 175

Cys Phe Pro Ala Pro Leu Ala Gln Pro Asp Gly Ser Gly Leu Leu Ala
            180                 185                 190

Phe Ser Met Gln Asp Ser Ser Pro Pro Gly Leu Asp Leu Asp Ser Ser
        195                 200                 205

Pro Val Leu Gln Asp Trp Val Thr Ala Thr Asp Val Arg Val Val Leu
 210                 215                 220

Thr Arg Pro Ser Thr Ala Gly Asp Pro Arg Asp Met Glu Ala Val Val
225                 230                 235                 240

Pro Tyr Ser Tyr Ala Ala Thr Asp Leu Gln Val Gly Gly Arg Cys Lys
                245                 250                 255

Cys Asn Gly His Ala Ser Arg Cys Leu Leu Asp Thr Gln Gly His Leu
            260                 265                 270

Ile Cys Asp Cys Arg His Gly Thr Glu Gly Pro Asp Cys Gly Arg Cys
        275                 280                 285

Lys Pro Phe Tyr Cys Asp Arg Pro Trp Gln Arg Ala Thr Ala Arg Glu
 290                 295                 300

Ser His Ala Cys Leu Ala Cys Ser Cys Asn Gly His Ala Arg Arg Cys
305                 310                 315                 320

Arg Phe Asn Met Glu Leu Tyr Arg Leu Ser Gly Arg Arg Ser Gly Gly
                325                 330                 335

Val Cys Leu Asn Cys Arg His Asn Thr Ala Gly Arg His Cys His Tyr
            340                 345                 350

Cys Arg Glu Gly Phe Tyr Arg Asp Pro Gly Arg Ala Leu Ser Asp Arg
        355                 360                 365

Arg Ala Cys Arg Ala Cys Asp Cys His Pro Val Gly Ala Ala Gly Lys
 370                 375                 380

Thr Cys Asn Gln Thr Thr Gly Gln Cys Pro Cys Lys Asp Gly Val Thr
385                 390                 395                 400
```

```
Gly Leu Thr Cys Asn Arg Cys Ala Pro Gly Phe Gln Gln Ser Arg Ser
                405                 410                 415

Pro Val Ala Pro Cys Val Lys Thr Pro Ile Pro Gly Pro Thr Glu Asp
            420                 425                 430

Ser Ser Pro Val Gln Pro Gln Asp Cys Asp Ser His Cys Lys Pro Ala
        435                 440                 445

Arg Gly Ser Tyr Arg Ile Ser Leu Lys Lys Phe Cys Lys Lys Asp Tyr
    450                 455                 460

Ala Val Gln Val Ala Val Gly Ala Arg Gly Glu Ala Arg Gly Ala Trp
465                 470                 475                 480

Thr Arg Phe Pro Val Ala Val Leu Ala Val Phe Arg Ser Gly Glu Glu
                485                 490                 495

Arg Ala Arg Arg Gly Ser Ser Ala Leu Trp Val Pro Ala Gly Asp Ala
            500                 505                 510

Ala Cys Gly Cys Pro Arg Leu Leu Pro Gly Arg Arg Tyr Leu Leu Leu
        515                 520                 525

Gly Gly Gly Pro Gly Ala Ala Ala Gly Gly Ala Gly Gly Arg Gly Pro
    530                 535                 540

Gly Leu Ile Ala Ala Arg Gly Ser Leu Val Leu Pro Trp Arg Asp Ala
545                 550                 555                 560

Trp Thr Arg Arg Leu Arg Arg Leu Gln Arg Arg Glu Arg Arg Gly Arg
                565                 570                 575

Cys Ser Ala Ala
            580

<210> SEQ ID NO 7
<211> LENGTH: 4212
<212> TYPE: DNA
<213> ORGANISM: Mouse

<400> SEQUENCE: 7
ggtgtctgaa tctgcttctg attctggctg tcgggacaag gcccctccc ctccttcctt      60 cccggcccga gcagctccgc ccctggctag gaccaggctt gctcctgctg agcccccac     120 ccccttctgg cacagctcct ctgctctcgc tgcagccagg agaagccggc agcccgggcg    180
ccccaggccc cgcccgccca aggcccttcc cgggaggccg ggagacctgc tcctcctggc    240
cctccgtggg tgagtgctgg cggcggcgg cgggtgggc ctccgcgggc ggaggcaccg      300
ggagcggggg cgacgcctgt caacgcttca ggcctagcag gaggactcgc aacatccct    360 gctcctgtgc tcggccccgg gcgtgccggt ggctgctccc acttctgggc ctgtgctggg    420
ggccgccctg gtgctctgct atcttggcac tgcagacccg gcacgcagag tagcggacta    480
ggctctctct tcgagggcag actcgttagg cggaagctgg ctggttgact tacagcggcc    540
acggccatgc ccacctggct ctggggctg ctgctgaccg cgggcacgct ctccgctgca     600
ctgagcccag gctgccggc ctctgccgac ccctgctatg atgaggcgag ggagcctcgc      660
tcttgtattc ctggccttgt gaacgctgct ctgggccgag aggtgctggc gtccagcacg    720
tgcgggaggt cggccaatcg cgtctgcgat tcctcggacc cgcagcgggc acactctgca    780
gacctcctga cctctgctcc gggcactgca agtcctctct gttggcgctc cgatttgctg    840
caacaggcac ctttcaacgt aaccctcaca gtgcccctgg ggaaggcttt tgagctggtc    900
ttcgtgagcc tgcgcttctg ctcagctcct ccaacctccg tggccctgct taagtcgcag    960
gaccatggcc gcagctgggt ccccttgggc ttcttctctt ccagctgtac cctggactat   1020
ggccgtctgc ctgctcctgc tgatggccct tctggtccag ggccagaagc cctctgcttt   1080
```

| | |
|---|---|
| ccagccccc aggctcagcc tgatggtgga ggccttctgg ccttcagtgt gcaggatggc | 1140 |
| agcccacagg gcctggatct ggacaacagc cccgtgctcc aagactgggt gactgccaca | 1200 |
| gatattcgca tagtactcac aaggcctgcc attcaggag acaccaggga cggtggggtg | 1260 |
| acagtccct actcctactc agccactgag cttcaggtgg gaggtcgatg caagtgcaat | 1320 |
| gggcatgcct cacggtgtct gttggacacc catggccacc tggtctgcga ctgccagcat | 1380 |
| ggtacagagg gccctgattg cagccgctgc aagcccttct actgcgacag gccatggcag | 1440 |
| cgggctacag gcaggaagc ccacgcttgc cttgcttgct cctgcaacgg ccatgcgcga | 1500 |
| agatgccgct caacatgga gctctaccga ctgtccggcc gccgcagtgg gggcgtgtgc | 1560 |
| ctcaactgcc ggcacaatac agctggtcgt cactgccact actgccggga gggcttctat | 1620 |
| cgtgatccag gccgtgtcct gagtgaccgt cgtgcttgca gagcttgtga ctgccaccca | 1680 |
| gttggtgctg ctggcaaaac ctgtaaccag accacaggcc agtgtccctg taaggatggt | 1740 |
| gttactggcc tcacctgtaa ccgctgtgcc ccaggtttcc agcagagccg ttctcctgtg | 1800 |
| gcaccttgcg ttaagactcc tgtccctgga cccaccgaag aaagcagtcc tgtggagcca | 1860 |
| caggactgtg agtcacattg cagacctgcg cgtggcagtt accgaatcag cctgaagaag | 1920 |
| ttctgccgga aggactatgc ggtgcaggtg gcagtgggtg cacgcggtga ggcccgcggc | 1980 |
| tcgtggacac gctttccggt agcggtgctt gctgtgttcc gcagcggcga ggaacgcgct | 2040 |
| cgacgcggga gcagcgcgct gtgggtacca actctagacg cggcctgcgg ttgcccgcgc | 2100 |
| ctcctgcccg gccggcgtta cttgctgctg ggaggtgggc cggggctgc agctgggagc | 2160 |
| acagcgggcc ggggacaggg gctcagtgct gcccgtggaa gcctcgtgct gccttggaga | 2220 |
| gacgcctgga cccggcgcct gcggaggctg cagaggagag agcggcgggg gcgctgcggg | 2280 |
| accgcctgaa tctgcaagct gggcgtggac tgggcggact cagctctctt atcactgggc | 2340 |
| gcggcgcgtt aatcagagca ctaggctgga agtgtcacgt gcatcgccat ctaatttccc | 2400 |
| cctaccccca tccccgcttg aaacctattt ggcgatacc taccccaac ttagaggagt | 2460 |
| atgatggccc ctaagagcta tctggaggct cctagggcag ctcagaggac cctgatctta | 2520 |
| tccctcttgg ctgatacccg acgtctctta aaggtgtgaa cccgcctatt cccaggggat | 2580 |
| gctaggatga tccctctggg gtttgagcac atcccacggg ccaatgtgat tcatcaactc | 2640 |
| tctgatgctg tgatacacta gagttctcca acctctccaa aaccactgtt gccaccataa | 2700 |
| ttgcctgtac accgctgcag gggctgtggc tcaattgcac agccaagaca gcgacgtctc | 2760 |
| tgccctccag ccgggaatgt acaaagagta ttgtaggctc ccctgtccag tgtcatggat | 2820 |
| cttgtcccca tatccattct ggcctgcctc tgccggtcac gtgaccgtgt ccccatccgc | 2880 |
| agctgcatca ctgcctgtgt cccatatctt tcttgttccg ttgtacccctt ttctggggtc | 2940 |
| catccagctg tcgctttcta ccacgactcc taccagtctt ggcctcttgg ctccatgaca | 3000 |
| caggtcctgc ccctagctag gagccctaca ctctatccgc tcaagactgg acgtcgagaa | 3060 |
| ggggcagatc aggtccacgt gtgaccggac cagaggcgac ttccacgggc agccgtcgga | 3120 |
| gttctagtcg tccgtgactt tgccttacac caggcgctag ggtccccacc tctttaggcg | 3180 |
| agccccgcc ccttagcgcg ggaaccgctg tttggctagc gcatgctccc gacttggccg | 3240 |
| ccgccgggcc caaatgcgca tgctcagagc cggcagcact gagacgcggg gcactcgggg | 3300 |
| tgggcagccc gcaagcgcgt gcttgtgggg cggggccgcc tacgcgcgtg cgcagaaagt | 3360 |
| ccagtgcggt ccagcggaga gccgaaggga gaggtgcggt gcggcgcgcc gaggtgggtg | 3420 |
| cgcggcgggg gcgtggcggc tggacgcggg gtgtggggt gtcactgcca cggtgcgctg | 3480 |

-continued

```
accggcggca cggatgtact gagggagggg ggcacgggtt gtgctccgtg tcttggtcgc    3540
tgcgggttag ggggctccag agtctaatgc tgcgtgcgtg acgtgggccc cggagtcaga    3600
acccttgggg caggcccggc tttcctcgat catccctgcc ttctctgggc tctgtgtcgt    3660
gggcaagaac tgcctctgtg tcaaccttcc cttggggcac tttccgtccc tgcggaatag    3720
gaaatcctct ttctgtattc gttcgaaatt gcagcagtgt tcatataccct ttgccctcgg   3780 agacctgcaa caacccaggc ccttcacttg ccaaagatga cacaactgcc cacctgaagc    3840
ttagggactt tcccagcctg agagccctat ccagccagtg tccctgacat gccttggtca    3900
cctgtgcctt agcttggccc tgtgcttcag gagttttgaa taacagctgg agggcagagc    3960
tggcaccaca cggggtgggc tgcacatgac agaagtcagt ctgctgggtg ctggcagcct    4020
gaccacagat tttccttgac agacctgact cagttcagaa atagtgctct ggccttcttg    4080
gatggggact cactgggcta actttaaagg ccaaagattg tctagcccag cccggacata    4140
tgcaggcata ggttggccat ttgggcggtt gtgttgctgt ctttccaagg taaataaagg    4200
attttccttg tc                                                       4212

<210> SEQ ID NO 8
<211> LENGTH: 580
<212> TYPE: PRT
<213> ORGANISM: Mouse

<400> SEQUENCE: 8

Met Pro Thr Trp Leu Trp Gly Leu Leu Leu Thr Ala Gly Thr Leu Ser
1               5                   10                  15

Ala Ala Leu Ser Pro Gly Leu Pro Ala Ser Ala Asp Pro Cys Tyr Asp
                20                  25                  30

Glu Ala Arg Glu Pro Arg Ser Cys Ile Pro Gly Leu Val Asn Ala Ala
            35                  40                  45

Leu Gly Arg Glu Val Leu Ala Ser Ser Thr Cys Gly Arg Ser Ala Asn
        50                  55                  60

Arg Val Cys Asp Ser Ser Asp Pro Gln Arg Ala His Ser Ala Asp Leu
65                  70                  75                  80

Leu Thr Ser Ala Pro Gly Thr Ala Ser Pro Leu Cys Trp Arg Ser Asp
                85                  90                  95

Leu Leu Gln Gln Ala Pro Phe Asn Val Thr Leu Thr Val Pro Leu Gly
            100                 105                 110

Lys Ala Phe Glu Leu Val Phe Ser Leu Arg Phe Cys Ser Ala Pro
        115                 120                 125

Pro Thr Ser Val Ala Leu Leu Lys Ser Gln Asp His Gly Arg Ser Trp
    130                 135                 140

Val Pro Leu Gly Phe Phe Ser Ser Ser Cys Thr Leu Asp Tyr Gly Arg
145                 150                 155                 160

Leu Pro Ala Pro Ala Asp Gly Pro Ser Gly Pro Gly Pro Glu Ala Leu
                165                 170                 175

Cys Phe Pro Ala Pro Gln Ala Gln Pro Asp Gly Gly Leu Leu Ala
            180                 185                 190

Phe Ser Val Gln Asp Gly Ser Pro Gln Gly Leu Asp Leu Asp Asn Ser
        195                 200                 205

Pro Val Leu Gln Asp Trp Val Thr Ala Thr Asp Ile Arg Ile Val Leu
    210                 215                 220

Thr Arg Pro Ala Ile Gln Gly Asp Thr Arg Asp Gly Val Thr Val
225                 230                 235                 240

Pro Tyr Ser Tyr Ser Ala Thr Glu Leu Gln Val Gly Gly Arg Cys Lys
```

245                 250                 255
Cys Asn Gly His Ala Ser Arg Cys Leu Leu Asp Thr His Gly His Leu
                260                 265                 270

Val Cys Asp Cys Gln His Gly Thr Glu Gly Pro Asp Cys Ser Arg Cys
                275                 280                 285

Lys Pro Phe Tyr Cys Asp Arg Pro Trp Gln Arg Ala Thr Gly Gln Glu
                290                 295                 300

Ala His Ala Cys Leu Ala Cys Ser Cys Asn Gly His Ala Arg Arg Cys
305                 310                 315                 320

Arg Phe Asn Met Glu Leu Tyr Arg Leu Ser Gly Arg Arg Ser Gly Gly
                    325                 330                 335

Val Cys Leu Asn Cys Arg His Asn Thr Ala Gly Arg His Cys His Tyr
                340                 345                 350

Cys Arg Glu Gly Phe Tyr Arg Asp Pro Gly Arg Val Leu Ser Asp Arg
                355                 360                 365

Arg Ala Cys Arg Ala Cys Asp Cys His Pro Val Gly Ala Ala Gly Lys
                370                 375                 380

Thr Cys Asn Gln Thr Thr Gly Gln Cys Pro Cys Lys Asp Gly Val Thr
385                 390                 395                 400

Gly Leu Thr Cys Asn Arg Cys Ala Pro Gly Phe Gln Gln Ser Arg Ser
                    405                 410                 415

Pro Val Ala Pro Cys Val Lys Thr Pro Val Pro Gly Pro Thr Glu Glu
                420                 425                 430

Ser Ser Pro Val Glu Pro Gln Asp Cys Glu Ser His Cys Arg Pro Ala
                435                 440                 445

Arg Gly Ser Tyr Arg Ile Ser Leu Lys Lys Phe Cys Arg Lys Asp Tyr
                450                 455                 460

Ala Val Gln Val Ala Val Gly Ala Arg Gly Glu Ala Arg Gly Ser Trp
465                 470                 475                 480

Thr Arg Phe Pro Val Ala Val Leu Ala Val Phe Arg Ser Gly Glu Glu
                    485                 490                 495

Arg Ala Arg Arg Gly Ser Ser Ala Leu Trp Val Pro Thr Leu Asp Ala
                500                 505                 510

Ala Cys Gly Cys Pro Arg Leu Leu Pro Gly Arg Arg Tyr Leu Leu Leu
                515                 520                 525

Gly Gly Gly Pro Gly Ala Ala Ala Gly Ser Thr Ala Gly Arg Gly Gln
                530                 535                 540

Gly Leu Ser Ala Ala Arg Gly Ser Leu Val Leu Pro Trp Arg Asp Ala
545                 550                 555                 560

Trp Thr Arg Arg Leu Arg Arg Leu Gln Arg Arg Glu Arg Arg Gly Arg
                    565                 570                 575

Cys Gly Thr Ala
            580

<210> SEQ ID NO 9
<211> LENGTH: 2174
<212> TYPE: DNA
<213> ORGANISM: Mouse

<400> SEQUENCE: 9
cagggccgct cagccggcag cggccaggcc ggctatgatc ccggggctcc cgccgctgct      60
gagctgcccg ggccccgcca ggccggtgcg cgacggtcac cccgccgcct ggcgcggccc     120
cggcccgcgc ctctgtgccc acggtgccca ctgagcgagc tggcgctcc gggaggagga     180 agaaccacag agcccccggt gctcccgagg accactgccg cttcatccca cccgctcccg     240

```
cagctgcccg gccatgggga gctgcgcacg gctgctgctg ctctgggct gctccgcggt    300 ggccgcaggc ttgaatggag tagccggagc gaactcccgc tgtgagaagg catgcaaccc    360
tcgcatggga aacttggctt tgggaagaaa gctccgggca gacactatgt gtggccagaa    420
cgccaccgaa ctcttctgct tctacagtga gaatgctgac ctcacttgcc ggcagcccaa    480
gtgtgataaa tgcaacgctg cccattctca cctagctcac ccaccctctg ccatggcaga    540
ctcatccttc aggtttcccc ggacatggtg gcagtctgca gaggatgtgc acagggaaaa    600
gattcagcta gacctggaag cagaattcta cttcactcac ctaattatgg tgttcaagtc    660
tcccaggcct gcagccatgg tgctggaccg gtcccaggac tttgggaaga cctggaagcc    720
ttacaagtac tttgcaacaa actgctcggc tacttttggc ctggaagatg atgttgtcaa    780
gaagggagct atttgcacgt ctagatactc aaatcctttc ccgtgcaccg aggagaggt    840 tattttcaga gccctgtcac caccatacga catagaaaac ccttacagtg ccaaagtgca    900
ggagcagctg aagatcacca acctccgagt gcggctgctc aagcgacagt cctgcccttg    960
tcagataaac gacctgaacg caaaacctca ccattttatg cactacgcag tctatgactt   1020
catcgtcaag ggcagctgct tctgcaacgg ccacgctgac cagtgcttac ctgtggaggg   1080
cttcagaccc atcaaggccc cgggagcgtt ccacgtggtc cacggaggt gtatgtgtaa   1140 gcacaacaca gcaggcagcc actgccagca ctgtgcacca ttgtacaatg accgccctg    1200 ggaggcagca gatggcagaa caggggctcc taacgaatgc agaacttgca agtgcaatgg   1260
gcacgcggac acctgtcact cgacgtcaa cgtgtgggag cgtcgggga accgcagcgg    1320 cggtgtctgc aacaactgtc agcacaacac tgagggtcag cactgtcagc gctgtaagcc   1380
cggtttctac cgcgacctca gaagacccctt ctccgcccct gacgcttgca aagcgtgttc   1440
ctgccacccg gttggatcag cgatccttcc tttcagctca gtgaccttct gcgaccccag   1500
caatggtgac tgcccctgca gcctggggt ggcggggcca cattgtgaca gatgcatggt   1560
gggatactgg ggttttggag actacggctg cagaccttgc gattgtgcgg ggagctgcga   1620
cccgctcacg ggagactgca tcagcagtaa cgctgatgta gactggtacc acgaagtccc   1680 caccttttcac tcgatgcaca ataagagtga gcccagctgg gaatgggagg atgagcaagg   1740 atttctctgcc ctccgacact caggtaaatg tgaatgtaag gaacaggtgt taggaaaccc   1800
caaagccttc tgtggaatga agtattcata tgtgttaaaa atcaagatct tatcagccca   1860
tgacaaaggc tcccatgccg aagtcaatgt gaagattaag aaagtcttaa agtccaccaa   1920
actgaagatc ttacgaggca agagaacgct atacccagag tcctggacta acagaggctg   1980
cacctgtcca atcctcaatc caggattgga gtacctggtc gccggccacg aggacgtaag   2040
aacgggcaaa ttaattgtga atatgaaag ctttgtccag cactggaaac cagctctttgg   2100 cagaagagtc atgcacatct taaaaagaga ctgcgtgtag cactgaaggt cttaagcaca   2160
caagggcttt tcta                                                     2174
```

<210> SEQ ID NO 10
<211> LENGTH: 628
<212> TYPE: PRT
<213> ORGANISM: Mouse

<400> SEQUENCE: 10

Met Gly Ser Cys Ala Arg Leu Leu Leu Leu Trp Gly Cys Ser Ala Val
1               5                   10                  15

Ala Ala Gly Leu Asn Gly Val Ala Gly Ala Asn Ser Arg Cys Glu Lys
            20                  25                  30

```
Ala Cys Asn Pro Arg Met Gly Asn Leu Ala Leu Gly Arg Lys Leu Arg
         35                  40                  45

Ala Asp Thr Met Cys Gly Gln Asn Ala Thr Glu Leu Phe Cys Phe Tyr
     50                  55                  60

Ser Glu Asn Ala Asp Leu Thr Cys Arg Gln Pro Lys Cys Asp Lys Cys
 65                  70                  75                  80

Asn Ala Ala His Ser His Leu Ala His Pro Pro Ser Ala Met Ala Asp
                 85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Met Val Phe Lys Ser Pro Arg Pro Ala Ala Met Val Leu
        130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Arg Tyr Ser Asn Pro Phe Pro Cys Thr
            180                 185                 190

Gly Gly Glu Val Ile Phe Arg Ala Leu Ser Pro Pro Tyr Asp Ile Glu
        195                 200                 205

Asn Pro Tyr Ser Ala Lys Val Gln Glu Gln Leu Lys Ile Thr Asn Leu
        210                 215                 220

Arg Val Arg Leu Leu Lys Arg Gln Ser Cys Pro Cys Gln Ile Asn Asp
225                 230                 235                 240

Leu Asn Ala Lys Pro His His Phe Met His Tyr Ala Val Tyr Asp Phe
                245                 250                 255

Ile Val Lys Gly Ser Cys Phe Cys Asn Gly His Ala Asp Gln Cys Leu
            260                 265                 270

Pro Val Glu Gly Phe Arg Pro Ile Lys Ala Pro Gly Ala Phe His Val
        275                 280                 285

Val His Gly Arg Cys Met Cys Lys His Asn Thr Ala Gly Ser His Cys
        290                 295                 300

Gln His Cys Ala Pro Leu Tyr Asn Asp Arg Pro Trp Glu Ala Ala Asp
305                 310                 315                 320

Gly Arg Thr Gly Ala Pro Asn Glu Cys Arg Thr Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asn Asn Cys Gln His Asn Thr Glu Gly
        355                 360                 365

Gln His Cys Gln Arg Cys Lys Pro Gly Phe Tyr Arg Asp Leu Arg Arg
        370                 375                 380

Pro Phe Ser Ala Pro Asp Ala Cys Lys Ala Cys Ser Cys His Pro Val
385                 390                 395                 400

Gly Ser Ala Ile Leu Pro Phe Ser Ser Val Thr Phe Cys Asp Pro Ser
                405                 410                 415

Asn Gly Asp Cys Pro Cys Lys Pro Gly Val Ala Gly Pro His Cys Asp
            420                 425                 430

Arg Cys Met Val Gly Tyr Trp Gly Phe Gly Asp Tyr Gly Cys Arg Pro
        435                 440                 445

Cys Asp Cys Ala Gly Ser Cys Asp Pro Leu Thr Gly Asp Cys Ile Ser
```

```
                  450                 455                 460
Ser Asn Ala Asp Val Asp Trp Tyr His Glu Val Pro Thr Phe His Ser
465                 470                 475                 480

Met His Asn Lys Ser Glu Pro Ser Trp Glu Trp Glu Asp Glu Gln Gly
                485                 490                 495

Phe Ser Ala Leu Arg His Ser Gly Lys Cys Glu Cys Lys Glu Gln Val
            500                 505                 510

Leu Gly Asn Pro Lys Ala Phe Cys Gly Met Lys Tyr Ser Tyr Val Leu
        515                 520                 525

Lys Ile Lys Ile Leu Ser Ala His Asp Lys Gly Ser His Ala Glu Val
    530                 535                 540

Asn Val Lys Ile Lys Lys Val Leu Lys Ser Thr Lys Leu Lys Ile Leu
545                 550                 555                 560

Arg Gly Lys Arg Thr Leu Tyr Pro Glu Ser Trp Thr Asn Arg Gly Cys
                565                 570                 575

Thr Cys Pro Ile Leu Asn Pro Gly Leu Glu Tyr Leu Val Ala Gly His
            580                 585                 590

Glu Asp Val Arg Thr Gly Lys Leu Ile Val Asn Met Lys Ser Phe Val
        595                 600                 605

Gln His Trp Lys Pro Ala Leu Gly Arg Arg Val Met His Ile Leu Lys
    610                 615                 620

Arg Asp Cys Val
625

<210> SEQ ID NO 11
<211> LENGTH: 3607
<212> TYPE: DNA
<213> ORGANISM: Homo sapiens

<400> SEQUENCE: 11
gggacgggag gagccggggc agccagaaga ggtgggaaaa gcggaggagg acgcccagga      60
ggaggcggcg gcggcggccg ggaagtgaaa ggtctcgcaa agttcatgcg gcggctgcgg     120
gcgccgagcc ccgggatagc ggcagacgag cccgcagggc cgctccgcgg ggcagcgcag     180
ccaggccggc tatggtcccg gggctcccgc cgcccccag gtgcccggga cccgccaggc      240
cggtgcgcga gggtcacccc acctccccgc gcggtcccgg ccctggctc ccagctgccg      300
gcgaccgctg accgagcccg cgcccccagg aggaggaaga aaccagggcc ccgttccctc     360
ccgaggacgg cggcgcttca tcccgcagcc cagaggtctc ggctccctcc ggcaccccgcc    420
cggcccggct gctccctggc tcctcccggc catggggagc tgcgcgcggc tgctgctgct     480
ctggggctgc acggtggtgg ccgcaggact gagtggagta gctggagtga gttcccgctg     540
tgaaaaagcc tgcaaccctc ggatgggaaa tttggctttg gggcgaaaac tctgggcaga     600
caccacctgc ggtcagaatg ctaccgaact gtactgcttc tacagtgaga acaaggatct     660
gacttgtcgg cagcccaaat gtgacaagtg caatgctgcc tatcctcacc tggctcacct     720
gccatctgcc atggcagact catccttccg gtttcctcgc acatggtggc agtctgcgga     780
ggatgtgcac agagaaaaga tccagttaga cctggaagct gaattctact tcactcacct     840
aattgtgatg ttcaagtccc ccaggccggc tgccatggtg ctggaccgct cccaggactt     900
tgggaaaaca tggaagcctt ataagtactt tgcgactaac tgctccgcta catttggcct     960
ggaagatgat gttgtcaaga agggcgctat ttgtacttct aaatactcca gtccttttcc    1020
atgcactgga ggagggtta ttttcaaagc tttgtcacca ccacacgata cagagaaccc     1080
ttacagtgcc aaagttcagg agcagctgaa gatcaccaac cttcgcgtgc agctgctgaa    1140
```

```
acgacagtct tgtccctgtc agagaaatga cctgaacgaa gagcctcaac attttacaca    1200
ctatgcgatc tatgatttca ttgtcaaggg cagctgcttc tgcaatggcc acgccgatca    1260
atgcatacct gttcatggct tcagacctgt caaggcccca ggaacattcc acatggtcca    1320
tgggaagtgt atgtgtaagc acaacacagc aggcagccac tgccagcact gtgcccgtt     1380 atacaatgac cggccatggg aggcagctga tggcaaaacg ggggctccca acgagtgcag    1440
agcctgcaag tgtaatgggc atgctgatac ctgtcacttc gacgttaatg tgtgggaggc    1500
atcagggaat cgtagtggtg gtgtctgtga tgactgtcag cacaacacag aaggacagta    1560
ttgccagagg tgcaagccag gcttctatcg tgacctgcgg agaccttct cagctccaga    1620 tgcttgcaaa ccgtgttcct gccatccagt aggatcagct gtccttcctg ccaactcagt    1680
gaccttctgc gaccccagca atggtgactg cccttgcaag cctggggtgg cagggcgacg    1740
ttgtgacagg tgcatggtgg atactgggg cttcggagac tatggctgtc gaccatgtga     1800
ctgtgcgggg agctgtgacc ctatcaccgg agactgcatc agcagccaca cagacataga    1860
ctggtgtcat gaagttcctg acttccgtcc cgtgcacaat aagagcgaac cagcctggga    1920
gtgggaggat gcgcaggggt tttctgcact tctacactca ggtaaatgcg aatgtaagga    1980
acagacatta ggaaatgcca aggcattctg tggaatgaaa tattcatatg tgctaaaaat    2040
aaagatttta tcagctcatg ataaaggtac tcatgttgag gtcaatgtga agattaaaaa    2100
ggtcttaaaa tctaccaaac tgaagatttt ccgaggaaag cgaacattat atccagaatc    2160
atggacggac agaggatgca cttgtccaat cctcaatcct ggtttggaat accttgtagc    2220
aggacatgag gatataagaa caggcaaact aattgtgaat atgaaaagct tgtccagca     2280 ctggaaacct tctcttggaa gaaaagtcat ggatatttta aaaagagagt gcaagtagca    2340
ttaagatgga tagcacataa tggcacttgt ctatgtacaa acacaaaact ttagagcaag    2400
aagacctcag acaggaaact ggaatttttt aaagtgccaa acatataga atgtttgaa      2460 tgcatgggtc ttatctaatt tatctcttct ggacccatgt ttaaatacag ttttatttca    2520
tgaagagaaa tgaaaacccc tacactgata tctgttttct atgggactga ttctgaaatt    2580
cttaactatt aagaatattt taatagcagc atgacattta gcagtaatcc attaagggca    2640
gtacctctaa caaggacgcc ttccagcttc agctatgtta cttacgtttg atgctactta    2700
aagtaatgaa tgacgtttta aggaatccct aaccctacta tcagaaaagg tgtttgttaa    2760
agagccttct cttgtgtgtt acgcatgaac tttggtctgt aggtgttaaa tggaacctct    2820
ccatgtgtat atagtatttc cttgtataaa gcactttact acctaccact tgtgttgtga    2880
acgtttggtg actgctgttg aaagaaggaa aagggtgtgt gagaaagcct actgaagcag    2940
ctgcacggcc actacatgtg gacaaaagtg aacatataaa agaagttgtg ctatttaact    3000
ctgaatactt ggagaaacta ggtgaagatg caaccagaaa ggagaatatg tatgcgtgaa    3060
gtctcagctt tgagckggag gctagaaaga gcagccagag aacttttta aaactaacca    3120 gaagagcttt aaaataagag aaagaaatca taaatgtaga catatgcttg gctaaagggg    3180
aaatggactt taaattttaa agagctcatt tgcaatgcac ttgtatacac ttcaaaaatt    3240
attgtagaca cagaatttgt tatattttg tgcttagtat ttaaacctga acattgaaac     3300
agttttcctc cttgtctttc ttaacagtaa tagtcattat atttacctgt tttttaacac    3360
aatgtatgtg atagtcaaaa atcacagtt tttcattatt attcatcttc tgtacccacg     3420
cataaccact atacatagtt tcttttgtac ttgaatatac aaaacatgaa cacagtgcca    3480
tatgaataat ttcacataca gaaccttttt ttctctgaag tcctgtggac ttgcaaatat    3540
```

```
atatatatat tgctttgtta atttgttttt atatttcata tatgtaataa aggaatatga   3600
tctgaaa                                                              3607
```

<210> SEQ ID NO 12
<211> LENGTH: 628
<212> TYPE: PRT
<213> ORGANISM: Homo sapiens

<400> SEQUENCE: 12

```
Met Gly Ser Cys Ala Arg Leu Leu Leu Leu Trp Gly Cys Thr Val Val
 1               5                  10                  15

Ala Ala Gly Leu Ser Gly Val Ala Gly Val Ser Ser Arg Cys Glu Lys
            20                  25                  30

Ala Cys Asn Pro Arg Met Gly Asn Leu Ala Leu Gly Arg Lys Leu Trp
        35                  40                  45

Ala Asp Thr Thr Cys Gly Gln Asn Ala Thr Glu Leu Tyr Cys Phe Tyr
    50                  55                  60

Ser Glu Asn Lys Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Val Met Phe Lys Ser Pro Arg Pro Ala Ala Met Val Leu
    130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro His Asp Thr Glu
        195                 200                 205

Asn Pro Tyr Ser Ala Lys Val Gln Glu Gln Leu Lys Ile Thr Asn Leu
    210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
        275                 280                 285

Val His Gly Lys Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Ala Cys Lys Cys Asn Gly
                325                 330                 335

His Ala Asp Thr Cys His Phe Asp Val Asn Val Trp Glu Ala Ser Gly
            340                 345                 350

Asn Arg Ser Gly Gly Val Cys Asp Asp Cys Gln His Asn Thr Glu Gly
```

```
                 355                 360                 365
Gln Tyr Cys Gln Arg Cys Lys Pro Gly Phe Tyr Arg Asp Leu Arg Arg
            370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415

Asn Gly Asp Cys Pro Cys Lys Pro Gly Val Ala Gly Arg Arg Cys Asp
            420                 425                 430

Arg Cys Met Val Gly Tyr Trp Gly Phe Gly Asp Tyr Gly Cys Arg Pro
        435                 440                 445

Cys Asp Cys Ala Gly Ser Cys Asp Pro Ile Thr Gly Asp Cys Ile Ser
    450                 455                 460

Ser His Thr Asp Ile Asp Trp Cys His Glu Val Pro Asp Phe Arg Pro
465                 470                 475                 480

Val His Asn Lys Ser Glu Pro Ala Trp Glu Trp Glu Asp Ala Gln Gly
                485                 490                 495

Phe Ser Ala Leu Leu His Ser Gly Lys Cys Glu Cys Lys Glu Gln Thr
            500                 505                 510

Leu Gly Asn Ala Lys Ala Phe Cys Gly Met Lys Tyr Ser Tyr Val Leu
        515                 520                 525

Lys Ile Lys Ile Leu Ser Ala His Asp Lys Gly Thr His Val Glu Val
    530                 535                 540

Asn Val Lys Ile Lys Lys Val Leu Lys Ser Thr Lys Leu Lys Ile Phe
545                 550                 555                 560

Arg Gly Lys Arg Thr Leu Tyr Pro Glu Ser Trp Thr Asp Arg Gly Cys
                565                 570                 575

Thr Cys Pro Ile Leu Asn Pro Gly Leu Glu Tyr Leu Val Ala Gly His
            580                 585                 590

Glu Asp Ile Arg Thr Gly Lys Leu Ile Val Asn Met Lys Ser Phe Val
        595                 600                 605

Gln His Trp Lys Pro Ser Leu Gly Arg Lys Val Met Asp Ile Leu Lys
    610                 615                 620

Arg Glu Cys Lys
625

<210> SEQ ID NO 13
<211> LENGTH: 3992
<212> TYPE: DNA
<213> ORGANISM: Mouse

<400> SEQUENCE: 13
gtcggtgcgc ggcgcggctg cgctgcgct ccgccccggc tgcattgctg cgctccgggt      60
gcccagggga ccacgcgcc cgtgcgccc cgcagccggc cgcccggagg cagcgctgtc     120
ctctggcatg ggccccgggg cgccccgag gtggggctct cggctgaggc gctgacagcc     180
tctctcccgc ccgcggggcc cctagtccag cccgctcgtc cgcccgcggc catggccgtc     240
cggcccggcc tgtggccagc gctcctgggc atagtcctca ctgcctggct tcgtggttcg     300
ggtgcccagc agagtgccac agtggccaac ccagtgcctg gtgccaaccc agacctgctg     360
ccccacttcc tggtagagcc ggaggacgtg tacattgtca agaacaagcc cgtgctgctg     420
gtgtgcaagg ctgtgcccgc cacccagatc ttcttcaagt gcaacgggga atgggttcgc     480
caggtcgatc acgtcatcga acgcagcact gacggcagca gcggattgcc aaccatggag     540
gtccggatca acgtatcaag gcagcaggtc gagaaagtgt ttgggctgga ggagtactgg     600
```

```
tgccagtgtg tggcatggag ctcctcagga accaccaaaa gccagaaggc ctacatccgg    660
attgcctatt tgcgcaagaa ctttgagcag gagccgctgg ccaaggaagt gtcactggag    720
caaggcattg tgctaccttg tcgccccccg gaaggaatcc cccagctga ggtggagtgg     780 ctccgaaatg aggacctcgt ggaccctcc ctcgaccca atgtgtacat cacacgggag      840
cacagcctag tcgtgcggca ggcccgcctg gccgacactg ccaactacac ctgcgtggcc    900
aagaacatcg tggcccgtcg ccgaagcgcc tctgcggccg tcattgttta tgtgaacggt    960
gggtggtcga cgtggaccga gtggtccgtc tgcagtgcca gctgtgggcg tggctggcag   1020
aaacggagcc ggagctgcac caacccggca cctctcaacg ggggcgcctt ctgtgagggg   1080
cagaatgtcc agaaaacagc ctgcgccact ctgtgcccag tggatgggag ctggagccca   1140
tggagtaagt ggtcagcctg cgggcttgac tgcacccact ggcggagccg ggagtgctcc   1200
gacccagcgc cccgcaacgg aggtgaggag tgccggggtg ctgacctgga cacccgcaac   1260
tgtaccagtg acctctgcct gcacacctct tccggccccg aggacgtggc tctctacatc   1320
ggcctcgtcg ccgtggccgt gtgcctcatc ttgctgctgc tggtcctcgt cctcatctac   1380
tgccgcaaga aggaaggact ggactcagac gtggctgact catccatcct tacctcaggc   1440
ttccagcctg tcagcatcaa gcccagcaaa gcagacaatc ccatctgct caccatccaa    1500 ccggacctca gcaccaccac gaccacctac cagggcagcc tgtgtcccg gcaggatgga    1560 cccagcccca agttccagct ctctaatggt cacctgctca gcccactggg cagtggccgc   1620
catacgctgc accacagctc ccccacctct gaggctgagg acttcgtctc ccgcctctcc   1680
acccaaaact actttcgttc tctgccccgc ggtaccagca acatggccta tgggaccttc   1740
aacttcctcg ggggccggct gatgatccct aacacaggaa tcagcctcct catacccccg   1800
gacgccatcc cccgaggaaa gatctacgag atctacctca ctctgcacaa gccagaagac   1860
gtgaggttgc ccctagctgg ctgtcagacc ctgctgagtc ctatcgttag ctgtgggccc   1920
ccaggagtcc tgctcacccg gccagtcatc cttgccatgg accactgcgg ggagcccagt   1980
cccgacagct ggagcctgcg cctcaaaaag cagtcctgtg agggcagctg gaggacgtg    2040 ctgcaccttg gtgaggagtc gccctctcat ctctactact gccagctgga ggccggggcc   2100
tgctatgtct tcaccgagca gctaggccgc tttgccctgg tgggagaggc cctcagcgtg   2160
gctgccacca agcgcctcag gctccttctg tttgcccctg tggcctgtac gtccctcgag   2220
tacaacatcc gagtgtactg cctgcacgac acccacgatg ctctcaagga ggtggtgcag   2280
ctggagaagc agctgggtgg acagctgatc caggagcccc gtgtcctgca cttcaaagac   2340
agttaccaca acctacgtct gtccatccac gacgtgccca gctccctgtg aagagcaag    2400 ctccttgtca gctaccagga gatccctttt taccacatct ggaatggcac tcagcagtat   2460
ctgcactgca ccttcaccct ggagcgcgtc aatgccagca ccagcgacct ggcctgcaag   2520
gtgtgggtgt ggcaggtgga gggagatgga cagagcttca acatcaactt taacatcact   2580
aaggacacga ggtttgctga aatgctggct ctggagagtg aagggggggt cccagccctg   2640
gtgggcccca gtgccttcaa gatccccttc ctcattcggc aaaagatcat taccagcctg   2700
gacccaccct gcagccgggg cgccgactgg cgaactctag cccagaaact tcacctggac   2760
agccatctta gcttctttgc ctccaagccc agccctacag ccatgatcct caacctatgg   2820
gaggcgcggc acttccccaa cggcaacctc ggccagctgg ccgcagctgt ggccggactg   2880
ggccagccag atgctggcct cttcaccgtg tcagaggccg agtgctgaga ccagccaggc   2940
cggtcacgcc tacactctca ccagctttgg cacctgccag ggacaggcaa aagccagaca   3000
```

-continued

```
gggccctac ccccacaccc ggggagagct gcttggacag gccccctcc tggctgaagt   3060 tgtccctcga tgctggtcct tcagaccctg cccaaactcc atccctccat ggcctgcctg   3120
gccaggttgg tttagccacc tgttctcgct ctgccctggt cccggggccc agagtggaca   3180
gtgcctggag cctgggctga gcccagccca tctgtgtgtg tgtgtgtatg tgtgtgatgc   3240
tacctctctt cctgtccctt gcagggggcc ccgcatacac acagcatgcg cacacatgct   3300
gggcttggga cacggccccc agagctcctg cctgaggtgg gccttatgca aacatttctg   3360
tgcctgctgg gtaggggtct atttgagggg cctggcttca agcctggggg gactaagggt   3420
cccagctgga caggggctgg cccttggatt caggcacacg atcaccacac aggcgtgtgt   3480
tcatgcatgc ctcgtgtgct catctcacac gcacccctct cccaggtcat gcaggacccc   3540
tccccccacc acacacacat ctcatgctgt gcacccggag gctgctcacg tctctcacac   3600
ccggtgtcgg tgtcggtaca catctgcctc tcacatgctg cccttctccc acccacccag   3660
ggacacccga cggctcctcc ctgatccttt ccctgtaccc cggcctcgag gtgccctgcc   3720
cagcggggcg tgtgaatatg caatgggagt cccgggctgt acaatggcaa gtgtgtgtgc   3780
cgtggcgtgc ccgttcctgg ggctggccaa tgccctgtg tggggcctgt tgtgtgaagc   3840
ttgtgtcctg actctgtctt aagtgcattc ctgcacttac acttggcctt atgtacacag   3900
ccttgcccgg ctgccggggc acgtagggat tttagcggat gtgaatgtaa ataaattata   3960
tatatatatt gctaaaaaaa aaaaaaaaaa aa                                 3992
```

<210> SEQ ID NO 14
<211> LENGTH: 898
<212> TYPE: PRT
<213> ORGANISM: Mouse

<400> SEQUENCE: 14

```
Met Ala Val Arg Pro Gly Leu Trp Pro Ala Leu Leu Gly Ile Val Leu
 1               5                  10                  15

Thr Ala Trp Leu Arg Gly Ser Gly Ala Gln Gln Ser Ala Thr Val Ala
            20                  25                  30

Asn Pro Val Pro Gly Ala Asn Pro Asp Leu Leu Pro His Phe Leu Val
        35                  40                  45

Glu Pro Glu Asp Val Tyr Ile Val Lys Asn Lys Pro Val Leu Leu Val
    50                  55                  60

Cys Lys Ala Val Pro Ala Thr Gln Ile Phe Phe Lys Cys Asn Gly Glu
65                  70                  75                  80

Trp Val Arg Gln Val Asp His Val Ile Glu Arg Ser Thr Asp Gly Ser
                85                  90                  95

Ser Gly Leu Pro Thr Met Glu Val Arg Ile Asn Val Ser Arg Gln Gln
            100                 105                 110

Val Glu Lys Val Phe Gly Leu Glu Glu Tyr Trp Cys Gln Cys Val Ala
        115                 120                 125

Trp Ser Ser Ser Gly Thr Thr Lys Ser Gln Lys Ala Tyr Ile Arg Ile
    130                 135                 140

Ala Tyr Leu Arg Lys Asn Phe Glu Gln Glu Pro Leu Ala Lys Glu Val
145                 150                 155                 160

Ser Leu Glu Gln Gly Ile Val Leu Pro Cys Arg Pro Pro Glu Gly Ile
                165                 170                 175

Pro Pro Ala Glu Val Glu Trp Leu Arg Asn Glu Asp Leu Val Asp Pro
            180                 185                 190

Ser Leu Asp Pro Asn Val Tyr Ile Thr Arg Glu His Ser Leu Val Val
```

```
                195                 200                 205
Arg Gln Ala Arg Leu Ala Asp Thr Ala Asn Tyr Thr Cys Val Ala Lys
            210                 215                 220

Asn Ile Val Ala Arg Arg Ser Ala Ser Ala Val Ile Val Tyr
225                 230                 235                 240

Val Asn Gly Gly Trp Ser Thr Trp Thr Glu Trp Ser Val Cys Ser Ala
                    245                 250                 255

Ser Cys Gly Arg Gly Trp Gln Lys Arg Ser Arg Ser Cys Thr Asn Pro
            260                 265                 270

Ala Pro Leu Asn Gly Gly Ala Phe Cys Glu Gly Gln Asn Val Gln Lys
            275                 280                 285

Thr Ala Cys Ala Thr Leu Cys Pro Val Asp Gly Ser Trp Ser Pro Trp
        290                 295                 300

Ser Lys Trp Ser Ala Cys Gly Leu Asp Cys Thr His Trp Arg Ser Arg
305                 310                 315                 320

Glu Cys Ser Asp Pro Ala Pro Arg Asn Gly Gly Glu Glu Cys Arg Gly
                325                 330                 335

Ala Asp Leu Asp Thr Arg Asn Cys Thr Ser Asp Leu Cys Leu His Thr
            340                 345                 350

Ser Ser Gly Pro Glu Asp Val Ala Leu Tyr Ile Gly Leu Val Ala Val
        355                 360                 365

Ala Val Cys Leu Ile Leu Leu Leu Val Leu Val Leu Ile Tyr Cys
        370                 375                 380

Arg Lys Lys Glu Gly Leu Asp Ser Asp Val Ala Asp Ser Ser Ile Leu
385                 390                 395                 400

Thr Ser Gly Phe Gln Pro Val Ser Ile Lys Pro Ser Lys Ala Asp Asn
                405                 410                 415

Pro His Leu Leu Thr Ile Gln Pro Asp Leu Ser Thr Thr Thr Thr
            420                 425                 430

Tyr Gln Gly Ser Leu Cys Pro Arg Gln Asp Gly Pro Ser Pro Lys Phe
            435                 440                 445

Gln Leu Ser Asn Gly His Leu Leu Ser Pro Leu Gly Ser Gly Arg His
            450                 455                 460

Thr Leu His His Ser Ser Pro Thr Ser Glu Ala Glu Asp Phe Val Ser
465                 470                 475                 480

Arg Leu Ser Thr Gln Asn Tyr Phe Arg Ser Leu Pro Arg Gly Thr Ser
                485                 490                 495

Asn Met Ala Tyr Gly Thr Phe Asn Phe Leu Gly Gly Arg Leu Met Ile
            500                 505                 510

Pro Asn Thr Gly Ile Ser Leu Leu Ile Pro Pro Asp Ala Ile Pro Arg
            515                 520                 525

Gly Lys Ile Tyr Glu Ile Tyr Leu Thr Leu His Lys Pro Glu Asp Val
        530                 535                 540

Arg Leu Pro Leu Ala Gly Cys Gln Thr Leu Leu Ser Pro Ile Val Ser
545                 550                 555                 560

Cys Gly Pro Pro Gly Val Leu Leu Thr Arg Pro Val Ile Leu Ala Met
                565                 570                 575

Asp His Cys Gly Glu Pro Ser Pro Asp Ser Trp Ser Leu Arg Leu Lys
            580                 585                 590

Lys Gln Ser Cys Glu Gly Ser Trp Glu Asp Val Leu His Leu Gly Glu
        595                 600                 605

Glu Ser Pro Ser His Leu Tyr Tyr Cys Gln Leu Glu Ala Gly Ala Cys
        610                 615                 620
```

```
Tyr Val Phe Thr Glu Gln Leu Gly Arg Phe Ala Leu Val Gly Glu Ala
625                 630                 635                 640

Leu Ser Val Ala Ala Thr Lys Arg Leu Arg Leu Leu Leu Phe Ala Pro
            645                 650                 655

Val Ala Cys Thr Ser Leu Glu Tyr Asn Ile Arg Val Tyr Cys Leu His
        660                 665                 670

Asp Thr His Asp Ala Leu Lys Glu Val Val Gln Leu Glu Lys Gln Leu
    675                 680                 685

Gly Gly Gln Leu Ile Gln Glu Pro Arg Val Leu His Phe Lys Asp Ser
690                 695                 700

Tyr His Asn Leu Arg Leu Ser Ile His Asp Val Pro Ser Ser Leu Trp
705                 710                 715                 720

Lys Ser Lys Leu Leu Val Ser Tyr Gln Glu Ile Pro Phe Tyr His Ile
                725                 730                 735

Trp Asn Gly Thr Gln Gln Tyr Leu His Cys Thr Phe Thr Leu Glu Arg
            740                 745                 750

Val Asn Ala Ser Thr Ser Asp Leu Ala Cys Lys Val Trp Val Trp Gln
        755                 760                 765

Val Glu Gly Asp Gly Gln Ser Phe Asn Ile Asn Phe Asn Ile Thr Lys
    770                 775                 780

Asp Thr Arg Phe Ala Glu Met Leu Ala Leu Glu Ser Glu Gly Gly Val
785                 790                 795                 800

Pro Ala Leu Val Gly Pro Ser Ala Phe Lys Ile Pro Phe Leu Ile Arg
                805                 810                 815

Gln Lys Ile Ile Thr Ser Leu Asp Pro Pro Cys Ser Arg Gly Ala Asp
            820                 825                 830

Trp Arg Thr Leu Ala Gln Lys Leu His Leu Asp Ser His Leu Ser Phe
        835                 840                 845

Phe Ala Ser Lys Pro Ser Pro Thr Ala Met Ile Leu Asn Leu Trp Glu
    850                 855                 860

Ala Arg His Phe Pro Asn Gly Asn Leu Gly Gln Leu Ala Ala Ala Val
865                 870                 875                 880

Ala Gly Leu Gly Gln Pro Asp Ala Gly Leu Phe Thr Val Ser Glu Ala
                885                 890                 895

Glu Cys

<210> SEQ ID NO 15
<211> LENGTH: 2892
<212> TYPE: DNA
<213> ORGANISM: Homo sapiens

<400> SEQUENCE: 15
atgaccgagc tgaggggtg cagcccttg ctgtggaaca cgcagaaccg tgggggtgcc      60
cagcagagtg ccaccgtggc caacccagtg cctggtgcca acccggacct gcttccccac     120
ttcctggtgg agcccgagga tgtgtacatc gtcaagaaca agccagtgct gcttgtgtgc     180
aaggccgtgc cgccacgca gatcttcttc aagtgcaacg ggagtgggt gcgccaggtg      240 gaccacgtga tcgagcgcag cacagacggg agcagtgggt cctcttctgc cccgagcatc    300
cgactccagc ctcccatggc cggaacatct gaacgttcat tgatctcatc gatttctcaa    360
cccaaagcca tcgagtgctt tgaggtgaag aaaaaggctt tccttaccca cggcagatac   420
cacggcagtg cgccacgcc gccaaagacc aaagacccca accagaaac gttctgtggt    480 cagacagggc tgcccaccat ggaggtccgc attaatgtct caaggcagca ggtcgagaag   540
gtgttcgggc tggaggaata ctggtgccag tgcgtggcat ggagctcctc gggcaccacc    600
```

```
aagagtcaga aggcctacat ccgcatagcc tatttgcgca agaacttcga gcaggagccg    660
ctggccaagg aggtgtccct ggagcagggc atcgtgctgc cctgccgtcc accggagggc    720
atccctccag ccgaggtgga gtggctccgg aacgaggacc tggtggaccc gtccctggac    780
cccaatgtat acatcacgcg ggagcacagc ctggtggtgc gacaggcccg ccttgctgac    840
acggccaact acacctgcgt ggccaagaac atcgtggcac gtcgccgcag cgcctccgct    900
gctgtcatcg tctacgtgaa cggtgggtgg tcgacgtgga ccgagtggtc cgtctgcagc    960
gccagctgtg ggcgcggctg gcagaaacgg agccggagct gcaccaaccc ggcgcctctc   1020 aacggggcg ctttctgtga ggggcagaat gtccagaaaa cagcctgcgc caccctgtgc   1080
ccagtggacg gcagctggag cccgtggagc aagtggtcgg cctgtgggct ggactgcacc   1140
cactggcgga gccgtgagtg ctctgaccca gcaccccgca acgaggggga ggagtgccag   1200
ggcactgacc tggacacccg caactgtacc agtgacctct gtgtacacaa ctcctacacc   1260
cctgccccca ccaaggccat gctgtctccc gcagctgctt ctggccctga ggacgtggcc   1320
ctctatgtgg gcctcatcgc cgtggccgtc tgcctggtcc tgctgctgct tgtcctcatc   1380
ctcgtttatt gccggaagaa ggaggggctg gactcagatg tggctgactc gtccattctc   1440
acctcaggct ccagcccgt cagcatcaag cccagcaaag cagacaaccc ccatctgctc   1500
accatccagc cggacctcag caccaccacc accacctacc agggcagtct ctgtccccgg   1560
caggatgggc ccagccccaa gttccagctc accaatgggc acctgctcag ccccctgggt   1620
ggcggccgcc acacactgca ccacagctct cccacctctg aggccgagga gttcgtctcc   1680
cgcctctcca cccagaacta cttccgctcc ctgccccgag gcaccagcaa catgacctat   1740
gggaccttca acttcctcgg gggccggctg atgatcccta atacaggaat cagcctcctc   1800
atccccccag atgccatacc ccgagggaag atctatgaga tctacctcac gctgcacaag   1860
ccggaagacg tgagctgtgg acccctggc gtcctgctca cccggccagt catcctggct   1920
atggaccact gtgggagcc cagccctgac agctggagcc tgcgcctcaa aaagcagtcg   1980
tgcgagggca gctgggagga tgtgctgcac ctgggcgagg aggcgccctc ccacctctac   2040
tactgccagc tggaggccag tgcctgctac gtcttcaccg agcagctggg ccgctttgcc   2100
ctggtgggag aggccctcag cgtggctgcc gccaagcgcc tcaagctgct tctgtttgcg   2160
ccggtggcct gcacctccct cgagtacaac atccgggtct actgcctgca tgacacccac   2220
gatgcactca aggaggtggt gcagctggag aagcagctgg ggggacagct gatccaggag   2280
ccacgggtcc tgcacttcaa ggacagttac cacaacctgc gcctatccat ccacgatgtg   2340
cccagctccc tgtggaagag taagctcctt gtcagctacc aggagatccc cttttatcac   2400
atctggaatg gcacgcagcg gtacttgcac tgcaccttca ccctggagcg tgtcagcccc   2460
agcactagtg acctggcctg caagctgtgg gtgtggcagg tggagggcga cgggcagagc   2520
ttcagcatca acttcaacat caccaaggac acaaggtttg ctgagctgct ggctctggag   2580
agtgaagcgg gggtcccagc cctggtgggc cccagtgcct tcaagatccc cttcctcatt   2640
cggcagaaga taatttccag cctggaccca ccctgtaggc ggggtgccga ctggcggact   2700
ctggcccaga aactccacct ggacagccat ctcagcttct ttgcctccaa gcccagcccc   2760
acagccatga tcctcaacct gtgggaggcg cggcacttcc ccaacggcaa cctcagccaa   2820
ctggctgcag cagtggctgg actgggccag ccagacgctg gcctcttcac agtgtcggag   2880
gctgagtgct ga                                                       2892
```

<210> SEQ ID NO 16
<211> LENGTH: 963
<212> TYPE: PRT
<213> ORGANISM: Homo sapiens

<400> SEQUENCE: 16

Met Thr Glu Leu Arg Gly Cys Ser Pro Leu Leu Trp Asn Thr Gln Asn
 1               5                   10                  15

Arg Gly Gly Ala Gln Gln Ser Ala Thr Val Ala Asn Pro Val Pro Gly
            20                  25                  30

Ala Asn Pro Asp Leu Leu Pro His Phe Leu Val Glu Pro Glu Asp Val
        35                  40                  45

Tyr Ile Val Lys Asn Lys Pro Val Leu Leu Val Cys Lys Ala Val Pro
    50                  55                  60

Ala Thr Gln Ile Phe Phe Lys Cys Asn Gly Glu Trp Val Arg Gln Val
65                  70                  75                  80

Asp His Val Ile Glu Arg Ser Thr Asp Gly Ser Ser Gly Ser Ser Ser
                85                  90                  95

Ala Pro Ser Ile Arg Leu Gln Pro Pro Met Ala Gly Thr Ser Glu Arg
            100                 105                 110

Ser Leu Ile Ser Ser Ile Ser Gln Pro Lys Ala Ile Glu Cys Phe Glu
        115                 120                 125

Val Lys Lys Lys Ala Phe Leu Thr His Gly Arg Tyr His Gly Ser Gly
    130                 135                 140

Ala Thr Pro Pro Lys Thr Lys Asp Pro Lys Pro Glu Thr Phe Cys Gly
145                 150                 155                 160

Gln Thr Gly Leu Pro Thr Met Glu Val Arg Ile Asn Val Ser Arg Gln
                165                 170                 175

Gln Val Glu Lys Val Phe Gly Leu Glu Glu Tyr Trp Cys Gln Cys Val
            180                 185                 190

Ala Trp Ser Ser Ser Gly Thr Thr Lys Ser Gln Lys Ala Tyr Ile Arg
        195                 200                 205

Ile Ala Tyr Leu Arg Lys Asn Phe Glu Gln Glu Pro Leu Ala Lys Glu
    210                 215                 220

Val Ser Leu Glu Gln Gly Ile Val Leu Pro Cys Arg Pro Pro Glu Gly
225                 230                 235                 240

Ile Pro Pro Ala Glu Val Glu Trp Leu Arg Asn Glu Asp Leu Val Asp
                245                 250                 255

Pro Ser Leu Asp Pro Asn Val Tyr Ile Thr Arg Glu His Ser Leu Val
            260                 265                 270

Val Arg Gln Ala Arg Leu Ala Asp Thr Ala Asn Tyr Thr Cys Val Ala
        275                 280                 285

Lys Asn Ile Val Ala Arg Arg Ser Ala Ser Ala Ala Val Ile Val
    290                 295                 300

Tyr Val Asn Gly Gly Trp Ser Thr Trp Thr Glu Trp Ser Val Cys Ser
305                 310                 315                 320

Ala Ser Cys Gly Arg Gly Trp Gln Lys Arg Ser Arg Ser Cys Thr Asn
                325                 330                 335

Pro Ala Pro Leu Asn Gly Gly Ala Phe Cys Glu Gly Gln Asn Val Gln
            340                 345                 350

Lys Thr Ala Cys Ala Thr Leu Cys Pro Val Asp Gly Ser Trp Ser Pro
        355                 360                 365

Trp Ser Lys Trp Ser Ala Cys Gly Leu Asp Cys Thr His Trp Arg Ser
    370                 375                 380

Arg Glu Cys Ser Asp Pro Ala Pro Arg Asn Gly Gly Glu Glu Cys Gln

```
385                 390                 395                 400
Gly Thr Asp Leu Asp Thr Arg Asn Cys Thr Ser Asp Leu Cys Val His
                405                 410                 415
Asn Ser Tyr Thr Pro Ala Pro Thr Lys Ala Met Leu Ser Pro Ala Ala
                420                 425                 430
Ala Ser Gly Pro Glu Asp Val Ala Leu Tyr Val Gly Leu Ile Ala Val
                435                 440                 445
Ala Val Cys Leu Val Leu Leu Leu Val Leu Ile Leu Val Tyr Cys
        450                 455                 460
Arg Lys Lys Glu Gly Leu Asp Ser Asp Val Ala Asp Ser Ser Ile Leu
465                 470                 475                 480
Thr Ser Gly Phe Gln Pro Val Ser Ile Lys Pro Ser Lys Ala Asp Asn
                485                 490                 495
Pro His Leu Leu Thr Ile Gln Pro Asp Leu Ser Thr Thr Thr Thr Thr
                500                 505                 510
Tyr Gln Gly Ser Leu Cys Pro Arg Gln Asp Gly Pro Ser Pro Lys Phe
                515                 520                 525
Gln Leu Thr Asn Gly His Leu Leu Ser Pro Leu Gly Gly Arg His
530                 535                 540
Thr Leu His His Ser Ser Pro Thr Ser Glu Ala Glu Phe Val Ser
545                 550                 555                 560
Arg Leu Ser Thr Gln Asn Tyr Phe Arg Ser Leu Pro Arg Gly Thr Ser
                565                 570                 575
Asn Met Thr Tyr Gly Thr Phe Asn Phe Leu Gly Gly Arg Leu Met Ile
                580                 585                 590
Pro Asn Thr Gly Ile Ser Leu Leu Ile Pro Pro Asp Ala Ile Pro Arg
                595                 600                 605
Gly Lys Ile Tyr Glu Ile Tyr Leu Thr Leu His Lys Pro Glu Asp Val
                610                 615                 620
Ser Cys Gly Pro Pro Gly Val Leu Leu Thr Arg Pro Val Ile Leu Ala
625                 630                 635                 640
Met Asp His Cys Gly Glu Pro Ser Pro Asp Ser Trp Ser Leu Arg Leu
                645                 650                 655
Lys Lys Gln Ser Cys Glu Gly Ser Trp Glu Asp Val Leu His Leu Gly
                660                 665                 670
Glu Glu Ala Pro Ser His Leu Tyr Tyr Cys Gln Leu Glu Ala Ser Ala
                675                 680                 685
Cys Tyr Val Phe Thr Glu Gln Leu Gly Arg Phe Ala Leu Val Gly Glu
                690                 695                 700
Ala Leu Ser Val Ala Ala Ala Lys Arg Leu Lys Leu Leu Phe Ala
705                 710                 715                 720
Pro Val Ala Cys Thr Ser Leu Glu Tyr Asn Ile Arg Val Tyr Cys Leu
                725                 730                 735
His Asp Thr His Asp Ala Leu Lys Glu Val Gln Leu Glu Lys Gln
                740                 745                 750
Leu Gly Gly Gln Leu Ile Gln Glu Pro Arg Val Leu His Phe Lys Asp
                755                 760                 765
Ser Tyr His Asn Leu Arg Leu Ser Ile His Asp Val Pro Ser Ser Leu
                770                 775                 780
Trp Lys Ser Lys Leu Leu Val Ser Tyr Gln Glu Ile Pro Phe Tyr His
785                 790                 795                 800
Ile Trp Asn Gly Thr Gln Arg Tyr Leu His Cys Thr Phe Thr Leu Glu
                805                 810                 815
```

```
Arg Val Ser Pro Ser Thr Ser Asp Leu Ala Cys Lys Leu Trp Val Trp
            820                 825                 830
Gln Val Glu Gly Asp Gly Gln Ser Phe Ser Ile Asn Phe Asn Ile Thr
        835                 840                 845
Lys Asp Thr Arg Phe Ala Glu Leu Leu Ala Leu Glu Ser Glu Ala Gly
    850                 855                 860
Val Pro Ala Leu Val Gly Pro Ser Ala Phe Lys Ile Pro Phe Leu Ile
865                 870                 875                 880
Arg Gln Lys Ile Ile Ser Ser Leu Asp Pro Pro Cys Arg Arg Gly Ala
                885                 890                 895
Asp Trp Arg Thr Leu Ala Gln Lys Leu His Leu Asp Ser His Leu Ser
            900                 905                 910
Phe Phe Ala Ser Lys Pro Ser Pro Thr Ala Met Ile Leu Asn Leu Trp
        915                 920                 925
Glu Ala Arg His Phe Pro Asn Gly Asn Leu Ser Gln Leu Ala Ala Ala
    930                 935                 940
Val Ala Gly Leu Gly Gln Pro Asp Ala Gly Leu Phe Thr Val Ser Glu
945                 950                 955                 960
Ala Glu Cys

<210> SEQ ID NO 17
<211> LENGTH: 3866
<212> TYPE: DNA
<213> ORGANISM: Mouse

<400> SEQUENCE: 17
attgtggccg gcggcagggc gggcgagggc gcggagccgc ggggagcggc agggcgcaga    60
gggaagcaca cccccactc ggacagactt cgccggcgcgg ccgctacgag cgccgctgag   120
cgcactccac tgggatcgca caacttcgga gcagggcgcg gacggcgctc gcagcgggag   180
agcgcggaaa gggcgcacca gagccgggat ccccagcggc gtccgactcc cggagcgctc   240
ctagtcgccg gcggcctcc cggcgctgcg cggttgcctc tgcgcctacg gagggcacgg    300
gctggcgctg ccgggcgcct gcgagaacgg cgaggcggcg gcgaaggcga aggcggcgag   360
gctggggacc gggaaagaac cccgagggag aggcgcccgg gccggggac aggagcatga   420
gggcccggag cggggtgcgg agcgcgctgc tgctggcgct gctgctttgc tgggatccga   480
caccgagcct agcaggcgtt gactctgctg gccaggtgct cccagactcc tacccatcag   540
cccctgcgga gcagctgccg tacttcctat tggagccaca ggacgcctac atcgtaaaga   600
acaagccagt ggaactgcac tgcagagcct tccctgccac gcagatctac ttcaagtgta   660
atggcgagtg ggtcagccag aatgaccacg tcacacagga gagcctggat gaggccacag   720
gcttgcgggt gcgagaggtg cagatcgagg tgtcacggca gcaagtggag gaactcttcg   780
ggctcgagga ctactggtgc cagtgcgtgg cctggagctc ttcgggaact accaagagtc   840
gccgagccta catccgcatt gcctacttgc gcaagaactt tgaccaggag cctctggcca   900
aggaggtacc cttggatcat gaggtccttc tgcagtgccg cccaccggag ggagtgcctg   960
tggctgaggt ggaatggctc aagaatgaag atgtcattga ccccgctcag gacactaact  1020
tcctgctcac cattgaccac aacctcatca tccgccaggc gcgcctctca gacacggcca  1080
actacacctg tgtggccaag aatatcgtgg ccaagcgccg gagcaccgcg ccacagtca   1140
tcgtctatgt gaatggaggc tggtccagct gggcagagtg gtcaccctgt tccaatcgct  1200
gtggccgagg ctggcagaag cgtactcgga cctgcaccaa tccagcccca ctcaatggag  1260
gcgccttctg tgagggacag gccttccaga agacagcttg caccaccgtg tgcccagtgg  1320
```

```
atggagcgtg gaccgagtgg agcaagtggt ctgcctgcag cacagagtgt gcgcactggc    1380
gcagccgcga gtgcatggca ccgccacccc agaacggagg ccgtgactgc agcgggacgc    1440
tacttgactc caagaactgc actgatgggc tgtgcgtgct gaatcagaga actctaaacg    1500
accctaaaag ccaccccctg gagacatcgg agatgtggc actgtacgca ggccttgtgg     1560
tggccgtctt tgtggtggta gcggttctca tggccgaggg agtgatcgta taccggagaa    1620
actgccggga cttcgacacg gacatcaccg actcctctgc ggccctcact ggtggcttcc    1680
accctgtcaa cttcaagact gcaaggccca caacccgca gctcctgcac ccgtccgccc     1740
ctccagacct aacggccagt gctggcatct accgcgggcc tgtgtatgcc ctgcaggact    1800
ccgccgacaa gatccccatg actaattcgc ccctgctgga tccctgccc agcctcaaga     1860 tcaaggtcta taactccagc accatcggtt ctgggtctgg cctggctgat ggagccgacc    1920
tgctgggtgt cctcccgccg ggcacgtacc caggcgattt ctcccgggac acccatttcc    1980
tgcacctgcg cagtgccagc cttggttccc agcacctcct gggcctacct cgggaccca     2040 gcagcagtgt cagcggcacc tttggttgcc tgggaggaag gctgagcctc cccggcacag    2100
gggtcagcct gttggtacca aatggagcca ttccccaggg caagttctat gacctgtatc    2160
tacatatcaa caaggccgaa agcaccctcc cactttcaga aggttcccag acagtattga    2220
gcccctcggt gacctgtggg cccacaggcc tactcctgtg ccgccctgtc gtcctcaccg    2280
tgccccactg tgctgaagtc atcgctggag actggatctt tcagctcaag acccaggccc    2340
atcagggcca ctgggaggag gtggtgacct tggatgagga accctcaac acaccctgct      2400 actgccagct ggaggctaag tcctgccaca tcctgctgga ccagctgggt tcctacgtat    2460
tcatgggcga gtcctactct cgctctgcag tcaagcggct ccagctggcc atcttcgccc    2520
cagccctctg cacctccctg gagtatagcc tcagggtcta ctgtctggag gacacacctg    2580
tagcactgaa ggaggtcctg gagctggaga ggactctggg tggctacttg gtggaggagc    2640
ccaagccttt gctctttaag gacagttacc acaacctacg cctctccctc catgacatcc    2700
cccatgccca ctggaggagc aaactactgg ccaagtacca ggagattccc ttctaccacg    2760
tctggaatgg cagccagaga gccctgcact gcactttcac cctggagagg catagcctgg    2820
cctccacgga gttcacctgt aaggtctgcg tgcggcaggt cgaagggaa ggccagattt      2880 tccagctgca cacaacgttg gccgagacgc ctgctggctc cctggatgct ctctgctctg    2940
ccccgggcaa tgccatcacc acccagctgg accctatgc cttcaagata ccctgtccca     3000
tccgccaaaa gatctgcagc agcctggacg ccccgactc ccgggcaac gactggagg         3060 tgttggcgca gaagctgtcc atggaccggt acctaaacta cttcgccacc aaagctagtc    3120
ccacaggtgt catcttagac tctgggaag ctcggcaaca ggatgacggg gacctcaaca       3180
gcctggccag tgccttggag gagatgggca agagtgagat gctggtagcc atggccacag     3240
atggcgattg ctgagtgcct gtgaccacag gcctgtgggg atcagtagga gacggtgcaa    3300
ggaggcctgg cagcctctgc acaggggtgc ccagcctcca ccactcctgg ctcacagcag    3360
gaatggtcct tcaactccct ccccgccaca accctcagac caccaccacc agccttagaa    3420
agtctctgtg ctctactgcc aagaggccgg gatcctctgg cccactgttt ccccagctca    3480
ctctggggtg gctgaggcc tctggacag ctgaaagcca gaggctttcc cctgcgacaa       3540
cacaccaccc tcagccctgt gactttgggg acccacaggt ttcaattctg tgttcacatg    3600
gtcctgggct agggaccgct ctcttatccc gggtcgagtt cagttcaggc aaactgctttt    3660 ttcctgtcca caagcagaga gggaagatta ggggagtggg ggtgggggt gggggatgag       3720
```

```
cctcagaagt cagcgagact caggtagtga gagagcaaaa acagtaaggg caaagaaaga   3780
cccagttttt tagggaacgc aaatgattta ttatccagat acttggatag ttccttttta   3840
agaaaacaaa acaaacaaaa aaaagt                                       3866
```

<210> SEQ ID NO 18
<211> LENGTH: 945
<212> TYPE: PRT
<213> ORGANISM: Mouse

<400> SEQUENCE: 18

```
Met Arg Ala Arg Ser Gly Val Arg Ser Ala Leu Leu Leu Ala Leu Leu
 1               5                  10                  15

Leu Cys Trp Asp Pro Thr Pro Ser Leu Ala Gly Val Asp Ser Ala Gly
             20                  25                  30

Gln Val Leu Pro Asp Ser Tyr Pro Ser Ala Pro Ala Glu Gln Leu Pro
         35                  40                  45

Tyr Phe Leu Leu Glu Pro Gln Asp Ala Tyr Ile Val Lys Asn Lys Pro
     50                  55                  60

Val Glu Leu His Cys Arg Ala Phe Pro Ala Thr Gln Ile Tyr Phe Lys
 65                  70                  75                  80

Cys Asn Gly Glu Trp Val Ser Gln Asn Asp His Val Thr Gln Glu Ser
                 85                  90                  95

Leu Asp Glu Ala Thr Gly Leu Arg Val Arg Glu Val Gln Ile Glu Val
            100                 105                 110

Ser Arg Gln Gln Val Glu Glu Leu Phe Gly Leu Glu Asp Tyr Trp Cys
        115                 120                 125

Gln Cys Val Ala Trp Ser Ser Ser Gly Thr Thr Lys Ser Arg Arg Ala
    130                 135                 140

Tyr Ile Arg Ile Ala Tyr Leu Arg Lys Asn Phe Asp Gln Glu Pro Leu
145                 150                 155                 160

Ala Lys Glu Val Pro Leu Asp His Glu Val Leu Leu Gln Cys Arg Pro
                165                 170                 175

Pro Glu Gly Val Pro Val Ala Glu Val Glu Trp Leu Lys Asn Glu Asp
            180                 185                 190

Val Ile Asp Pro Ala Gln Asp Thr Asn Phe Leu Leu Thr Ile Asp His
        195                 200                 205

Asn Leu Ile Ile Arg Gln Ala Arg Leu Ser Asp Thr Ala Asn Tyr Thr
    210                 215                 220

Cys Val Ala Lys Asn Ile Val Ala Lys Arg Arg Ser Thr Ala Ala Thr
225                 230                 235                 240

Val Ile Val Tyr Val Asn Gly Gly Trp Ser Ser Trp Ala Glu Trp Ser
                245                 250                 255

Pro Cys Ser Asn Arg Cys Gly Arg Gly Trp Gln Lys Arg Thr Arg Thr
            260                 265                 270

Cys Thr Asn Pro Ala Pro Leu Asn Gly Gly Ala Phe Cys Glu Gly Gln
        275                 280                 285

Ala Phe Gln Lys Thr Ala Cys Thr Thr Val Cys Pro Val Asp Gly Ala
    290                 295                 300

Trp Thr Glu Trp Ser Lys Trp Ser Ala Cys Ser Thr Glu Cys Ala His
305                 310                 315                 320

Trp Arg Ser Arg Glu Cys Met Ala Pro Pro Gln Asn Gly Gly Arg
                325                 330                 335

Asp Cys Ser Gly Thr Leu Leu Asp Ser Lys Asn Cys Thr Asp Gly Leu
            340                 345                 350
```

-continued

```
Cys Val Leu Asn Gln Arg Thr Leu Asn Asp Pro Lys Ser His Pro Leu
        355                 360                 365
Glu Thr Ser Gly Asp Val Ala Leu Tyr Ala Gly Leu Val Ala Val
370                 375                 380
Phe Val Val Val Ala Val Leu Met Ala Glu Gly Val Ile Val Tyr Arg
385                 390                 395                 400
Arg Asn Cys Arg Asp Phe Asp Thr Asp Ile Thr Asp Ser Ser Ala Ala
            405                 410                 415
Leu Thr Gly Gly Phe His Pro Val Asn Phe Lys Thr Ala Arg Pro Asn
                420                 425                 430
Asn Pro Gln Leu Leu His Pro Ser Ala Pro Pro Asp Leu Thr Ala Ser
        435                 440                 445
Ala Gly Ile Tyr Arg Gly Pro Val Tyr Ala Leu Gln Asp Ser Ala Asp
    450                 455                 460
Lys Ile Pro Met Thr Asn Ser Pro Leu Leu Asp Pro Leu Pro Ser Leu
465                 470                 475                 480
Lys Ile Lys Val Tyr Asn Ser Ser Thr Ile Gly Ser Gly Ser Gly Leu
            485                 490                 495
Ala Asp Gly Ala Asp Leu Leu Gly Val Leu Pro Pro Gly Thr Tyr Pro
                500                 505                 510
Gly Asp Phe Ser Arg Asp Thr His Phe Leu His Leu Arg Ser Ala Ser
        515                 520                 525
Leu Gly Ser Gln His Leu Leu Gly Leu Pro Arg Asp Pro Ser Ser Ser
    530                 535                 540
Val Ser Gly Thr Phe Gly Cys Leu Gly Gly Arg Leu Ser Leu Pro Gly
545                 550                 555                 560
Thr Gly Val Ser Leu Leu Val Pro Asn Gly Ala Ile Pro Gln Gly Lys
            565                 570                 575
Phe Tyr Asp Leu Tyr Leu His Ile Asn Lys Ala Glu Ser Thr Leu Pro
                580                 585                 590
Leu Ser Glu Gly Ser Gln Thr Val Leu Ser Pro Ser Val Thr Cys Gly
        595                 600                 605
Pro Thr Gly Leu Leu Leu Cys Arg Pro Val Val Leu Thr Val Pro His
    610                 615                 620
Cys Ala Glu Val Ile Ala Gly Asp Trp Ile Phe Gln Leu Lys Thr Gln
625                 630                 635                 640
Ala His Gln Gly His Trp Glu Glu Val Val Thr Leu Asp Glu Thr
            645                 650                 655
Leu Asn Thr Pro Cys Tyr Cys Gln Leu Glu Ala Lys Ser Cys His Ile
                660                 665                 670
Leu Leu Asp Gln Leu Gly Ser Tyr Val Phe Met Gly Glu Ser Tyr Ser
        675                 680                 685
Arg Ser Ala Val Lys Arg Leu Gln Leu Ala Ile Phe Ala Pro Ala Leu
    690                 695                 700
Cys Thr Ser Leu Glu Tyr Ser Leu Arg Val Tyr Cys Leu Glu Asp Thr
705                 710                 715                 720
Pro Val Ala Leu Lys Glu Val Leu Glu Leu Glu Arg Thr Leu Gly Gly
            725                 730                 735
Tyr Leu Val Glu Glu Pro Lys Pro Leu Leu Phe Lys Asp Ser Tyr His
                740                 745                 750
Asn Leu Arg Leu Ser Leu His Asp Ile Pro His Ala His Trp Arg Ser
        755                 760                 765
Lys Leu Leu Ala Lys Tyr Gln Glu Ile Pro Phe Tyr His Val Trp Asn
```

```
                770             775             780
Gly Ser Gln Arg Ala Leu His Cys Thr Phe Thr Leu Glu Arg His Ser
785                 790                 795                 800

Leu Ala Ser Thr Glu Phe Thr Cys Lys Val Cys Val Arg Gln Val Glu
                805                 810                 815

Gly Glu Gly Gln Ile Phe Gln Leu His Thr Thr Leu Ala Glu Thr Pro
                820                 825                 830

Ala Gly Ser Leu Asp Ala Leu Cys Ser Ala Pro Gly Asn Ala Ile Thr
                835                 840                 845

Thr Gln Leu Gly Pro Tyr Ala Phe Lys Ile Pro Leu Ser Ile Arg Gln
                850                 855                 860

Lys Ile Cys Ser Ser Leu Asp Ala Pro Asp Ser Arg Gly Asn Asp Trp
865                 870                 875                 880

Arg Leu Leu Ala Gln Lys Leu Ser Met Asp Arg Tyr Leu Asn Tyr Phe
                885                 890                 895

Ala Thr Lys Ala Ser Pro Thr Gly Val Ile Leu Asp Leu Trp Glu Ala
                900                 905                 910

Arg Gln Gln Asp Asp Gly Asp Leu Asn Ser Leu Ala Ser Ala Leu Glu
                915                 920                 925

Glu Met Gly Lys Ser Glu Met Leu Val Ala Met Ala Thr Asp Gly Asp
    930                 935                 940

Cys
945

<210> SEQ ID NO 19
<211> LENGTH: 3935
<212> TYPE: DNA
<213> ORGANISM: Homo sapiens

<400> SEQUENCE: 19
cccacgcgtc cgggctaggg cgccggagcc gcacgcagcc gcggggctcc gagaggcgcg      60
cactggggct gggactgcgc ggcgccgccg ctgcgagcgc cactgagcgg tcgcgcaact     120
tcggaggcac agcgccggag ccaggcgagc gctcagagac ccggagccag aggggcgcgc     180
cggagcctcg ttcgagagcc ggcgccaggc acccaccgcg ctccgagtgc aggcggccc      240 tccgcgcagc gtggcttccg ctgcccccac ggaaggcacg ggctggcgct gccgggcgcc     300
ggggaggacg gcgaggagga ggcggcggcg gcggagacgg cggcggcgag actggggcca     360
gggagacagc cctgggggag aggcgcccga accaggccgc gggagcatgg gggcccggag     420
cggagctcgg ggcgcgctgc tgctggcact gctgctctgc tgggacccga ggctgagcca     480
agcaggcact gattctggca gcgaggtgct ccctgactcc ttcccgtcag cgccagcaga     540
gccgctgccc tacttcctgc aggagccaca ggacgcctac attgtgaaga caagcctgt     600 ggagctccgc tgccgcgcct cccccgccac acagatctac ttcaagtgca acggcgagtg     660
ggtcagccag aacgaccacg tcacacagga aggcctggat gaggccaccg gcctgcgggt     720
gcgcgaggtg cagatcgagg tgtcgcggca gcaggtggag gagctctttg gctggagga     780 ttactggtgc cagtgcgtgg cctggagctc cgcgggcacc accaagagtc gccgagccta     840
cgtccgcatc gcctacctgc gcaagaactt cgatcaggag cctctgggca aggaggtgcc     900
cctggaccat gaggttctcc tgcagtgccg ccgccggagg gggtgcctg tggccgaggt     960 ggaatggctc aagaatgagg atgtcatcga ccccacccag gacaccaact cctgctcac    1020 catcgaccac aacctcatca tccgccaggc ccgcctgtcg acactgcca actataccg    1080 cgtggccaag aacatcgtgg ccaaacgccg gagcaccact gccaccgtca tcgtctacgt   1140
```

```
gaatggcggc tggtccagct gggcagagtg gtcaccctgc tccaaccgct gtggccgagg    1200
ctggcagaag cgcacccgga cctgcaccaa ccccgctcca ctcaacggag gggccttctg    1260
cgagggccag gcattccaga agaccgcctg caccaccatc tgcccagtcg atggggcgtg    1320
gacggagtgg agcaagtggt cagcctgcag cactgagtgt gcccactggc gtagccgcga    1380
gtgcatggcg ccccaccccc agaacggagg ccgtgactgc agcgggacgc tgctcgactc    1440
taagaactgc acagatgggc tgtgcatgca aaataagaaa actctaagcg accccaacag    1500
ccacctgctg gaggcctcag gggatgcggc gctgtatgcg gggctcgtgg tggccatctt    1560
cgtggtcgtg gcaatcctca tggcggtggg ggtggtggtg taccgccgca actgccgtga    1620
cttcgacaca gacatcactg actcatctgc tgccctgact ggtggtttcc accccgtcaa    1680
ctttaagacg gcaaggccca gcaacccgca gctcctacac ccctctgtgc ctcctgacct    1740
gacagccagc gccggcatct accgcggacc cgtgtatgcc ctgcaggact ccaccgacaa    1800
aatccccatg accaactctc ctctgctgga ccccttaccc agccttaagg tcaaggtcta    1860
cagctccagc accacgggct ctgggccagg cctggcagac ggggctgacc tgctggggt    1920 cttgccgcct ggcacatacc ctagcgattt cgcccgggac acccacttcc tgcacctgcg    1980
cagcgccagc ctcggttccc agcagctctt gggcctgccc cgagaccag ggagcagcgt    2040 cagcggcacc tttggctgcc tgggtgggag gctcagcatc cccggcacag gggtcagctt    2100
gctggtgccc aatggagcca ttccccaggg caagttctac gagatgtatc tactcatcaa    2160
caaggcagaa agtaccctcc cgcttcaga agggacccag acagtattga gccctcggt    2220 gacctgtgga cccacaggcc tcctgctgtg ccgccccgtc atcctcacca tgccccactg    2280
tgccgaagtc agtgcccgtg actggatctt tcagctcaag acccaggccc accagggcca    2340
ctgggaggag gtggtgaccc tggatgagga gaccctgaac acaccctgct actgccagct    2400
ggagcccagg gcctgtcaca tcctgctgga ccagctgggc acctacgtgt tcacgggcga    2460
gtcctattcc cgctcagcag tcaagcggct ccagctggcc gtcttcgccc ccgccctctg    2520
cacctccctg gagtacagcc tccgggtcta ctgcctggag gacacgcctg tagcactgaa    2580
ggaggtgctg gagctggagc ggactctggg cggatacttg gtggaggagc cgaaaccgct    2640
aatgttcaag gacagttacc acaacctgcg cctctccctc catgacctcc ccatgccca    2700 ttggaggagc aagctgctgg ccaaatacca ggagatcccc ttctatcaca tttggagtgg    2760
cagccagaag gccctccact gcactttcac cctggagagg cacagcttgg cctccacaga    2820
gctcacctgc aagatctgcg tgcggcaagt ggaagggag ggccagatat tccagctgca    2880
taccactctg gcagagacac ctgctggctc cctggacact ctctgctctg ccctggcag    2940 cactgtcacc acccagctgg gacccttatgc cttcaagatc ccactgtcca tccgccagaa    3000
gatatgcaac agcctagatg cccccaactc acggggcaat gactggcgga tgttagcaca    3060
gaagctctct atggaccggt acctgaatta ctttgccacc aaagcgagcc ccacgggtgt    3120
gatcctggac ctctgggaag ctctgcagca ggacgatggg gacctcaaca gcctggcgag    3180
tgccttggag gagatgggca agagtgagat gctggtggct gtggccaccg acggggactg    3240
ctgagcctcc tgggacaggcg ggctggcagg gactggcagg aggcaggtgc agggaggcct    3300
ggggcagcct cctgatgggg atgtttggcc tctgcttcct cccagttcac agccagagtt    3360
gcctctcctc ctcctcttcc ccaaccccca gaccatgacc agccttagaa aatccatgta    3420
ctctgttgtt agagggccca gagttccttc tccaccccg ctctctctct cttggcctga    3480
gatctctgtg caggaaccaa gatggggctg aagcctctgg aggcagttgg ttgggggcgg    3540
```

```
gcaggcagga ggccctccct ccacccccc  accctcagcc cggcaacttc tgggttccat    3600
gggttttagt tccgttctcg ttttcttcct ccgttattga tttctccttt ctccctaagc    3660 cccttctgc  ttccacgccc ttttcctctt tgaagagtca agtacaattc agacaaactg    3720
ctttctcctg tccaaaagca aaaggcaaa  ggaaagaaag aaagcttcag accgctagta    3780
aggctcaaag aagaagaaaa acaccaaaac cacaagggaa agaaaaacc  cagtttctta    3840 ggaaacgcaa acgatttatt atccagatta tttggataag tccttttta  gaaaaaaaaa    3900 agaaaatgaa aacaacaca  aaaaaaaaaa aaaaa                               3935

<210> SEQ ID NO 20
<211> LENGTH: 945
<212> TYPE: PRT
<213> ORGANISM: Homo sapiens

<400> SEQUENCE: 20

Met Gly Ala Arg Ser Gly Ala Arg Gly Ala Leu Leu Ala Leu Leu
 1               5                  10                  15

Leu Cys Trp Asp Pro Arg Leu Ser Gln Ala Gly Thr Asp Ser Gly Ser
                20                  25                  30

Glu Val Leu Pro Asp Ser Phe Pro Ser Ala Pro Ala Glu Pro Leu Pro
            35                  40                  45

Tyr Phe Leu Gln Glu Pro Gln Asp Ala Tyr Ile Val Lys Asn Lys Pro
    50                  55                  60

Val Glu Leu Arg Cys Arg Ala Phe Pro Ala Thr Gln Ile Tyr Phe Lys
65                  70                  75                  80

Cys Asn Gly Glu Trp Val Ser Gln Asn Asp His Val Thr Gln Glu Gly
                85                  90                  95

Leu Asp Glu Ala Thr Gly Leu Arg Val Arg Glu Val Gln Ile Glu Val
            100                 105                 110

Ser Arg Gln Gln Val Glu Glu Leu Phe Gly Leu Glu Asp Tyr Trp Cys
        115                 120                 125

Gln Cys Val Ala Trp Ser Ser Ala Gly Thr Thr Lys Ser Arg Arg Ala
    130                 135                 140

Tyr Val Arg Ile Ala Tyr Leu Arg Lys Asn Phe Asp Gln Glu Pro Leu
145                 150                 155                 160

Gly Lys Glu Val Pro Leu Asp His Glu Val Leu Leu Gln Cys Arg Pro
                165                 170                 175

Pro Glu Gly Val Pro Val Ala Glu Val Glu Trp Leu Lys Asn Glu Asp
            180                 185                 190

Val Ile Asp Pro Thr Gln Asp Thr Asn Phe Leu Leu Thr Ile Asp His
        195                 200                 205

Asn Leu Ile Ile Arg Gln Ala Arg Leu Ser Asp Thr Ala Asn Tyr Thr
    210                 215                 220

Cys Val Ala Lys Asn Ile Val Ala Lys Arg Arg Ser Thr Thr Ala Thr
225                 230                 235                 240

Val Ile Val Tyr Val Asn Gly Gly Trp Ser Ser Trp Ala Glu Trp Ser
                245                 250                 255

Pro Cys Ser Asn Arg Cys Gly Arg Gly Trp Gln Lys Arg Thr Arg Thr
            260                 265                 270

Cys Thr Asn Pro Ala Pro Leu Asn Gly Gly Ala Phe Cys Glu Gly Gln
        275                 280                 285

Ala Phe Gln Lys Thr Ala Cys Thr Thr Ile Cys Pro Val Asp Gly Ala
    290                 295                 300
```

```
Trp Thr Glu Trp Ser Lys Trp Ser Ala Cys Ser Thr Glu Cys Ala His
305                 310                 315                 320

Trp Arg Ser Arg Glu Cys Met Ala Pro Pro Gln Asn Gly Gly Arg
                325                 330                 335

Asp Cys Ser Gly Thr Leu Leu Asp Ser Lys Asn Cys Thr Asp Gly Leu
            340                 345                 350

Cys Met Gln Asn Lys Lys Thr Leu Ser Asp Pro Asn Ser His Leu Leu
        355                 360                 365

Glu Ala Ser Gly Asp Ala Ala Leu Tyr Ala Gly Leu Val Val Ala Ile
    370                 375                 380

Phe Val Val Val Ala Ile Leu Met Ala Val Gly Val Val Tyr Arg
385                 390                 395                 400

Arg Asn Cys Arg Asp Phe Asp Thr Asp Ile Thr Asp Ser Ser Ala Ala
                405                 410                 415

Leu Thr Gly Gly Phe His Pro Val Asn Phe Lys Thr Ala Arg Pro Ser
            420                 425                 430

Asn Pro Gln Leu Leu His Pro Ser Val Pro Pro Asp Leu Thr Ala Ser
        435                 440                 445

Ala Gly Ile Tyr Arg Gly Pro Val Tyr Ala Leu Gln Asp Ser Thr Asp
    450                 455                 460

Lys Ile Pro Met Thr Asn Ser Pro Leu Leu Asp Pro Leu Pro Ser Leu
465                 470                 475                 480

Lys Val Lys Val Tyr Ser Ser Thr Thr Gly Ser Gly Pro Gly Leu
                485                 490                 495

Ala Asp Gly Ala Asp Leu Leu Gly Val Leu Pro Pro Gly Thr Tyr Pro
        500                 505                 510

Ser Asp Phe Ala Arg Asp Thr His Phe Leu His Leu Arg Ser Ala Ser
    515                 520                 525

Leu Gly Ser Gln Gln Leu Leu Gly Leu Pro Arg Asp Pro Gly Ser Ser
530                 535                 540

Val Ser Gly Thr Phe Gly Cys Leu Gly Gly Arg Leu Ser Ile Pro Gly
545                 550                 555                 560

Thr Gly Val Ser Leu Leu Val Pro Asn Gly Ala Ile Pro Gln Gly Lys
                565                 570                 575

Phe Tyr Glu Met Tyr Leu Leu Ile Asn Lys Ala Glu Ser Thr Leu Pro
            580                 585                 590

Leu Ser Glu Gly Thr Gln Thr Val Leu Ser Pro Ser Val Thr Cys Gly
        595                 600                 605

Pro Thr Gly Leu Leu Leu Cys Arg Pro Val Ile Leu Thr Met Pro His
    610                 615                 620

Cys Ala Glu Val Ser Ala Arg Asp Trp Ile Phe Gln Leu Lys Thr Gln
625                 630                 635                 640

Ala His Gln Gly His Trp Glu Glu Val Val Thr Leu Asp Glu Glu Thr
                645                 650                 655

Leu Asn Thr Pro Cys Tyr Cys Gln Leu Glu Pro Arg Ala Cys His Ile
            660                 665                 670

Leu Leu Asp Gln Leu Gly Thr Tyr Val Phe Thr Gly Glu Ser Tyr Ser
        675                 680                 685

Arg Ser Ala Val Lys Arg Leu Gln Leu Ala Val Phe Ala Pro Ala Leu
    690                 695                 700

Cys Thr Ser Leu Glu Tyr Ser Leu Arg Val Tyr Cys Leu Glu Asp Thr
705                 710                 715                 720

Pro Val Ala Leu Lys Glu Val Leu Glu Leu Glu Arg Thr Leu Gly Gly
                725                 730                 735
```

| | | | | | | | | | | | |
|---|---|---|---|---|---|---|---|---|---|---|---|
|Tyr|Leu|Val|Glu|Glu|Pro|Lys|Pro|Leu|Met|Phe|Lys|Asp|Ser|Tyr|His|
| | | |740| | |745| | | |750| |

Asn Leu Arg Leu Ser Leu His Asp Leu Pro His Ala His Trp Arg Ser
           755                 760                 765

Lys Leu Leu Ala Lys Tyr Gln Glu Ile Pro Phe Tyr His Ile Trp Ser
770                 775                 780

Gly Ser Gln Lys Ala Leu His Cys Thr Phe Thr Leu Glu Arg His Ser
785                 790                 795                 800

Leu Ala Ser Thr Glu Leu Thr Cys Lys Ile Cys Val Arg Gln Val Glu
                805                 810                 815

Gly Glu Gly Gln Ile Phe Gln Leu His Thr Thr Leu Ala Glu Thr Pro
                820                 825                 830

Ala Gly Ser Leu Asp Thr Leu Cys Ser Ala Pro Gly Ser Thr Val Thr
                835                 840                 845

Thr Gln Leu Gly Pro Tyr Ala Phe Lys Ile Pro Leu Ser Ile Arg Gln
850                 855                 860

Lys Ile Cys Asn Ser Leu Asp Ala Pro Asn Ser Arg Gly Asn Asp Trp
865                 870                 875                 880

Arg Met Leu Ala Gln Lys Leu Ser Met Asp Arg Tyr Leu Asn Tyr Phe
                885                 890                 895

Ala Thr Lys Ala Ser Pro Thr Gly Val Ile Leu Asp Leu Trp Glu Ala
                900                 905                 910

Leu Gln Gln Asp Asp Gly Asp Leu Asn Ser Leu Ala Ser Ala Leu Glu
                915                 920                 925

Glu Met Gly Lys Ser Glu Met Leu Val Ala Val Ala Thr Asp Gly Asp
    930                 935                 940

Cys
945

```
<210> SEQ ID NO 21
<211> LENGTH: 9299
<212> TYPE: DNA
<213> ORGANISM: Mouse

<400> SEQUENCE: 21
ccttggagaa agtggagtgt ggcgctcagg ctgctgttat ttctcaggac tgcctggcgg      60
tggccggatc cagcctcctg cctggctggg ctttcggctg tttgcgcgtc tcctggtggc     120
gtttcccttc cccgtacacc tctgccgacg atgaggaaag gtctgagggc gacagcggcc     180
cgctgcggac tgggactagg atacttgctg cagatgcttg tgttacctgc cctggccctg     240
ctaagcgcca gtggcaccgg ctccgccgct caagatgatg aatttttttca cgaactccca     300 gaaacctttc catctgaccc acctgagcca ttgccacact tcctcattga gcccgaggaa     360
gcttacattg tgaagaacaa gcctgtgaac ctgtattgta agccagccc tgccacccag     420 atctacttca gtgcaacag cgagtgggtt catcagaagg accacgtagt agacgagaga     480
gtagatgaaa cctctggtct aattgtgaga gaagtgagca ttgagatttc acgccagcag     540
gtggaggaac tgtttgggcc tgaagattac tggtgccagt gtgtggcctg gagctcagca     600
ggcactacga agagtcggaa ggcatacgtg cgcattgcgt atctgcggaa gacattcgag     660
caggaaccct tgggaaagga agtgtccttg gagcaggaag tcttactcca gtgtcggcca     720
cctgaaggga tcccagtggc tgaggtggaa tggctaaaga tgaagacat aattgatcct     780 gctgaagatc ggaactttta tattactatc gatcacaacc tgatcatcaa gcaagcccga     840
ctctcagata cagcaaatta tacctgtgtt gccaaaaata ttgttgccaa gagaaaaagc     900
```

```
accacagcca ctgtcatcgt gtatgttaat ggtggctggt ccacctggac agagtggtct    960
gtgtgtaaca gccgctgtgg gcgaggatat cagaaacgca caagaacctg caccaaccca   1020
gccccactca atggtggggc cttctgtgag gggcagagtg tgcagaaaat agcatgcact   1080
acgttatgtc cagtggatgg taggtggact tcatggagca aatggtcaac ctgtgggact   1140
gaatgcaccc actggcgcag agggagtgt acagcaccag cccccaagaa cgggggtaag    1200
gactgtgatg gcctggtcct ccaatccaag aactgcactg atgggctgtg catgcaggct   1260
gctcctgact cagatgatgt ggctctctac gtggggattg tgatcgctgt aacagtctgt   1320
ctggcgatca ctgttgtggt ggccctgttt gtgtatcgga agaaccaccg tgactttgag   1380
tctgacatca ttgactcctc agcactcaat ggcggctttc agcctgtgaa catcaaggct   1440
gccagacaag atctcctggc tgtccccct gacctcacct cagctgcagc catgtacagg    1500
ggacctgtct atgctctgca tgatgtctca gacaaaatcc caatgaccaa ctctccaatt   1560
ctggacccac tacccaactt gaaaatcaaa gtgtacaaca gctcaggtgc tgtcactcct   1620
caggatgacc ttgccgagtt ctcatccaaa ctgtcacccc agatgaccca gtccttgcta   1680
gagaatgagg cccttaacct gaagaaccag agcctcgcaa gacagactga cccatcctgc   1740
acagcatttg gtaccttcaa ctctcttggg ggtcacctca tcattcctaa ttcaggagta   1800
agcttgctga ttcccgctgg ggccattcct caggggagag tctatgaaat gtatgtgact   1860
gtacacagga agaaaatat gaggcccccc atggaagact ctcagaccct acttacccct    1920
gtggtgagct gtgggcctcc tggagctctg ctgacccgcc ctgtcatcct cactctgcat   1980
cactgtgcag accccagcac cgaggactgg aagatccagc tcaaaaacca ggcagtgcag   2040
ggacaatggg aggatgttgt ggtggttggg gaggagaact tcacaacccc ctgttacatt   2100
cagctggatg cagaggcttg ccatatcctc acagagaacc tcagtaccta tgccctggtt   2160
gggcagtcca ccaccaaagc agctgccaag cgtcttaaac tggccatctt tgggcccctc   2220
tgctgctctt ccctggagta cagcattaga gtctactgcc tggatgacac acaggatgcc   2280
ctgaaggaag ttctacaact ggagaggcaa atgggaggac agctcctaga agaacccaag   2340
gctcttcatt ttaaaggcag catccacaac ctgcgcctgt ctattcatga catcgcccat   2400
tccctctgga gagcaaatt gctggctaag tatcaggaaa ttccattta ccacatctgg     2460
agtggctctc aaagaaacct ccactgcacc ttcactctgg aaagactcag cctaaacaca   2520
gtggaactgg tttgcaaact ctgtgtgcgg caggttgaag gagaagggca gatcttccag   2580
ctcaactgta ctgtgtcaga ggaacctact ggcatcgact acctctcct ggaccctgct    2640
agtaccatca ccactgtcac cggaccaagt gctttcagca ttcctctccc tatccggcag   2700
aagctatgca gcagcctgga tgcccctcaa acaagaggcc atgactggag gatgctggcc   2760
cataaactca acctgacag gtacttgaat tactttgcca ccaaatcgag cccaactggc    2820
gtaatcctgg atctttggga agcacagaac ttcccagatg gaaacctgag catgctggca   2880
gccgtcctgg aagaaatggg aagacatgag acagtggtgt ccttggcagc agaaggacag   2940
tattgatcac actggaacta aagctgaagg acacaattac acagggagtc tgtgttcagg   3000
ggaaccacat ctgaggagga aatccagata ggaccaaggc gctctacagg caagatggca   3060
acaggaaact tggggacgg atataaccac caaggtacac gcccacttca ttcggacagt    3120
accaccgcgg gagttaagaa aaattgtgta aatttgtacc ttgaatttaa gaatcaatct   3180
aattttctct tcgttgggct gtatgctgta tggtacagga tcttacagtt tcctaggaaa   3240
cgcttttat tgctatccag atgtatggat aaactttctt aacaaaccca gtttctacaa    3300
```

```
atgttgttta catcaaattg gacagggatg cagacactgt ccatggctcg ttctattttt      3360
gttcagatca tttgaagttg aagctgtgga cggtttattg tgtctatttc agattagtaa      3420
tttacagaga aatcacagac ttttgctaaa aatcatgtac atcaagtgtc tcagataatc      3480
ttcccatcag tgttctgttt ctgaaacttg ttggaccagt attggcattg gtatcaggga      3540
agtggagaat ctaaatgtaa aggagaaact gagaaaattc cttatatcct ggggtaaccc      3600
cgttggtatc ctttgggaac agagctctag cattacaggg gaggtagcta ttcatgttcc      3660
tccacacaaa catttctgta ccacatgtgt gtttgtaata agcaatttca agtgtttttt      3720
aaaaaaatat tatcattatt attgatgatt attacaaata ttctagtaaa aagaatttcc      3780
ttttgtttta gttagcaata ctgctagtgt ttggtgttga ctagacctgc ctccctttct      3840
tgcctaaaga ggtgggcatg gtcaccagtt tagttcaata gcttttgctt ccttgacctt      3900
tggtctacca ttctgtggtg gaaaagacag aaatgctcaa tggctatgtc tgctctttca      3960
gcttgctcgg tcagagtctt tctgctcttg cttttatcat gaggagagtt ctctatgtaa      4020
agttcattta ctcttgtggc tatctgggag gcagtatggt tgtgggaaca gtatctgaac      4080
taggaatctg gaaaccagtt atccttgtgg agttggtccc tgtatggctg tgtgactttg      4140
gggaaaacat cgaaactcac tggcgctcat tgcccttctt tgtaaacttt gtggtgagac      4200
cagatcatct caaggttcca gaatgctgat ctcccattca aatgtcatca gccttttcta      4260
tcttgcaggc aggattgact tgaacaggga ttacttcaac acacatttgt ttgtctttat      4320
ctttgtgtca ttattgcatg atgttgttcg cttagagatg gcatcctttt cttaccattg      4380
tcttgacctc tgctggggcc ctaatgtcca gccttccaac taactgtaaa ttctacttta      4440
ctcatttatt gatctccaga tctcaagacc atttctacaa aaagcccatg cggctgaatg      4500
aattggtaac attttttcttt ctttattact ctttgcttta gtaatattca gttgtattta      4560
tgtagattag tgctatagga ccatcctata aaacgttagt tgtgcatact ccttgggacc      4620
atcctgggtt ttgtttgtat gttagtttgt ttttattttt tgatatagga actccattca      4680
gcagatagta aatgaaaact tagcagcccc actgacatag ttaaatagaa agcacctatg      4740
tccttaagtc agaaacttca aaatgtggct gtggtgtact ttggggctag aagtattcag      4800
gttgctgaat ggattccatt gggaatcatt ttgcctaata ccctctgatt ctgttacttc      4860
ctgatacacg ctaactcttc tatcctagtc attaaagaac tgtgggtaca gttgtggagc      4920
ctcttccttc atgctgtttg tcttctcttt cagagatgta ttctacagtc tctttctcta      4980
accatattca tatataaaaa tcctggtccc actgactgtg gaagggaaat tctatactcc      5040
taaggaagtt tgttggctga tatctgtaag catgagtttg ttcgaacttt taagagtttg      5100
attgatattc ttaaaaagta agaggaagaa agactttgct gcctcttgaa acaagtgtga      5160
aggttcctct tcacttcttg gattttggaa ccatcaaaga aatccaatct gagaggtctg      5220
gactggatgt tctgtgtaac ttcaatgctt tgtgctaagt caagaggaac aaatatgttg      5280
ctattctggt taatttatcc taaaaactgt taagtcacca acacagaaat actgaatata      5340
accaaagcaa cattattgaa tattttgaga gtcctcgtgt tcaagcatct agagatactt      5400
gcttttgtat tcagactctc acaacaggca aaggaaaaat gactgatctc ttatgaagga      5460
atcatatgtc ataaaaccac tttctatcat gtgaatgaca gttccaaaac tagaacatac      5520
catacatcaa ataattttca ctaagcagtc tgctctttct ccttgggaag aaaatgatag      5580
ttgttagatt gctgctttcc aacacacacg tttcacctgc cacagttcat cttagaggaa      5640
gcttcatcat caccccctgtg gcatgtctga cttctacaga gcttctcagg aatgccttgc      5700
```

```
ttgctgtggg tgggtagaaa aacaaattat ttgtgcctgg tgccatctag tggcctgcca    5760
catagttact caatgtcata tacagcttac aaaaaattag caaagagagt taagtacctg    5820
tggagttcga catttgtgac aaatagacat ggtgaaattt acctacatgt gtaattctct    5880
tattctcgta ttcttcagtt aaattatcca ttttacaact ttctgggtat agcacgtcat    5940
caacttactc atacacatct taagttactt tcttgtgata cacatgtatg gaatctgtat    6000
ttttaaaagt ctctgaaaat tgtcattggg ctttgcatat ttgaaatctt ttaactccca    6060
aacactgact tttagaaata taaactgtat tcacaaagaa ggaagattcc ctgcccaaca    6120
gctccacaca catggcatca ccttgggcat atatattctt gctaggtatc ccagaacatc    6180
atcaaatcca tgaccctatt tccacagcct ctcaagtggt gagagtttaa ctatgtacca    6240
ctatacctgt tcaaacctgc tctacatttg taaatgagaa tcctgtctct atggacatgg    6300
aagttgtggc tgttaatcaa gacgaatgat cttcagatga agtagacctg agattaggaa    6360
tctaaaactt catgttctct tcttattgac attaattcaa attggcttga gtctaagcat    6420
gtgtcaagaa agtcacagcc aaacattttc aaagcagaca cattgtctct gctacacaaa    6480
gaattccatc ctgacctgag caaattaatc tcttctggga aaggataatt tggggaataa    6540
gaggtccaag atcaaagtat atcattagct attttcatat attctatgat tctacagatt    6600
ttaattattc cactatcaaa gagtagagac atccttaggg ggaaagttgc aatgactata    6660
tttaggatcc tctaggaaat aggtattaaa actaggtttt aaagacattt ctcctaaaaa    6720
tgattgaaag ggaaacactc agagggtagg atttagacag ttcacatctg gaagagagta    6780
gatggttgcc tacatctctg tgtgtctctg atgatgacct ggcacctatg atcctgggtc    6840
attcacacac acctacatag ccataggaca aagagagctt atagggagaa tgttctatcc    6900
cacaatccat acacatccct acagtctgcg ctctggagct acatcaatgt agaaggatgt    6960
tagataatat gagagaaaaa gtaagaaaga tttacttatt ccccggtctt caagatgaac    7020
acgaatttga gctgagtaat tgctctggaa aagtattcta ttcagagata tgtgctggtg    7080
taagtccaag gccagtggtg gcaaaggagg attacagaaa cacagtgtgg gtggacttag    7140
gctcgagaca cctttactga gcagctttgt caaccaggac atcattgttc aaatcaatca    7200
tttgtaaaga tgataatggc caatgagcat cttattttat agatccaaaa gaaaatatt    7260 tttattatta ttctcaagat aataaaactg gttttttgcc ttctgagtgc ctcgtgggac    7320
caactatctt actcctttag tttttgtattg tttttgtatt tttaaagcat actgagctga    7380
cattgactga aaacctttta actctctgtc tatacaacaa aatcctgttt ctctacccca    7440
agatatccga ttgtgtcacc tctgcttaca ctgaccactt tgacagtcac ccgataactt    7500
tttgatggga ttgggactat gaggaataca cttattataa ccaatactaa tttatggtca    7560
tataggctaa ataagccata tgaagtcata cctgttttcca aaaagctgac acttaagctc    7620
attggtttaa tgagtagaga tggcctgcat gtaccagggt ggaatatctc ttcaaactaa    7680
caatgcagtt gtgaatcctt tagttctttt ggtcaaatgg ttgcccccctt ttctgaaaac    7740 ttactgcaat agtcttcaga aagtccagtg ggcttgccta cttcctttct tgatctgtgg    7800
tgggatatta acaggcttat tcaaccaaag gtgttttcag aggcctattt aattgtggct    7860
ggggtatcct caggacaaat agatgcactc cataaatata ctagcaggca aagccaaaga    7920
gatgtaagtg gcgacctgca agtcttcagt atactaaact ttatatgaag gtatctatcc    7980
caagagtacc aaaatgctac attggaaacc cttgccatat atcaggacag tcatggccaa    8040
acccactagt tactaagcag aaaaccagag agtgtcctga aatacaatca gctgtccacc    8100
```

```
agccatgtta tttgctatgg tacaccagct ttttatatat catttgggaa cctgtgctat    8160
ggcagaatta taaattgcag gtaaaattac tgtaaaaccc attttaaata agcctaaacc    8220
ccataccatc tttatatgcc aaaggcctaa tgccatggag cctgatgacc cgtggccatg    8280
gtgactgtca actgtgggct agttgtcttg atgggcagcc taagggatga gctctctgcc    8340
tttgatcttc actcagtgat gatgtggcaa catcaaagca tcctgatgag ctctgtgctg    8400
tattaaaccc atttaaagat agcattccaa acaaatccac agctagtaga aaatgccttt    8460
gcccatttct gtgttcctaa agacattaat ggcacctata actgcataca tatgtattca    8520
gatatatttt tctccagatt attggaaaga aagaggagcc agttgaagac atgactcgca    8580
ttctttcttt cacttgttcc tagtcccgac tatgggtatt gatgccctca cccttcagac    8640
aatgtattta gccaagttgc agggaatatc attattgtat gtatactgtg tgtatgtgtg    8700
tgtgtgtgta tgtgtgtgta agatgtcaca gtgttgtgtt tattaagctt aatgttgagc    8760
tgtaaggaac cagtaatctt cctccgtgct ctaaagaaga aaacccatat tcatgagaga    8820
acaatcccag ctttctgctt taaaaaaaaa aaaaagggga agaagaagct gggtagctgg    8880
gtcaccctcc tgctgtcttc tttggaccag ttcaacttca gaagtatcag gttgaaattt    8940
tatgctttgt cagttttttct tttttttagca aaacaacatg accttggctt ctcagatatg    9000
gagcacttct tccttccttt gttatggaat tctgtcttgc tgtatattct atgcaactcc    9060
tttcctaatg accccagtg gctgcggagt gctctccagc attctgctca tcctcatcgc    9120
cttgctgtgt ggttgaggtg taccggcttt gggtgtgcct cttttctctc tctggttgcc    9180
tcacccaatt tacctgccgt ccccttggtt tgtaaactgc ctgcatttac tcttgtcagc    9240
caacatgtac aaatgtaaga aagaattttt aaacaggtaa taaattatat ttataagcg     9299
```

<210> SEQ ID NO 22
<211> LENGTH: 931
<212> TYPE: PRT
<213> ORGANISM: Mouse

<400> SEQUENCE: 22

Met Arg Lys Gly Leu Arg Ala Thr Ala Ala Arg Cys Gly Leu Gly Leu
1               5                   10                  15

Gly Tyr Leu Leu Gln Met Leu Val Leu Pro Ala Leu Ala Leu Leu Ser
            20                  25                  30

Ala Ser Gly Thr Gly Ser Ala Ala Gln Asp Asp Glu Phe Phe His Glu
        35                  40                  45

Leu Pro Glu Thr Phe Pro Ser Asp Pro Pro Glu Pro Leu Pro His Phe
    50                  55                  60

Leu Ile Glu Pro Glu Glu Ala Tyr Ile Val Lys Asn Lys Pro Val Asn
65                  70                  75                  80

Leu Tyr Cys Lys Ala Ser Pro Ala Thr Gln Ile Tyr Phe Lys Cys Asn
                85                  90                  95

Ser Glu Trp Val His Gln Lys Asp His Val Val Asp Glu Arg Val Asp
            100                 105                 110

Glu Thr Ser Gly Leu Ile Val Arg Glu Val Ser Ile Glu Ile Ser Arg
        115                 120                 125

Gln Gln Val Glu Glu Leu Phe Gly Pro Glu Asp Tyr Trp Cys Gln Cys
    130                 135                 140

Val Ala Trp Ser Ser Ala Gly Thr Thr Lys Ser Arg Lys Ala Tyr Val
145                 150                 155                 160

Arg Ile Ala Tyr Leu Arg Lys Thr Phe Glu Gln Glu Pro Leu Gly Lys

```
                            165                 170                 175
        Glu Val Ser Leu Glu Gln Glu Val Leu Leu Gln Cys Arg Pro Pro Glu
                    180                 185                 190
        Gly Ile Pro Val Ala Glu Val Glu Trp Leu Lys Asn Glu Asp Ile Ile
                    195                 200                 205
        Asp Pro Ala Glu Asp Arg Asn Phe Tyr Ile Thr Ile Asp His Asn Leu
                    210                 215                 220
        Ile Ile Lys Gln Ala Arg Leu Ser Asp Thr Ala Asn Tyr Thr Cys Val
        225                 230                 235                 240
        Ala Lys Asn Ile Val Ala Lys Arg Lys Ser Thr Thr Ala Thr Val Ile
                    245                 250                 255
        Val Tyr Val Asn Gly Gly Trp Ser Thr Trp Thr Glu Trp Ser Val Cys
                    260                 265                 270
        Asn Ser Arg Cys Gly Arg Gly Tyr Gln Lys Arg Thr Arg Thr Cys Thr
                    275                 280                 285
        Asn Pro Ala Pro Leu Asn Gly Gly Ala Phe Cys Glu Gly Gln Ser Val
                    290                 295                 300
        Gln Lys Ile Ala Cys Thr Thr Leu Cys Pro Val Asp Gly Arg Trp Thr
        305                 310                 315                 320
        Ser Trp Ser Lys Trp Ser Thr Cys Gly Thr Glu Cys Thr His Trp Arg
                    325                 330                 335
        Arg Arg Glu Cys Thr Ala Pro Ala Pro Lys Asn Gly Gly Lys Asp Cys
                    340                 345                 350
        Asp Gly Leu Val Leu Gln Ser Lys Asn Cys Thr Asp Gly Leu Cys Met
                    355                 360                 365
        Gln Ala Ala Pro Asp Ser Asp Asp Val Ala Leu Tyr Val Gly Ile Val
                    370                 375                 380
        Ile Ala Val Thr Val Cys Leu Ala Ile Thr Val Val Val Ala Leu Phe
        385                 390                 395                 400
        Val Tyr Arg Lys Asn His Arg Asp Phe Glu Ser Asp Ile Ile Asp Ser
                    405                 410                 415
        Ser Ala Leu Asn Gly Gly Phe Gln Pro Val Asn Ile Lys Ala Ala Arg
                    420                 425                 430
        Gln Asp Leu Leu Ala Val Pro Pro Asp Leu Thr Ser Ala Ala Ala Met
                    435                 440                 445
        Tyr Arg Gly Pro Val Tyr Ala Leu His Asp Val Ser Asp Lys Ile Pro
                    450                 455                 460
        Met Thr Asn Ser Pro Ile Leu Asp Pro Leu Pro Asn Leu Lys Ile Lys
        465                 470                 475                 480
        Val Tyr Asn Ser Ser Gly Ala Val Thr Pro Gln Asp Asp Leu Ala Glu
                    485                 490                 495
        Phe Ser Ser Lys Leu Ser Pro Gln Met Thr Gln Ser Leu Leu Glu Asn
                    500                 505                 510
        Glu Ala Leu Asn Leu Lys Asn Gln Ser Leu Ala Arg Gln Thr Asp Pro
                    515                 520                 525
        Ser Cys Thr Ala Phe Gly Thr Phe Asn Ser Leu Gly Gly His Leu Ile
                    530                 535                 540
        Ile Pro Asn Ser Gly Val Ser Leu Leu Ile Pro Ala Gly Ala Ile Pro
        545                 550                 555                 560
        Gln Gly Arg Val Tyr Glu Met Tyr Val Thr Val His Arg Lys Glu Asn
                    565                 570                 575
        Met Arg Pro Pro Met Glu Asp Ser Gln Thr Leu Leu Thr Pro Val Val
                    580                 585                 590
```

| | | | | | | | | | | | | |
|---|---|---|---|---|---|---|---|---|---|---|---|---|
|Ser|Cys|Gly|Pro|Pro|Gly|Ala|Leu|Leu|Thr|Arg|Pro|Val|Ile|Leu|Thr|
| |595| | | |600| | | | |605| | |

Ser Cys Gly Pro Pro Gly Ala Leu Leu Thr Arg Pro Val Ile Leu Thr
    595             600             605

Leu His His Cys Ala Asp Pro Ser Thr Glu Asp Trp Lys Ile Gln Leu
610             615             620

Lys Asn Gln Ala Val Gln Gly Gln Trp Glu Asp Val Val Val Gly
625             630             635             640

Glu Glu Asn Phe Thr Thr Pro Cys Tyr Ile Gln Leu Asp Ala Glu Ala
            645             650             655

Cys His Ile Leu Thr Glu Asn Leu Ser Thr Tyr Ala Leu Val Gly Gln
            660             665             670

Ser Thr Thr Lys Ala Ala Lys Arg Leu Lys Leu Ala Ile Phe Gly
            675             680             685

Pro Leu Cys Cys Ser Ser Leu Glu Tyr Ser Ile Arg Val Tyr Cys Leu
    690             695             700

Asp Asp Thr Gln Asp Ala Leu Lys Glu Val Leu Gln Leu Glu Arg Gln
705             710             715             720

Met Gly Gly Gln Leu Leu Glu Pro Lys Ala Leu His Phe Lys Gly
                725             730             735

Ser Ile His Asn Leu Arg Leu Ser Ile His Asp Ile Ala His Ser Leu
            740             745             750

Trp Lys Ser Lys Leu Leu Ala Lys Tyr Gln Glu Ile Pro Phe Tyr His
            755             760             765

Ile Trp Ser Gly Ser Gln Arg Asn Leu His Cys Thr Phe Thr Leu Glu
    770             775             780

Arg Leu Ser Leu Asn Thr Val Glu Leu Val Cys Lys Leu Cys Val Arg
785             790             795             800

Gln Val Glu Gly Glu Gly Gln Ile Phe Gln Leu Asn Cys Thr Val Ser
            805             810             815

Glu Glu Pro Thr Gly Ile Asp Leu Pro Leu Asp Pro Ala Ser Thr
            820             825             830

Ile Thr Thr Val Thr Gly Pro Ser Ala Phe Ser Ile Pro Leu Pro Ile
    835             840             845

Arg Gln Lys Leu Cys Ser Ser Leu Asp Ala Pro Gln Thr Arg Gly His
850             855             860

Asp Trp Arg Met Leu Ala His Lys Leu Asn Leu Asp Arg Tyr Leu Asn
865             870             875             880

Tyr Phe Ala Thr Lys Ser Ser Pro Thr Gly Val Ile Leu Asp Leu Trp
            885             890             895

Glu Ala Gln Asn Phe Pro Asp Gly Asn Leu Ser Met Leu Ala Ala Val
            900             905             910

Leu Glu Glu Met Gly Arg His Glu Thr Val Val Ser Leu Ala Ala Glu
            915             920             925

Gly Gln Tyr
    930

<210> SEQ ID NO 23
<211> LENGTH: 3646
<212> TYPE: DNA
<213> ORGANISM: Homo sapiens

<400> SEQUENCE: 23
ctgcctttgg agaaagtgga gtgtggcgct tggttgtcgt tatttcttcg gactgcttcg    60
cggtgcacgg attcagcttc tgcccagtgg ggctttcagc tgtttgcgcg tctctctgtc   120
cccctcccct ccccccggca cacctctgtc tacgatgagg aaaggtctgc gggcgacagc   180

```
ggcccgctgc ggactgggac tgggatactt gctgcaaatg ctcgtgctac ctgccctggc    240
cctgctcagc gccagcggca ctggctccgc cgcccaagat gatgactttt ttcatgaact    300
cccagaaact tttccttctg atccacctga gcctctgcca catttcctta ttgagcctga    360
agaagcttat attgtgaaga ataagcctgt gaacctgtac tgtaaagcaa gccctgccac    420
ccagatctat ttcaagtgta atagtgaatg ggttcatcag aaggaccaca tagtagatga    480
aagagtagat gaaacttccg gtctcattgt ccgggaagtg agcattgaga tttcgcgcca    540
gcaagtggaa gaactctttg gacctgaaga ttactggtgc cagtgtgtgg cctggagctc    600
cgcgggtacc acaaagagcc ggaaggcgta tgtgcgcatt gcatatctac ggaagacatt    660
tgagcaggaa cccctaggaa aggaagtgtc tttggaacag gaagtcttac tccagtgtcg    720
accacctgaa gggatcccag tggctgaggt ggaatggttg aaaaatgaag acataattga    780
tcccgttgaa gatcggaatt tttatattac tattgatcac aacctcatca taaagcaggc    840
ccgactctct gatactgcaa attacacctg tgttgccaaa acattgttg ccaagaggaa     900 aagtacaact gccactgtca tagtctatgt caacggtggc tggtccacct ggacggagtg    960
gtctgtgtgt aacagccgct gtggacgagg gtatcagaaa cgtacaagga cttgtaccaa   1020
cccggcacca ctcaatgggg gtgccttctg tgaagggcag agtgtgcaga aaatagcctg   1080
tactacgtta tgcccagtgg atggcaggtg gacgccatgg agcaagtggt ctacttgtgg   1140
aactgagtgc acccactggc gcaggaggga gtgcacggcg ccagccccca gaatggagg    1200 caaggactgc gacggcctcg tcttgcaatc caagaactgc actgatgggc tttgcatgca   1260
gactgctcct gattcagatg atgttgctct ctatgttggg attgtgatag cagtgatcgt   1320
ttgcctggcg atctctgtag ttgtggcctt gtttgtgtat cggaagaatc atcgtgactt   1380
tgagtcagat attattgact cttcggcact caatgggggc tttcagcctg tgaacatcaa   1440
ggcagcaaga caagatctgc tggctgtacc cccagacctc acgtcagctg cagccatgta   1500
cagaggacct gtctatgccc tgcatgacgt ctcagacaaa atcccaatga ccaactctcc   1560
aattctggat ccactgccca acctgaaaat caaagtgtac aacacctcag gtgctgtcac   1620
cccccaagat gacctctctg agtttacgtc caagctgtcc cctcagatga cccagtcgtt   1680
gttggagaat gaagccctca gcctgaagaa ccagagtcta gcaaggcaga ctgatccatc   1740
ctgtaccgca tttggcagct tcaactcgct gggaggtcac cttattgttc caattcagg    1800 agtcagcttg ctgattcccg ctggggccat tccccaaggg agagtctacg aaatgtatgt   1860
gactgtacac aggaaagaaa ctatgaggcc acccatggat gactctcaga cactttttgac  1920 ccctgtggtg agctgtgggc cccaggagc tctgctcacc cgccccgtcg tcctcactat    1980
gcatcactgc gcagacccca ataccgagga ctggaaaata ctgctcaaga accaggcagc   2040
acagggacag tgggaggatg tggtggtggt cggggaggaa aacttccacca cccctgcta   2100 cattaagctg gatgcagagg cctgccacat cctcacagag aacctcagca cctacgccct   2160
ggtaggacat tccaccacca aagcggctgc aaagcgcctc aagctggcca tctttgggcc   2220
cctgtgctgc tcctcgctgg agtacagcat ccgagtctac tgtctggatg acacccagga   2280
tgccctgaag gaaattttac atcttgagag acagacggga ggacagctcc tagaagaacc   2340
taaggctctt catttttaaag gcagcaccca caacctgcgc ctgtcaattc acgatatcgc   2400
ccattccctc tggaagagca aattgctggc taaatatcag gaaattccat tttaccatgt   2460
ttggagtgga tctcaaagaa acctgcactg caccttcact ctggaaagat ttagcctgaa   2520
cacagtggag ctggtttgca aactctgtgt gcggcaggtg gaaggagaag ggcagatctt   2580
```

```
ccagctcaac tgcaccgtgt cagaggaacc tactggcatc gatttgccgc tgctggatcc    2640
tgcgaacacc atcaccacgg tcacggggcc cagtgctttc agcatccctc tccctatccg    2700
gcagaagctc tgtagcagcc tggatgcccc ccagacgaga ggccatgact ggaggatgct    2760
ggcccataag ctgaacctgg acaggtactt gaattacttt gccaccaaat ccagcccaac    2820
tggcgtaatc ctggatcttt gggaagcaca gaacttccca gatggaaacc tgagcatgct    2880
ggcagctgtc ttgaagaaa tgggaagaca tgaaacggtg gtgtccttag cagcagaagg    2940
gcagtattaa ccaccatgct ggaaggggaa atgaaggaca aaatgcaca gggagtctgt     3000 ggccgtccag gtgaatcaca gctgaggagg aaatccagat gagaccaatg cacttcacag    3060
gcaagaatgc agcaggagcc agaaggaaaa cagatacaac tgcccatgta catgcccact    3120
ttactcggag atcatcacgg gagttaagaa aaattgtgta aatttgtacc ttgaatttag    3180
ctatcaacct aattttcctc ttagttgggc tgtatgctgt gtggtacagg atcttacagt    3240
ttcctaggaa acgcttttta ttgctatcca gatatatgga taaactttct taacaaaccc    3300
aatttctaca aatgttgttt acatcaaatt ggacagggat gcagacactg tccatggctc    3360
gttctatttt tgttcaaatc atttgaagtt gaagctgtgg acgtttgtt gtgtctatttt     3420 cagattagta atttacagag aaatcacaga cttttgctac aaatcgtgtg catcaagtgt    3480
ctcagataat cctcccatca gtgttctgtt tctagaactt gtagaaccag tgttactgtt    3540
tgtatcaggg aagtggagaa tctaagtgta aaaagaaat aactaagact cctattcctt     3600
ggagggaccc ttctggtgcc ctttgggaat aaagctgtag cactgc                   3646
```

<210> SEQ ID NO 24
<211> LENGTH: 931
<212> TYPE: PRT
<213> ORGANISM: Homo sapiens

<400> SEQUENCE: 24

```
Met Arg Lys Gly Leu Arg Ala Thr Ala Ala Arg Cys Gly Leu Gly Leu
 1               5                  10                  15

Gly Tyr Leu Leu Gln Met Leu Val Leu Pro Ala Leu Ala Leu Leu Ser
            20                  25                  30

Ala Ser Gly Thr Gly Ser Ala Ala Gln Asp Asp Asp Phe Phe His Glu
        35                  40                  45

Leu Pro Glu Thr Phe Pro Ser Asp Pro Pro Glu Pro Leu Pro His Phe
    50                  55                  60

Leu Ile Glu Pro Glu Glu Ala Tyr Ile Val Lys Asn Lys Pro Val Asn
65                  70                  75                  80

Leu Tyr Cys Lys Ala Ser Pro Ala Thr Gln Ile Tyr Phe Lys Cys Asn
                85                  90                  95

Ser Glu Trp Val His Gln Lys Asp His Ile Val Asp Glu Arg Val Asp
            100                 105                 110

Glu Thr Ser Gly Leu Ile Val Arg Glu Val Ser Ile Glu Ile Ser Arg
        115                 120                 125

Gln Gln Val Glu Glu Leu Phe Gly Pro Glu Asp Tyr Trp Cys Gln Cys
    130                 135                 140

Val Ala Trp Ser Ser Ala Gly Thr Thr Lys Ser Arg Lys Ala Tyr Val
145                 150                 155                 160

Arg Ile Ala Tyr Leu Arg Lys Thr Phe Glu Gln Glu Pro Leu Gly Lys
                165                 170                 175

Glu Val Ser Leu Glu Gln Glu Val Leu Leu Gln Cys Arg Pro Pro Glu
            180                 185                 190
```

-continued

```
Gly Ile Pro Val Ala Glu Val Glu Trp Leu Lys Asn Glu Asp Ile Ile
        195                 200                 205

Asp Pro Val Glu Asp Arg Asn Phe Tyr Ile Thr Ile Asp His Asn Leu
    210                 215                 220

Ile Ile Lys Gln Ala Arg Leu Ser Asp Thr Ala Asn Tyr Thr Cys Val
225                 230                 235                 240

Ala Lys Asn Ile Val Ala Lys Arg Lys Ser Thr Thr Ala Thr Val Ile
                245                 250                 255

Val Tyr Val Asn Gly Gly Trp Ser Thr Trp Thr Glu Trp Ser Val Cys
                    260                 265                 270

Asn Ser Arg Cys Gly Arg Gly Tyr Gln Lys Arg Thr Arg Thr Cys Thr
            275                 280                 285

Asn Pro Ala Pro Leu Asn Gly Gly Ala Phe Cys Glu Gly Gln Ser Val
    290                 295                 300

Gln Lys Ile Ala Cys Thr Thr Leu Cys Pro Val Asp Gly Arg Trp Thr
305                 310                 315                 320

Pro Trp Ser Lys Trp Ser Thr Cys Gly Thr Glu Cys Thr His Trp Arg
                325                 330                 335

Arg Arg Glu Cys Thr Ala Pro Ala Pro Lys Asn Gly Gly Lys Asp Cys
                    340                 345                 350

Asp Gly Leu Val Leu Gln Ser Lys Asn Cys Thr Asp Gly Leu Cys Met
            355                 360                 365

Gln Thr Ala Pro Asp Ser Asp Val Ala Leu Tyr Val Gly Ile Val
    370                 375                 380

Ile Ala Val Ile Val Cys Leu Ala Ile Ser Val Val Ala Leu Phe
385                 390                 395                 400

Val Tyr Arg Lys Asn His Arg Asp Phe Glu Ser Asp Ile Ile Asp Ser
                405                 410                 415

Ser Ala Leu Asn Gly Gly Phe Gln Pro Val Asn Ile Lys Ala Ala Arg
            420                 425                 430

Gln Asp Leu Leu Ala Val Pro Pro Asp Leu Thr Ser Ala Ala Ala Met
    435                 440                 445

Tyr Arg Gly Pro Val Tyr Ala Leu His Asp Val Ser Asp Lys Ile Pro
    450                 455                 460

Met Thr Asn Ser Pro Ile Leu Asp Pro Leu Pro Asn Leu Lys Ile Lys
465                 470                 475                 480

Val Tyr Asn Thr Ser Gly Ala Val Thr Pro Gln Asp Asp Leu Ser Glu
                485                 490                 495

Phe Thr Ser Lys Leu Ser Pro Gln Met Thr Gln Ser Leu Leu Glu Asn
            500                 505                 510

Glu Ala Leu Ser Leu Lys Asn Gln Ser Leu Ala Arg Gln Thr Asp Pro
    515                 520                 525

Ser Cys Thr Ala Phe Gly Ser Phe Asn Ser Leu Gly Gly His Leu Ile
530                 535                 540

Val Pro Asn Ser Gly Val Ser Leu Leu Ile Pro Ala Gly Ala Ile Pro
545                 550                 555                 560

Gln Gly Arg Val Tyr Glu Met Tyr Val Thr Val His Arg Lys Glu Thr
                565                 570                 575

Met Arg Pro Pro Met Asp Asp Ser Gln Thr Leu Leu Thr Pro Val Val
            580                 585                 590

Ser Cys Gly Pro Pro Gly Ala Leu Leu Thr Arg Pro Val Val Leu Thr
        595                 600                 605

Met His His Cys Ala Asp Pro Asn Thr Glu Asp Trp Lys Ile Leu Leu
610                 615                 620
```

-continued

```
Lys Asn Gln Ala Ala Gln Gly Gln Trp Glu Asp Val Val Val Gly
625                 630                 635                 640

Glu Glu Asn Phe Thr Thr Pro Cys Tyr Ile Lys Leu Asp Ala Glu Ala
            645                 650                 655

Cys His Ile Leu Thr Glu Asn Leu Ser Thr Tyr Ala Leu Val Gly His
        660                 665                 670

Ser Thr Thr Lys Ala Ala Lys Arg Leu Lys Leu Ala Ile Phe Gly
        675                 680                 685

Pro Leu Cys Cys Ser Ser Leu Glu Tyr Ser Ile Arg Val Tyr Cys Leu
    690                 695                 700

Asp Asp Thr Gln Asp Ala Leu Lys Glu Ile Leu His Leu Glu Arg Gln
705                 710                 715                 720

Thr Gly Gly Gln Leu Leu Glu Glu Pro Lys Ala Leu His Phe Lys Gly
                725                 730                 735

Ser Thr His Asn Leu Arg Leu Ser Ile His Asp Ile Ala His Ser Leu
            740                 745                 750

Trp Lys Ser Lys Leu Leu Ala Lys Tyr Gln Glu Ile Pro Phe Tyr His
        755                 760                 765

Val Trp Ser Gly Ser Gln Arg Asn Leu His Cys Thr Phe Thr Leu Glu
    770                 775                 780

Arg Phe Ser Leu Asn Thr Val Glu Leu Val Cys Lys Leu Cys Val Arg
785                 790                 795                 800

Gln Val Glu Gly Glu Gly Gln Ile Phe Gln Leu Asn Cys Thr Val Ser
                805                 810                 815

Glu Glu Pro Thr Gly Ile Asp Leu Pro Leu Leu Asp Pro Ala Asn Thr
            820                 825                 830

Ile Thr Thr Val Thr Gly Pro Ser Ala Phe Ser Ile Pro Leu Pro Ile
        835                 840                 845

Arg Gln Lys Leu Cys Ser Ser Leu Asp Ala Pro Gln Thr Arg Gly His
850                 855                 860

Asp Trp Arg Met Leu Ala His Lys Leu Asn Leu Asp Arg Tyr Leu Asn
865                 870                 875                 880

Tyr Phe Ala Thr Lys Ser Ser Pro Thr Gly Val Ile Leu Asp Leu Trp
                885                 890                 895

Glu Ala Gln Asn Phe Pro Asp Gly Asn Leu Ser Met Leu Ala Ala Val
            900                 905                 910

Leu Glu Glu Met Gly Arg His Glu Thr Val Val Ser Leu Ala Ala Glu
        915                 920                 925

Gly Gln Tyr
    930
```

<210> SEQ ID NO 25
<211> LENGTH: 5414
<212> TYPE: DNA
<213> ORGANISM: Mouse

<400> SEQUENCE: 25

```
gcaggaggga ggcgcccgga gtctttcccc ctgggcgcgc gaggggggccg cgcgggccgg    60 gccgggccgg gctggagccg agccctgcgg cgcagagacc ggctgaggcg cgctgaggga   120
agggcgcgag cgctccgcgg cgctatcgcc gccgccgccg ccgccactcg tggggtagag   180
atggcggcgg agcgcgaagc cgggcgactc ctctgcacct cctcctcccg gcgctgctgt   240
ccgccaccgc cgctgctgct gttgctgccg ctgctgctgc tgctcggacg cccggcgtcc   300
ggcgccgcgg ccacgaagag cggccccccgc cggcagtccc aaggagccag tgttcgaaca   360
```

```
ttcactccgt tttattttct ggtggagcca gtagacaccc tctcagttag aggctcttct    420
gttatattaa attgctcggc atattctgag ccctctccaa acattgaatg gaagaaagat    480 gggactttt  taaacttaga atcagatgat cgacgccagc tactcccaga tggatcttta    540
ttcatcagca acgtggtgca ttccaaacac aataagcctg acgaaggttt ctatcagtgt    600
gtagccactg tggataatct tggaaccatt gtcagcagaa cagccaagct cacagtagca    660
ggtcttccaa gatttaccag ccaaccagaa ccttcttcag tctatgttgg aaacagtgca    720
attctgaatt gtgaagttaa tgcagatttg gtcccatttg ttaggtggga acagaatcga    780
cagccccttc ttctagatga caggattgtc aaacttccaa gtggaacact ggttatcagc    840
aatgctactg aaggagatgg gggactctac cgctgcattg ttgaaagtgg tgggccacca    900
aagtttagtg acgaagctga attgaaagtt cttcaagatc ctgaggaaat tgtagacttg    960
gtatttctga tgcgaccatc ttctatgatg aaagtcactg gtcagagtgc agtgttgcca   1020
tgtgttgtct cagggcttcc tgctccagtt gttagatgga tgaaaacgaa gaagtgctt   1080 gacacagaaa gctctggcag gttggtcttg ctagcaggag gttgcttgga gatcagtgat   1140
gtcactgagg atgatgctgg gacttatttt tgcatagctg ataatggaaa taagacagtt   1200
gaagctcagg cggagcttac tgtgcaagtg ccacctggat tcctgaaaca acctgctaac   1260
atatatgctc acgaatccat ggacattgta tttgaatgtg aagtcactgg gaagccaact   1320
ccaactgtga agtgggtcaa gaatggggat gtggttatcc ccagtgataa ctttaaaatt   1380
gtaaaggaac ataatcttca agttttgggt ctggtgaaat cagatgaagg gttctatcaa   1440
tgcattgctg agaatgatgt tggaaatgca caagctggag cccagctgat aatccttgag   1500
catgatgttg ccatcccaac attacctccc acttcactga ccagtgccac tactgaccat   1560
ctagcaccag ccacaacggg accattacct tcagctcctc gagacgtcgt ggcctccctg   1620
gtctctactc gcttcattaa attgacatgg cgtacacctg catcagaccc tcatggagac   1680
aatctcacct actctgtgtt ctacaccaag gaaggggttg atagggagcg tgttgagaat   1740
accagccagc caggagagat gcaggtgact attcaaaact tgatgccagc aactgtgtac   1800
atcttcaaag ttatggctca aaataagcat ggctctggag aaagttcagc tcctcttcga   1860
gtagagacac agcctgaggt tcagctccct ggcccagcac ctaatatccg tgcttatgca   1920
acgtcaccta cttctatcac tgtcacctgg gaaacaccgt tatctggcaa tggggaaatt   1980
caaaattaca aattgtacta catggaaaaa ggaactgata agaacagga tattgatgtt   2040 tcaagtcact cctacaccat taatggactg aagaaataca cagaatacag tttccgagtg   2100
gtggcctaca ataaacatgg tcctggagtt tctacacaag atgttgctgt tcgaacatta   2160
tcagatgttc ccagtgctgc tcctcagaat ctgtccttag aagtgagaaa ttcaaagagt   2220
atagtgatcc actggcagcc cccttcctca accacacaaa atgggcagat aactggctac   2280
aagattcgat atcgaaaggc ctcccgaaaa agtgatgtca ctgagacctt ggtaactggg   2340
acacagctgt ctcagctgat tgaaggtctt gatcggggga cagaatataa cttccgagtc   2400
gctgctctca cagtcaatgg tacaggtcca gcaactgatt ggctgtctgc tgaaactttt   2460
gaaagcgacc tagatgaaac tcgtgttcct gaagtgccca gctctcttca tgtccgtccg   2520
ctcgtcacta gcattgtagt gagctggact cctccagaga accagaacat tgtggtccga   2580
ggttatgcca tcggttacgg cattggcagc cctcatgccc agaccatcaa agtggactat   2640
aaacaacgtt attacaccat cgaaaacttg gatccaagct ctcattacgt gattaccttg   2700
aaagcattta acaatgttgg cgaaggcatc cccctttatg agagtgctgt gaccagacct   2760
```

```
cacacagaca cttctgaagt tgatttattt gttattaatg ctccatacac tccagtgcca    2820
gatcccactc ccatgatgcc accagtggga gttcaggctt ccattctgag tcacgacacc    2880
ataaggatta cctgggcaga caactccctg cccaaacacc agaagattac agactcccgc    2940
tactacacag tccggtggaa gaccaacatc ccagcaaaca cgaagtacaa gaatgcaaat    3000
gcaacgacgt taagctattt ggttactggt ttaaagccaa atacgctcta tgagttctct    3060
gtgatggtga ccaaaggcag aaggtcaagc acgtggagta tgacagctca tggcgctacc    3120
tttgaattag ttcctacttc tccacctaag gatgtgacag ttgtgagtaa ggaaggaaaa    3180
cctagaacca tcatagtgaa ttggcagcct ccctctgaag ctaacggcaa gattacaggt    3240
tacatcatct attacagcac ggatgtgaat gcagagatac atgactgggt tattgaacca    3300
gttgtgggaa acagactgac tcaccagatt caagagttaa cacttgatac gccatactac    3360
ttcaaaatcc aggcccggaa ctcaaagggc atggggccca tgtctgaagc tgtacagttc    3420
agaacaccta aagcggactc ctctgataaa atgcctaatg accaagcctt agggtcagca    3480
ggaaaaggaa gccgactacc agacctggga tctgactaca aacctccaat gagtggcagc    3540
aacagccctc acgggagccc cacctcccct ctggacagca catgctgct ggtcatcatt    3600 gtctctgttg gcgtcatcac tatcgtggtg gttgtggtca ttgctgtctt ttgtacccgg    3660
cgcaccacct ctcaccagaa gaagaaacga gctgcgtgca atcagtgaa tggctcccat    3720 aagtacaagg gcaattgcaa agatgtgaag cctccagacc tatggatcca tcacgagaga    3780
ctagagttga agcctattga caagtctcca gatcctaacc ctgtcatgac tgatactcca    3840
atccctcgaa actctcaaga tatcacacca gtggacaatt ccatggatag caatatccat    3900
caaaggcgga attcatacag agggcatgag tcagaggaca gcatgtctac actggctgga    3960
aggaggggaa tgagaccaaa aatgatgatg ccctttgact ctcagccacc tcagcctgtg    4020
attagtgccc atcccatcca ttccctcgat aaccctcacc atcatttcca ctccagcagc    4080
ctcgcttctc cagcccgcag tcatctctac cacccaagca gcccatggcc cattggcaca    4140
tccatgtccc tttcagacag ggccaattcc acagaatctg ttcgaaatac ccccagcacg    4200
gacaccatgc cagcgtcctc gtctcagacg tgctgcactg accatcagga ccctgagggt    4260
gctactagct cctcttactt ggccagctcc aagaggaag actcaggcca gagtcttccc    4320
acagcccatg tccgcccttc ccaccctctg aagagcttcg ctgtgccagc aatcccaccc    4380
ccaggacctc ctctctatga tcctgcactg ccaagcacac cattactgtc ccagcaagct    4440
ctggaaccat caacattcca ctcagtgaaa acagcctcca tcgggacgtt aggaaggagc    4500
cggcctccta tgccagtggt tgttccgagt gcccctgaag tacaggagac caccaggatg    4560
ctggaagact ccgagagtag ctatgaacca gatgagctga ccaaagagat ggcccacctg    4620
gaaggactaa tgaaggacct aaatgccatc acaacagcct gatgaccttt cgcctggaca    4680
tgactccaag cctgagtcta caagtctcgg aacttaacct tgaaaacaag gaattgtaca    4740
gagtacgaga ggacagcact tgagagcagg agccagcaaa ccagccagtg cctccatgtg    4800
gggttggctc caggcacagc caacctgcct tcctcctggt cagcctggat tacacttgtg    4860
tggaggcagc ttccctttgc ctgctgagag cctgcaggac tggacactat gggccaaaat    4920
tttgtgtcca gggaagaggc aagaagtacg acctgccttt tgctttgtgg tcagtggctt    4980
gtgtctttgt gctgcaactg catcactttt atggagtgta gacattggca tttatgtaca    5040
attttgtgtc ctattttatt ttaccttaaa acactatcag aagccaaggg agtctgtgat    5100
gttctctcaa gcagttgaca cttgactgtg gttccagtta cttacggaaa gtcatcaaca    5160
```

```
gtgaggttgt ttgacaccac tgacaggcat tggcttgttg tgggtttcat ttttattctt   5220
aattctgaga cattgcatcc tctgccagct gttaatccca tcactttgag gggaggacat   5280
gttgcattgc tgtttgtaag cttttttatt atttttttat tataattatt aaaggcctga   5340
ctttctcctc tcatcactgt gagattacag atctatttga atgaaatgta acattgaaaa   5400
aaaaaaaaaa aaaa                                                     5414
```

<210> SEQ ID NO 26
<211> LENGTH: 1493
<212> TYPE: PRT
<213> ORGANISM: Mouse

<400> SEQUENCE: 26

```
Met Ala Ala Glu Arg Glu Ala Gly Arg Leu Leu Cys Thr Ser Ser Ser
 1               5                  10                  15

Arg Arg Cys Cys Pro Pro Pro Leu Leu Leu Leu Pro Leu Leu
            20                  25                  30

Leu Leu Leu Gly Arg Pro Ala Ser Gly Ala Ala Ala Thr Lys Ser Gly
        35                  40                  45

Pro Arg Arg Gln Ser Gln Gly Ala Ser Val Arg Thr Phe Thr Pro Phe
    50                  55                  60

Tyr Phe Leu Val Glu Pro Val Asp Thr Leu Ser Val Arg Gly Ser Ser
65                  70                  75                  80

Val Ile Leu Asn Cys Ser Ala Tyr Ser Glu Pro Ser Pro Asn Ile Glu
                85                  90                  95

Trp Lys Lys Asp Gly Thr Phe Leu Asn Leu Glu Ser Asp Asp Arg Arg
            100                 105                 110

Gln Leu Leu Pro Asp Gly Ser Leu Phe Ile Ser Asn Val Val His Ser
        115                 120                 125

Lys His Asn Lys Pro Asp Glu Gly Phe Tyr Gln Cys Val Ala Thr Val
    130                 135                 140

Asp Asn Leu Gly Thr Ile Val Ser Arg Thr Ala Lys Leu Thr Val Ala
145                 150                 155                 160

Gly Leu Pro Arg Phe Thr Ser Gln Pro Glu Pro Ser Ser Val Tyr Val
                165                 170                 175

Gly Asn Ser Ala Ile Leu Asn Cys Glu Val Asn Ala Asp Leu Val Pro
            180                 185                 190

Phe Val Arg Trp Glu Gln Asn Arg Gln Pro Leu Leu Leu Asp Asp Arg
        195                 200                 205

Ile Val Lys Leu Pro Ser Gly Thr Leu Val Ile Ser Asn Ala Thr Glu
    210                 215                 220

Gly Asp Gly Gly Leu Tyr Arg Cys Ile Val Glu Ser Gly Gly Pro Pro
225                 230                 235                 240

Lys Phe Ser Asp Glu Ala Glu Leu Lys Val Leu Gln Asp Pro Glu Glu
                245                 250                 255

Ile Val Asp Leu Val Phe Leu Met Arg Pro Ser Ser Met Met Lys Val
            260                 265                 270

Thr Gly Gln Ser Ala Val Leu Pro Cys Val Val Ser Gly Leu Pro Ala
        275                 280                 285

Pro Val Val Arg Trp Met Lys Asn Glu Glu Val Leu Asp Thr Glu Ser
    290                 295                 300

Ser Gly Arg Leu Val Leu Leu Ala Gly Gly Cys Leu Glu Ile Ser Asp
305                 310                 315                 320

Val Thr Glu Asp Asp Ala Gly Thr Tyr Phe Cys Ile Ala Asp Asn Gly
```

```
                    325                 330                 335
Asn Lys Thr Val Glu Ala Gln Ala Glu Leu Thr Val Gln Val Pro Pro
                340                 345                 350

Gly Phe Leu Lys Gln Pro Ala Asn Ile Tyr Ala His Glu Ser Met Asp
                355                 360                 365

Ile Val Phe Glu Cys Glu Val Thr Gly Lys Pro Thr Pro Thr Val Lys
                370                 375                 380

Trp Val Lys Asn Gly Asp Val Val Ile Pro Ser Asp Asn Phe Lys Ile
385                 390                 395                 400

Val Lys Glu His Asn Leu Gln Val Leu Gly Leu Val Lys Ser Asp Glu
                405                 410                 415

Gly Phe Tyr Gln Cys Ile Ala Glu Asn Asp Val Gly Asn Ala Gln Ala
                420                 425                 430

Gly Ala Gln Leu Ile Ile Leu Glu His Asp Val Ala Ile Pro Thr Leu
                435                 440                 445

Pro Pro Thr Ser Leu Thr Ser Ala Thr Thr Asp His Leu Ala Pro Ala
                450                 455                 460

Thr Thr Gly Pro Leu Pro Ser Ala Pro Arg Asp Val Val Ala Ser Leu
465                 470                 475                 480

Val Ser Thr Arg Phe Ile Lys Leu Thr Trp Arg Thr Pro Ala Ser Asp
                485                 490                 495

Pro His Gly Asp Asn Leu Thr Tyr Ser Val Phe Tyr Thr Lys Glu Gly
                500                 505                 510

Val Asp Arg Glu Arg Val Glu Asn Thr Ser Gln Pro Gly Glu Met Gln
                515                 520                 525

Val Thr Ile Gln Asn Leu Met Pro Ala Thr Val Tyr Ile Phe Lys Val
                530                 535                 540

Met Ala Gln Asn Lys His Gly Ser Gly Glu Ser Ser Ala Pro Leu Arg
545                 550                 555                 560

Val Glu Thr Gln Pro Glu Val Gln Leu Pro Gly Pro Ala Pro Asn Ile
                565                 570                 575

Arg Ala Tyr Ala Thr Ser Pro Thr Ser Ile Thr Val Thr Trp Glu Thr
                580                 585                 590

Pro Leu Ser Gly Asn Gly Glu Ile Gln Asn Tyr Lys Leu Tyr Tyr Met
                595                 600                 605

Glu Lys Gly Thr Asp Lys Glu Gln Asp Ile Asp Val Ser Ser His Ser
                610                 615                 620

Tyr Thr Ile Asn Gly Leu Lys Lys Tyr Thr Glu Tyr Ser Phe Arg Val
625                 630                 635                 640

Val Ala Tyr Asn Lys His Gly Pro Gly Val Ser Thr Gln Asp Val Ala
                645                 650                 655

Val Arg Thr Leu Ser Asp Val Pro Ser Ala Ala Pro Gln Asn Leu Ser
                660                 665                 670

Leu Glu Val Arg Asn Ser Lys Ser Ile Val Ile His Trp Gln Pro Pro
                675                 680                 685

Ser Ser Thr Thr Gln Asn Gly Gln Ile Thr Gly Tyr Lys Ile Arg Tyr
                690                 695                 700

Arg Lys Ala Ser Arg Lys Ser Asp Val Thr Glu Thr Leu Val Thr Gly
705                 710                 715                 720

Thr Gln Leu Ser Gln Leu Ile Glu Gly Leu Asp Arg Gly Thr Glu Tyr
                725                 730                 735

Asn Phe Arg Val Ala Ala Leu Thr Val Asn Gly Thr Gly Pro Ala Thr
                740                 745                 750
```

```
Asp Trp Leu Ser Ala Glu Thr Phe Glu Ser Asp Leu Asp Glu Thr Arg
        755                 760                 765

Val Pro Glu Val Pro Ser Ser Leu His Val Arg Pro Leu Val Thr Ser
770                 775                 780

Ile Val Ser Trp Thr Pro Pro Glu Asn Gln Asn Ile Val Val Arg
785                 790                 795                 800

Gly Tyr Ala Ile Gly Tyr Gly Ile Gly Ser Pro His Ala Gln Thr Ile
                805                 810                 815

Lys Val Asp Tyr Lys Gln Arg Tyr Tyr Thr Ile Glu Asn Leu Asp Pro
                820                 825                 830

Ser Ser His Tyr Val Ile Thr Leu Lys Ala Phe Asn Asn Val Gly Glu
            835                 840                 845

Gly Ile Pro Leu Tyr Glu Ser Ala Val Thr Arg Pro His Thr Asp Thr
        850                 855                 860

Ser Glu Val Asp Leu Phe Val Ile Asn Ala Pro Tyr Thr Pro Val Pro
865                 870                 875                 880

Asp Pro Thr Pro Met Met Pro Val Gly Val Gln Ala Ser Ile Leu
                885                 890                 895

Ser His Asp Thr Ile Arg Ile Trp Ala Asp Asn Ser Leu Pro Lys
            900                 905                 910

His Gln Lys Ile Thr Asp Ser Arg Tyr Tyr Thr Val Arg Trp Lys Thr
            915                 920                 925

Asn Ile Pro Ala Asn Thr Lys Tyr Lys Asn Ala Asn Ala Thr Thr Leu
930                 935                 940

Ser Tyr Leu Val Thr Gly Leu Lys Pro Asn Thr Leu Tyr Glu Phe Ser
945                 950                 955                 960

Val Met Val Thr Lys Gly Arg Arg Ser Ser Thr Trp Ser Met Thr Ala
                965                 970                 975

His Gly Ala Thr Phe Glu Leu Val Pro Thr Ser Pro Lys Asp Val
                980                 985                 990

Thr Val Val Ser Lys Glu Gly Lys Pro Arg Thr Ile Ile Val Asn Trp
            995                 1000                1005

Gln Pro Pro Ser Glu Ala Asn Gly Lys Ile Thr Gly Tyr Ile Ile Tyr
        1010                1015                1020

Tyr Ser Thr Asp Val Asn Ala Glu Ile His Asp Trp Val Ile Glu Pro
1025                1030                1035                1040

Val Val Gly Asn Arg Leu Thr His Gln Ile Gln Glu Leu Thr Leu Asp
                1045                1050                1055

Thr Pro Tyr Tyr Phe Lys Ile Gln Ala Arg Asn Ser Lys Gly Met Gly
        1060                1065                1070

Pro Met Ser Glu Ala Val Gln Phe Arg Thr Pro Lys Ala Asp Ser Ser
            1075                1080                1085

Asp Lys Met Pro Asn Asp Gln Ala Leu Gly Ser Ala Gly Lys Gly Ser
            1090                1095                1100

Arg Leu Pro Asp Leu Gly Ser Asp Tyr Lys Pro Pro Met Ser Gly Ser
1105                1110                1115                1120

Asn Ser Pro His Gly Ser Pro Thr Ser Pro Leu Asp Ser Asn Met Leu
                1125                1130                1135

Leu Val Ile Ile Val Ser Val Gly Val Ile Thr Ile Val Val Val Val
                1140                1145                1150

Val Ile Ala Val Phe Cys Thr Arg Arg Thr Ser His Gln Lys Lys
            1155                1160                1165

Lys Arg Ala Ala Cys Lys Ser Val Asn Gly Ser His Lys Tyr Lys Gly
        1170                1175                1180
```

Asn Cys Lys Asp Val Lys Pro Pro Asp Leu Trp Ile His His Glu Arg
1185                1190                1195                1200

Leu Glu Leu Lys Pro Ile Asp Lys Ser Pro Asp Pro Asn Pro Val Met
            1205                1210                1215

Thr Asp Thr Pro Ile Pro Arg Asn Ser Gln Asp Ile Thr Pro Val Asp
        1220                1225                1230

Asn Ser Met Asp Ser Asn Ile His Gln Arg Arg Asn Ser Tyr Arg Gly
    1235                1240                1245

His Glu Ser Glu Asp Ser Met Ser Thr Leu Ala Gly Arg Arg Gly Met
1250                1255                1260

Arg Pro Lys Met Met Met Pro Phe Asp Ser Gln Pro Gln Pro Val
1265                1270                1275                1280

Ile Ser Ala His Pro Ile His Ser Leu Asp Asn Pro His His Phe
            1285                1290                1295

His Ser Ser Ser Leu Ala Ser Pro Ala Arg Ser His Leu Tyr His Pro
        1300                1305                1310

Ser Ser Pro Trp Pro Ile Gly Thr Ser Met Ser Leu Ser Asp Arg Ala
    1315                1320                1325

Asn Ser Thr Glu Ser Val Arg Asn Thr Pro Ser Thr Asp Thr Met Pro
1330                1335                1340

Ala Ser Ser Ser Gln Thr Cys Cys Thr Asp His Gln Asp Pro Glu Gly
1345                1350                1355                1360

Ala Thr Ser Ser Ser Tyr Leu Ala Ser Ser Gln Glu Glu Asp Ser Gly
            1365                1370                1375

Gln Ser Leu Pro Thr Ala His Val Arg Pro Ser His Pro Leu Lys Ser
        1380                1385                1390

Phe Ala Val Pro Ala Ile Pro Pro Gly Pro Leu Tyr Asp Pro
    1395                1400                1405

Ala Leu Pro Ser Thr Pro Leu Leu Ser Gln Gln Ala Leu Glu Pro Ser
1410                1415                1420

Thr Phe His Ser Val Lys Thr Ala Ser Ile Gly Thr Leu Gly Arg Ser
1425                1430                1435                1440

Arg Pro Pro Met Pro Val Val Val Pro Ser Ala Pro Glu Val Gln Glu
            1445                1450                1455

Thr Thr Arg Met Leu Glu Asp Ser Glu Ser Ser Tyr Gly Pro Asp Glu
        1460                1465                1470

Leu Thr Lys Glu Met Ala His Leu Glu Gly Leu Met Lys Asp Leu Asn
    1475                1480                1485

Ala Ile Thr Thr Ala
    1490

<210> SEQ ID NO 27
<211> LENGTH: 5297
<212> TYPE: DNA
<213> ORGANISM: Homo sapiens

<400> SEQUENCE: 27
gggccgggcc gggctgggct ggagcagcgg cgcccgggag ccgagcttgc agcgagggac    60
cggctgaggc gcgcgggagg gaaggaggca agggctccgc ggcgctgtcg cgctgccgct   120
cactctcggg gaagagatgg cggcggagcg gggagcccgg cgactcctca gcacccctc    180 cttctggctc tactgcctgc tgctgctcgg gcgccgggcg ccgggcgccg cggcggccag   240
gagcggctcc gcgccgcagt ccccaggagc cagcattcga acgttcactc cattttattt   300
tctggtggag ccggtggata cactctcagt tagaggctct tctgttatat taaactgttc   360

```
agcatattct gagccttctc caaaaattga atggaaaaaa gatggaactt ttttaaactt    420
agtatcagat gatcgacgcc agcttctccc ggatggatct ttatttatca gcaatgtggt    480
gcattccaaa cacaataaac ctgatgaagg ttattatcag tgtgtggcca ctgttgagag    540
tcttggaact attatcagta gaacagcgaa gctcatagta gcaggtcttc caagatttac    600
cagccaacca gaaccttcct cagtttatgc tgggaacgga gcaattctga attgtgaagt    660
taatgcagat ttggtcccat tgtgaggtg ggaacagaac agacaacccc ttcttctgga     720
tgatagagtt atcaaacttc caagtggaat gctggttatc agcaatgcaa ctgaaggaga    780
tggcgggctt tatcgctgcg tagtgaaag tggtgggcca ccaaagtata gtgatgaagt     840
tgaattgaag gttcttccag atcctgaggt gatatcagac ttggtatttt tgaaacagcc    900
ttctccctta gtcagagtca ttggtcagga tgtagtgttg ccatgtgttg cttcaggact    960
tcctactcca accattaaat ggatgaaaaa tgaggaggca cttgacacag aaagctctga   1020
aagattggta ttgctggcag gtggtagcct ggagatcagt gatgttactg aggatgatgc   1080
tgggacttat ttttgtatag ctgataatgg aaatgagaca attgaagctc aagcagagct   1140
tacagtgcaa gctcaacctg aattcctgaa gcagcctact aatatatatg ctcacgaatc   1200
tatggatatt gtatttgaat gtgaagtgac tggaaaacca actccaactg tgaagtgggt   1260
caaaaatggg gatatggtta tcccaagtga ttatttttaag attgtaaagg aacataatct   1320
tcaagttttg ggtctggtga atcagatga agggttctat cagtgcattg ctgaaaatga   1380
tgttggaaat gcacaagctg agcccaact gataatcctt gaacatgcac cagccacaac    1440
gggaccactg ccttcagctc ctcgggatgt cgtggcctcc ctggtctcta cccgcttcat   1500
caaattgacg tggcggacac ctgcatcaga tcctcacgga gacaaccta cctactctgt    1560 gttctacacc aaggaaggga ttgctaggga acgtgttgag aataccagtc acccaggaga   1620
gatgcaagta accattcaaa acctaatgcc agcgaccgtg tacatcttta gagttatggc   1680
tcaaaataag catggctcag agagagttc agctccactg cgagtagaaa cacaacctga    1740
ggttcagctc cctggcccag cacctaacct tcgtgcatat gcagcttcgc ctacctccat   1800
cactgttacg tgggaaacac cagtgtctgg caatggggaa attcagaatt ataagttgta   1860
ctacatggaa aaggggactg ataaagaaca ggatgttgat gtttcaagtc actcttacac   1920
cattaatggg ttgaaaaaat atacagagta tagtttccga gtggtggcct acaataaaca   1980
tggtcctgga gtttccacac cagatgttgc tgttcgaaca ttgtcagatg ttcccagtgc   2040
tgctcctcag aatctgtcct tggaagtgag aaattcaaag agtattatga ttcactggca   2100
gccacctgct ccagccacac aaaatgggca gattactggc tacaagattc gctaccgaaa   2160
ggcctcccga aagagtgatg tcactgagac cttggtaagc gggacacagc tgtctcagct   2220
gattgaaggt cttgatcggg ggactgagta taatttccga gtggctgctc taacaatcaa   2280
tggtacaggc ccggcaactg actggctgtc tgctgaaact tttgaaagtg acctagatga   2340
aactcgtgtt cctgaagtgc ctagctctct tcacgtacgc ccgctcgtta ctagcatcgt   2400
agtgagctgg actcctccag agaatcagaa cattgtggtc agaggttacg ccattggtta   2460
tggcattggc agccctcatg cccagaccat caaagtggac tataaacagc gctattacac   2520
cattgaaaat ctggatccca gctctcacta tgtgattacc ctgaaagcat taataacgt    2580 gggtgaaggc atcccctgt atgagagtgc tgtgaccagg cctcacacag acacttctga    2640
agttgattta tttgttatta atgctccata cactccagtg ccagatccca ctcccatgat   2700
gccaccagtg ggagttcagg cttccattct gagtcatgac accatcagga ttacgtgggc   2760
```

```
agacaactcg ctgcccaagc accagaagat tacagactcc cgatactaca ccgtccgatg   2820
gaaaaccaac atcccagcaa acaccaagta caagaatgca aatgcaacca ctttgagtta   2880
tttggtgact ggtttaaagc cgaatacact ctatgaattc tctgtgatgg tgaccaaagg   2940
tcgaagatca agtacatgga gtatgacagc ccatgggacc acctttgaat tagttccgac   3000
ttctccaccc aaggatgtga ctgttgtgag taaagagggg aaacctaaga ccataattgt   3060
gaattggcag cctccctctg aagccaatgg caaaattaca ggttacatca tatattacag   3120
tacagatgtg aatgcagaga tacatgactg ggttattgag cctgttgtgg gaaacagact   3180
gactcaccag atacaagagt taactcttga cacaccatac tacttcaaaa tccaggcacg   3240
gaactcaaag ggcatgggac ccatgtctga agctgtccaa ttcagaacac ctaaagcgga   3300
ctcctctgat aaaatgccta atgatcaagc ctcagggtct ggaggaaaag gaagccggct   3360
gccagaccta ggatccgact acaaacctcc aatgagcggc agtaacagcc ctcatgggag   3420
ccccacctct cctctggaca gtaatatgct gctggtcata attgtttctg ttggcgtcat   3480
caccatcgtg gtggttgtga ttatcgctgt cttttgtacc cgtcgtacca cctctcacca   3540
gaaaaagaaa cgagctgcct gcaaatcagt gaatggctct cataagtaca agggaattc    3600 caaagatgtg aaacctccag atctctggat ccatcatgag agactggagc tgaaacccat   3660
tgataagtct ccagacccaa accccatcat gactgatact ccaattcctc gcaactctca   3720
agatatcaca ccagttgaca actccatgga cagcaatatc catcaaaggc gaaattcata   3780
cagagggcat gagtcagagg acagcatgtc tacactggct ggaaggcgag gaatgagacc   3840
aaaaatgatg atgcccttg actcccagcc accccagcct gtgattagtg cccatcccat    3900
ccattccctc gataaccctc accatcattt ccactccagc agcctcgctt ctccagctcg   3960
cagtcatctc taccacccgg gcagcccatg gcccattggc acatccatgt cccttttcaga  4020 cagggccaat tccacagaat ccgttcgaaa taccccagc actgacacca tgccagcctc    4080
ttcgtctcaa acatgctgca ctgatcacca ggaccctgaa ggtgctacca gctcctctta   4140
cttggccagc tcccaagagg aagattcagg ccagagtctt cccactgccc atgttcgccc   4200
ttcccaccca ttgaagagct tcgccgtgcc agcaatcccg cctccaggac ctcccaccta   4260
tgatcctgca ttgccaagca caccattact gtcccagcaa gctctgaacc atcacattca   4320
ctcagtgaag acagcctcca tcgggactct aggaaggagc cggcctccta tgccagtggt   4380
tgttcccagt gcccctgaag tgcaggagac acaaggatg ttggaagact ccgagagtag    4440
ctatgaacca gatgagctga ccaaagagat ggcccacctg aaggactaa tgaaggacct    4500 aaacgctatc acaacagcat gacgaccttc accaggacct gacttcaaac ctgagtctgg   4560
aagtcttgga acttaaccct tgaaaacaag gaattgtaca gagtacgaga ggacagcact   4620
tgagaacaca gaatgagcca gcagactggc cagcgcctct gtgtagggct ggctccaggc   4680
atggccacct gccttcccct ggtcagcctg gaagaagcct gtgtcgaggc agcttccctt   4740
tgcctgctga tattctgcag gactgggcac catgggccaa aattttgtgt ccagggaaga   4800
ggcgagaagt gcaacctgca tttcactttg tggtcaggcc gtgtctttgt gctgtgactg   4860
catcaccttt atggagtgta gacattggca tttatgtaca attttatttg tgtcttattt   4920
tattttacct tcaaaaacaa aaacgccatc caaaaccaag gaagtccttg gtgttctcca   4980
caagtggttg acatttgact gcttgttcca attatgtatg gaaagtcttt gacagtgtgg   5040
gtcgttcctg gggttggctt gttttttggt ttcatttta tttttttaatt ctgagtcatt   5100 gcatcctcta ccagctgtta atccatcact ctgagggga ggaaatgttg cattgctgtt    5160
```

```
tgtaagcttt ttttattatt tttttattat aattattaaa ggcctgactc tttcctctca    5220
tcactgtgag attacagatc tatttgaatt gaatgaaatg taacattgaa aaaaaaaaaa    5280
aaaaaaaaaa aaaaaaa                                                   5297
```

<210> SEQ ID NO 28
<211> LENGTH: 1461
<212> TYPE: PRT
<213> ORGANISM: Homo sapiens

<400> SEQUENCE: 28

```
Met Ala Ala Glu Arg Gly Ala Arg Arg Leu Leu Ser Thr Pro Ser Phe
  1               5                  10                  15

Trp Leu Tyr Cys Leu Leu Leu Gly Arg Arg Ala Pro Gly Ala Ala
                 20                  25                  30

Ala Ala Arg Ser Gly Ser Ala Pro Gln Ser Pro Gly Ala Ser Ile Arg
             35                  40                  45

Thr Phe Thr Pro Phe Tyr Phe Leu Val Glu Pro Val Asp Thr Leu Ser
         50                  55                  60

Val Arg Gly Ser Ser Val Ile Leu Asn Cys Ser Ala Tyr Ser Glu Pro
 65                  70                  75                  80

Ser Pro Lys Ile Glu Trp Lys Lys Asp Gly Thr Phe Leu Asn Leu Val
                 85                  90                  95

Ser Asp Asp Arg Arg Gln Leu Leu Pro Asp Gly Ser Leu Phe Ile Ser
                100                 105                 110

Asn Val Val His Ser Lys His Asn Lys Pro Asp Glu Gly Tyr Tyr Gln
            115                 120                 125

Cys Val Ala Thr Val Glu Ser Leu Gly Thr Ile Ile Ser Arg Thr Ala
        130                 135                 140

Lys Leu Ile Val Ala Gly Leu Pro Arg Phe Thr Ser Gln Pro Glu Pro
145                 150                 155                 160

Ser Ser Val Tyr Ala Gly Asn Gly Ala Ile Leu Asn Cys Glu Val Asn
                165                 170                 175

Ala Asp Leu Val Pro Phe Val Arg Trp Glu Gln Asn Arg Gln Pro Leu
            180                 185                 190

Leu Leu Asp Asp Arg Val Ile Lys Leu Pro Ser Gly Met Leu Val Ile
        195                 200                 205

Ser Asn Ala Thr Glu Gly Asp Gly Gly Leu Tyr Arg Cys Val Val Glu
    210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Val Leu Pro Cys Val Ala
            260                 265                 270

Ser Gly Leu Pro Thr Pro Thr Ile Lys Trp Met Lys Asn Glu Glu Ala
        275                 280                 285

Leu Asp Thr Glu Ser Ser Glu Arg Leu Val Leu Ala Gly Gly Ser
    290                 295                 300

Leu Glu Ile Ser Asp Val Thr Glu Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
            340                 345                 350
```

```
His Glu Ser Met Asp Ile Val Phe Glu Cys Glu Val Thr Gly Lys Pro
            355                 360                 365

Thr Pro Thr Val Lys Trp Val Lys Asn Gly Asp Met Val Ile Pro Ser
    370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
                420                 425                 430

Ala Thr Thr Gly Pro Leu Pro Ser Ala Pro Arg Asp Val Val Ala Ser
            435                 440                 445

Leu Val Ser Thr Arg Phe Ile Lys Leu Thr Trp Arg Thr Pro Ala Ser
    450                 455                 460

Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
                485                 490                 495

Gln Val Thr Ile Gln Asn Leu Met Pro Ala Thr Val Tyr Ile Phe Arg
                500                 505                 510

Val Met Ala Gln Asn Lys His Gly Ser Gly Glu Ser Ser Ala Pro Leu
            515                 520                 525

Arg Val Glu Thr Gln Pro Glu Val Gln Leu Pro Gly Pro Ala Pro Asn
    530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
                565                 570                 575

Met Glu Lys Gly Thr Asp Lys Glu Gln Asp Val Asp Val Ser Ser His
                580                 585                 590

Ser Tyr Thr Ile Asn Gly Leu Lys Lys Tyr Thr Glu Tyr Ser Phe Arg
            595                 600                 605

Val Val Ala Tyr Asn Lys His Gly Pro Gly Val Ser Thr Pro Asp Val
    610                 615                 620

Ala Val Arg Thr Leu Ser Asp Val Pro Ser Ala Ala Pro Gln Asn Leu
625                 630                 635                 640

Ser Leu Glu Val Arg Asn Ser Lys Ser Ile Met Ile His Trp Gln Pro
                645                 650                 655

Pro Ala Pro Ala Thr Gln Asn Gly Gln Ile Thr Gly Tyr Lys Ile Arg
                660                 665                 670

Tyr Arg Lys Ala Ser Arg Lys Ser Asp Val Thr Glu Thr Leu Val Ser
            675                 680                 685

Gly Thr Gln Leu Ser Gln Leu Ile Glu Gly Leu Asp Arg Gly Thr Glu
    690                 695                 700

Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
                725                 730                 735

Arg Val Pro Glu Val Pro Ser Ser Leu His Val Arg Pro Leu Val Thr
                740                 745                 750

Ser Ile Val Val Ser Trp Thr Pro Pro Glu Asn Gln Asn Ile Val Val
            755                 760                 765

Arg Gly Tyr Ala Ile Gly Tyr Gly Ile Gly Ser Pro His Ala Gln Thr
```

```
              770             775             780
Ile Lys Val Asp Tyr Lys Gln Arg Tyr Tyr Thr Ile Glu Asn Leu Asp
785                 790                 795                 800

Pro Ser Ser His Tyr Val Ile Thr Leu Lys Ala Phe Asn Asn Val Gly
                805                 810                 815

Glu Gly Ile Pro Leu Tyr Glu Ser Ala Val Thr Arg Pro His Thr Asp
                820                 825                 830

Thr Ser Glu Val Asp Leu Phe Val Ile Asn Ala Pro Tyr Thr Pro Val
                835                 840                 845

Pro Asp Pro Thr Pro Met Met Pro Pro Val Gly Val Gln Ala Ser Ile
850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
                885                 890                 895

Thr Asn Ile Pro Ala Asn Thr Lys Tyr Lys Asn Ala Asn Ala Thr Thr
                900                 905                 910

Leu Ser Tyr Leu Val Thr Gly Leu Lys Pro Asn Thr Leu Tyr Glu Phe
                915                 920                 925

Ser Val Met Val Thr Lys Gly Arg Arg Ser Ser Thr Trp Ser Met Thr
                930                 935                 940

Ala His Gly Thr Thr Phe Glu Leu Val Pro Thr Ser Pro Pro Lys Asp
945                 950                 955                 960

Val Thr Val Val Ser Lys Glu Gly Lys Pro Lys Thr Ile Ile Val Asn
                965                 970                 975

Trp Gln Pro Pro Ser Glu Ala Asn Gly Lys Ile Thr Gly Tyr Ile Ile
                980                 985                 990

Tyr Tyr Ser Thr Asp Val Asn Ala Glu Ile His Asp Trp Val Ile Glu
                995                 1000                1005

Pro Val Val Gly Asn Arg Leu Thr His Gln Ile Gln Glu Leu Thr Leu
                1010                1015                1020

Asp Thr Pro Tyr Tyr Phe Lys Ile Gln Ala Arg Asn Ser Lys Gly Met
1025                1030                1035                1040

Gly Pro Met Ser Glu Ala Val Gln Phe Arg Thr Pro Lys Ala Asp Ser
                1045                1050                1055

Ser Asp Lys Met Pro Asn Asp Gln Ala Ser Gly Ser Gly Gly Lys Gly
                1060                1065                1070

Ser Arg Leu Pro Asp Leu Gly Ser Asp Tyr Lys Pro Pro Met Ser Gly
                1075                1080                1085

Ser Asn Ser Pro His Gly Ser Pro Thr Ser Pro Leu Asp Ser Asn Met
                1090                1095                1100

Leu Leu Val Ile Ile Val Ser Val Gly Val Ile Thr Ile Val Val Val
1105                1110                1115                1120

Val Ile Ile Ala Val Phe Cys Thr Arg Arg Thr Thr Ser His Gln Lys
                1125                1130                1135

Lys Lys Arg Ala Ala Cys Lys Ser Val Asn Gly Ser His Lys Tyr Lys
                1140                1145                1150

Gly Asn Ser Lys Asp Val Lys Pro Pro Asp Leu Trp Ile His His Glu
                1155                1160                1165

Arg Leu Glu Leu Lys Pro Ile Asp Lys Ser Pro Asp Pro Asn Pro Ile
                1170                1175                1180

Met Thr Asp Thr Pro Ile Pro Arg Asn Ser Gln Asp Ile Thr Pro Val
1185                1190                1195                1200
```

-continued

Asp Asn Ser Met Asp Ser Asn Ile His Gln Arg Arg Asn Ser Tyr Arg
            1205                1210                1215

Gly His Glu Ser Glu Asp Ser Met Ser Thr Leu Ala Gly Arg Arg Gly
        1220                1225                1230

Met Arg Pro Lys Met Met Met Pro Phe Asp Ser Gln Pro Pro Gln Pro
        1235                1240                1245

Val Ile Ser Ala His Pro Ile His Ser Leu Asp Asn Pro His His His
    1250                1255                1260

Phe His Ser Ser Ser Leu Ala Ser Pro Ala Arg Ser His Leu Tyr His
1265                1270                1275                1280

Pro Gly Ser Pro Trp Pro Ile Gly Thr Ser Met Ser Leu Ser Asp Arg
            1285                1290                1295

Ala Asn Ser Thr Glu Ser Val Arg Asn Thr Pro Ser Thr Asp Thr Met
        1300                1305                1310

Pro Ala Ser Ser Ser Gln Thr Cys Cys Thr Asp His Gln Asp Pro Glu
        1315                1320                1325

Gly Ala Thr Ser Ser Ser Tyr Leu Ala Ser Ser Gln Glu Glu Asp Ser
        1330                1335                1340

Gly Gln Ser Leu Pro Thr Ala His Val Arg Pro Ser His Pro Leu Lys
1345                1350                1355                1360

Ser Phe Ala Val Pro Ala Ile Pro Pro Pro Gly Pro Pro Thr Tyr Asp
            1365                1370                1375

Pro Ala Leu Pro Ser Thr Pro Leu Leu Ser Gln Gln Ala Leu Asn His
        1380                1385                1390

His Ile His Ser Val Lys Thr Ala Ser Ile Gly Thr Leu Gly Arg Ser
        1395                1400                1405

Arg Pro Pro Met Pro Val Val Val Pro Ser Ala Pro Glu Val Gln Glu
    1410                1415                1420

Thr Thr Arg Met Leu Glu Asp Ser Glu Ser Ser Tyr Glu Pro Asp Glu
1425                1430                1435                1440

Leu Thr Lys Glu Met Ala His Leu Glu Gly Leu Met Lys Asp Leu Asn
            1445                1450                1455

Ala Ile Thr Thr Ala
        1460

<210> SEQ ID NO 29
<211> LENGTH: 20
<212> TYPE: DNA
<213> ORGANISM: Artificial Sequence
<220> FEATURE:
<223> OTHER INFORMATION: forward primer

<400> SEQUENCE: 29
acaggcctca aaccaaacac                                              20

<210> SEQ ID NO 30
<211> LENGTH: 20
<212> TYPE: DNA
<213> ORGANISM: Artificial Sequence
<220> FEATURE:
<223> OTHER INFORMATION: reverse primer

<400> SEQUENCE: 30
acctccatct ccatgacgac                                              20

<210> SEQ ID NO 31
<211> LENGTH: 20
<212> TYPE: DNA
<213> ORGANISM: Artificial Sequence

```
<220> FEATURE:
<223> OTHER INFORMATION: forward primer

<400> SEQUENCE: 31
accccagcct gtgattagtg                                              20

<210> SEQ ID NO 32
<211> LENGTH: 20
<212> TYPE: DNA
<213> ORGANISM: Artificial Sequence
<220> FEATURE:
<223> OTHER INFORMATION: reverse primer

<400> SEQUENCE: 32
tgtgatggtt cagagcttgc                                              20

<210> SEQ ID NO 33
<211> LENGTH: 20
<212> TYPE: DNA
<213> ORGANISM: Artificial Sequence
<220> FEATURE:
<223> OTHER INFORMATION: forward primer

<400> SEQUENCE: 33
agttgcctct cctcctcctc                                              20

<210> SEQ ID NO 34
<211> LENGTH: 20
<212> TYPE: DNA
<213> ORGANISM: Artificial Sequence
<220> FEATURE:
<223> OTHER INFORMATION: reverse primer

<400> SEQUENCE: 34
ctttgccttt ttgcttttgg                                              20

<210> SEQ ID NO 35
<211> LENGTH: 20
<212> TYPE: DNA
<213> ORGANISM: Artificial Sequence
<220> FEATURE:
<223> OTHER INFORMATION: forward primer

<400> SEQUENCE: 35
acccagaaga ctgtggatgg                                              20

<210> SEQ ID NO 36
<211> LENGTH: 20
<212> TYPE: DNA
<213> ORGANISM: Artificial Sequence
<220> FEATURE:
<223> OTHER INFORMATION: reverse primer

<400> SEQUENCE: 36
tgctgtagcc aaattcgttg                                              20

<210> SEQ ID NO 37
<211> LENGTH: 4090
<212> TYPE: DNA
<213> ORGANISM: Mouse

<400> SEQUENCE: 37
gaattcggca cgagaaaaaa cccacagtaa aagtttaagg cgagaagtgg tggcggcggc      60
ggcggcggcg cggggaagct gcgagcggag aaggttgccg agacctcgga aggcggcgat     120
ttggttccta atcccactgt attttttggag ggagaggcac ctttctcatc ctcccttcct    180
```

```
ctccgcccac ccctctccct cccctcatc tacctgtcaa agtcactgat cttttgcatt      240
ttggaagagg acgtcaacgg gaaggaattc ccctgtcag ggtcccggct ccgagagggg      300
gcgacgcgcg acaaggctgc cccaggggca agagaccaag gttgctggtg ccagaagagg    360
gaagagaaaa gattgaaggg aaacagatac aggacgatag acaccatccc tttgcttctg    420
atgctgatac ttcagctcat ctgaggagcc ctgatgaacc cagaacagca aggatcactc    480
aggattattg gatgtacaac gggagagccg tcactttgct aaattattat ctgctcctgg    540
acatccctgg acatctttca caaaagtcaa atagatatgt tctacgagga gaaatggctg    600
caagctgtta atgcctaaca gataagcatg ttaggcttct accaaagtcc tcagcatacc    660
tgaccgcata gaatatttca atctgtcaca tttggttttg gaatctgctt tgagatctca    720
gcctattttt ttatacatat acagacctac ctacataaag atacatatag acacgtgcac    780
acacacacac acacacacat ataagatact catgtatatt taaaagagac actgattgca    840
tagaagacac gaagattgcc aagattttag agatgtattt gtcaagattc ctgtcgatcc    900
atgccctgtg ggtgacagtg tcctctgtga tgcagcccta ccttttcgtg tggggacatt    960
atgatgtatg taagagcctg atttacacag aagaaggcaa agtttgggat tacacagcct   1020
gccagccgga atccacggac atgaccaagt atctgaaagt gaaactggac cctccggata   1080
ttacctgtgg agaccctcca gagtccttct gtgcaatggg caaccttac atgtgcaata   1140
atgagtgtga tgcgagtacc cctgaactgg cacaccctcc tgagctgatg tttgattttg   1200
aaggaagaca tccctccaca ttttggcagt ctgctacttg gaaggagtac cccaaacctc   1260
tccaggttaa catcactctg tcttggagca aaaccattga actcacagac aacatagtta   1320
ttacctttga atcggggcgt ccagaccaaa tgatcctaga gaaatctctc gactacggac   1380
gaacatggca gccctatcag tattatgcca cagactgcct ccatgcattc cacatggacc   1440
cgaaatccgt gaaggattta tctcagcaca cggtcttgga aatcatttgc acggaagagt   1500
actccactgg gtactccacg aatagcaaaa taatccactt cgagatcaaa gacaggtttg   1560
cgttttcgc tggaccctcg gctacgaaata tggcttccct ctatggacag ctggatacaa   1620
ccaagaaact cagagatttc ttcactgtca cagacctgag gatcaggctg ttgagacccg   1680
ccgttgggga aatatttgta gatgaactac atttggcacg ttactttat gcgatctcag   1740
acataaaggt gcgaggaagg tgcaagtgca acctgcatgc cacttcgtgt ttgtatgaca   1800
acagcaaact gacatgtgaa tgtgagcaca acactacagg tcccgactgt gggaaatgca   1860
agaagaacta ccagggccga ccttggagcc ccggctcata cctccccatc cccaaaggca   1920
ccgcaaacac ctgtatcccc agcatttcca gtatcggtaa ctgtgaatgc ttcggccact   1980
ccaatcggtg cagttatatc gatctgctaa acacagtcat ttgcgtgagc tgtaaacaca   2040
acactagagg gcagcactgt gagttatgca ggctgggcta cttcagaaat gcttctgcac   2100
agctggacga tgagaatgtg tgcatagagt gttattgtaa ccctttgggc tcaatccatg   2160
atcgttgtaa tggctcagga tttttgtgagt gtaagactgg aacaacaggg cctaaatgtg   2220
atgagtgtct gccaggaaat tcctggtact acggctgtca acctaatgtc tgcgacaatg   2280
agctcctgca ctgccagaat ggagggacct gccagaacaa tgtgcgctgc gcgtgcccag   2340
acgcctacac cggcatcctc tgtgagaagc tacggtgcga agaggcgggc agctgtggct   2400
ccgaatccgg ccaggagca cccccgcggg gctccccagc actgctgctg ctgaccatgc   2460
tgctggggac tgccggtccc ctggtgttct aggggtcaca cccagccctc cgacaggcct   2520
gtgctgtggg gaagcaaaca caacccaagc gattgccact gacatagaaa acacgcacac   2580
```

```
ccactccaac acagtgtata aaagaagagg gcctaactga actaagccat atctctcaga    2640
accggacagc acatcgcaca tcggagttga gactgttcat cattgactcc agaggaattg    2700
gcagctgttg ctattctcac tgcaaatctc attgccagct gcagagctga ttgcggattg    2760
gaaaggctgt gagagcgccc ccaagaggaa agacggaaaa caaactgatc aaccaaccta    2820
aaaacattcg ctactctacc gtggtgcacc ctagtaccgc tctgctcagt gtgtgggcca    2880
accaaataaa agcattcttc gctgtcaggt gcattgtggg tataaggaaa tctgttacaa    2940
gctgccatat tggcctgctt cagtccccccc gaccccaaa tcccttccaa cctgtgcttt    3000
agtgaacgtt gctctgtaac ccttgttggt tgaaagattt ctttgtctga tgttagtgat    3060
acacacgtgt aacagccccc tccaaagcgc aagccagtca tacccctgta tattttagca    3120
gcactgcggt cccagtgcca gctcacgtcc acttcacaag agtggttaga ggaaaagaga    3180
aagtgtatct atcctttgt attcaaatga agttattttt cttgaaataa tgtaatatgt    3240 agatttttg tattattgcc aatttatgtt accagacaat ctgttaatgt atctaattcg    3300
aatcagcaaa gactgactga tgtttgagtt tttggtcctc tttggttttg tttcgtttcg    3360
tcatgcagag atttctctgt aagggcaacg agcgtgctgg catcaaagaa tatcggttta    3420
catatagcaa gtgtaataag attccaccaa aggacatttt aaatgttttt tcttgttgct    3480
ttaacactgg aagatttaaa gaataaaaat tcctgcagaa atgttatcag gaaattgtat    3540
ggccgtttct taagacgaaa ggagcaacca cccagcagtt tcccagtcac gtcactgatt    3600
tttgtgtgga ctgaacacag tcagctgaca actttaataa ccaggaagac ggattgatgg    3660
tcactagctt ggacaacgtc tgcaaaatat gagactattt tccacctggg aaaaaattat    3720
aaccacaaaa acagagagaa agaaatatct aagtgattgc caagattatg ccaaagcctg    3780
ttggcagagc actaagagac ttttatttt aagtcatgct attttcacag atttatggtg    3840
atcatgtgac tctagggatg ccgatctatg tatccttcca aatacagtgt ttacatggag    3900
tatcataaga ggccacctgg ggaaccagga cagcagcagg gaaattgagt gattagcaat    3960
ttgactttga atatattcta agtatttaaa tgaaatatca aaatatacag cagcaagtag    4020
acataactgc tgttcctgaa aataaagtct gtttcaagta ctgccaaaaa aaaaaaaaaa    4080
aaaactcgag                                                         4090
```

<210> SEQ ID NO 38
<211> LENGTH: 539
<212> TYPE: PRT
<213> ORGANISM: Mouse

<400> SEQUENCE: 38

Met Tyr Leu Ser Arg Phe Leu Ser Ile His Ala Leu Trp Val Thr Val
1               5                   10                  15

Ser Ser Val Met Gln Pro Tyr Leu Phe Val Trp Gly His Tyr Asp Val
            20                  25                  30

Cys Lys Ser Leu Ile Tyr Thr Glu Glu Gly Lys Val Trp Asp Tyr Thr
        35                  40                  45

Ala Cys Gln Pro Glu Ser Thr Asp Met Thr Lys Tyr Leu Lys Val Lys
    50                  55                  60

Leu Asp Pro Pro Asp Ile Thr Cys Gly Asp Pro Glu Ser Phe Cys
65                  70                  75                  80

Ala Met Gly Asn Pro Tyr Met Cys Asn Asn Glu Cys Asp Ala Ser Thr
                85                  90                  95

Pro Glu Leu Ala His Pro Pro Glu Leu Met Phe Asp Phe Glu Gly Arg

```
                100                 105                 110
His Pro Ser Thr Phe Trp Gln Ser Ala Thr Trp Lys Glu Tyr Pro Lys
            115                 120                 125
Pro Leu Gln Val Asn Ile Thr Leu Ser Trp Ser Lys Thr Ile Glu Leu
        130                 135                 140
Thr Asp Asn Ile Val Ile Thr Phe Glu Ser Gly Arg Pro Asp Gln Met
145                 150                 155                 160
Ile Leu Glu Lys Ser Leu Asp Tyr Gly Arg Thr Trp Gln Pro Tyr Gln
                165                 170                 175
Tyr Tyr Ala Thr Asp Cys Leu His Ala Phe His Met Asp Pro Lys Ser
            180                 185                 190
Val Lys Asp Leu Ser Gln His Thr Val Leu Glu Ile Cys Thr Glu
        195                 200                 205
Glu Tyr Ser Thr Gly Tyr Ser Thr Asn Ser Lys Ile Ile His Phe Glu
        210                 215                 220
Ile Lys Asp Arg Phe Ala Phe Ala Gly Pro Arg Leu Arg Asn Met
225                 230                 235                 240
Ala Ser Leu Tyr Gly Gln Leu Asp Thr Thr Lys Lys Leu Arg Asp Phe
            245                 250                 255
Phe Thr Val Thr Asp Leu Arg Ile Arg Leu Leu Arg Pro Ala Val Gly
        260                 265                 270
Glu Ile Phe Val Asp Glu Leu His Leu Ala Arg Tyr Phe Tyr Ala Ile
        275                 280                 285
Ser Asp Ile Lys Val Arg Gly Arg Cys Lys Cys Asn Leu His Ala Thr
        290                 295                 300
Ser Cys Leu Tyr Asp Asn Ser Lys Leu Thr Cys Glu Cys Glu His Asn
305                 310                 315                 320
Thr Thr Gly Pro Asp Cys Gly Lys Cys Lys Lys Asn Tyr Gln Gly Arg
                325                 330                 335
Pro Trp Ser Pro Gly Ser Tyr Leu Pro Ile Pro Lys Gly Thr Ala Asn
            340                 345                 350
Thr Cys Ile Pro Ser Ile Ser Ile Gly Asn Cys Glu Cys Phe Gly
        355                 360                 365
His Ser Asn Arg Cys Ser Tyr Ile Asp Leu Leu Asn Thr Val Ile Cys
        370                 375                 380
Val Ser Cys Lys His Asn Thr Arg Gly Gln His Cys Glu Leu Cys Arg
385                 390                 395                 400
Leu Gly Tyr Phe Arg Asn Ala Ser Ala Gln Leu Asp Asp Glu Asn Val
            405                 410                 415
Cys Ile Glu Cys Tyr Cys Asn Pro Leu Gly Ser Ile His Asp Arg Cys
        420                 425                 430
Asn Gly Ser Gly Phe Cys Glu Cys Lys Thr Gly Thr Thr Gly Pro Lys
        435                 440                 445
Cys Asp Glu Cys Leu Pro Gly Asn Ser Trp Tyr Tyr Gly Cys Gln Pro
450                 455                 460
Asn Val Cys Asp Asn Glu Leu Leu His Cys Gln Asn Gly Gly Thr Cys
465                 470                 475                 480
Gln Asn Asn Val Arg Cys Ala Cys Pro Asp Ala Tyr Thr Gly Ile Leu
            485                 490                 495
Cys Glu Lys Leu Arg Cys Glu Ala Gly Ser Cys Gly Ser Glu Ser
        500                 505                 510
Gly Gln Gly Ala Pro Pro Arg Gly Ser Pro Ala Leu Leu Leu Leu Thr
        515                 520                 525
```

Met Leu Leu Gly Thr Ala Gly Pro Leu Val Phe
    530                 535

<210> SEQ ID NO 39
<211> LENGTH: 3015
<212> TYPE: DNA
<213> ORGANISM: Homo sapiens

<400> SEQUENCE: 39

| | | | | | |
|---|---|---|---|---|---|
| tgcagccgga | gcagcaccag | caacagcaac | agcgagcggg | acggagttag | gaccgctcgg | 60 |
| agcgcacagg | tctcgagggt | gttggtgcca | gaagaaaaga | atgattgatg | ggaaacagac | 120 |
| accgggctat | agacactcat | ccttttgctt | cagatactga | tatctcagcc | tgcttgagca | 180 |
| tcccttgtga | gctgtgaaca | ttgaggatca | ctcagggtta | tcggatgtac | aacgggagag | 240 |
| ccatcgcttt | gctaaattat | tatctgcaat | tggacatctt | ttacaaaaac | caaactagac | 300 |
| ctgagtctaa | tagatatgtt | ctaagacaaa | gaaaaagctg | caagttgtta | acgcctaaca | 360 |
| cacaagtatg | ttaggcttcc | accaaagtcc | tcaatatacc | tgaatacgca | caatatctta | 420 |
| actcttcata | tttggttttg | ggatctgctt | tgaggtccca | tcttcattta | aaaaaaaata | 480 |
| cagagaccta | cctacccgta | cgcatacata | catatgtgta | tatatatgta | aactagacaa | 540 |
| agatcgcaga | tcataaagca | agctctgctt | tagtttccaa | gaagattaca | aagaatttag | 600 |
| agatgtattt | gtcaagattc | ctgtcgattc | atgcccttg | ggttacggtg | tcctcagtga | 660 |
| tgcagcccta | cccttggtt | tggggacatt | atgatttgtg | taagactcag | atttacacgg | 720 |
| aagaagggaa | agtttgggat | tacatggcct | gccagccgga | atccacggac | atgacaaaat | 780 |
| atctgaaagt | gaaactcgat | cctccggata | ttacctgtgg | agaccctcct | gagacgttct | 840 |
| gtgcaatggg | caatccctac | atgtgcaata | atgagtgtga | tgcgagtacc | ctgagctgg | 900 |
| cacacccccc | tgagctgatg | tttgattttg | aaggaagaca | tccctccaca | ttttggcagt | 960 |
| ctgccacttg | gaaggagtat | cccaagcctc | tccaggttaa | catcactctg | tcttggagca | 1020 |
| aaaccattga | gctaacagac | aacatagtta | ttacctttga | atctgggcgt | ccagaccaaa | 1080 |
| tgatcctgga | gaagtctctc | gattatggac | gaacatggca | gccctatcag | tattatgcca | 1140 |
| cagactgctt | agatgctttt | cacatggatc | ctaaatccgt | gaaggattta | tcacagcata | 1200 |
| cggtcttaga | aatcatttgc | acagaagagt | actcaacagg | gtatacaaca | aatagcaaaa | 1260 |
| taatccactt | tgaaatcaaa | gacaggttcg | cgttttttgc | tggacctcgc | ctacgcaata | 1320 |
| tggcttccct | ctacggacag | ctggatacaa | ccaagaaact | cagagatttc | tttacagtca | 1380 |
| cagacctgag | gataaggctg | ttaagaccag | ccgttgggga | atatttgta | gatgagctac | 1440 |
| acttggcacg | ctacttttac | gcgatctcag | acataaaggt | gcgaggaagg | tgcaagtgta | 1500 |
| atctccatgc | cactgtatgt | gtgtatgaca | acagcaaatt | gacatgcgaa | tgtgagcaca | 1560 |
| acactacagg | tccagactgt | gggaaatgca | agaagaatta | tcaggccgaa | ccttggagtc | 1620 |
| caggctccta | tctcccccatc | cccaaaggca | ctgcaaatac | ctgtatcccc | agtatttcca | 1680 |
| gtattggtac | gaatgtctgc | gacaacgagc | tcctgcactg | ccagaacgga | gggacgtgcc | 1740 |
| acaacaacgt | gcgctgcctg | tgcccggccg | catacacggg | catcctctgc | gagaagctgc | 1800 |
| ggtgcgagga | ggctggcagc | tgcggctccg | actctggcca | gggcgcgccc | ccgcacggct | 1860 |
| ccccagcgct | gctgctgctg | accacgctgc | tgggaaccgc | cagcccctg | gtgttctagg | 1920 |
| tgtcacctcc | agccacaccg | gacgggcctg | tgccgtgggg | aagcagacac | aacccaaaca | 1980 |
| tttgctacta | cataggaaa | cacacacata | cagcacccc | cactcagaca | gtgtacaaac | 2040 |
| taagaaggcc | taactgaact | aagccatatt | tatcacccgt | ggacagcaca | tccgagtcaa | 2100 |

-continued

```
gactgttaat ttctgactcc agaggagttg gcagctgttg atattatcac tgcaaatcac    2160
attgccagct gcagagcata ttgtggattg gaaaggctgc gacagccccc caaacaggaa    2220
agacaaaaaa caaacaaatc aaccgaccta aaaacattgg ctactctagc gtggtgcgcc    2280
ctagtacgac tccgcccagt gtgtggacca accaaatagc attctttgct gtcaggtgca    2340
ttgtgggcat aaggaaatct gttacaagct gccatattgg cctgcttccg tccctgaatc    2400
ccttccaacc tgtgctttag tgaacgttgc tctgtaaccc ttgttggttg aaagatttct    2460
ttgtctgatg ttagtgatgc acatgtgtaa cagcccctc taaaagcgca agccagtcat     2520
acccctgtat atcttagcag cactgagtcc agtgcgagca cacacccact atacaagagt    2580
ggctatagga aaaagaaag tgtatctatc cttttgtatt caaatgaagt tattttttct     2640
gaactactgt aatatgtaga ttttttgtat tattgccaat ttgtgttacc agacaatctg    2700
ttaatgtatc taattcgaat cagcaaagac tgacatttta ttttgtcctc tttcgttctg    2760
ttttgtttca ctgtgcagag atttctctgt aagggcaacg aacgtgctgg catcaaagaa    2820
tatcagttta catatataac aagtgtaata agattccacc aaaggacatt ctaaatgttt    2880
tcttgttgct ttaacactgg aagatttaaa gaataaaaac tcctgcataa acaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaa                                                    3015
```

<210> SEQ ID NO 40
<211> LENGTH: 438
<212> TYPE: PRT
<213> ORGANISM: Homo sapiens

<400> SEQUENCE: 40

```
Met Tyr Leu Ser Arg Phe Leu Ser Ile His Ala Leu Trp Val Thr Val
  1               5                  10                  15

Ser Ser Val Met Gln Pro Tyr Pro Leu Val Trp Gly His Tyr Asp Leu
             20                  25                  30

Cys Lys Thr Gln Ile Tyr Thr Glu Glu Gly Lys Val Trp Asp Tyr Met
         35                  40                  45

Ala Cys Gln Pro Glu Ser Thr Asp Met Thr Lys Tyr Leu Lys Val Lys
     50                  55                  60

Leu Asp Pro Pro Asp Ile Thr Cys Gly Asp Pro Glu Thr Phe Cys
 65                  70                  75                  80

Ala Met Gly Asn Pro Tyr Met Cys Asn Asn Glu Cys Asp Ala Ser Thr
                 85                  90                  95

Pro Glu Leu Ala His Pro Pro Glu Leu Met Phe Asp Phe Glu Gly Arg
            100                 105                 110

His Pro Ser Thr Phe Trp Gln Ser Ala Thr Trp Lys Glu Tyr Pro Lys
        115                 120                 125

Pro Leu Gln Val Asn Ile Thr Leu Ser Trp Ser Lys Thr Ile Glu Leu
    130                 135                 140

Thr Asp Asn Ile Val Ile Thr Phe Glu Ser Gly Arg Pro Asp Gln Met
145                 150                 155                 160

Ile Leu Glu Lys Ser Leu Asp Tyr Gly Arg Thr Trp Gln Pro Tyr Gln
                165                 170                 175

Tyr Tyr Ala Thr Asp Cys Leu Asp Ala Phe His Met Asp Pro Lys Ser
            180                 185                 190

Val Lys Asp Leu Ser Gln His Thr Val Leu Glu Ile Ile Cys Thr Glu
        195                 200                 205
```

```
Glu Tyr Ser Thr Gly Tyr Thr Thr Asn Ser Lys Ile Ile His Phe Glu
            210                 215                 220

Ile Lys Asp Arg Phe Ala Phe Phe Ala Gly Pro Arg Leu Arg Asn Met
225                 230                 235                 240

Ala Ser Leu Tyr Gly Gln Leu Asp Thr Thr Lys Lys Leu Arg Asp Phe
                245                 250                 255

Phe Thr Val Thr Asp Leu Arg Ile Arg Leu Leu Arg Pro Ala Val Gly
            260                 265                 270

Glu Ile Phe Val Asp Glu Leu His Leu Ala Arg Tyr Phe Tyr Ala Ile
            275                 280                 285

Ser Asp Ile Lys Val Arg Gly Arg Cys Lys Cys Asn Leu His Ala Thr
            290                 295                 300

Val Cys Val Tyr Asp Asn Ser Lys Leu Thr Cys Glu Cys Glu His Asn
305                 310                 315                 320

Thr Thr Gly Pro Asp Cys Gly Lys Cys Lys Lys Asn Tyr Gln Gly Arg
                325                 330                 335

Pro Trp Ser Pro Gly Ser Tyr Leu Pro Ile Pro Lys Gly Thr Ala Asn
            340                 345                 350

Thr Cys Ile Pro Ser Ile Ser Ser Ile Gly Thr Asn Val Cys Asp Asn
            355                 360                 365

Glu Leu Leu His Cys Gln Asn Gly Gly Thr Cys His Asn Asn Val Arg
    370                 375                 380

Cys Leu Cys Pro Ala Ala Tyr Thr Gly Ile Leu Cys Glu Lys Leu Arg
385                 390                 395                 400

Cys Glu Glu Ala Gly Ser Cys Gly Ser Asp Ser Gly Gln Gly Ala Pro
                405                 410                 415

Pro His Gly Ser Pro Ala Leu Leu Leu Leu Thr Thr Leu Leu Gly Thr
            420                 425                 430

Ala Ser Pro Leu Val Phe
            435

<210> SEQ ID NO 41
<211> LENGTH: 1770
<212> TYPE: DNA
<213> ORGANISM: Mouse

<400> SEQUENCE: 41
atgctgcgcc tgctggctct cttcctgcac tgcctcccgc tggtctctgg ggactatgac      60
atctgcaaat cctgggtgac cacagatgag ggccccacct gggaattcta tgcctgccag     120
cccaaggtga tgcgcctgaa ggattatgtc aaggtcaaag tggagccctc aggcatcacg     180
tgcggagacc ccctgaaaag gttctgttcc catgagaacc cctacctgtg cagtaatgag     240
tgtgatgcct ccaatcccga cctggcccac cgccccggc ttatgtttga cagggaagat     300
gagggactgg ctacctactg caaagcgtc acgtggagtc gctacccag tccactagag      360 gccaacatca ccctctcatg aacaagagc gtggagttga cagacgacgt ggtggtgact      420
tttgagtatg gccggcccac ggtcatggtc ctcgagaagt ccctggacaa tggccgcacc     480
tggcagccct accagttcta tgcagaggac tgcatggagg ccttcggcat gtctgcccga     540
cgtgcccgag acatgtcacc ctccagcgcc caccgggtgc tctgcaccga ggagtactca     600
cgctgggcag ggtccaagaa agagaagcat gtgcgctttg aggtaaggga ccgctttgcc     660
atctttgccg gcctgacct gcgtaacatg gacaacctgt acacgaggat ggagagcgcc     720
aagggcctca aggagttctt caccttcact gacctgcgca tgcgcctgct gcgtcctgcg     780
ctgggtggca cctacgtgca gcgagagaac ctctacaagt acttctatgc catctccaat     840
```

```
atcgaagtca ttggcaggtg taagtgcaac ctgcatgcca acctgtgcac agtgcgagag      900
ggcagcctgc agtgtgagtg tgaacacaac accacgggcc ccgactgtgg caggtgcaag      960
aagaacttcc gcacacgcgc ctggcgagct ggctcctacc tgccgctgcc ccacggctct     1020
cccaatgcct gtgcggccgc gggctccgcc tttggcagtc agaccaagcc acctactatg     1080
gcccccttg gggacagctc cttctggccc caggtgtcct ccagtgcaga agctgtagct      1140
atctctgtcg ctgtcccttc ccaagccaag gactctacgc ttttcgagct caagcccaga     1200
tctcctcagg tgatacccat tgaagaattt caagactgcg agtgctacgg ccactccaac     1260
cgttgcagct acattgactt cctgaacgtg gtgacctgcg tcagctgtaa acacaacact     1320
cgaggccaac actgtcagca ctgccgcctg ggctactatc gcaatggctc cgcagagctg     1380
gatgatgaga acgtctgcat tgaatgtaac tgtaaccaga tcggctctgt gcacgatcga     1440
tgcaatgaga caggcttctg cgagtgcagg gagggcgcag tggggcccaa gtgcgacgac     1500
tgccttccta cacactactg cgccaaggga tgctatccca atgtgtgcga cgatgaccag     1560
ctgctctgcc agaatggcgg cacctgccag cagaaccaac gctgcgcctg ccgcccggc      1620
tacaccggca ttcgctgtga gcagcccgc tgtgacctcg ccgacgacgc tggcccggac      1680
tgtgaccgcg cgccaggcat cgtcccgcgc cccgacaccc tgctcggatg cctgctgctg     1740
ctcgggctgg ccgcccgtct ggcctgctga                                      1770
```

<210> SEQ ID NO 42
<211> LENGTH: 589
<212> TYPE: PRT
<213> ORGANISM: Mouse

<400> SEQUENCE: 42

```
Met Leu Arg Leu Leu Ala Leu Phe Leu His Cys Leu Pro Leu Val Ser
 1               5                   10                  15

Gly Asp Tyr Asp Ile Cys Lys Ser Trp Val Thr Thr Asp Glu Gly Pro
             20                  25                  30

Thr Trp Glu Phe Tyr Ala Cys Gln Pro Lys Val Met Arg Leu Lys Asp
         35                  40                  45

Tyr Val Lys Val Lys Val Glu Pro Ser Gly Ile Thr Cys Gly Asp Pro
     50                  55                  60

Pro Glu Arg Phe Cys Ser His Glu Asn Pro Tyr Leu Cys Ser Asn Glu
 65                  70                  75                  80

Cys Asp Ala Ser Asn Pro Asp Leu Ala His Pro Pro Arg Leu Met Phe
                 85                  90                  95

Asp Arg Glu Asp Glu Gly Leu Ala Thr Tyr Trp Gln Ser Val Thr Trp
            100                 105                 110

Ser Arg Tyr Pro Ser Pro Leu Glu Ala Asn Ile Thr Leu Ser Trp Asn
        115                 120                 125

Lys Ser Val Glu Leu Thr Asp Asp Val Val Thr Phe Glu Tyr Gly
    130                 135                 140

Arg Pro Thr Val Met Val Leu Glu Lys Ser Leu Asp Asn Gly Arg Thr
145                 150                 155                 160

Trp Gln Pro Tyr Gln Phe Tyr Ala Glu Asp Cys Met Glu Ala Phe Gly
                165                 170                 175

Met Ser Ala Arg Arg Ala Arg Asp Met Ser Pro Ser Ser Ala His Arg
            180                 185                 190

Val Leu Cys Thr Glu Glu Tyr Ser Arg Trp Ala Gly Ser Lys Lys Glu
        195                 200                 205
```

-continued

```
Lys His Val Arg Phe Glu Val Arg Asp Arg Phe Ala Ile Phe Ala Gly
    210                 215                 220

Pro Asp Leu Arg Asn Met Asp Asn Leu Tyr Thr Arg Met Glu Ser Ala
225                 230                 235                 240

Lys Gly Leu Lys Glu Phe Phe Thr Phe Thr Asp Leu Arg Met Arg Leu
                245                 250                 255

Leu Arg Pro Ala Leu Gly Gly Thr Tyr Val Gln Arg Glu Asn Leu Tyr
            260                 265                 270

Lys Tyr Phe Tyr Ala Ile Ser Asn Ile Glu Val Ile Gly Arg Cys Lys
        275                 280                 285

Cys Asn Leu His Ala Asn Leu Cys Thr Val Arg Glu Gly Ser Leu Gln
    290                 295                 300

Cys Glu Cys Glu His Asn Thr Thr Gly Pro Asp Cys Gly Arg Cys Lys
305                 310                 315                 320

Lys Asn Phe Arg Thr Arg Ala Trp Arg Ala Gly Ser Tyr Leu Pro Leu
                325                 330                 335

Pro His Gly Ser Pro Asn Ala Cys Ala Ala Gly Ser Ala Phe Gly
            340                 345                 350

Ser Gln Thr Lys Pro Pro Thr Met Ala Pro Leu Gly Asp Ser Ser Phe
        355                 360                 365

Trp Pro Gln Val Ser Ser Ala Glu Ala Val Ala Ile Ser Val Ala
    370                 375                 380

Val Pro Ser Gln Ala Lys Asp Ser Thr Leu Phe Glu Leu Lys Pro Arg
385                 390                 395                 400

Ser Pro Gln Val Ile Pro Ile Glu Glu Phe Asp Cys Glu Cys Tyr
                405                 410                 415

Gly His Ser Asn Arg Cys Ser Tyr Ile Asp Phe Leu Asn Val Val Thr
            420                 425                 430

Cys Val Ser Cys Lys His Asn Thr Arg Gly Gln His Cys Gln His Cys
        435                 440                 445

Arg Leu Gly Tyr Tyr Arg Asn Gly Ser Ala Glu Leu Asp Asp Glu Asn
    450                 455                 460

Val Cys Ile Glu Cys Asn Cys Asn Gln Ile Gly Ser Val His Asp Arg
465                 470                 475                 480

Cys Asn Glu Thr Gly Phe Cys Glu Cys Arg Glu Gly Ala Val Gly Pro
                485                 490                 495

Lys Cys Asp Asp Cys Leu Pro Thr His Tyr Trp Arg Gln Gly Cys Tyr
            500                 505                 510

Pro Asn Val Cys Asp Asp Gln Leu Leu Cys Gln Asn Gly Gly Thr
        515                 520                 525

Cys Gln Gln Asn Gln Arg Cys Ala Cys Pro Pro Gly Tyr Thr Gly Ile
    530                 535                 540

Arg Cys Glu Gln Pro Arg Cys Asp Leu Ala Asp Ala Gly Pro Asp
545                 550                 555                 560

Cys Asp Arg Ala Pro Gly Ile Val Pro Arg Pro Asp Thr Leu Leu Gly
                565                 570                 575

Cys Leu Leu Leu Leu Gly Leu Ala Ala Arg Leu Ala Cys
            580                 585
```

```
<210> SEQ ID NO 43
<211> LENGTH: 2428
<212> TYPE: DNA
<213> ORGANISM: Homo sapiens

<400> SEQUENCE: 43
```

| | |
|---|---|
| ccatgctgag gccgcgagtc ccgcctgacc ccgtcgctgc ctctccaggg cttctctggg | 60 |
| ccgcgcctct gcagactgcg cagccatgct gcatctgctg gcgctcttcc tgcactgcct | 120 |
| ccctctggcc tctggggact atgacatctg caaatcctgg gtgaccacag atgagggccc | 180 |
| cacctgggag ttctacgcct gccagcccaa ggtgatgcgc ctgaaggact acgtcaaggt | 240 |
| gaaggtggag ccctcaggca tcacatgtgg agaccccct gagaggttct gctcccatga | 300 |
| gaatccctac ctatgcagca acgagtgtga cgcctccaac ccggacctgg cccacccgcc | 360 |
| caggctcatg ttcgacaagg aggaggaggg cctggccacc tactggcaga gcatcacctg | 420 |
| gagccgctac cccagcccgc tggaagccaa catcacccctt tcgtggaaca agaccgtgga | 480 |
| gctgaccgac gacgtggtga tgaccttcga gtacggccgg cccacggtca tggtcctgga | 540 |
| gaagtccctg gacaacgggc gcacctggca gccctaccag ttctacgccg aggactgcat | 600 |
| ggaggccttc ggtatgtccg cccgccgggc ccgcgacatg tcatcctcca gcgcgcaccg | 660 |
| cgtgctctgc accgaggagt actcgcgctg ggcaggctcc aagaaggaga agcacgtgcg | 720 |
| cttcgaggtg cgggaccgct cgccatcatt tgccggcccc gacctgcgca acatggacaa | 780 |
| cctctacacg cggctggaga cgccaagggc cctcaaggag ttcttcaccc tcaccgacct | 840 |
| gcgcatgcgg ctgctgcgcc cggcgctggg cggcacctat gtgcagcggg agaacctcta | 900 |
| caagtacttc tacgccatct ccaacatcga ggtcatcggc aggtgcaagt gcaacctgca | 960 |
| tgccaacctg tgctccatgc gcgagggcag cctgcagtgc gagtgcgagc acaacaccac | 1020 |
| cggcccccgac tgcggcaagt gcaagaagaa tttccgcacc cggtcctggc gggccggctc | 1080 |
| ctacctgccg ctgcccatg gctctcccaa cgcctgtgcc gctgcaggtt cctttggcaa | 1140 |
| ctgcgaatgc tacggtcact ccaaccgctg cagctacatt gacttcctga atgtggtgac | 1200 |
| ctgcgtcagc tgcaagcaca acacgcgagg tcagcactgc cagcactgcc ggctgggcta | 1260 |
| ctaccgcaac ggctcggcag agctggatga tgagaacgtc tgcattgagt gtaactgcaa | 1320 |
| ccagatagggc tccgtgcacg accggtgcaa cgagaccggc ttctgcgagt gccgcgaggg | 1380 |
| cgcggcgggc cccaagtgcg acgactgcct ccccacgcac tactggcgcc agggctgcta | 1440 |
| ccccaacgtg tgcgacgacg accagctgct gtgccagaac ggaggcacct gcctgcagaa | 1500 |
| ccagcgctgc gcctgcccgc gcggctacac cggcgtgcgc tgcgagcagc ccgctgcga | 1560 |
| cccccgccgac gatgacggcg gtctggactg cgaccgcgcg cccggggccg ccccgcgccc | 1620 |
| cgccacccctg ctcggctgcc tgctgctgct ggggctggcc gcccgcctgg gccgctgagc | 1680 |
| cccgcccgga ggacgctccc cgcacccgga ggccgggggt cccggggtcc cgggggcggg | 1740 |
| ccggcgtccg aggccgggcg gtgagaaggg tgcggcccga ggtgctccca ggtgctactc | 1800 |
| agcagggccc cccgcccggc ccgcgctccc gcccgcactg ccctcccccc gcagcagggg | 1860 |
| cgccttggga ctccggtccc cgcgcctgcg atttggtttc gttttctttt tgtattatcc | 1920 |
| gccgcccagt tccttttttg tctttctctc tctctctttt tttttttttt ttctggcggt | 1980 |
| gagccagagg gtcgggagaa acgctgctcg ccccacaccc cgtcctgcct cccaccacac | 2040 |
| ttacacacac gggactgtgg ccgacacccc ctggcctgtg ccaggctcac gggcggcggc | 2100 |
| ggaccccgac ctccagttgc ctacaattcc agtcgctgac ttggtcctgt tttctattct | 2160 |
| ttattttttcc tgcaacccac cagacccag gcctcaccgg aggccggtg accacggaac | 2220 |
| tcaccgtctg ggggaggagg agagaaggaa ggggtggggg gcctggaaac ttcgttctgt | 2280 |
| agagaactat ttttgtttgt attcactgtc ccctgcaagg gggacggggc gggagcactg | 2340 |
| gtcaccgcgg gggccgatgg tggagaatcc gaggagtaaa gagtttgctc actgctgcaa | 2400 | aaaaaaaaaa aaaaaaaaaa aaaaaaa                                        2428

<210> SEQ ID NO 44
<211> LENGTH: 530
<212> TYPE: PRT
<213> ORGANISM: Homo sapiens

<400> SEQUENCE: 44

Met Leu His Leu Leu Ala Leu Phe Leu His Cys Leu Pro Leu Ala Ser
1               5                   10                  15

Gly Asp Tyr Asp Ile Cys Lys Ser Trp Val Thr Thr Asp Glu Gly Pro
            20                  25                  30

Thr Trp Glu Phe Tyr Ala Cys Gln Pro Lys Val Met Arg Leu Lys Asp
        35                  40                  45

Tyr Val Lys Val Lys Val Glu Pro Ser Gly Ile Thr Cys Gly Asp Pro
50                  55                  60

Pro Glu Arg Phe Cys Ser His Glu Asn Pro Tyr Leu Cys Ser Asn Glu
65                  70                  75                  80

Cys Asp Ala Ser Asn Pro Asp Leu Ala His Pro Pro Arg Leu Met Phe
                85                  90                  95

Asp Lys Glu Glu Gly Leu Ala Thr Tyr Trp Gln Ser Ile Thr Trp
            100                 105                 110

Ser Arg Tyr Pro Ser Pro Leu Glu Ala Asn Ile Thr Leu Ser Trp Asn
        115                 120                 125

Lys Thr Val Glu Leu Thr Asp Asp Val Val Met Thr Phe Glu Tyr Gly
130                 135                 140

Arg Pro Thr Val Met Val Leu Glu Lys Ser Leu Asp Asn Gly Arg Thr
145                 150                 155                 160

Trp Gln Pro Tyr Gln Phe Tyr Ala Glu Asp Cys Met Glu Ala Phe Gly
                165                 170                 175

Met Ser Ala Arg Arg Ala Arg Asp Met Ser Ser Ser Ala His Arg
            180                 185                 190

Val Leu Cys Thr Glu Glu Tyr Ser Arg Trp Ala Gly Ser Lys Lys Glu
        195                 200                 205

Lys His Val Arg Phe Glu Val Arg Asp Arg Phe Ala Ile Phe Ala Gly
    210                 215                 220

Pro Asp Leu Arg Asn Met Asp Asn Leu Tyr Thr Arg Leu Glu Ser Ala
225                 230                 235                 240

Lys Gly Leu Lys Glu Phe Phe Thr Leu Thr Asp Leu Arg Met Arg Leu
                245                 250                 255

Leu Arg Pro Ala Leu Gly Gly Thr Tyr Val Gln Arg Glu Asn Leu Tyr
            260                 265                 270

Lys Tyr Phe Tyr Ala Ile Ser Asn Ile Glu Val Ile Gly Arg Cys Lys
        275                 280                 285

Cys Asn Leu His Ala Asn Leu Cys Ser Met Arg Glu Gly Ser Leu Gln
    290                 295                 300

Cys Glu Cys Glu His Asn Thr Thr Gly Pro Asp Cys Gly Lys Cys Lys
305                 310                 315                 320

Lys Asn Phe Arg Thr Arg Ser Trp Arg Ala Gly Ser Tyr Leu Pro Leu
                325                 330                 335

Pro His Gly Ser Pro Asn Ala Cys Ala Ala Gly Ser Phe Gly Asn
            340                 345                 350

Cys Glu Cys Tyr Gly His Ser Asn Arg Cys Ser Tyr Ile Asp Phe Leu
        355                 360                 365

Asn Val Val Thr Cys Val Ser Cys Lys His Asn Thr Arg Gly Gln His

-continued

```
                  370                 375                 380
Cys Gln His Cys Arg Leu Gly Tyr Tyr Arg Asn Gly Ser Ala Glu Leu
385                 390                 395                 400

Asp Asp Glu Asn Val Cys Ile Glu Cys Asn Cys Asn Gln Ile Gly Ser
                405                 410                 415

Val His Asp Arg Cys Asn Glu Thr Gly Phe Cys Glu Cys Arg Glu Gly
                420                 425                 430

Ala Ala Gly Pro Lys Cys Asp Asp Cys Leu Pro Thr His Tyr Trp Arg
                435                 440                 445

Gln Gly Cys Tyr Pro Asn Val Cys Asp Asp Gln Leu Leu Cys Gln
                450                 455                 460

Asn Gly Gly Thr Cys Leu Gln Asn Gln Arg Cys Ala Cys Pro Arg Gly
465                 470                 475                 480

Tyr Thr Gly Val Arg Cys Glu Gln Pro Arg Cys Asp Pro Ala Asp Asp
                485                 490                 495

Asp Gly Gly Leu Asp Cys Asp Arg Ala Pro Gly Ala Ala Pro Arg Pro
                500                 505                 510

Ala Thr Leu Leu Gly Cys Leu Leu Leu Gly Leu Ala Ala Arg Leu
                515                 520                 525

Gly Arg
    530
```